US011612619B2

(12) United States Patent
Honkanen et al.

(10) Patent No.: US 11,612,619 B2
(45) Date of Patent: Mar. 28, 2023

(54) COMPOSTIONS AND METHODS FOR ENABLING CHOLESTEROL CATABOLISM IN HUMAN CELLS

(71) Applicant: University of South Alabama Foundation for Research and Commercialization, Mobile, AL (US)

(72) Inventors: Richard Eric Honkanen, Mobile, AL (US); Brandon Marshall D'Arcy, Mobile, AL (US); Mark Raymond Swingle, Mobile, AL (US)

(73) Assignee: National Institute of Health (NIH), U.S. Dept. of Health and Human Services (DHHS), U.S. Government, Bethesda, MD (US)

( * ) Notice: Subject to any disclaimer, the term of this patent is extended or adjusted under 35 U.S.C. 154(b) by 505 days.

(21) Appl. No.: 16/672,185

(22) Filed: Nov. 1, 2019

(65) Prior Publication Data

US 2020/0179452 A1 Jun. 11, 2020

Related U.S. Application Data

(60) Provisional application No. 62/754,499, filed on Nov. 1, 2018.

(51) Int. Cl.

| | |
|---|---|
| ***A61K 35/17*** | (2015.01) |
| ***C12N 15/52*** | (2006.01) |
| ***C12N 15/62*** | (2006.01) |
| ***C12N 5/0783*** | (2010.01) |
| ***C12N 9/02*** | (2006.01) |
| ***C12N 9/04*** | (2006.01) |

(52) U.S. Cl.

CPC ............ *A61K 35/17* (2013.01); *C12N 5/0636* (2013.01); *C12N 15/52* (2013.01); *C12N 15/62* (2013.01); *C07K 2319/43* (2013.01); *C12N 9/001* (2013.01); *C12N 9/0006* (2013.01); *C12N 9/0077* (2013.01); *C12N 9/0095* (2013.01); *C12N 2710/16141* (2013.01); *C12N 2820/005* (2013.01); *C12N 2820/60* (2013.01); *C12Y 101/01051* (2013.01); *C12Y 101/01145* (2013.01); *C12Y 103/01021* (2013.01); *C12Y 103/99004* (2013.01); *C12Y 106/02004* (2013.01); *C12Y 114/15* (2013.01); *C12Y 114/15006* (2013.01); *C12Y 118/01002* (2013.01)

(58) Field of Classification Search

None

See application file for complete search history.

(56) References Cited

U.S. PATENT DOCUMENTS

| | | | | |
|---|---|---|---|---|
| 5,484,727 | A | 1/1996 | Chang | |
| 5,547,868 | A | 8/1996 | Miller et al. | |
| 5,939,318 | A | 8/1999 | Miller et al. | |
| 8,741,812 | B2 | 6/2014 | Javitt | |
| 2004/0121992 | A1 | 6/2004 | Javitt | |
| 2006/0172423 | A1 * | 8/2006 | Van Der Geize ...... | C07K 14/36 435/252.2 |
| 2006/0252705 | A1 | 11/2006 | Shaw | |
| 2012/0039929 | A1 | 2/2012 | Ginns | |
| 2015/0258081 | A1 | 9/2015 | Lukas | |
| 2016/0152955 | A1 * | 6/2016 | Sakamoto ................ | C12N 7/00 435/239 |
| 2016/0264615 | A1 | 9/2016 | Shunlin | |

FOREIGN PATENT DOCUMENTS

| | | | |
|---|---|---|---|
| CN | 102168098 | B | 3/2013 |
| JP | 5643643 | B2 | 12/2014 |
| WO | 2010103837 | A1 | 9/2010 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Arif, Kamil, Enabling Cholesterol Catabolism in Human Cells; Partial Thesis, University of South Alabama, May 2012, 32 Pages.
Chistiakov, et al., Journal of Cellular Molecular Medicine; 20(1): 17-28, Aug. 19, 2015.
Bednarska, et al., Mediators of Inflammation; 2014: 498395, Jul. 8, 2014.
Taylor, et al., Cardiovascular Research; 86: 526-534, Jan. 18, 2010.
Giovanna, et al., Protein Expression and Purification 79: 231-236, May 20, 2011.
Harikrishna, et al., DNA and Cell Biology; vol. 12, No. 5: 371-379, 1993.
D'Arcy, et al., Scientific Reports; 9:5969 www.nature.com/scientificreports, Apr. 12, 2019.

* cited by examiner

*Primary Examiner* — Christian L Fronda
(74) *Attorney, Agent, or Firm* — Dorsey & Whitney LLP

(57) ABSTRACT

Compositions, methods, and systems for modifying sterol metabolism in a subject is disclosed. In some embodiments, the subjects may be administered one or more mammalian cells modified to express at least one sterol degrading enzyme derived from a bacterium. In many embodiments, the cell is a macrophage or monocyte stably expressing three or more enzymes that aid in opening the β ring of cholesterol. The disclosed compositions and methods may be useful in lowering cholesterol levels in a subject in need thereof. In some embodiments, the subject may have a genetic predisposition to atherosclerosis.

17 Claims, 92 Drawing Sheets
(45 of 92 Drawing Sheet(s) Filed in Color)
Specification includes a Sequence Listing.

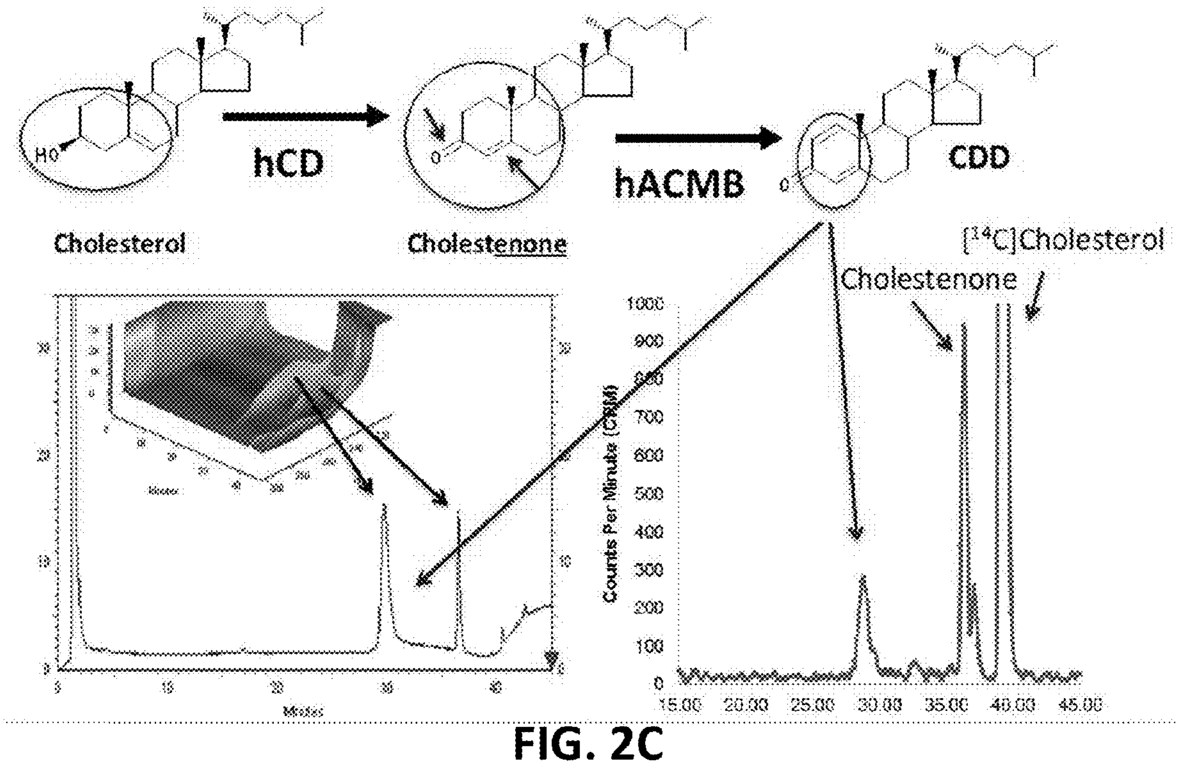
FIG. 2C
FIG. 2D
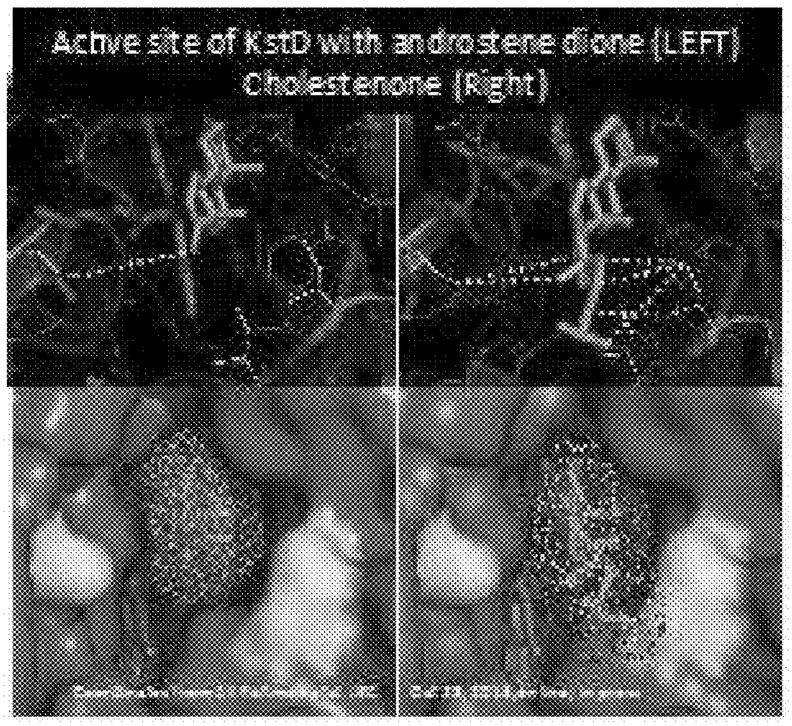

FIG. 9
a)
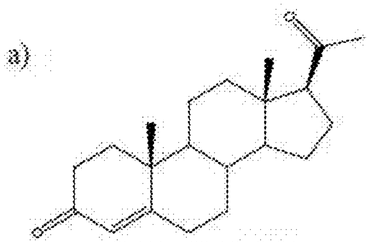
progesterone (PD)
b)
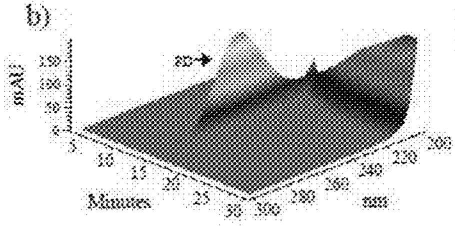
c)
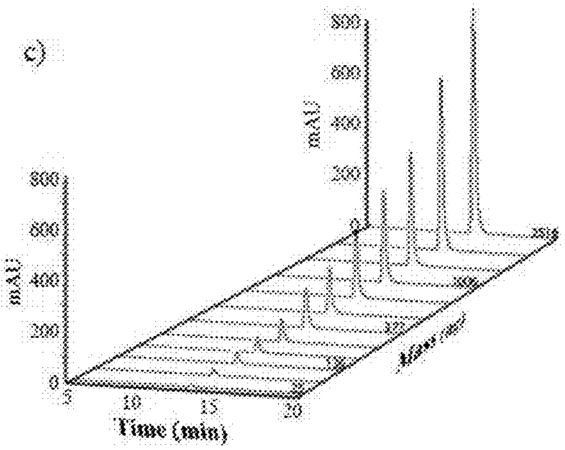
d)
| Mass (μg) | AUC |
|---|---|
| 0.025 | 385193 |
| 0.076 | 1144434 |
| 0.129 | 1932149 |
| 0.182 | 2726643 |
| 0.257 | 3850619 |
| 0.391 | 5851692 |
| 0.523 | 7824425 |
| 0.788 | 11772883 |
| 1.050 | 15689153 |
| 1.315 | 19632318 |
| 1.979 | 29545695 |
| 2.648 | 39529936 |
e)
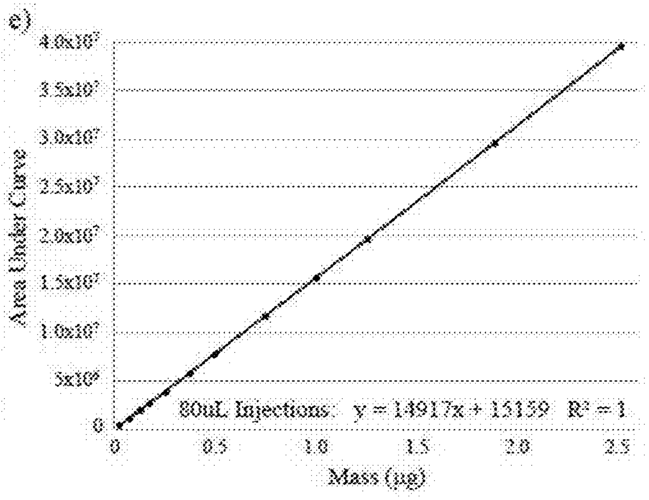

| Band | Pixel Area | Percentage |
|---|---|---|
| 1 | 6707.134 | 79.6% |
| 2 | 681.577 | 8.1% |
| 3 | 25.950 | 0.3% |
| 4 | 38.364 | 0.4% |
| 5 | 146.435 | 1.7% |
| 6 | 825.820 | 9.8% |

Progesterone (PD)

pregn-1,4-diene-3,20-dione (PDD)

Resazurin
(Weakly Fluorescent)

Resorufin
(Highly Fluorescent)

a) androsterone
b) hydrocortisone
c) hydrocortisone 21-hemisuccinate
d) mifepristone
e) cholesterol
f) pregnenolone
g) dehydroepiandrosterone
h) corticosterone
i) 7β-hydroxycholestanone
j)
k)
l)

P450-FdxR-Fdx Fusion Protein SEQ ID NO:5

MLAKGLPPRSVLVKGCQTFLSAPREGLGRLRVPTGEGAGISTRSPRPFNEIPSPGDNGWLNLYHFWRE
TGTHKVHLHHVQNFQKYGPIYREKLGNVESVYVIDPEDVALLFKSEGPNPERFLIPPWVAYHQYYQRPIG
VLLKKSAAWKKDRVALNQEVMAPEATKNFLPLLDAVSRDFVSVLHRRIKKAGSGNYSGDISDDLFRFAF
ESITNVIFGERQGMLEEVVNPEAQRFIDAIYQMFHTSVPMLNLPPDLFRLFRTKTWKDHVAAWDVIFSKA
DIYTQNFYWELRQKGSVHHDYRGILYRLLGDSKMSFEDIKANVTEMLAGGVDTTSMTLQWHLYEMARN
LKVQDMLRAEVLAARHQAQGDMATMLQLVPLLKASIKETLRLHPISVTLQRYLVNDLVLRDYMIPAKTL
VQVAIYALGREPTFFFDPENFDPTRWLSKDKNITYFRNLGFGWGVRQCLGRRIAELEMTIFLINMLENFRV
EIQHLSDVGTTFNLILMPEKPISFTFWPFNQEATQQTDGTSSTQEKTPQICVVGSGPAGFYTAQHLLKHPQA
HVDIYEKQPVPFGLVRFGVAPDHPEVKNVINTFTQTAHSGRCAFWGNVEVGRDVTVPELREAYHAVVLS
YGAEDHRALEIPGEELPGVCSARAFVGWYNGLPENQELEPDLSCDTAVILGQGNVALDVARILLTPPEHLE
RTDITKAALGVLRQSRVKTVWLVGRRGPLQVAFTIKELREMIQLPGARPILDPVDFLGLQDKIKEVPRPRK
RLTELLLRTATEKPGPAEAARQASASRAWGLRFFRSPQQVLPSPDGRRAAGVRLAVTRLEGVDEATRAVP
TGDMEDLPCGLVLSSIGYKSRPVDPSVPFDSKLGVIPNVEGRVMDVPGLYCSGWVKRGPTGVIATTMTDS
FLTGQMLLQDLKAGLLPSGPRPGYAAIQALLSSRGVRPVSFSDWEKLDAEEVARGQGTGKPREKLVDPQE
MLRLLGHTDGASSSSEDKITVHFINRDGETLTTKGKVGDSLLDVVVENNLDIDGFGACEGTLACSTCHLIF
EDHIYEKLDAITDEENDMLDLAYGLTDRSRLGCQICLTKSMDNMTVRVPETVADARQSIDVGKTSDYKD
DDDKGSGATNFSLLKQAGDVEENPGP

P450 http://www.uniprot.org/uniprot/P05108 SEQ ID NO:6

MLAKGLPPRSVLVKGCQTFLSAPREGLGRLRVPTGEGAGISTRSPRPFNEIPSPGDNGWLNLYHFWRE
TGTHKVHLHHVQNFQKYGPIYREKLGNVESVYVIDPEDVALLFKSEGPNPERFLIPPWVAYHQYYQRPIG
VLLKKSAAWKKDRVALNQEVMAPEATKNFLPLLDAVSRDFVSVLHRRIKKAGSGNYSGDISDDLFRFAF
ESITNVIFGERQGMLEEVVNPEAQRFIDAIYQMFHTSVPMLNLPPDLFRLFRTKTWKDHVAAWDVIFSKA
DIYTQNFYWELRQKGSVHHDYRGILYRLLGDSKMSFEDIKANVTEMLAGGVDTTSMTLQWHLYEMARN
LKVQDMLRAEVLAARHQAQGDMATMLQLVPLLKASIKETLRLHPISVTLQRYLVNDLVLRDYMIPAKTL
VQVAIYALGREPTFFFDPENFDPTRWLSKDKNITYFRNLGFGWGVRQCLGRRIAELEMTIFLINMLENFRV
EIQHLSDVGTTFNLILMPEKPISFTFWPFNQEATQQ

Ferrodoxin Reductase http://www.uniprot.org/uniprot/P22570 SEQ ID NO:7

MASRCWRWWGWSAWPRTRLPPAGSTPSFCHHFSTQEKTPQICVVGSGPAGFYTAQHLLKHPQAHVDI
YEKQPVPFGLVRFGVAPDHPEVKNVINTFTQTAHSGRCAFWGNVEVGRDVTVPELREAYHAVVLSYGAE
DHRALEIPGEELPGVCSARAFVGWYNGLPENQELEPDLSCDTAVILGQGNVALDVARILLTPPEHLERTDI
TKAALGVLRQSRVKTVWLVGRRGPLQVAFTIKELREMIQLPGARPILDPVDFLGLQDKIKEVPRPRKRLTE
LLLRTATEKPGPAEAARQASASRAWGLRFFRSPQQVLPSPDGRRAAGVRLAVTRLEGVDEATRAVPTGD
MEDLPCGLVLSSIGYKSRPVDPSVPFDSKLGVIPNVEGRVMDVPGLYCSGWVKRGPTGVIATTMTDSFLT
GQMLLQDLKAGLLPSGPRPGYAAIQALLSSRGVRPVSFSDWEKLDAEEVARGQGTGKPREKLVDPQEML
RLLGH

Ferrodoxin http://www.uniprot.org/uniprot/P10109 SEQ ID NO:8

MAAAGGARLLRAASAVLGGPAGRWLHHAGSRAGSSGLLRNRGPGGSAEASRSLSVSARARSSSEDK
ITVHFINRDGETLTTKGKVGDSLLDVVVENNLDIDGFGACEGTLACSTCHLIFEDHIYEKLDAITDEENDM
LDLAYGLTDRSRLGCQICLTKSMDNMTVRVPETVADARQSIDVGKTS

FIG. 84

FIG. 85
FIG. 86
Features :
| | |
|---|---|
| AttB1 | : [1 : 25] |
| TEV Site | : [43 : 63] |
| 6x His Tag | : [64 : 81] |
| Kozak Consensus Sequence | : [82 : 93] |
| Tetracysteine Tag | : [106 : 123] |
| Flag Tag | : [142 : 165] |
| CholD | : [166 : 1284] |
| AttB2 | : [1304 : 1328] |
FIG. 87
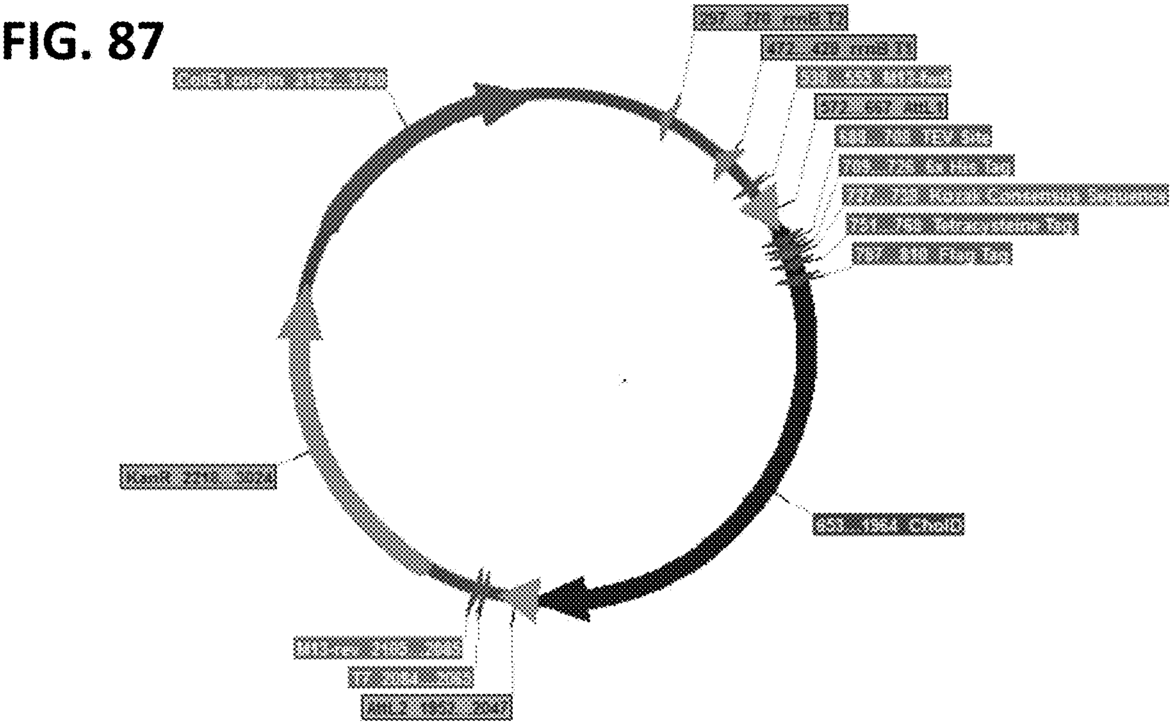

FIG. 88
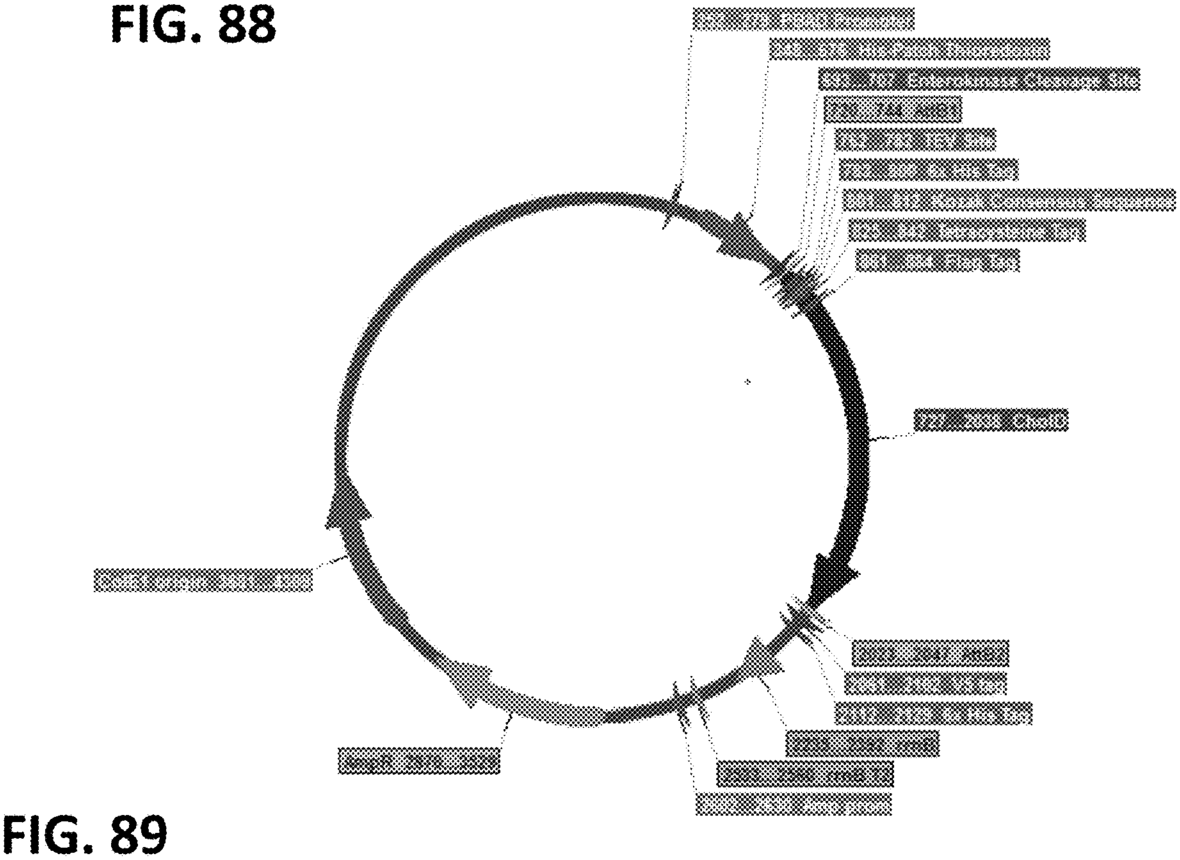
FIG. 89
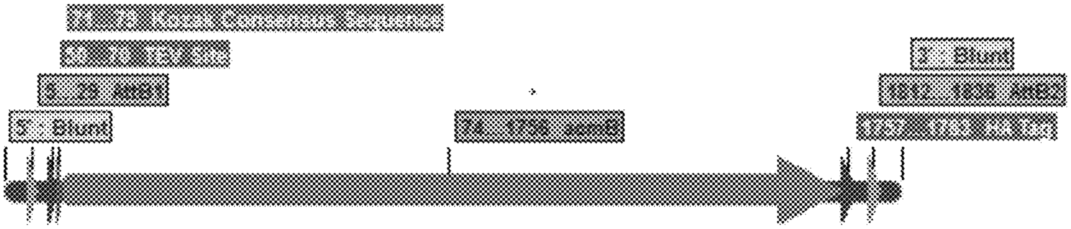
FIG. 90
| | | |
|---|---|---|
| Features : | | |
| AttB1 | : | [5 : 29] |
| TEV Site | : | [50 : 70] |
| Kozak Consensus Sequence | : | [71 : 79] |
| acmB | : | [74 : 1756] |
| HA Tag | : | [1757 : 1783] |
| AttB2 | : | [1812 : 1836] |

Features :

| | | |
|---|---|---|
| AttL1 | : | [18 : 113] |
| Kozak Consensus Sequence | : | [116 : 127] |
| P450-FdxR-Fdx | : | [122 : 3463] |
| Flag Tag | : | [3464 : 3487] |
| P2A Peptide | : | [3488 : 3553] |
| HSD2 | : | [3554 : 4672] |
| AttL2 | : | [4707 :4802] |

Features :

| | | |
|---|---|---|
| AttB1 | : | [5 : 29] |
| TEV Site | : | [47 : 67] |
| 6x His Tag | : | [68 : 85] |
| Kozak Consensus Sequence | : | [86 : 97] |
| Tetracysteine Tag | : | [110 : 127] |
| Flag Tag | : | [146 : 169] |
| KstD | : | [170 : 1704] |
| AttB2 | : | [1734 : 1758] |

FIG. 103
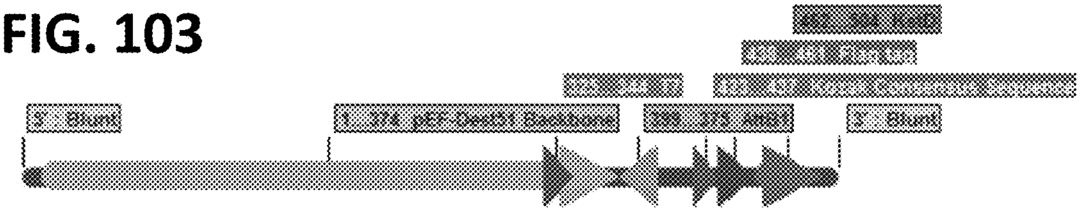
FIG. 104
Features :
| | | |
|---|---|---|
| pEF-Dest51 Backbone | : | [1 : 374] |
| T7 | : | [325 : 344] |
| AttB1 | : | [375 : 399] |
| Kozak Consensus Sequence | : | [423 : 437] |
| Flag tag | : | [438 : 461] |
| KstD | : | [462 : 504] |
FIG. 105
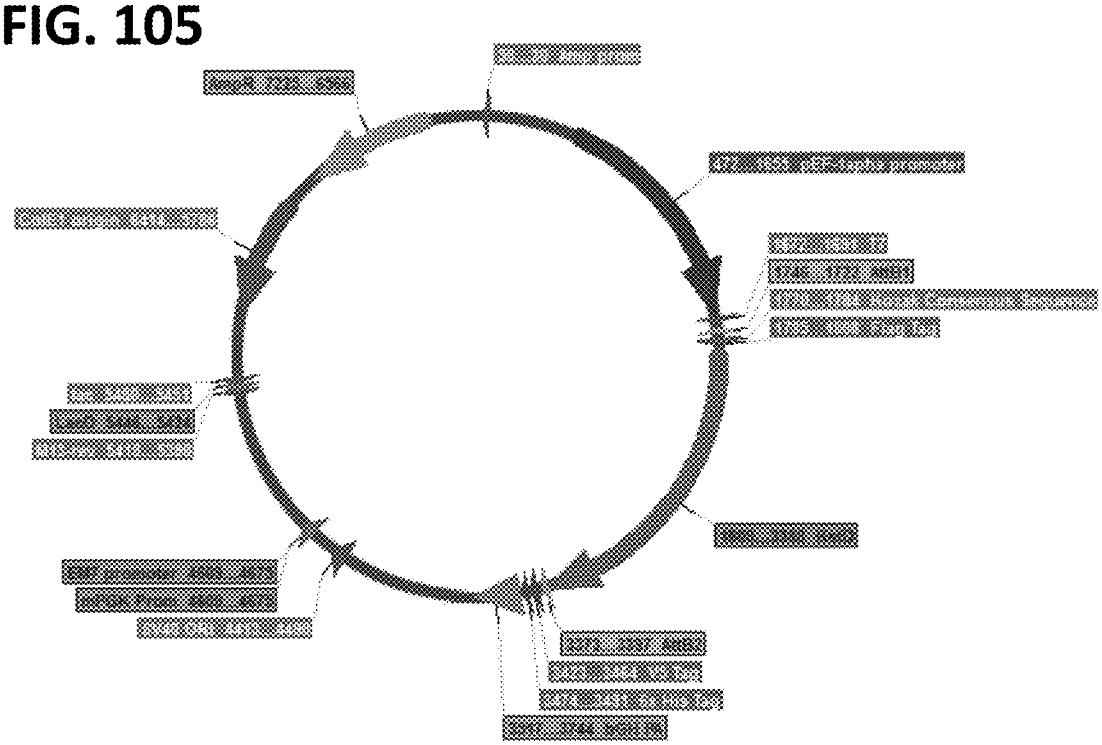

Features :

| | |
|---|---|
| Amp prom | : [30 : 58] |
| pEF-lapha promoter | : [472 : 1655] |
| T7 | : [1672 : 1691] |
| AttB1 | : [1722 : 1746] |
| Kozak Consensus Sequence | : [1770 : 1784] |
| Flag Tag | : [1785 : 1808] |
| KstD | : [1809 : 3388] |
| V5 Tag | : [3423 : 3464] |
| 6x His Tag | : [3474 : 3491] |
| AttB2 | : [3373 : 3397] |
| bGH PA | : [3517 : 3744] |
| EM7 promoter | : [4609 : 4675] |
| mPGK Prom | : [4609 : 4675] |
| M13-rev | : [5398 : 5418] |
| LacO | : [5424 : 5446] |
| lac | : [5451 : 5480] |
| SV40 ORI | : [4413 : 4490] |
| ColE1 origin | : [5786 : 6414] |
| AmpR | : [6566 : 7225] |

```
Features :
AttB1               : [69 : 45]
Shine Dalgarno      : [79 : 96]
TAT Peptide         : [97 : 141]
6x His Tag          : [142 : 159]
KshA                : [160 : 1338]
Shine Dalgarno      : [1346 : 1363]
TAT Peptide         : [1364 : 1408]
6x His Tag          : [1409 : 1426]
KshB                : [1427 : 2485]
AttB2               : [2496 : 2520]
```

Features :

| | | |
|---|---|---|
| AttB1 | : | [69 : 45] |
| Kozak Consensus Sequence | : | [93 : 107] |
| Flag Tag | : | [108 : 131] |
| KshA | : | [132 : 1316] |
| P2A Peptide | : | [1317 : 1382] |
| HA Tag | : | [1389 : 1415] |
| KshB | : | [1416 : 2483] |
| AttB2 | : | [2526 : 2550] |

FIG. 119
FIG. 120
Features :
attL1 : [1 : 4]
Kozak Consensus Sequence : [31 : 45]
Aconitase2 MTS : [37 : 141]
Flag Tag : [142 : 165]
KshA : [166 : 1000]
FIG. 121
FIG. 122
Features :
KshA : [1 : 387]
P2A Peptide : [388 : 453]
Aconitase2 MTS : [454 : 558]
HA Tag : [562 : 588]
KshB : [589 : 600]

Features :

| | |
|---|---|
| rrnB T2 | : [270 : 297] |
| rrnB T1 | : [429 : 472] |
| M13-fwd | : [538 : 555] |
| AttL1 | : [572 : 667] |
| Kozak Consensus Sequence | : [693 : 705] |
| KshA MTS | : [700 : 804] |
| Flag Tag | : [805 : 828] |
| KshA | : [700 : 2013] |
| P2A Peptide | : [2014 : 2079] |
| KshB MTS | : [2080 : 2184] |
| HA Tag | : [2188 : 2214] |
| KshB | : [2080 : 3279] |
| AttL2 | : [3328 : 3423] |
| T7 | : [3441 : 3460] |
| M13-rev | : [3461 : 3481] |
| KanR | : [3594 : 4400] |
| ColE1 origin | : [4528 : 5156] |

3' Blunt
5' Blunt
1..512 KshB No Stop
3' Blunt
5' Blunt
1..512 KshB No Stop

FIG. 127
FIG. 128
Features :
| | | |
|---|---|---|
| KshB No Stop | : | [1 : 512] |
| Thosea asigna 2A Peptide | : | [513 : 575] |
| Flag Tag | : | [576 : 599] |
| KstD | : | [600 : 656] |
FIG. 129
FIG. 130
Features :
| | | |
|---|---|---|
| KshB No Stop | : | [1 : 512] |
| Porcine Teschovirus 2A Peptide | : | [513 : 578] |
| Flag Tag | : | [579 : 602] |
| KstD | : | [603 : 659] |

Features :

| | | |
|---|---|---|
| rrnB T2 | : | [577 : 604] |
| rrnB T1 | : | [736 : 779] |
| M13-fwd | : | [845 : 862] |
| AttL1 | : | [879 : 974] |
| Kozak Consensus Sequence | : | [1001 : 1012] |
| KshA MTS | : | [1007 : 1111] |
| Flag Tag | : | [1112 : 1135] |
| **KshA** | : | [1007 : 2320] |
| P2A Peptide | : | [2321 : 2386] |
| KshB MTS | : | [2387 : 2491] |
| HA Tag | : | [2495 : 2521] |
| **KshB** | : | [2387 : 3586] |
| AttL2 | : | [5241 : 5336] |
| T2A Peptide | : | [3587 : 3649] |
| Flag Tag | : | [3650 : 3673] |
| KstD | : | [3674 : 5212] |
| KstD Stop | : | [5204 : 5212] |
| T7 | : | [5354 : 5373] |
| M13-rev | : | [5374 : 5394] |
| KanR | : | [5507 : 6313] |

5' Blunt
3' Blunt
41 : 434 P450-FdxR-Fdx
3' Blunt
3039 : 3221 HSD2
5' Blunt
3' Blunt
5' Blunt

FIG. 135
FIG. 136
Features :
| | | |
|---|---|---|
| Left Homology Arm pEntr221 | : | [1 : 40] |
| ATG Start for P450-FdxR-Fdx | : | [41 : 43] |
| **P450-FdxR-Fdx** | : | **[41 : 434]** |
| Right Homology Arm P450 | : | [435 : 474] |
FIG. 137
FIG. 138
Features :
| | | |
|---|---|---|
| **P450-FdxR-Fdx** | : | **[1 : 2948]** |
| Flag Tag | : | [2949 : 2972] |
| P2A | : | [2973 : 3038] |
| ATG Start for HSD2 | : | [3039 : 3041] |
| **HSD2** | : | **[3039 : 3221]** |
FIG. 139
FIG. 140
Features :
| | | |
|---|---|---|
| Left Homology Arm | : | [1 : 40] |
| **HSD** | : | **[41 : 973]** |
| T2A Peptide | : | [974 : 1036] |
| Right Homology Arm | : | [1037 : 1079] |

Features :

| | | |
|---|---|---|
| M13-fwd | : | [845 : 862] |
| AttL1 | : | [879 : 974] |
| rrnB T2 | : | [577 : 604] |
| rrnB T1 | : | [736 : 779] |
| Kozak Consensus Sequence | : | [1001 : 1012] |
| P450-FdxR-Fdx | : | [1007 : 4348] |
| Flag Tag | : | [4349 : 4372] |
| P2A Peptide | : | [4373 : 4438] |
| HSD2 | : | [4439 : 5554] |
| T2A Peptide | : | [5555 : 5617] |
| KshA MTS | : | [5618 : 5722] |
| Flag Tag | : | [5723 : 5746] |
| KshA | : | [5747 : 6931] |
| P2A Peptide | : | [6932 : 6997] |
| KshB MTS | : | [6998 : 7106] |
| HA Tag | : | [7106 : 7132] |
| KshB | : | [7133 : 8197] |
| T2A Peptide | : | [8198 : 8260] |
| Flag Tag | : | [8261 : 8284] |
| KstD | : | [8285 : 9814] |
| KstD Stop | : | [9815 : 9817] |
| AttL2 | : | [9852 : 9947] |
| T7 | : | [9965 : 9984] |
| M13-rev | : | [9985 : 10005] |
| KanR | : | [10116 : 10924] |

COMPOSTIONS AND METHODS FOR ENABLING CHOLESTEROL CATABOLISM IN HUMAN CELLS

CROSS-REFERENCE TO RELATED APPLICATIONS

This application claims benefit of priority pursuant to 35 U.S.C. § 119(e) of U.S. provisional patent application No. 62/754,499 entitled "ENABLING CHOLESTEROL CATABOLISM IN HUMAN CELLS," filed on 1 Nov. 2019, which is hereby incorporated by reference in its entirety.

GOVERNMENT RIGHTS

This invention was made with government support under grant number HL110937 awarded by the National Institutes of Health of the U.S. Department of Health and Human Services. The government has certain rights in the invention.

FIELD

The processes, methods, compositions, and systems disclosed herein are useful in regulating sterol concentrations in subjects in need thereof.

SEQUENCE LISTING

The instant application contains a Sequence Listing which has been submitted electronically in ASCII format and is hereby incorporated by reference in its entirety. Said ASCII copy, created on Oct. 29, 2019, is named P278091_US_03_507078-00005_SL.txt and is 105,499 bytes in size.

BACKGROUND

Atherosclerosis is a chronic maladaptive inflammatory response initiated by the retention of cholesterol rich apolipoprotein B-containing lipoproteins within the arterial wall. Atherosclerosis is an underlying cause of cardiovascular disease (CVD), myocardial infarction, stroke and peripheral vascular disease, which are leading causes of death in the United States. CVD originates from aberrations in normal lipid metabolism (some lifestyle choices, some genetic) that result in elevated plasma lipoproteins (principally LDLs) and/or low levels of high-density lipoproteins (HDLs). CVD is often an age dependent, progressive disease that is largely undetected or ignored until an event (i.e. myocardial infarction or stroke) occurs in the later stages of disease. Therefore, current therapies focus on preventing a second event (or a primary event in high risk individuals) by reducing the circulating levels of LDLs and/or increasing HDLs.

SUMMARY

The present disclosure is directed to therapies targeting the biochemical basis of CVD (at a biochemical level the inability of macrophages to modify cholesterol to degrade the cholestane ring of cholesterol is a fundamental component of CVD). Applicants hypothesized that if macrophages had the ability to degrade cholesterol, they might not become engorged with cholesterol/cholesterol esters and elicit the maladaptive immune response that leads to the onset and progression of atherosclerosis. The present compositions and methods are based, in part, on Applicant's surprising observation that during chronic infection *Mycobacteria tuberculosis* survival in humans is enabled by their ability to feed on cholesterol, while contained within foamy macrophages.

Disclosed herein are methods to humanize and express the enzymes that aid in catalyzing cholesterol degradation, including side chain modification, ring modifications, and modifications leading to ring opening. Disclosed herein are methods for enzyme-mediated cholestane ring opening in human cells. The present disclosure will aid the development of genetic and cell-based therapies allowing for an entirely new and inventive approach for the medical management of CVD.

Disclosed herein are methods, compositions, and systems for regulating sterol metabolism. In one embodiment, the disclosed compositions, methods, and systems may enable sterol catabolism in a mammal. In some embodiments, the disclosed methods, compositions, and systems may be useful in modifying mammalian cells to express one or more non-mammalian enzymes active in sterol catabolism. In some embodiments the mammalian cells may be immune cells, such as monocytes. In some embodiments the monocytes are macrophages. In some embodiments, the sterol may be cholesterol.

Disclosed herein are methods for modifying a mammalian cell with nucleic acid compositions that enable and/or promote expression of one or more proteins useful in degrading a sterol. In some embodiments, the composition includes a vector having one or more control sequences for promoting the expression of one or more protein coding sequences. In some embodiments, the vector is a viral vector or a transposable element.

Disclosed herein are methods of expressing proteins in a cell that does not normally express such proteins. In many embodiments the proteins may be enzymes capable of altering a sterol, such as cholesterol or derivatives thereof. In some embodiments, the enzymes are selected from cholesterol dehydrogenase (CholD), 3-ketosteroid Δ1-dehydrogenase (Δ1-KstD), anoxic cholesterol metabolism B enzyme (acmB), 3-ketosteroid 9α-hydroxylase (KshAB), 3β-hydroxysteroid dehydrogenase 2 (HSD2), and P450-ferredoxin reductase-ferredoxin fusion protein (P450-FdxR-Fdx). In some embodiments, the enzymes may be derived from one or more non-eukaryotic organisms, for example bacteria. In most embodiments, the amino acid sequences of and/or the coding sequences for these enzymes has been modified to aid in expressing the enzymes in a eukaryotic cell.

Disclosed herein are methods and compositions useful in creating modified human cells capable of degrading cholesterol. In many embodiments, the human cells are immune cells comprising one or more nucleic acid sequences coding for one or more proteins useful in degrading a sterol, or derivative thereof. In many embodiments, the proteins may be derived from a non-eukaryote, such as bacteria. In many embodiments, the cells are immune cells, for example monocytes or, more particularly, macrophages. In some embodiments, the macrophages may be modified to degrade low density lipoproteins associated with atherosclerotic plaques.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2C Shows HPLC-analysis of cholesterol catabolism. Humanized hCD and hACMB expressed in *E. coli* were partially purified. [$^{14}$C]-spiked cholesterol (100 nCi/10 μM) was then added to a mixture containing hCD and hAMCB. After 24 hours the samples were extracted with ethylacetate and catabolites were identified by their retention time when resolved using RP-HPLC (C-18 column) in combination with the spectral shift that is produced (ie. cholesterol does not absorb at 245 nm and elutes with a retention time of 40 minutes. Cholestenone and CDD absorb strongly at ~245 nm and have shorter retention times. Control *E. coli* extracts demonstrated no metabolic activity against cholesterol, CDD, or any of the catabolites produced prior to ring opening, which makes detection of sterol derived analytes robust.

FIG. 2D shows Co-crystal structure of bacterial KstD in complex with ADD (left). Model of cholesterol in the KstD active site (right). Isoleucine residues producing a steric clash with the C17-side chain are shown in yellow. Coordinates for Pymol generated figures and for modeling were kindly provided by Ali. Rohman et al.

FIG. 9. RP-HPLC calibration curve for progesterone. (Panel a) Molecular structure of progesterone (PD). (Panel b)(Panel b) 3-D spectral data showing progesterone's absorbance wavelength ($\lambda_{max}$: 245 nm) and retention time ($t_r$=13.8 min). (Panel c) Serial 2-D chromatograms with increasing concentrations of progesterone. (Panels d & e) Demonstration of the sensitivity and quantitative ability in assessing the number of micrograms in a serial dilution of progesterone by RP-HPLC. Injection volumes of 80 μL from serial dilutions between 0.025 μg to 2.5 μg progesterone resulted in a calibration curve with an $R^2$ of 1.

Figure 58:
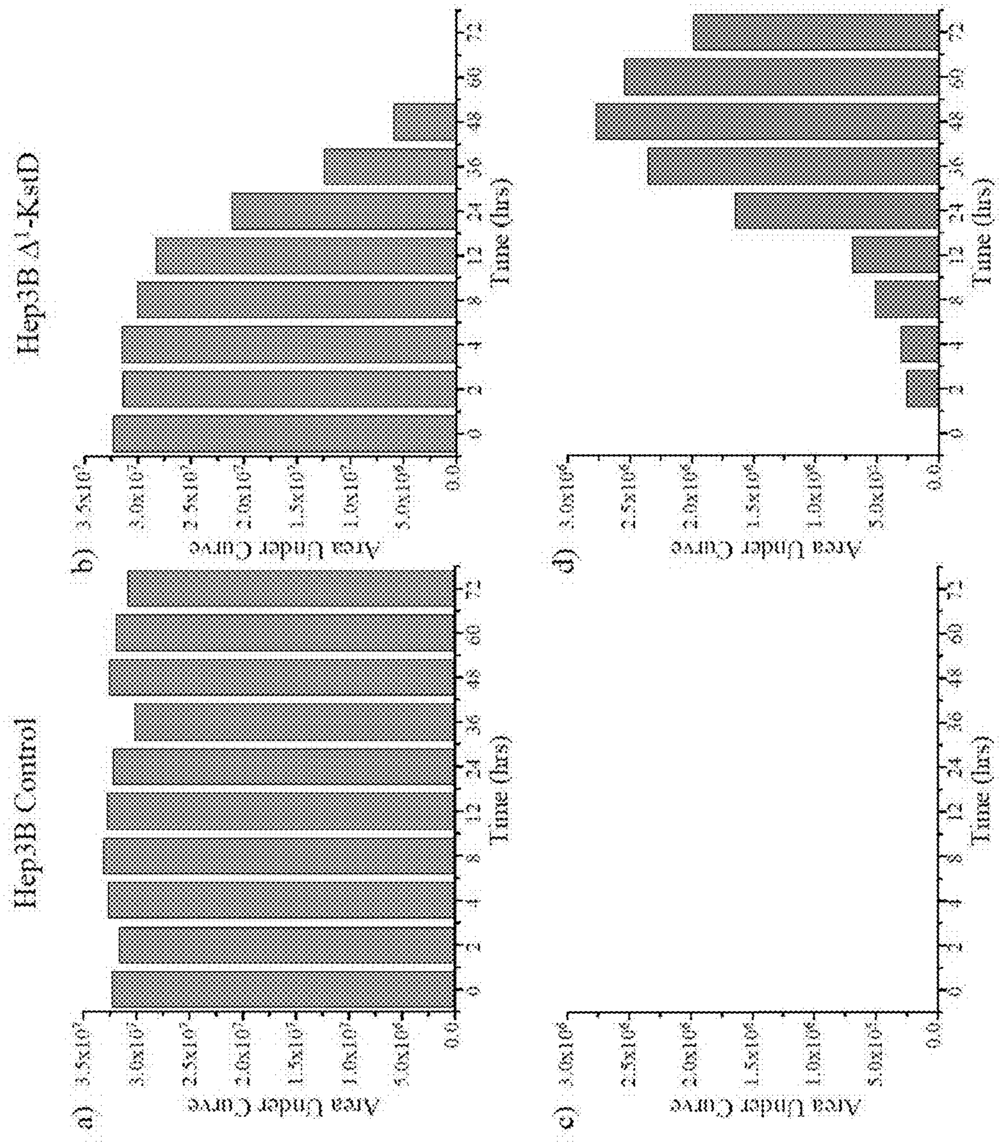

FIG. 58. Quantitative analysis of 3-hydroxy-9,10-seco-pregn-1,3,5(10)-triene-9,20-dione (3-HSP) product formation from 9-hdyroxypregn-4-ene-3,20-dione (9-OHPD) C1-C2 desaturation by Hep3B $\Delta^1$-KstD cells. Bar graphs representing the measured area under the curve (AUC) of (Panels a & b) 9-OHPD and (Panels c &d) 3-HSP from (Panels a & c) Hep3B control and (Panels b & d) Hep3B $\Delta^1$-KstD cells following incubation with 17 μg (10 μM) 9-OHPD produced and isolated from bacterial KshAB lysate. The AUC of 9-OHPD and 3-HSP were measured at λ245 nm and λ280 nm, respectively, from 2-D chromatograms at time points: 0, 2, 4, 8, 12, 24, 36, 48, 60, and 72 hours. Quantitative analysis of 9-OHPD AUC reveals (Panel b) Hep3B $\Delta^1$-KstD cells are equipped with the ability to catabolize the substrate as seen by its reduction and exhaustion over the 72 hour time course. Conversely, (Panel a) Hep3B control cells lack the metabolic ability to modify the substrate, as seen by the retention of 9-OHPD throughout the time course. Quantitative analysis of 3-HSP AUC reveals (Panel d) Hep3B $\Delta^1$-KstD cells are equipped with the ability to desaturate C1-C2 bond of 9-OHPD to form the ring opened product, 3-HSP. Conversely, (Panel c) Hep3B control cells lack the metabolic ability to catabolize 9-OHPD and therefore are unable to produce 3-HSP.

Figure 59:
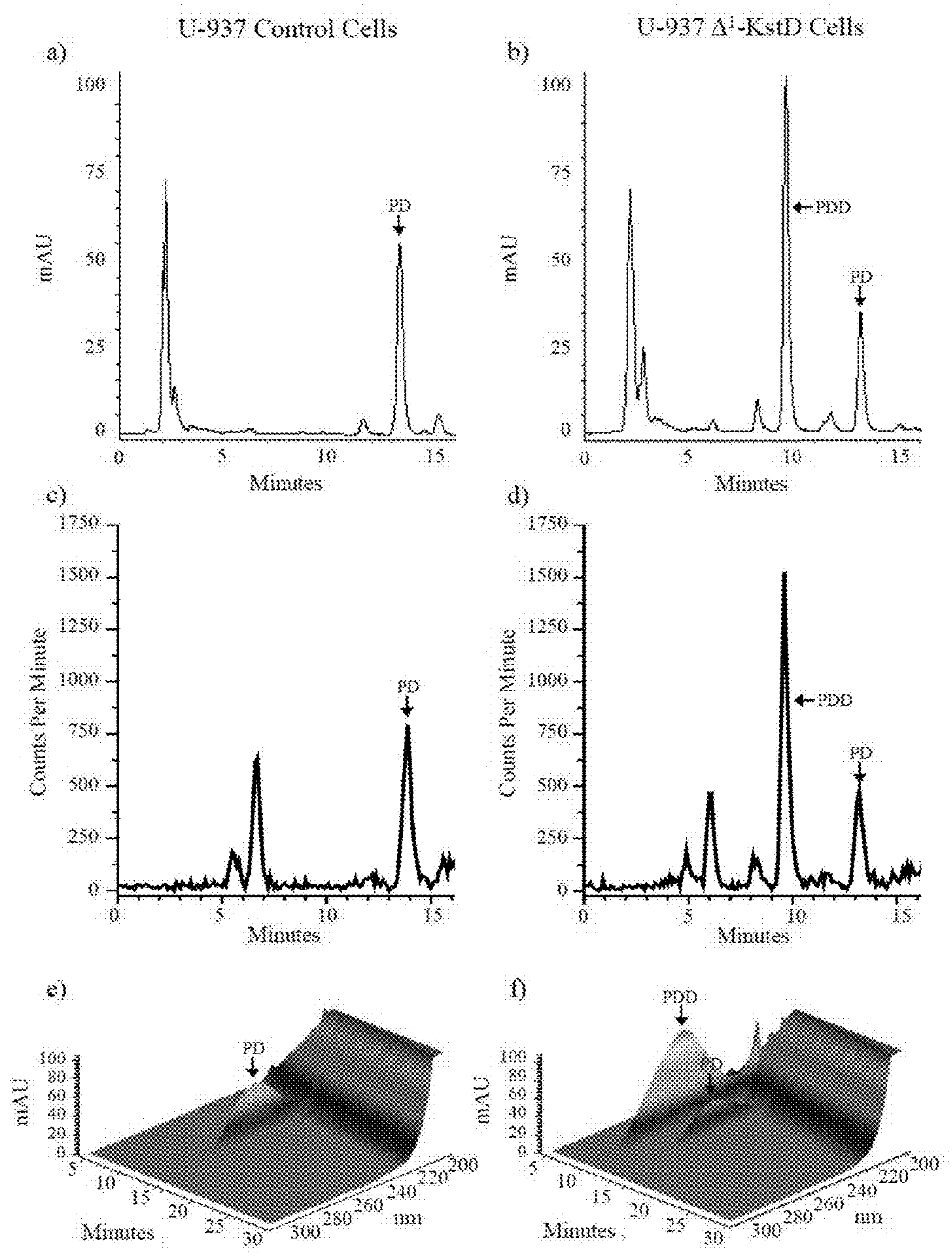

FIG. 59. RP-HPLC analysis of pregn-1,4-diene-3,20-dione (PDD) formation from progesterone (PD) by U-937 $\Delta^1$-KstD cells. Representative 2-D chromatograms of (Panels a & b) λ245 nm, (Panels c & d) C4-$^{14}$C scintillation events, and (Panels e & f) 3-D spectral data from (Panels a, c, & e) control macrophages and (Panels b, d, & f) $\Delta^1$-KstD expressing macrophages incubated with 15.7 μg (10 μM) progesterone spiked with 100 nCi C4-$^{14}$C labeled PD ($t_r$=13.8 min; $\lambda_{max}$ of 245 nm) for 72 hours. Analysis of U-937 $\Delta^1$-KstD cells shows formation of a new peak with a retention time of 10.0 min, a $\lambda_{max}$ of 247 nm, and containing C4-$^{14}$C scintillation events corresponding to the formation of PDD ($t_r$=10.0 min, $\lambda_{max}$ 247 nm) following 72 hours incubation with PD. In contrast, U-937 control cells lack the ability to catabolize PD to PDD, as seen by the absence of a peak with a 10.0 min retention time.

Figure 60:
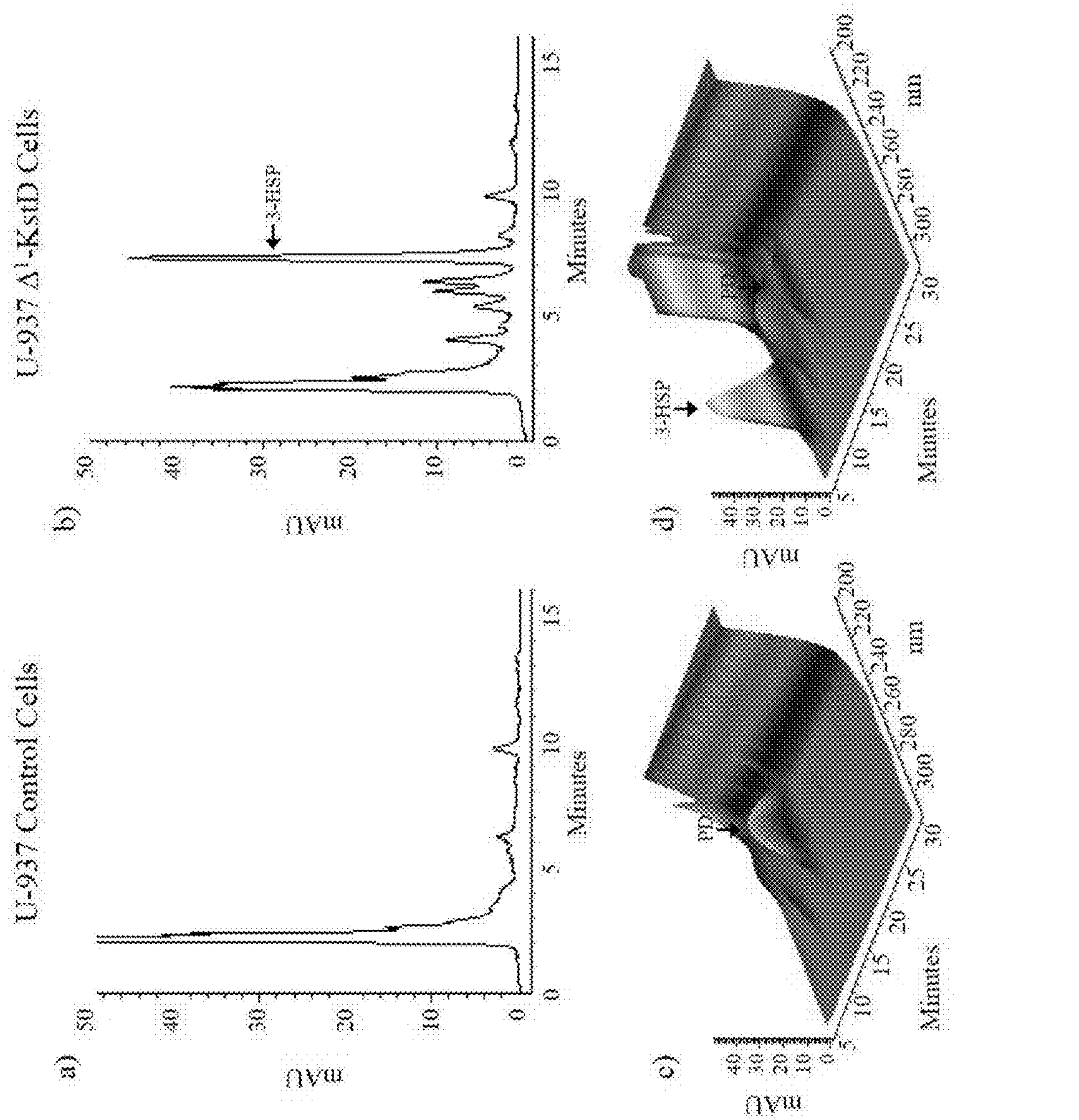

FIG. 60. RP-HPLC analysis of 3-hydroxy-9,10-seco-pregn-1,3,5(10)-triene-9,20-dione (3-HSP) formation by U-937-derived macrophages expressing $\Delta^1$-KstD. Representative 2-D chromatograms (λ280 nm) and 3-D spectral data from (Panels a & c) control U-937-derived macrophages and (Panels b & d) U-937-derived macrophages expressing $\Delta^1$-KstD incubated with 17 μg (10 μM) 9-hydroxypregn-4-ene-3,20-dione (9-OHPD, $t_r$=5.2 min)produced and isolated from bacterial KshAB lysate. Analysis of the U-937-derived macrophages expressing $\Delta^1$-KstD following 72 hours incubation shows the formation of 3-HSP ($t_r$=7.2 min; $\lambda_{max}$ 280 nm). In contrast, control U-937-derived macrophages lack the metabolic capability to produce 3-HSP.

Figure 61:
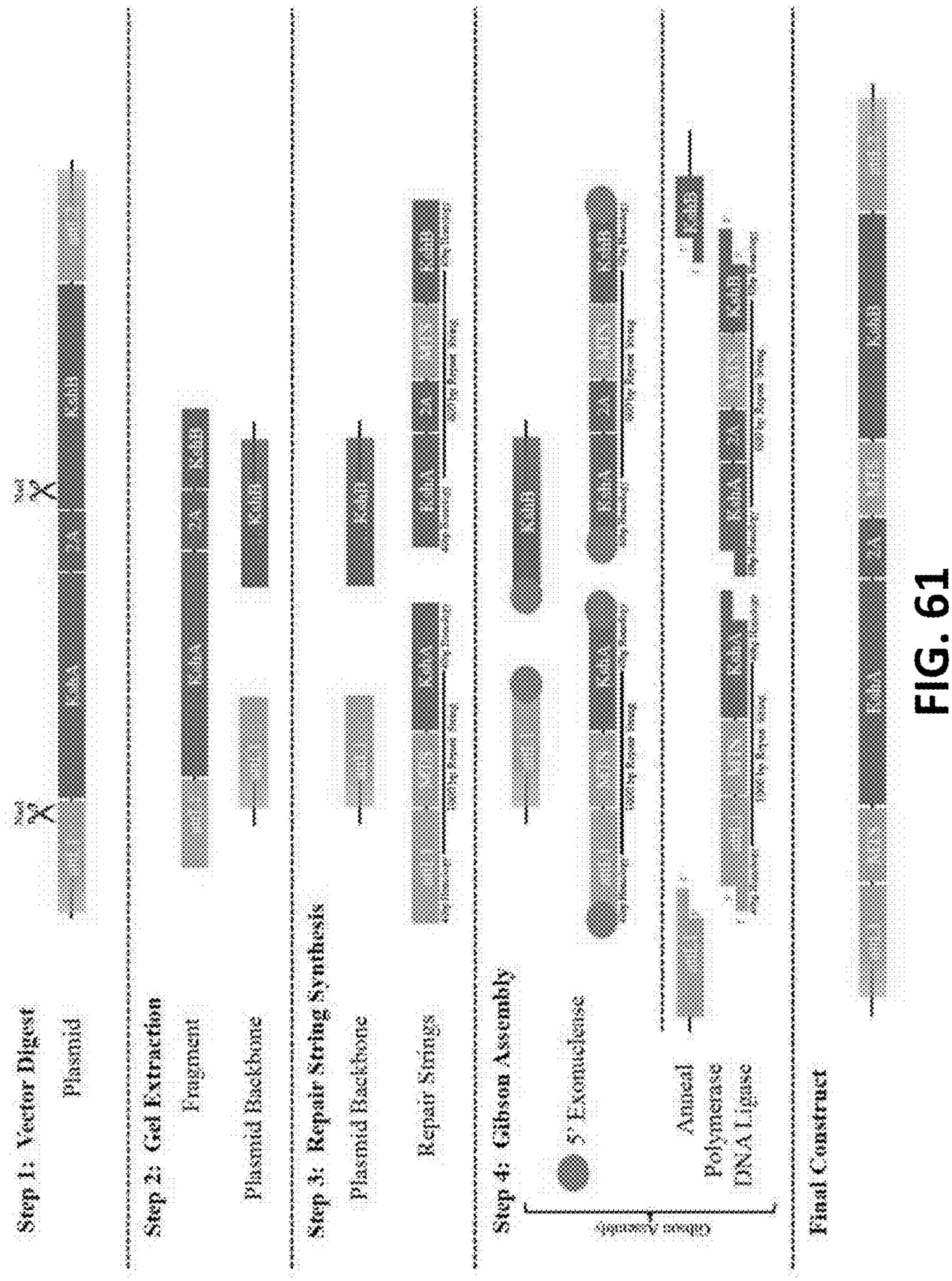

FIG. 61. Modification of the eukaryotic KshAB construct with mitochondrial targeting sequences using Gibson Assembly. The DNA encoding the Ksh A and B subunits was modified to include Aconitase2 mitochondrial targeting sequences (MTS) using Gibson Assembly and synthetic DNA. The starting vector was linearized by double restriction enzyme digest to remove the KshA subunit and N-terminus of KshB. The nucleotide sequence was replaced with synthetic DNA encoding KshA and the N-terminus of KshB with the addition of a 5' MTS attached to each subunit. Each repair string contained 40 bp of homology for correct incorporation into the backbone vector. The vector was reassembled using Gibson assembly as described in methods.

Figure 62:
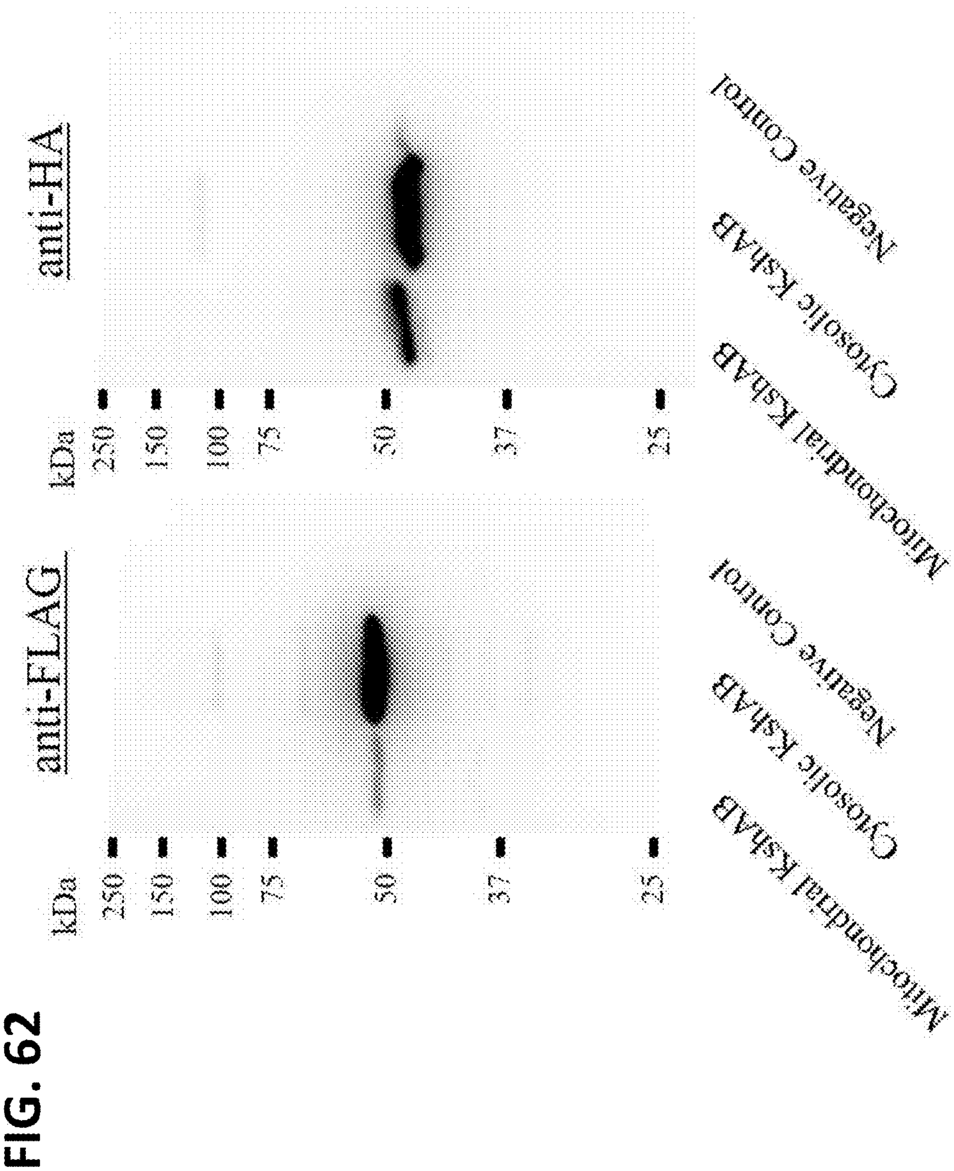

FIG. 62. Western blot analysis of Hep3B cells transiently expressing EF1α driven mitochondrial KshAB or cytosolic KshAB. Hep3B cells were transiently transfected with pDest51-MTS KshAB (mitochondrial) or pDest51-KshAB (cytosolic) plasmids in 60 mm dishes and protein expression was assessed following 48 hours incubation. Following incubation, cells were collected by scraping in 500 μL RIPA buffer and mechanically lysed on ice using a syringe with a 27 gauge needle. Protein samples were mixed with an equal volume of 2× Laemmli sample buffer, boiled for 5 min, and spun at 15,000×g for 10 min at 4cc. Protein samples (25 μg) were separated using SDS-PAGE on a 10% polyacrylamide gel, transferred to a PVDF membrane, and probed with anti-FLAG (1:1000) or anti-HA (1:3000). ECL anti-mouse IgG secondary antibody conjugated to HRP (1:10,000) and SuperSignal West Femto Substrate was used for detection. Samples include Hep3B cells expressing pDest51-MTS KshAB, pDest51-KshAB, and Hep3B negative control cells.

Figure 63:
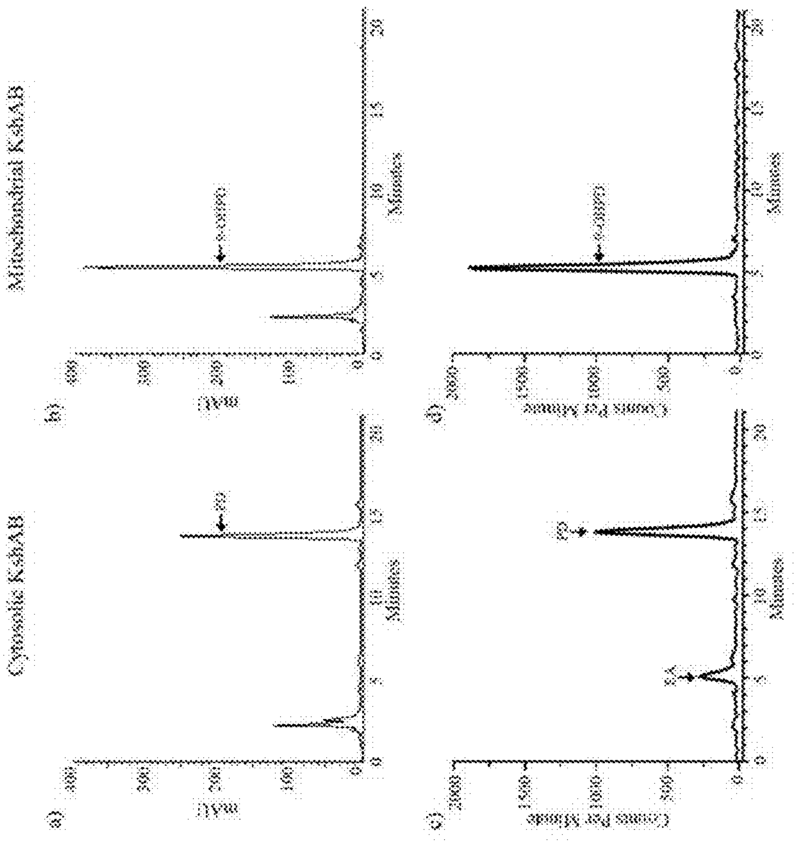

FIG. 63. RP-HPLC analysis of 9-hydroxypregn-4-ene-3,20-dione (9-OHPD) formation from progesterone (PD) utilization by the mitochondrial localized KshAB enzyme. Representative 2-D chromatograms of (Panels a & b) λ245 nm and (Panels c & d) C4-$^{14}$C scintillation events from (Panels a & c) Hep3B cells stably expressing cytosolic KshAB and (Panels b & d) Hep3B cells transiently expressing MTS-KshAB. Cells were incubated with 15.7 μg (10 μM) progesterone spiked with 100nCi C4-14C labeled PD ($t_r$=13.8 min) for 48 hour. Analysis of Hep3B cells expressing cytosolic KshAB (Panels a & c) shows a lack in ability to produce 9-OHPD ($t_r$=5.2 min, $\lambda_{max}$ 245 nm). In contrast, Hep3B MTS-KshAB cells demonstrate the ability to completely utilize the PD substrate to produce the 9-OHPD product.

Figure 64:
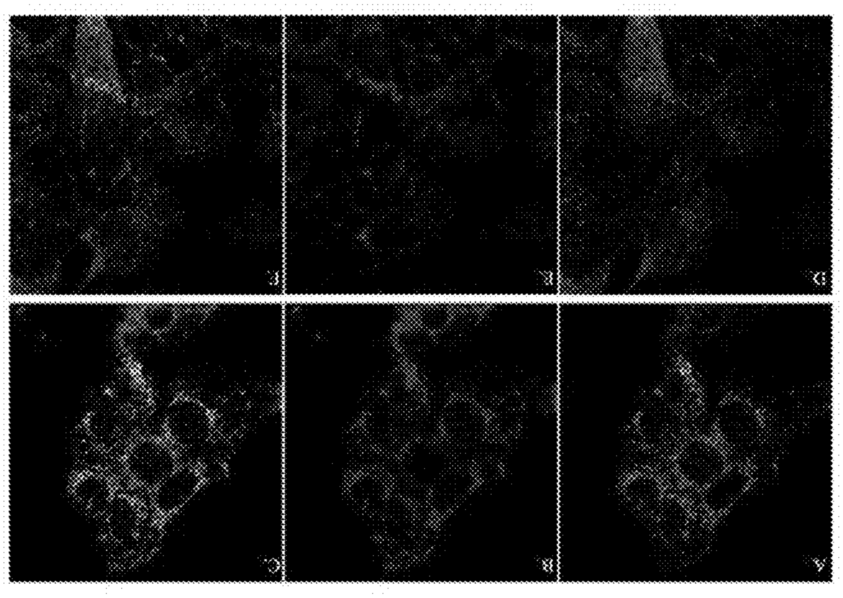

FIG. 64. Micrographs revealing addition of mitochondrial targeting sequences localizes KshAB to the mitochondria. Hep3B cells were transfected with either (A-C) pEF-Dest51-MTS-KshAB (mitochondrial) or (D-F) pEF-Dest51-KshAB (cytosolic) for 48 hours. Cells were immunostained with antibody against the HA-tag of the KshB subunit (green) and co-stained with MitoTracker Far-red (purple). Merged channels show greater signal colocalization(white) between the KshB subunit and Mitotracker in the pEF-Dest51-MTS-KshAB transfected cells (Pearson's coefficient=0.71) than between the KshB subunit and MitoTracker in the pEF-Dest51-KshAB (cytosolic) transfected cells (Pearson's coefficient=0.4).

Figure 65:
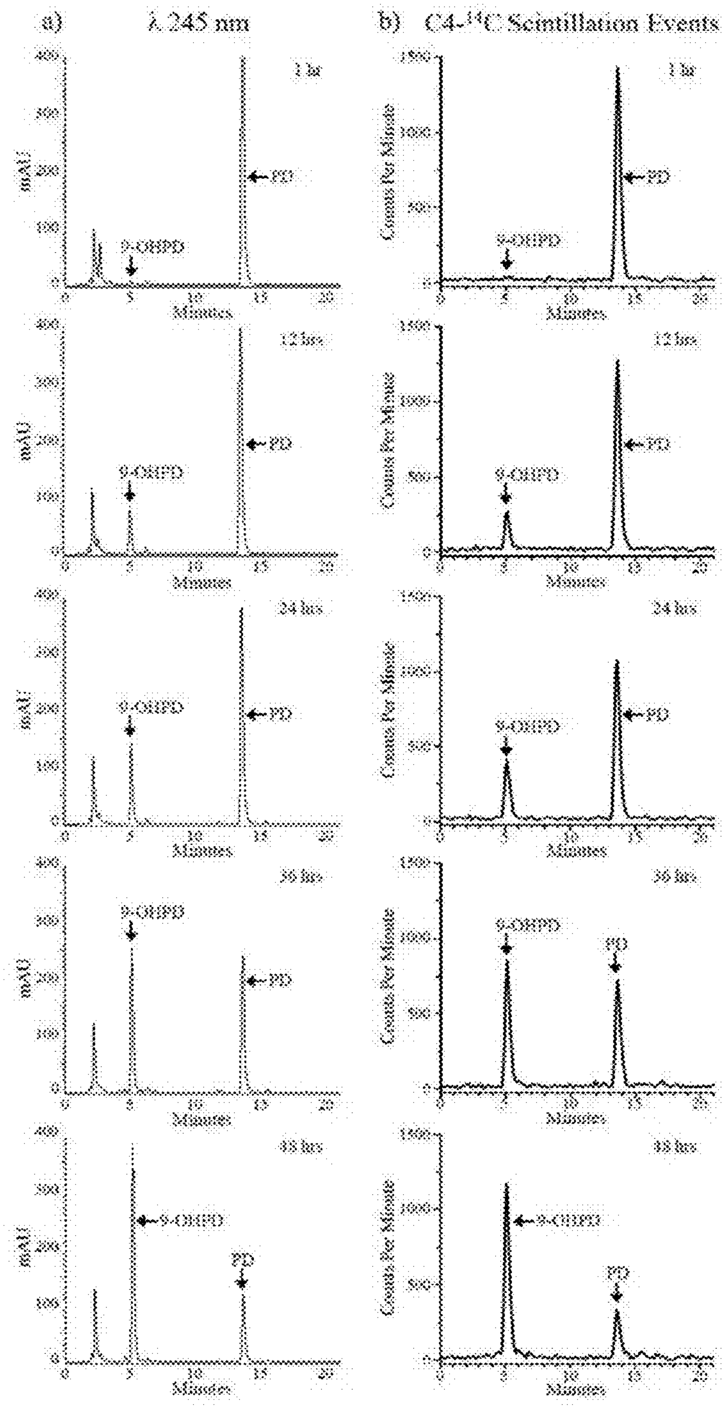

FIG. 65. RP-HPLC analysis of 9-hydroxypregn-4-ene-3,20-dione (9-OHPD) formation from progesterone (PD) utilization by Hep3B MTS-KshAB cells. Representative 2-D chromatograms of (Panel a) λ245 nm and (Panel b) C4-$^{14}$C scintillation events from Hep3B MTS-KshAB cells incubated with 15.7 μg (10 μM) progesterone spiked with 100nCi C4-14C labeled PD ($t_r$=13.8 min) at 1, 12, 24, 36, and 48 hour time points. Analysis of Hep3B MTS-KshAB cells reveal reduction in PD AUC and C4-$^{14}$C PD scintillation events over the 48 hour time course. Concomitant to PD catabolism, 9-OHPD ($t_r$=5.2 min; $\lambda_{max}$ 245 nm)accumulates with time as observed with a new peak forming at 5.2 min with a $\lambda_{max}$ of 245 nm and C4-$^{14}$C scintillation events.

Figure 66:
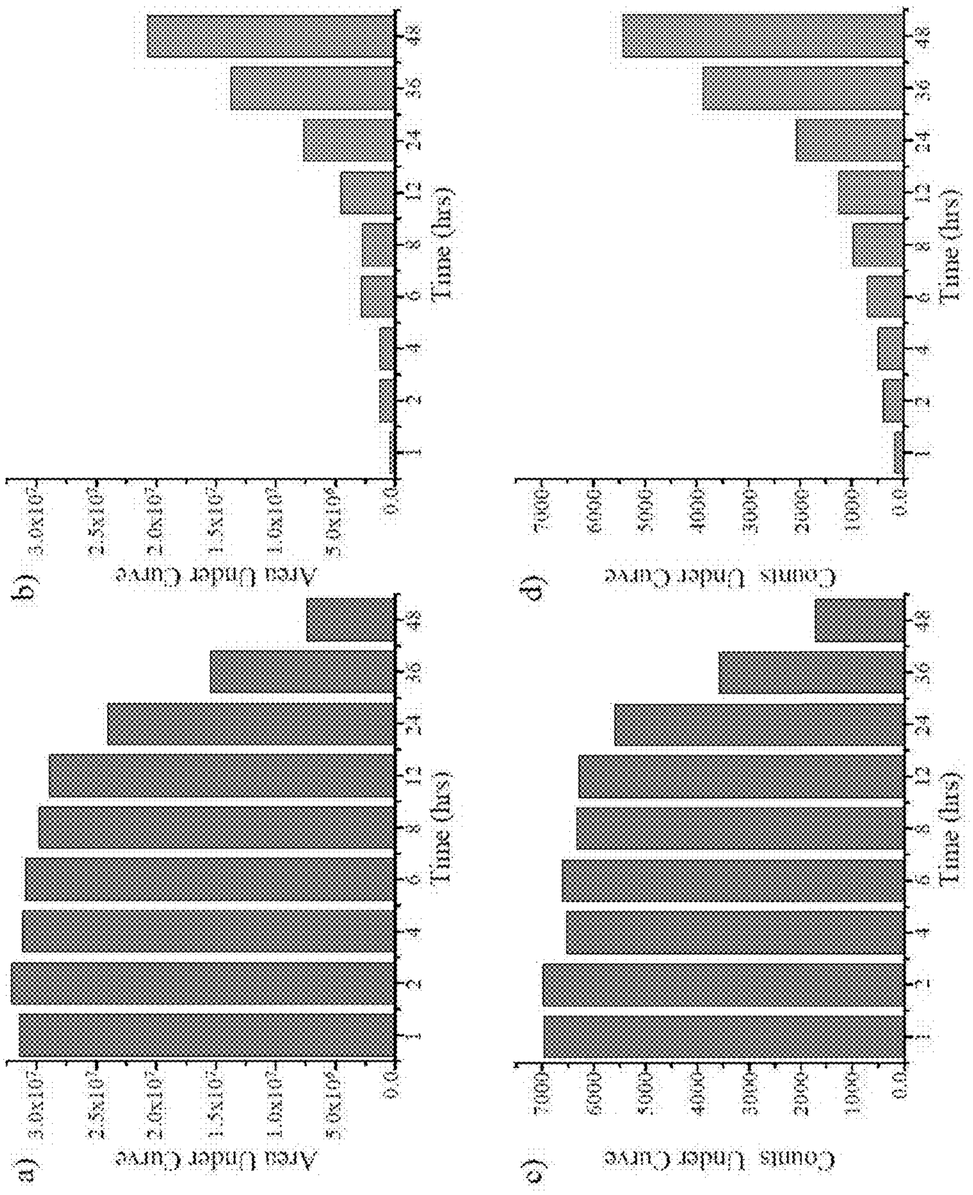

FIG. 66. Quantitative analysis of 9-hdyroxypregn-4-ene-3,20-dione (9-OHPD) product formation from progesterone (PD) catabolism by Hep3B MTS-KshAB cells. Bar graphs representing the measured (Panels a & b) area under the curve (AUC) and (Panels c & d) counts under the curve (CUC) of (Panels a & c) PD and (Panels b & d) 9-OHPD from Hep3B MTS-KshAB cells incubated with 15.7 μg (10 μM) progesterone spiked with 100 nCi C4-$^{14}$C labeled PD. The AUC (λ245) and CUC of PD and 9-OHPD were measured from 2-D chromatograms and C4-$^{14}$C scintillation events under the curve at time points: 1, 2, 4, 6, 8, 12, 24, 36, and 48 hours. Quantitative analysis of PD and 9-OHPD AUC and CUC reveals Hep3B MTS-KshAB cells are equipped with the ability to catabolize PD to form the hydroxylated product, 9-OHPD.

Figure 67:
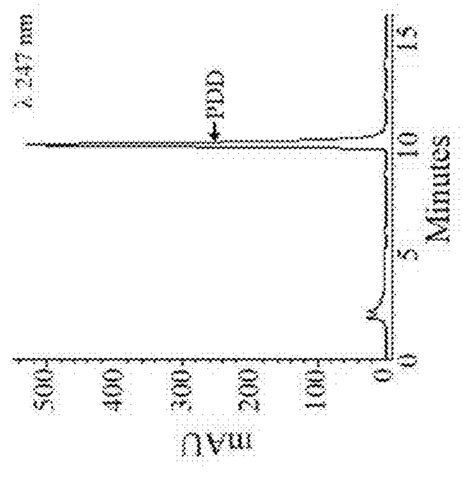

FIG. 67. RP-HPLC analysis of pregn-1,4-diene-3,20-dione (PDD) substrate. Representative 2-D chromatogram at λ247 nm of an 80 μL injection of 15.6 μg PDD in 500 μL HPLC running buffer 2. PDD was produced and isolated from partially purified $\Delta^1$-KstD enzyme incubated with progesterone (PD). The PDD was subsequently used as substrate for Hep3B MTS-KshAB cells. The PDD substrate standard in (Panel a) has a $\lambda_{max}$ of 247 nm and a 10.0 min retention time ($t_r$).

Figure 68:
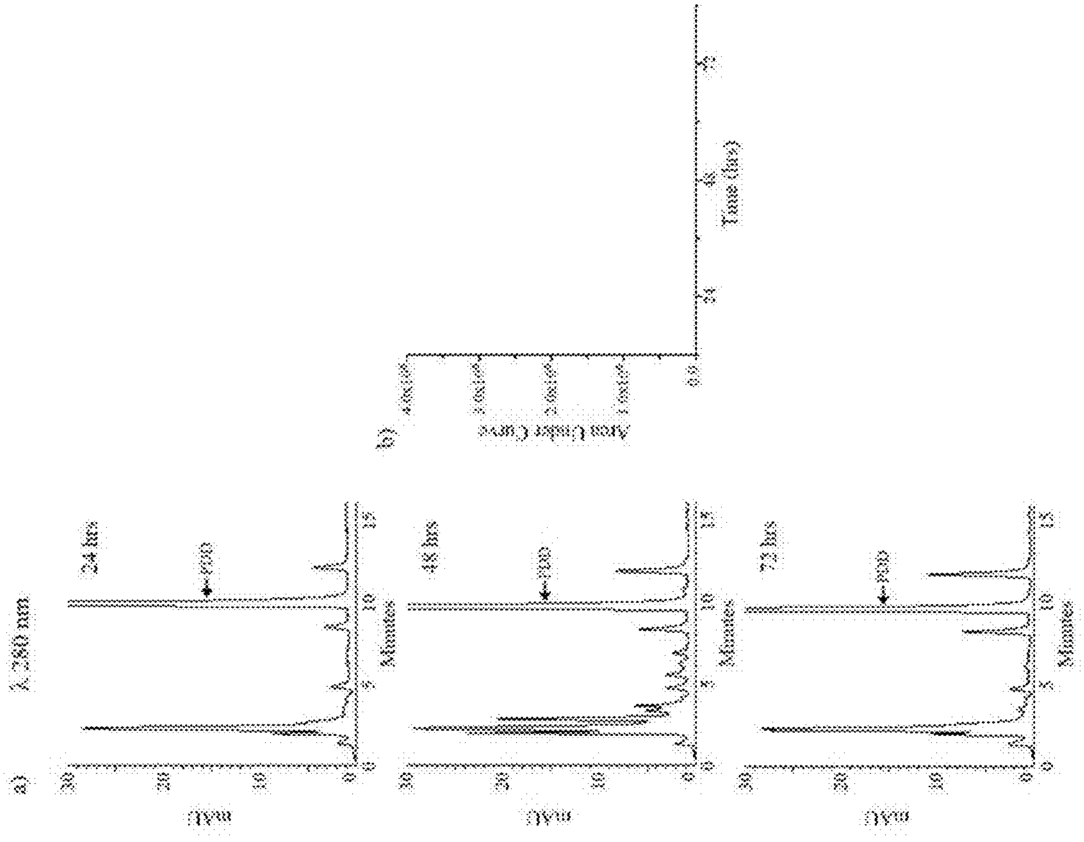

FIG. 68. RP-HPLC and quantitative analysis of Hep3B control cells and their inability to produce the ring opened product, 3-hydroxy-9,10-secopregn-1,3,5(10)-triene-9,20-dione (3-HSP). Representative 2-D chromatogram at (Panel a) λ280 nm from Hep3B control cells incubated with 15.6 μg (10 μM) pregn-1,4-diene-3,20-dione (PDD; $t_r$=10.0 min; $\lambda_{max}$ 247 nm) from 24, 48, and 72 hour time points. Analysis of Hep3B control cells at (Panel a) λ280 nm reveals Hep3B control cells lack the ability to produce 3-HSP ($t_r$=7.2 min, $\lambda_{max}$ 280 nm). (Panel b) Bar graphs representing the measured area under the curve (AUC) of 3-HSP from Hep3B control cells incubated with 7.85 μg (5 μM) PDD. The AUC of 3-HSP was measured at λ280 nm from 2-D chromatograms at time points: 24, 48, and 72 hours. Quantitative analysis of 3-HSP AUC reveals that Hep3B control cells lack 9α-hydroxylase activity, and thus are unable to produce 3-HSP.

Figure 69:
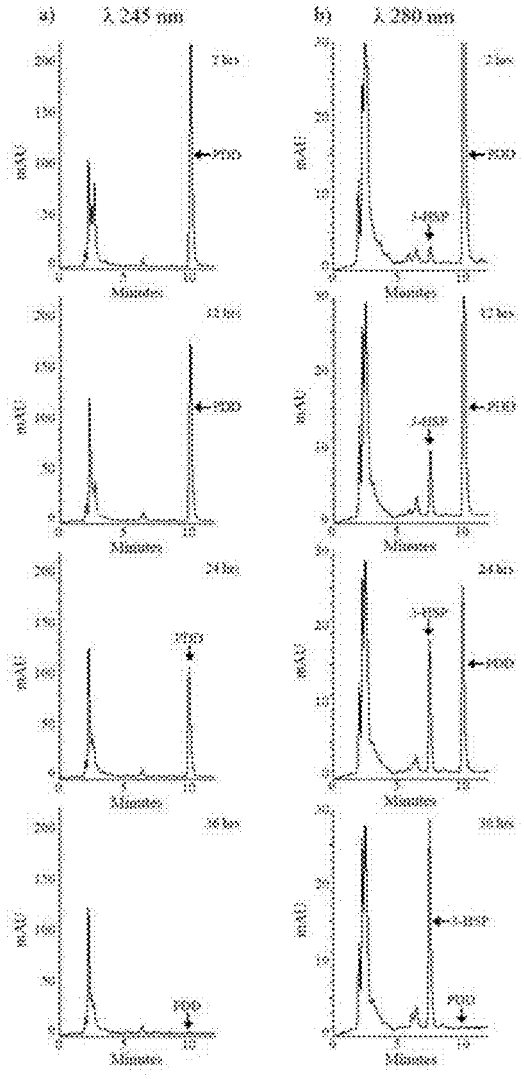

FIG. 69. RP-HPLC analysis of 3-hydroxy-9,10-secopregn-1,3,5(10)-triene-9,20-dione (3-HSP) product formation from pregn-1,4-diene-3,20-dione (PDD) C9 hydroxylation by Hep3B MTS-KshAB cells. Representative 2-D chromatograms at (Panel a) λ245 nm and (Panel b) λ280 nm from time points: 2, 12, 24, and 36 from Hep3B MTS-KshAB cells incubated with 7.85 μg (5 μM) pregn-1,4-diene-3,20-dione (PDD; $t_r$=10.2 min)produced and isolated from partially purified $\Delta^1$-KstD. Analysis of Hep3B MTS-KshAB cells at (Panel a) λ245 nm reveal reduction and exhaustion of the substrate PDD over the 36 hour time course. Concomitant to the catabolism of PDD, a new peak at (Panel b) λ280 nm, corresponding to the formation of 3-HSP ($t_r$=7.2 min, $\lambda_{max}$ 280 nm) is observed with time.

Figure 70:
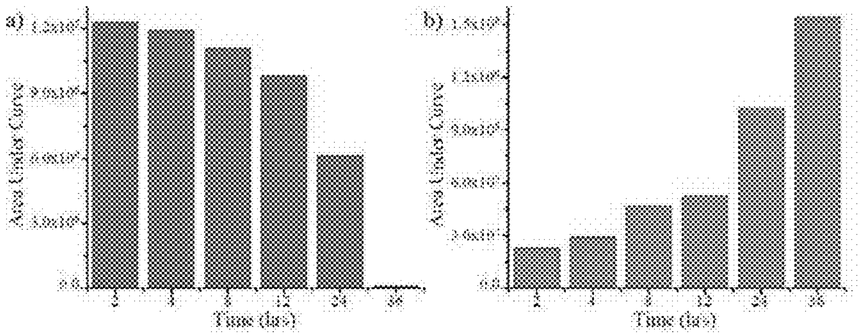

FIG. 70. Quantitative analysis of 3-hydroxy-9,10-secopregn-1,3,5(10)-triene-9,20-dione (3-HSP) product formation from pregn-1,4-diene-3,20-dione (PDD) C9 hydroxylation by Hep3B MTS-KshAB cells. Bar graphs representing the measured area under the curve (AUC) of (Panel a) PDD and (Panel b) 3-HSP from Hep3B MTS-KshAB cells incubated with 7.85 μg (5 μM) PDD. The AUC of PDD and 3-HSP were measured at λ245 nm and λ280 nm, respectively, from 2-D chromatograms at time points: 2, 4, 8, 12, 24, and 36 hours. Quantitative analysis of PDD AUC reveals Hep3B MTS-KshAB cells are equipped with the ability to hydroxylate C9 of PDD to form the ring opened product, 3-HSP.

Figure 71:
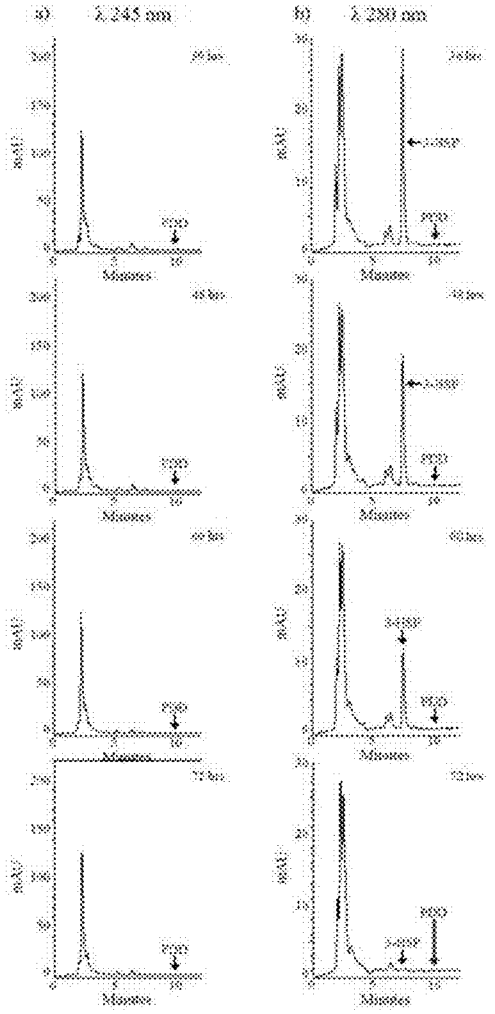

FIG. 71. RP-HPLC analysis of pregn-1,4-diene-3,20-dione (PDD) C9 hydroxylation by Hep3B MTS-KshAB cells. Representative 2-D chromatograms at (Panel a) λ245 nm and (Panel b) λ280 nm from time points: 36, 48, 60, and 72 hours from Hep3B MTS-KshAB cells incubated with 7.85 μg (5 μM) pregn-1,4-diene-3,20-dione (PDD; $t_r$=10.2 min; $\lambda_{max}$ 247 nm)produced and isolated from partially purified $\Delta^1$-KstD. Analysis of Hep3B MTS-KshAB cells at (Panel a) λ245 nm shows the substrate PDD was exhausted over the remaining 72 hour time course. In addition (Panel b) λ280 nm reveals that once the substrate PDD is exhausted, the new peak corresponding to 3-HSP ($t_r$=7.2 min, $\lambda_{max}$ 280 nm)decreases with time. This finding suggest that Hep3B cells are equipped with additional metabolic capability to catabolize 3-HSP resulting in further degradation of the ring opened product.

Figure 72:
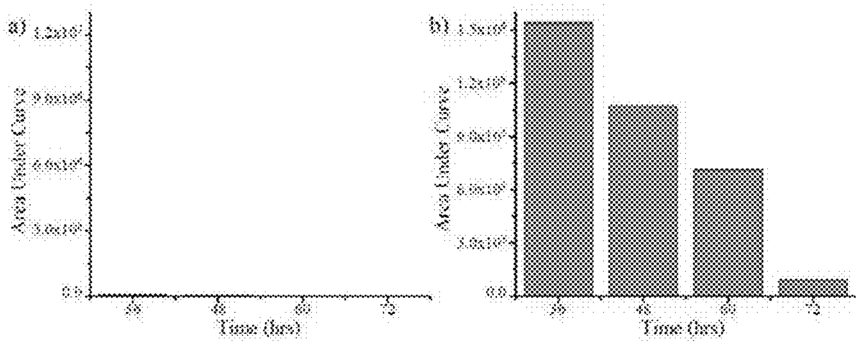

FIG. 72. Quantitative analysis of 3-hydroxy-9,10-secopregn-1,3,5(10)-triene-9,20-dione (3-HSP) formation and catabolism from pregn-1.4-diene-3,20-dione (PDD) C9 hydroxylation by Hep3B MTS-KshAB cells. Bar graphs representing the measured area under the curve (AUC) of (Panel a) PDD and (Panel b) 3-HSP by Hep3B MTS-KshAB cells following incubation with 7.85 μg (5 μM) PDD produced and isolated from partially purified $\Delta^1$-KstD. The AUC of PDD and 3-HSP were measured at λ245 nm and λ280 nm, respectively, from 2-D chromatograms at time points: 36, 48, 60, and 72 hours. Quantitative analysis of PDD AUC shows that by 36 hours, Hep3B MTS-KshAB cells catabolized all substrate. Additionally, analysis of 3-HSP AUC reveals Hep3B MTS-KshAB cells are equipped with the ability to further catabolize the ring opened product, 3-HSP.

Figure 73:
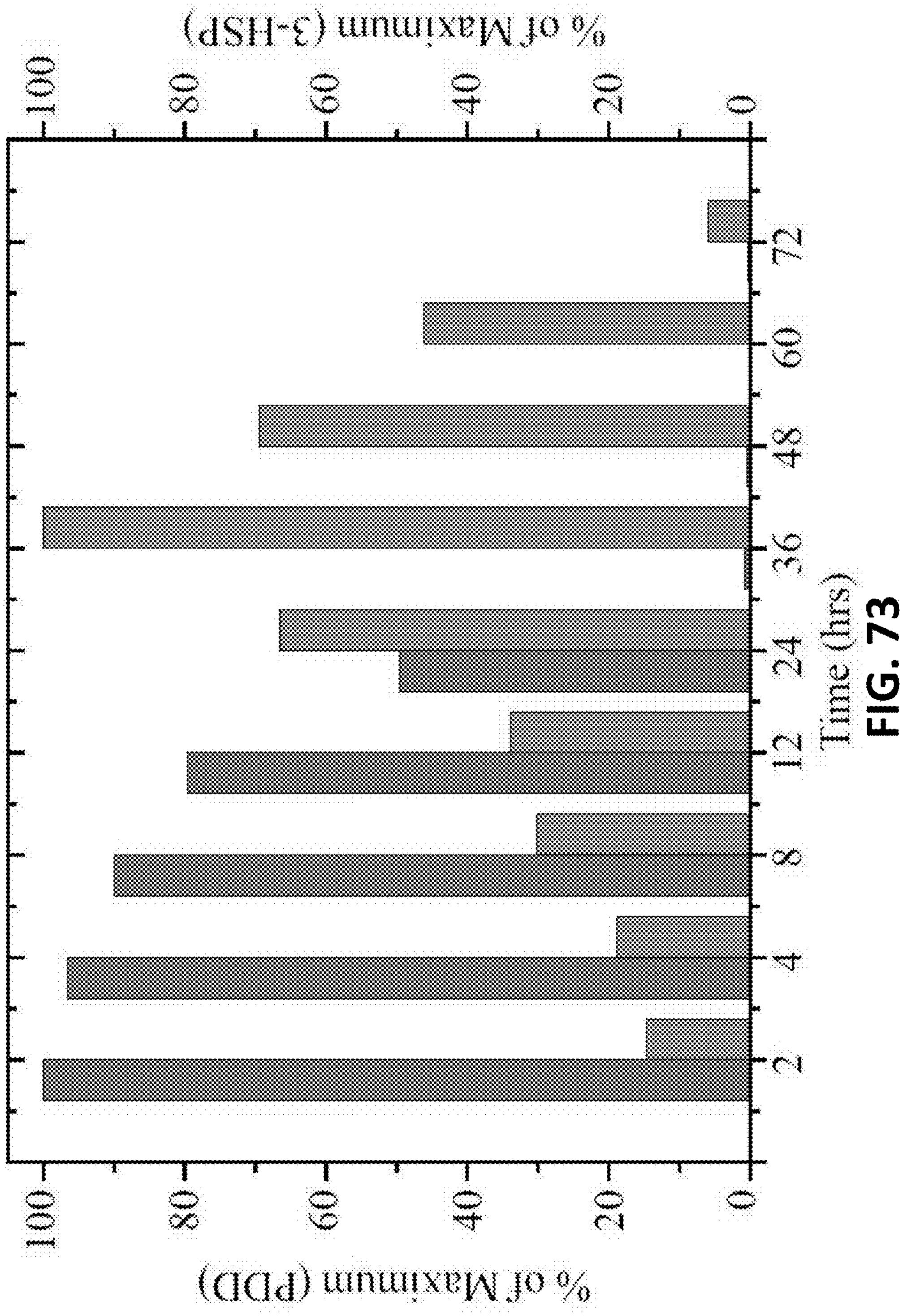

FIG. 73. Overview of the quantitative analysis of 3-hydroxy-9,10-secopregn-1,3,5(10)-triene-9,20-dione (3-HSP) formation and catabolism from pregn-1.4-diene-3,20-dione (PDD) C9 hydroxylation by Hep3B MTS-KshAB cells. Bar graphs representing the measured area under the curve (AUC) of PDD and 3-HSP by Hep3B MTS-KshAB cells following incubation with 7.85 μg (5 μM) PDD produced and isolated from partially purified $\Delta^1$-KstD. The AUC of PDD and 3-HSP were measured at λ245 nm and λ280 nm, respectively, from 2-D chromatograms at time points: 2, 4, 8, 12, 24, 36, 48, 60, and 72 hours. Quantitative analysis of PDD AUC shows Hep3B MTS-KshAB cells hydroxylated all PDD substrate to form 3-HSP by 36 hours. Analysis of 3-HSP AUC reveals Hep3B MTS-KshAB cells had maximal production of 3-HSP by 36 hours. In addition, it appears Hep3B cells are equipped with the ability to further catabolize the ring opened product 3-HSP, as seen by the reduction in accumulated product at subsequent time points.

Figure 74:
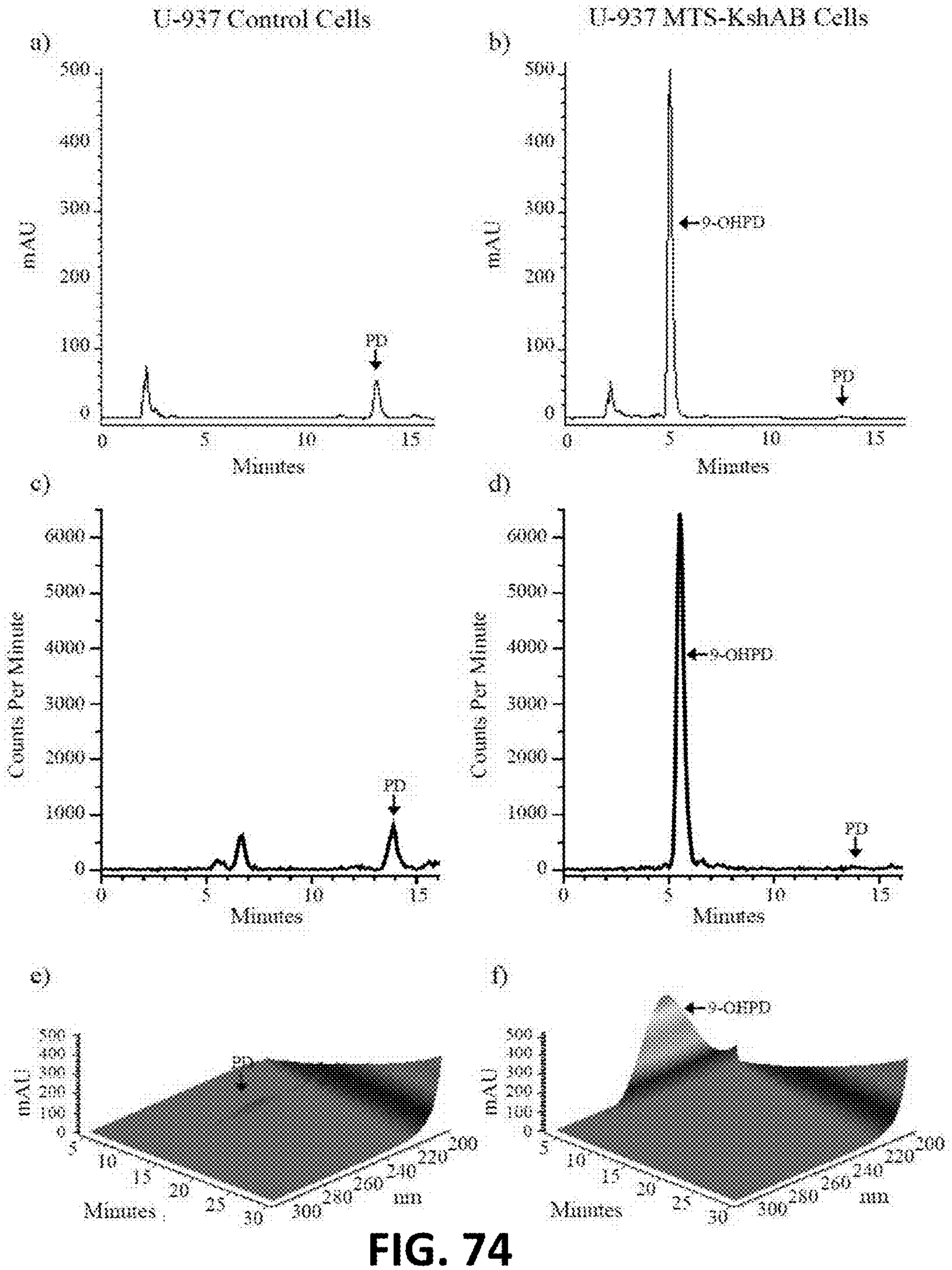

FIG. 74. RP-HPLC analysis of 9-hydroxypregn-4-ene-3,20-dione (9-OHPD) formation from progesterone (PD) utilization by MTS-KshAB expressing U-937-derived macrophages. Representative 2-D chromatograms of (Panels a & b) 1245 nm, (Panels c & d) C4-$^{14}$C scintillation events, and (Panels e & f) 3-D spectral data from (Panels a, c, & e) control macrophages and (Panels b, d, & f) MTS-KshAB expressing macrophages incubated with 15.7 μg (10 μM) progesterone (PD) spiked with 100nCi C4-$^{14}$C labeled PD ($t_r$=13.8 min) for 72 hours. Analysis of the MTS-KshAB expressing macrophages reveal the PD substrate was exhausted by 72 hours. Concomitant to PD catabolism, 9-OHPD ($t_r$=5.2 min) is observed by the formation of a new peak with a retention time of 5.2 min, a $\lambda_{max}$ of 245 nm, and confirmed by C4-$^{14}$C scintillation events. In contrast, U-937 control cells lack the ability to catabolize PD to 9-OHPD, as seen by the absence of a peak with a 5.2 min retention time.

Figure 75:
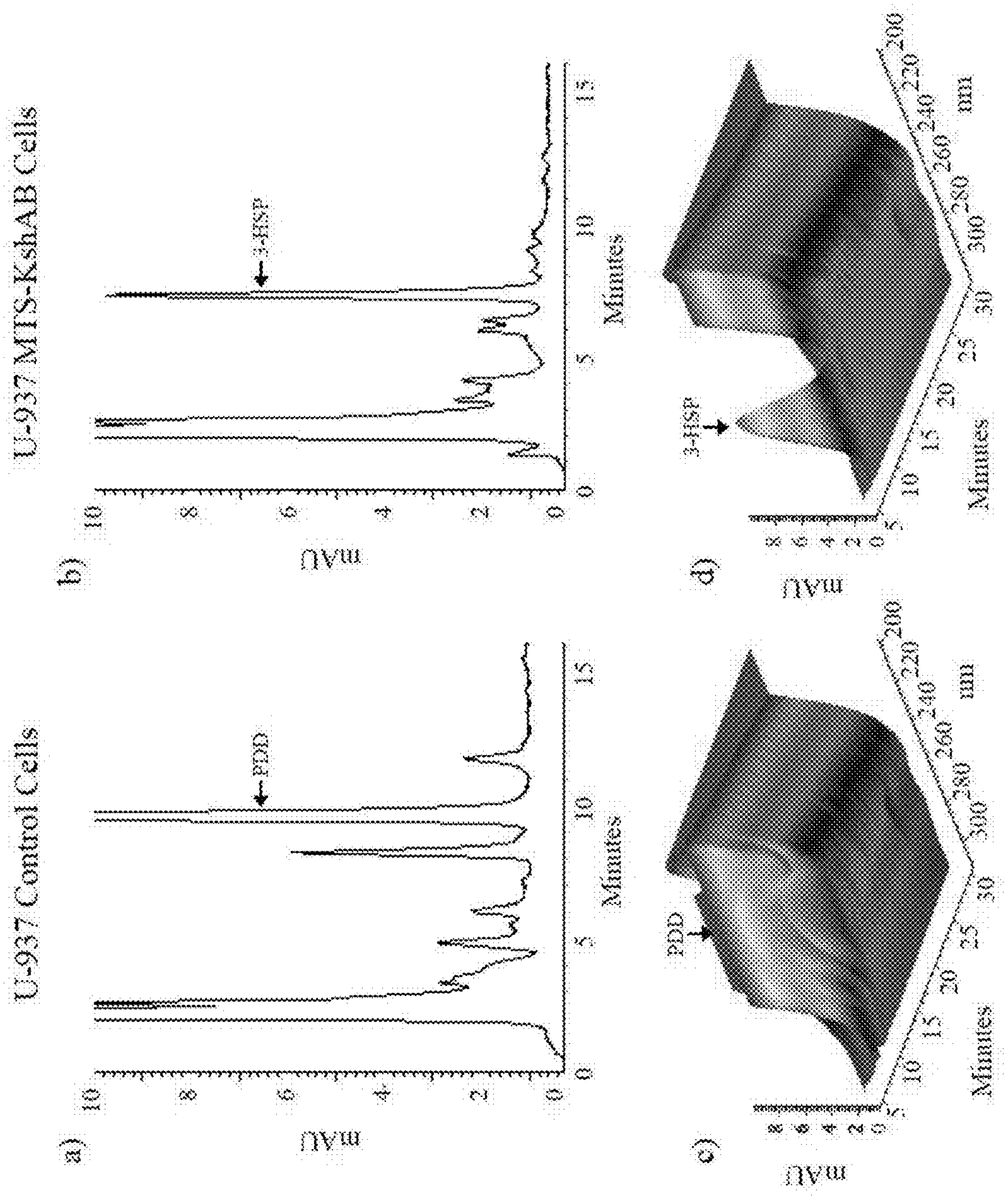

FIG. 75. RP-HPLC analysis of 3-hydroxy-9,10-seco-pregn-1,3,5(10)-triene-9,20-dione (3-HSP) formation by U-937-derived macrophages expressing MTS-KshAB. Representative 2-D chromatograms (λ280 nm) from (Panels a & c) control U-937-derived macrophages and (Panels b & d) U-937-derived macrophages expressing MTS-KshAB incubated with 15.6 μg (10 μM) pregn-1,4-diene-3,20-dione (PDD, $t_r$=10.0 min)produced and isolated from bacterial $\Delta^1$-KstD lysate. Analysis of U-937 MTS-KshAB cells following 72 hours incubation shows the formation of 3-HSP (4-7.2 min). In contrast, control U-937 cells lack the metabolic capability to produce 3-HSP.

Figure 76:
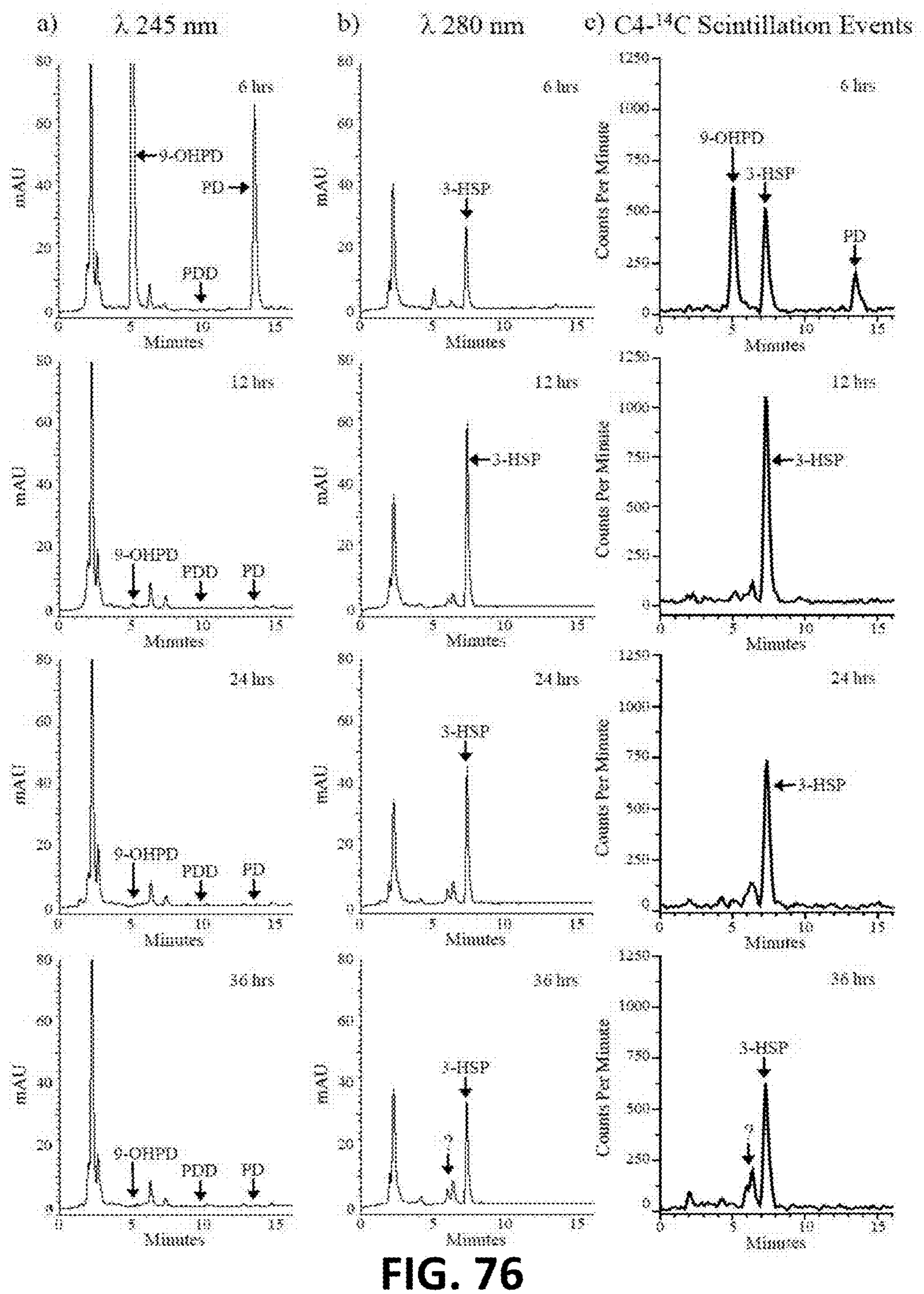

FIG. 76. RP-HPLC analysis of 3-hydroxy-9,10-seco-pregn-1,3,5(10)-triene-9,20-dione (3-HSP) product formation from progesterone (PD) by Hep3B cells transiently expressing MTS-KshAB and $\Delta^1$-KstD. Representative 2-D chromatograms at (Panel a) λ245 nm, (Panel b) λ280 nm, and (Panel c) C4-$^{14}$C scintillation events from Hep3B cells transiently expressing EF1α driven MTS-KshAB and $\Delta^1$-KstD. Cells were incubated with 15.7 μg (10 μM) progesterone spiked with 100nCi C4-$^{14}$C labeled PD ($t_r$=13.8 min) and time points taken at 6, 12, 24, and 36 hours. Analysis at (Panel a) λ245 nm reveals a large proportion of the PD substrate being converted to 9-hydroxypregn-4-ene-3,20, dione (9-OHPD, $t_r$=5.2 min) by 6 hours. Although pregn-1,4-diene-3,20-dione (PDD; $t_r$=10.0 min) is not observed at the 6 hour time point, analysis of (Panel b) λ280 nm and (Panel c) C4-$^{14}$C scintillation events reveals the formation of 3-HSP ($t_r$=7.2 min, $\lambda_{max}$ 280 nm). By 12 hours, the PD substrate and 9-OHPD product are exhausted resulting in maximal production of 3-HSP. Interestingly, both the area and counts under the curve of 3-HSP decreases at further time points, suggesting that Hep3B cells have ability to further modify the pregnanering once opened. Evidence of this can be observed at 24 and 36 hour time points as new C4-$^{14}$C scintillation events appear between 6.0-6.5 minutes.

Figure 77:
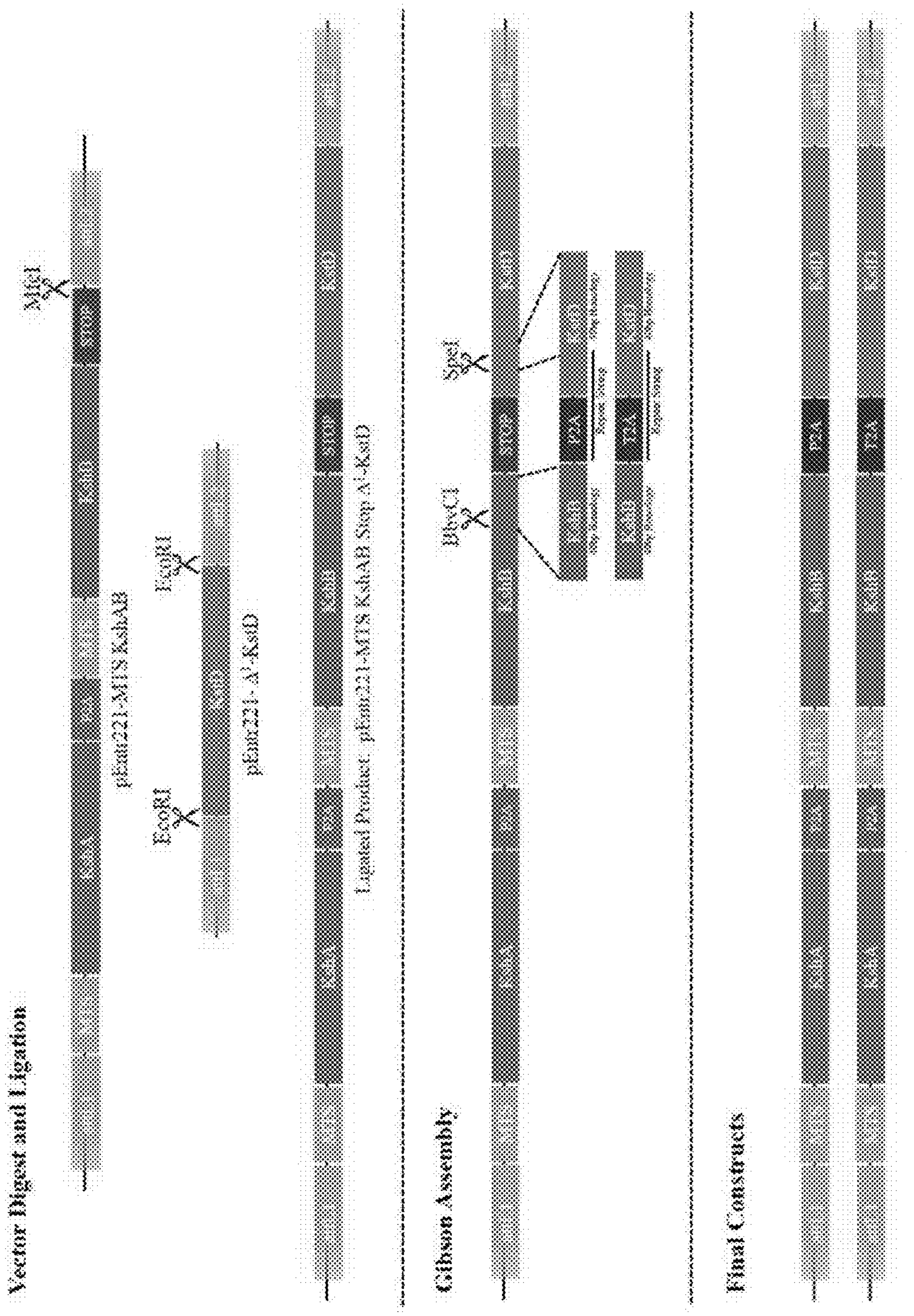

FIG. 77. Assembly of the MTS-KshAB-T2A-$\Delta^1$-KstD and MTS-KshAB-P2A-$\Delta^1$-KstD tricistronic vectors for co-expression of MTS-KshAB and $\Delta^1$-KstD from a single construct. The MTS-KshAB vector was linearized by restriction enzyme digest. The DNA encoding $\Delta^1$-KstD was obtained by double restriction enzyme digest. Following isolation by electrophoresis and gel extraction, $\Delta^1$-KstD was ligated into the MTS-KshAB vector. The preliminary MTS-KshAB $\Delta^1$-KstD vector was linearized by double restriction enzyme digest to remove the C-terminal end of KshB containing the native stop codon and the N-terminus of $\Delta^1$-KstD. Two repair strings were synthesized encoding the C-terminal end of KshB with the native stop codon omitted, a Thoseaasigna2A skipping peptide (T2A) or a Porcine teschnovirus-1 2A skipping peptide, a Flag tag for detection of $\Delta^1$-KstD, and the N-terminus of $\Delta^1$-KstD that was removed. The backbone vector and synthetic DNA were reassembled using Gibson assembly to produce two tricistronic constructs for the co-expression of MTS-KshAB and $\Delta^1$-KstD.

Figure 78:
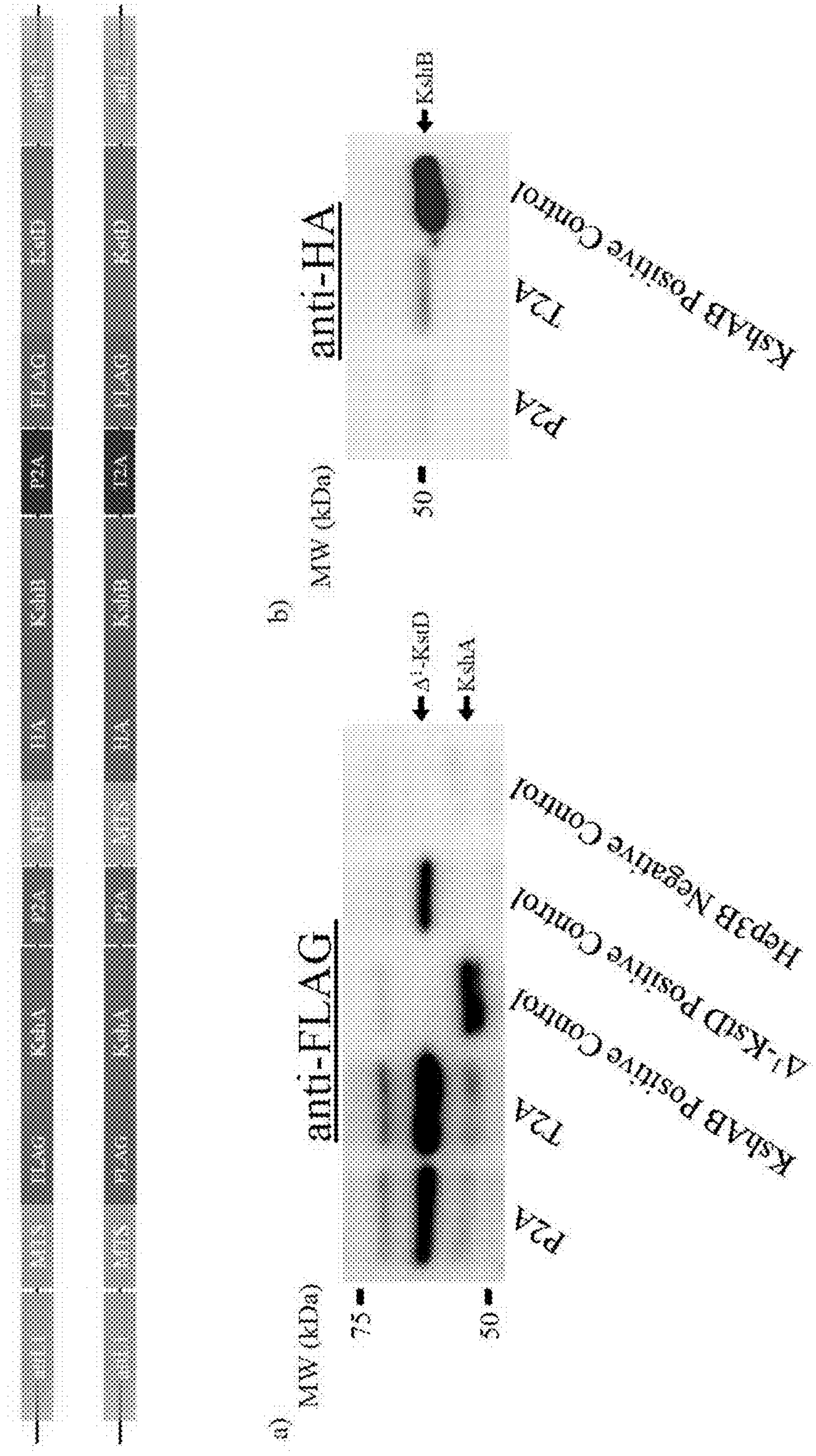

FIG. 78. Western blot analysis of Hep3B cells expressing EF1α driven MTS-KshAB-P2A-$\Delta^1$-KstD or MTS-KshAB-T2A-$\Delta^1$-KstD constructs. Hep3B cells were transiently transfected with pDest51-KshAB-P2A-$\Delta^1$-KstD or pDest51-KshAB-T2A-$\Delta^1$-KstD plasmids in 60 mm dishes and protein expression was assessed following 48 hours incubation. Cells were collected by scraping in 500 μL RIPA buffer and mechanically lysed on ice using a syringe with a 27 gauge needle. Protein samples were mixed with an equal volume of 2× Laemmli sample buffer, boiled for 5 min, and spun at 15,000×g for 10 min at 4cc. Protein samples (25 μg) were separated using SDS-PAGE on a 10% polyacrylamide gel, transferred to PVDF membranes, and probed with anti-FLAG (1:1000) or anti-HA (1:3000). ECL anti-mouse IgG secondary antibody conjugated to HRP (1:10,000) and SuperSignal West Femto Substrate was used for detection. Samples include the P2A construct, T2A construct, Hep3B CMV-MTS KshAB cell line (positive KshA FLAG and KshB HA control), Hep3B CMV-$\Delta^1$-KstD cell line (positive $\Delta^1$-KstD FLAG control), and non-transduced Hep3B cells (negative control).

Figure 79:
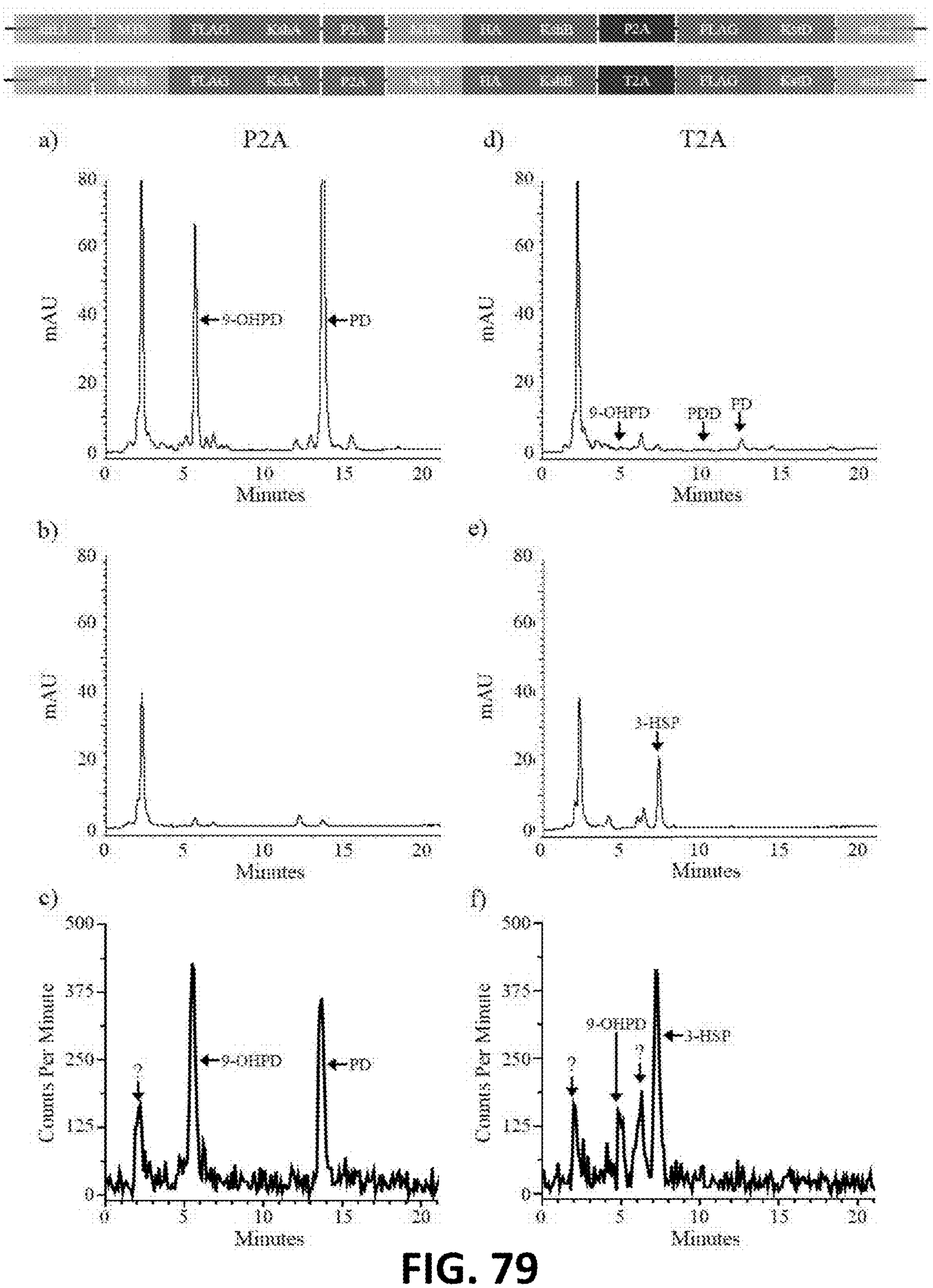

FIG. 79. RP-HPLC analysis of 3-hydroxy-9,10-seco-pregn-1,3,5(10)-triene-9,20-dione (3-HSP) product formation from progesterone (PD) catabolism by Hep3B cells expressing EF1α driven KshAB P2A $\Delta^1$-KstD or KshAB T2A $\Delta^1$-KstD constructs. Hep3B cells were transiently transfected with pDest51-KshAB P2A $\Delta^1$-KstD or pDest51-KshAB T2A $\Delta^1$-KstD plasmids in 60 mm dishes. Following 48 hours of protein expression, cells were incubated with 15.7 μg (10 μM) PD spiked with 100nCi C4-$^{14}$C labeled PD ($t_r$=13.8 min) for 48 hours. Representative 2-D chromatograms at (Panels a & d) λ245 nm, (Panels b & e) λ280 nm, and (Panels c & f) C4-$^{14}$C scintillation events demonstrate the efficiency of the P2A and T2A constructs in producing 3-HSP ($t_r$=7.2 min, $\lambda_{max}$ 280 nm) through PD catabolism. Analysis of the P2A construct at (Panel a) λ245 nm reveals a large proportion of the PD substrate being converted to 9-hydroxypregn-4-ene-3,20,dione (9-OHPD, $t_r$=5.2 min) by 48 hours. However, in comparison to the T2A construct at (Panel d) λ245 nm, residual 9-OHPD is observed, suggesting $\Delta^1$-KstD is the rate limiting step in 3-HSP($t_r$=7.2 min, $\lambda_{max}$ 280 nm) formation. Although 3-HSP is not observed at (Panel b) λ280 nm or in (Panel c) C4-$^{14}$C scintillation events, the accumulation of scintillation events from an unidentified metabolite ($t_r$=2.3 min) are detected prior to the 5.2 minute retention time of 9-OHPD. In contrast, the T2A construct at (Panel d) λ245 nm reveals complete reduction in the PD substrate, 9-OHPD, and pregn-1,4-diene-3,20-dione (PDD, $t_r$=10.0 min, $\lambda_{max}$ 247 nm) by 48 hours. In addition, (Panel e) λ280 nm reveals the formation of 3-HSP. Furthermore, (f) C4-$^{14}$C scintillation events confirm the formation of 3-HSP as well as additional scintillation events from unidentified metabolites prior to 3-HSP's 7.2 minute retention time.

Figure 80:
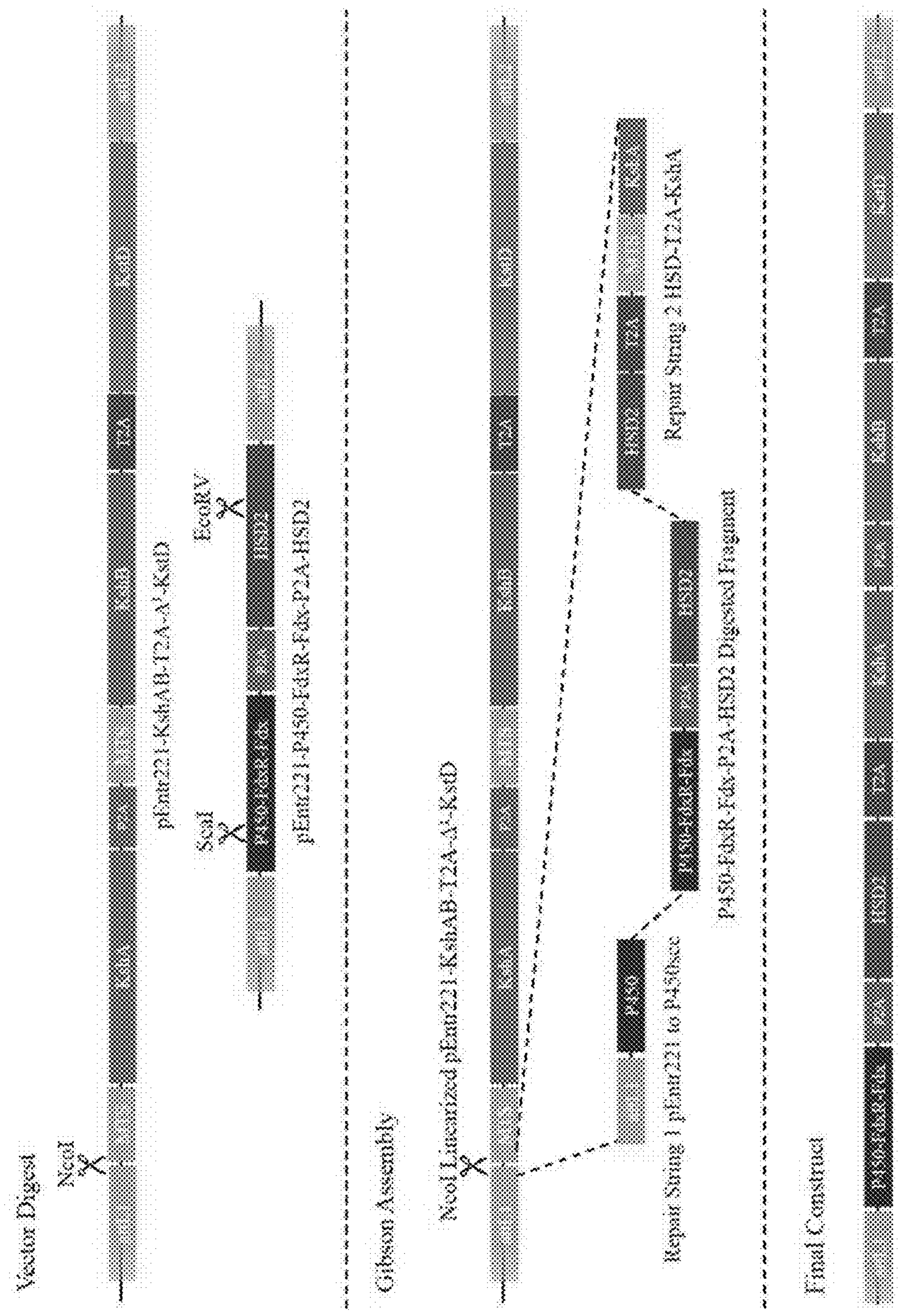

FIG. 80. Assembly of the P450-FdxR-Fdx-P2A-HSD2-T2A-KshA-P2A-KshB-T2A-$\Delta^1$-KstD pentacistronic vector for co-expression of all required cholesterol catabolizing enzymes from a single construct (cholesterol catabolism cassette or CCC). The cholesterol catabolizing cassette (CCC) was assembled by linearizing the MTS-KshAB-T2A-$L^1$-KstD vector by restriction enzyme digest. Additionally, the DNA encoding the P450-FdxR-Fdx-P2A-HSD2 was obtained by double restriction enzyme digest. Following isolation by electrophoresis and gel extraction, the MTS-KshAB-T2A-$\Delta^1$-KstD backbone vector and P450-FdxR-Fdx-P2A-HSD2 fragment were assembled using two repair strings and Gibson Assembly.

Figure 81:
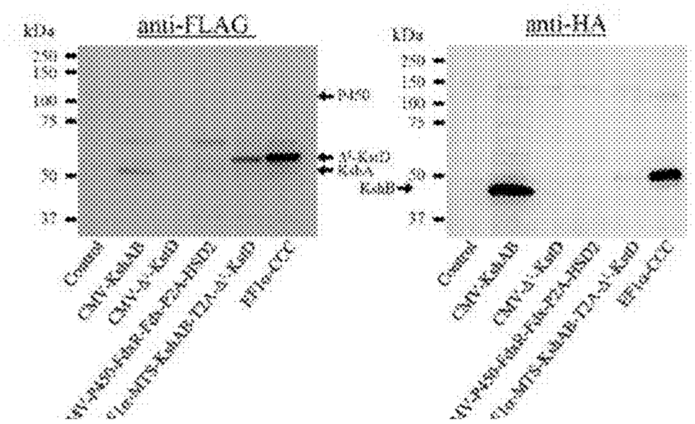

FIG. 81. Western blot analysis of Hep3B cells expressing EF1α driven P450-FdxR-Fdx-P2A-HSD2-T2A-KshA-P2A-KshB-T2A-$L^1$-KstD pentacistronic vector (cholesterol catabolizing cassette or CCC). Hep3B cells were transiently transfected with the pDest51-P450-FdxR-Fdx-P2A-HSD2-T2A-KshA-P2A-KshB-T2A-$\Delta^1$-KstD (CCC) plasmid in 60 mm dishes and protein expression was assessed following 48 hours incubation. Cells were collected by scraping in 500

µL RIPA buffer and mechanically lysed on ice using a syringe with a 27 gauge needle. Protein samples were mixed with an equal volume of 2× Laemmli sample buffer, boiled for 5 min, and spun at 15,000×g for 10 min at 4° c. Protein samples (25 µg) were separated using SDS-PAGE on a 10% polyacrylamide gel, transferred to PVDF membranes, and probed with anti-FLAG (1:1000) or anti-HA (1:3000). ECL anti-mouse IgG secondary antibody conjugated to HRP (1:10,000) and SuperSignal West Femto Substrate were used for detection. Samples include Hep3B control cells, Hep3B CMV-MTS KshAB cells (positive KshA FLAG and KshB HA control), Hep3B CMV-$\Delta^1$-KstD cells (positive $\Delta^1$-KstD FLAG control), Hep3B CMV-P450-FdxR-Fdx-P2A-HSD2 cells, Hep3B EF1α-MTS-KshAB-T2A-$\Delta^1$-KstD cells, and Hep3B EF1α-P450-FdxR-Fdx-P2A-HSD2-T2A-KshA-P2A-KshB-T2A-$\Delta^1$-KstD cells.

Figure 82:
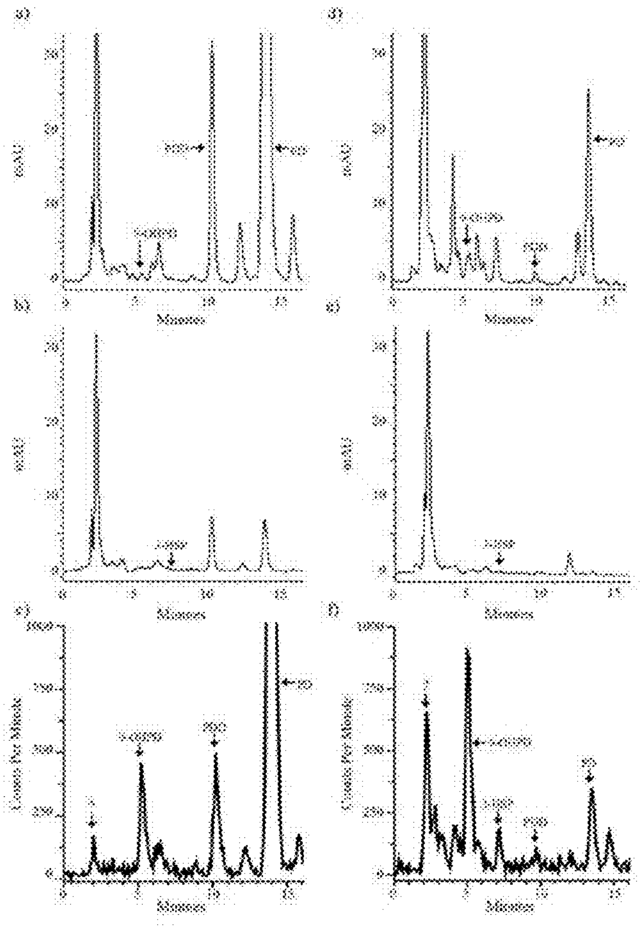

FIG. 82. RP-HPLC analysis of progesterone (PD) catabolism by Hep3B cells expressing EF1α driven P450-FdxR-FdxP2A-HSD2-T2A-MTS-KshA-P2A-MTS-KshB-T2A-$\Delta^1$-KstD construct (cholesterol catabolism cassette or CCC). Hep3B cells were transiently transfected with pDest51-CCC in 60 mm dishes. Following 48 hours, cells were incubated with 15.7 µg (10 µM) progesterone spiked with 100nCi C4-$^{14}$C labeled PD ($t_r$=13.8 min) for 24 (a, b, & c) and 72 (Panels d, e, & f) hours. Representative 2-D chromatograms at (Panels a & d) λ245 nm, (Panels b & e) λ280 nm, and (Panels c & f) C4-$^{14}$C scintillation events demonstrate the efficiency of the CCC at catabolizing PD. Analysis of the CCC at (Panel a) λ245 nm shows the formation of pregn-1,4-diene-3,20-dione (PDD). Analysis of the (Panel c) C4-$^{14}$C scintillation events reveals the formation of 9-hydroxypregn-4-ene-3,20-dione (9-OHPD) and confirms the production of PDD. By 72 hours, Hep3B cells expressing the CCC catabolized a large proportion of the PD substrate and only residual 9-OHPD, PDD, and 3-HSP were observed. Interestingly, (f) C4-$^{14}$C scintillation events were found to accumulate in the solvent front. The scintillation events in the solvent front are likely from an unidentified metabolite (s) ($t_r$=2-3 min) that form as a result of 3-HSP metabolism by endogenous enzymes.

Figure 83:
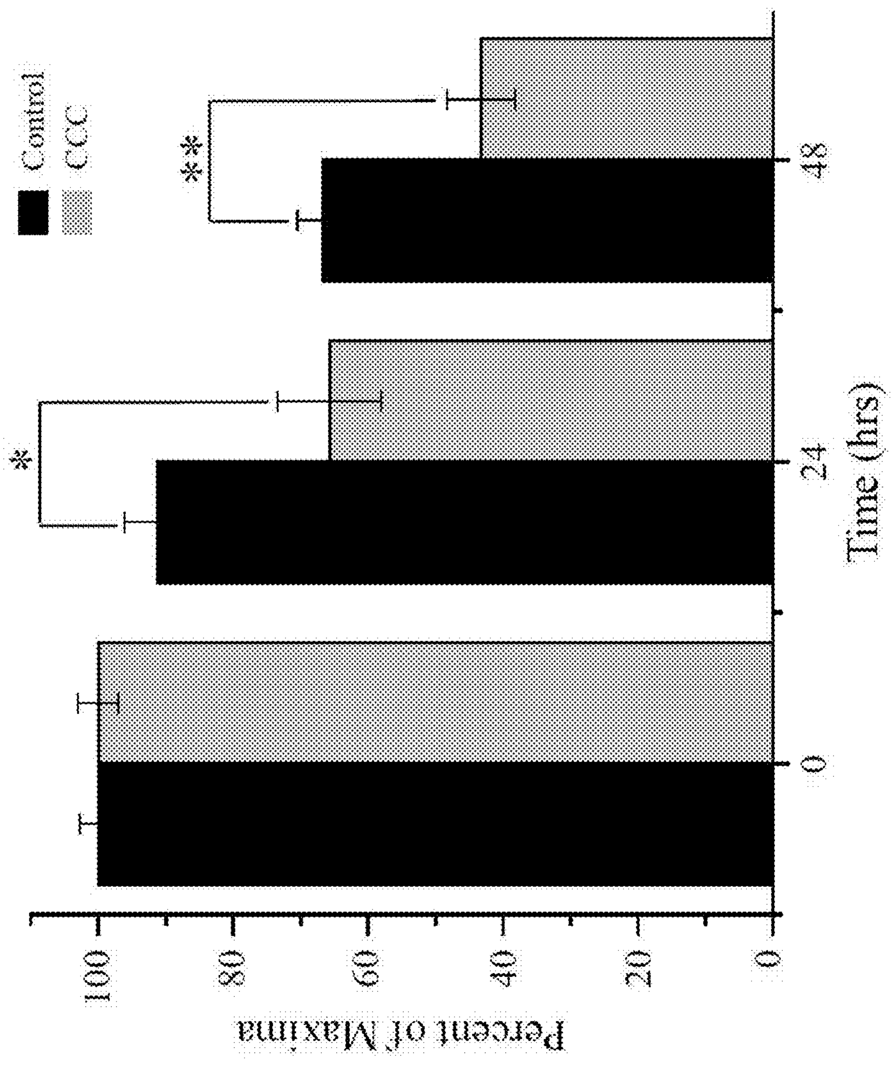

FIG. 83. Comparison of C4-$^{14}$C-cholesterol retention between U-937 control and CCC macrophages. U-937 monocytes (CCC and control) were plated in 60 mm dishes and differentiated into macrophages (as described in methods). Five day old macrophages were loaded with 5 µg C4-$^{14}$C-cholesterol labeled LDLs for 24 hours. Following incubation, media was removed, cells were washed with PBS, and new media was provided. Cholesterol retention was monitored by measuring C4-$^{14}$C scintillation events in cells at timed intervals for 48 hours. Total scintillation events per dish were normalized to cellular protein. Analysis of C4-$^{14}$C scintillation events reveal the CCC cell line retain less C4-14C-cholesterol in comparison to control macrophages. Data represents two experiments (N=2) with four replicates each. Error bars indicate the standard error of the mean.

FIG. 84. Amino acid sequence of the P450-FdxR-Fdx fusion protein construct. The minimal structures of the P450 cholesterol side chain cleavage enzyme (CYP11A1), ferredoxin reductase (FdxR), and ferredoxin (Fdx) enzymes were fused using short linkers. Green indicates the P450 enzyme, red indicates the Ferrodoxin Reductase enzyme, blue indicates the ferrodoxin enzyme, and purple indicates mitochondrial targeting sequence. Also shown in black are the linker peptides fusing the P450scc to FdxR and FdxR to Fdx. In addition, a Flag tag (orange) and P2A peptide (grey) were added to the 3' end of the Fdx protein. (SEQ ID NOs: 5-8)

FIG. 85. Humanized cholesterol dehydrogenase (CholD) map. The amino acid sequence of CholD from *Mycobacterium tuberculosis* (coding region 166-1284 nt, 371 amino acids) was reverse translated using GeneOptimizer software set to *H. sapiens* codon usage. GeneOptimizer software was also used to design flanking sequences that contained Gateway attachment sites (attB1 and attB2) and restriction enzyme recognition sites (5': MfeI and BamHI; 3': SmaI, EcoRI, and BgIII) to aid sub cloning. In addition, 5' of the CholD sequence a TEV site, a 6×His tag, Kozak consensus sequence, a tetracysteine tag, and a Flag tag were added to aid purification and detection of the recombinant protein after expression. This humanized CholD construct was then synthesized and inserted into the pMK-RQ vector (GeneArt).

FIG. 86 Features of the humanized cholesterol dehydrogenase (CholD) nucleotide sequence. SEQ ID NO: 10

FIG. 87. Map of humanized cholesterol dehydrogenase (CholD) in pEntr221. To generate the pEntr221-CholD entry vector, pMK-RQ-CholD and pDonr221 were recombined using BP Clonase II. The resulting 3,821 nt construct includes the humanized CholD coding sequence (653-1964 nt), 5' TEV site, 6×His Tag, Kozak consensus sequence, tetracysteine tag, and Flag tag flanked by attL attachment sites.

FIG. 88. Map of humanized cholesterol dehydrogenase (CholD) in pBAD-Dest49. To generate the pBAD-Dest49-CholD expression vector, pEntr221-CholD and pBAD-Dest49 were recombined using LR ClonaseII. The resulting 5,783 nt construct includes the humanized CholD coding sequence (727-2038 nt), 5' TEV site, 6×His Tag, Kozak consensus sequence, tetracysteine tag, and Flag tag flanked by attB attachment sites. The pBAD-Dest49 vector expresses CholD as an N-terminal His-Patch Thioredoxin fusion protein under the control of an arabinose inducible promoter.

FIG. 89. Humanized anoxic cholesterol catabolism B enzyme (acmB) map. The amino acid sequence of acmB from *Sterolibacterium denitrificans* (coding region 74-1756 nt, 569 amino acids) was reverse translated using GeneOptimizer software set to *H. sapiens* codon usage. GeneOptimizer software was also used to design flanking sequences that contained Gateway attachment sites (attB1 and attB2) and restriction enzyme recognition sites (5': MfeI and BamHI; 3': NaeI, SmaI, EcoRI, and BgIII) to aid sub cloning. In addition, 5' of the acmB sequence a TEV site, Kozak consensus sequence and 3' HA tag were added to aid in purification and detection of the recombinant protein after expression. This humanized CholD construct was then synthesized and inserted into the pMA-RQ vector (GeneArt).

FIG. 90. Features of the humanized anoxic cholesterol metabolism B enzyme (acmB) nucleotide sequence. SEQ ID NO: 11

Figure 91:
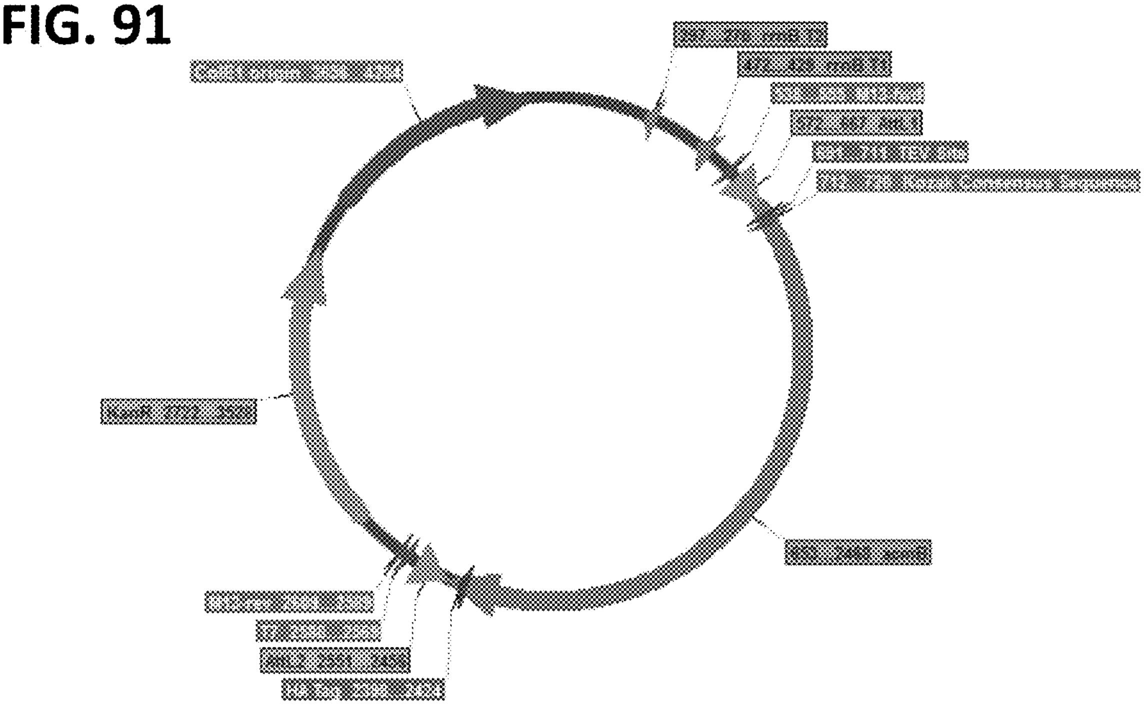

FIG. 91. Map of humanized anoxic cholesterol catabolism B enzyme (acmB) in pEntr221. To generate the pEntr221-acmB entry vector, pMA-RQ-acmB and pDonr221 were recombined using BP Clonase II. The resulting 4,325 nt construct includes the humanized acmB coding sequence (653-2468 nt), 5' TEV site, Kozak consensus sequence and 3' HA tag flanked by attL attachment sites.

Figure 92:
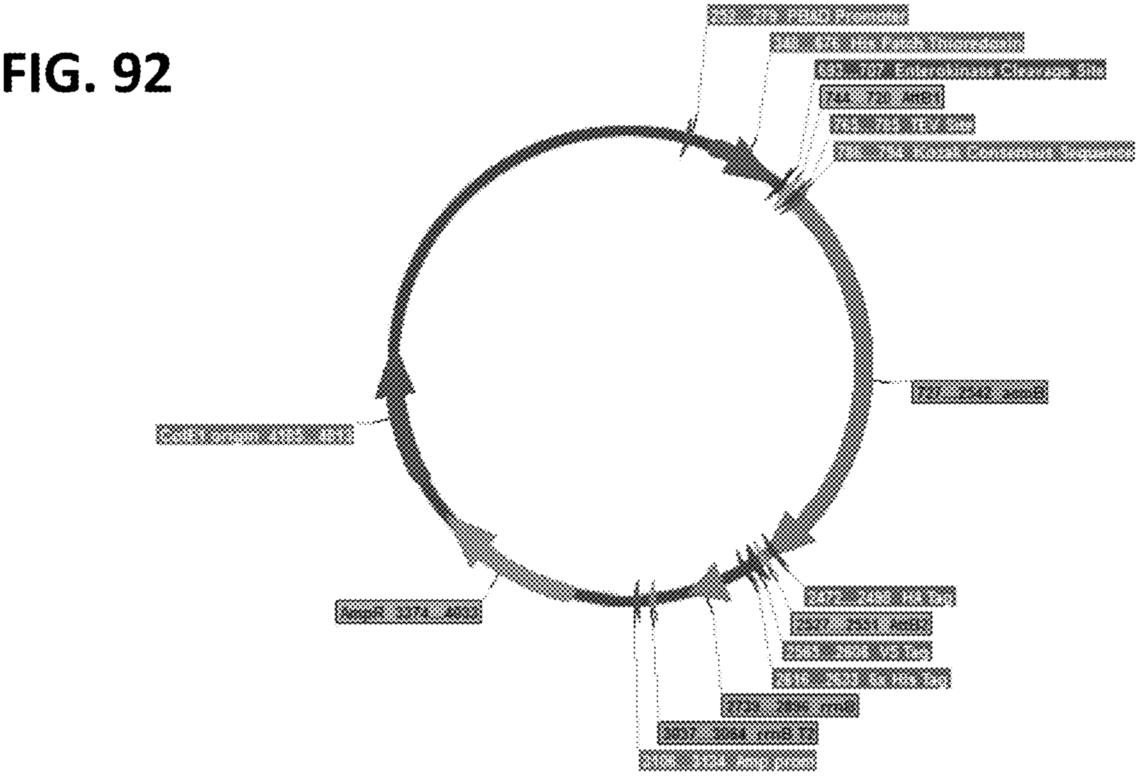

FIG. 92. Map of humanized anoxic cholesterol catabolism B enzyme (acmB) in pBAD-Dest49. To generate the pBAD-Dest49-acmB expression vector, pEntr221-acmB and pBAD-Dest49 were recombined using LR Clonase II. The resulting 6,287 nt construct includes the humanized acmB coding sequence (727-2542 nt), 5' TEV site, Kozak consensus sequence and 3' HA tag flanked by attB attachment sites.

The pBAD-Dest49 vector expresses acmB as an N-terminal His-Patch Thioredoxin fusion protein under the control of an arabinose inducible promoter.

Figure 93:
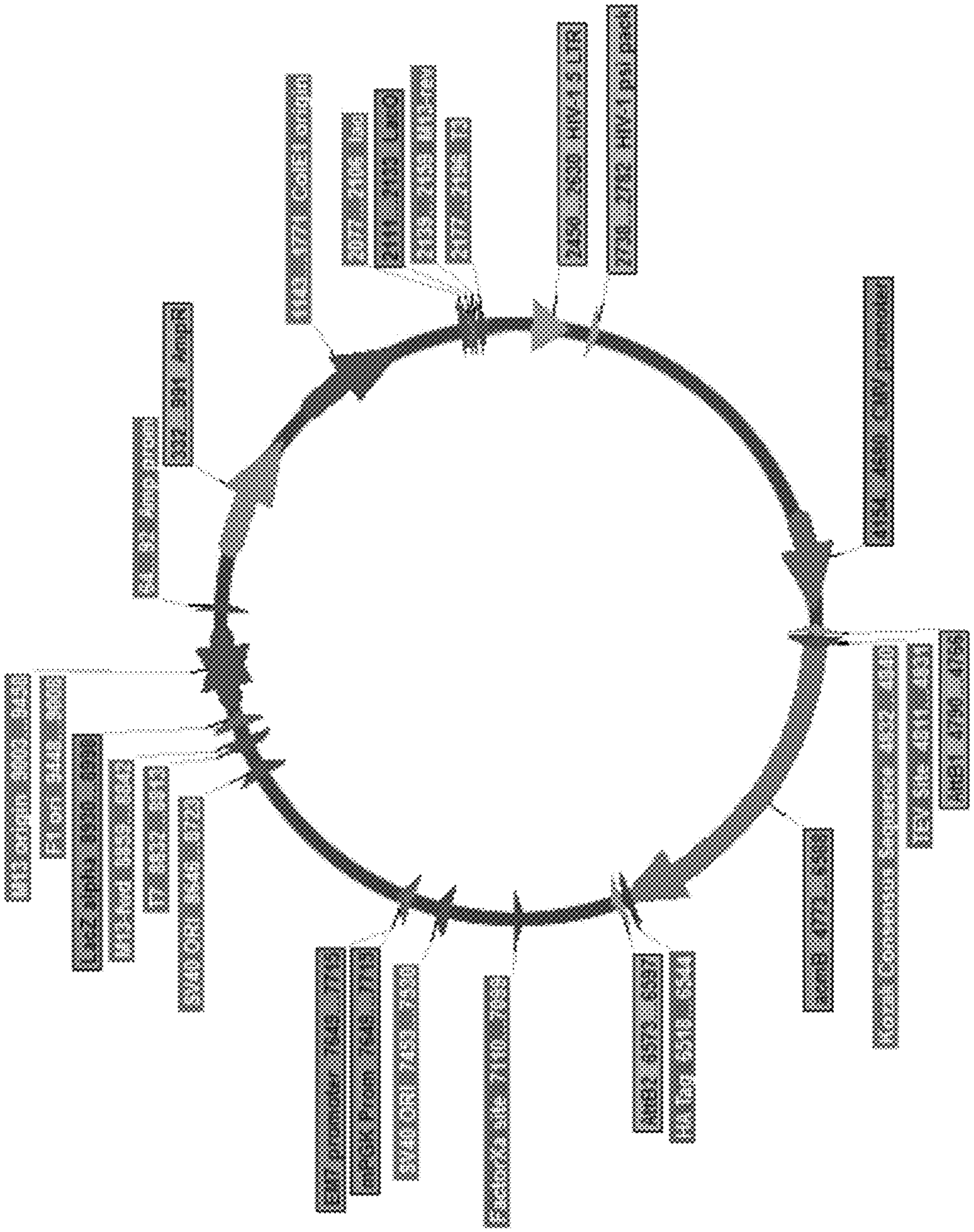

FIG. 93. Map of humanized anoxic cholesterol catabolism B enzyme (acmB) in pLenti CMV Blast DEST (706-1). To generate the pLenti CMV Blast DEST (706-1)—acmB lentiviral expression vector, pEntr221-acmB and pLenti CMV Blast DEST (706-1) were recombined using LR Clonase II. The resulting 9,458 nt construct includes the humanized acmB coding sequence (4773-6588 nt), 5' TEV site, Kozak consensus sequence and 3' HA tag flanked by attB attachment sites. The pLenti CMV Blast DEST (706-1) expression vector is a third generation lentiviral transfer vector that expresses acmB under the control of a CMV promoter and encodes for blasticidin resistance.

Figures 95, 96:
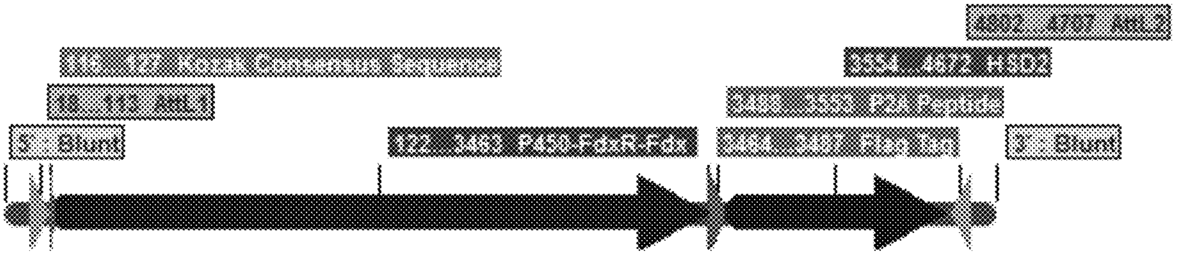

FIG. 95. P450-FdxR-Fdx-P2A-HSD2 construct map. The amino acid sequence of the P450-FdxR-Fdx-P2A-HSD2 construct (coding region 122-4672 nt; P450-FdxR-Fdx: 122-3,463 nt, 1,114 amino acids; HSD2: 2554-4672 nt, 372 amino acids) was reverse translated using GeneOptimizer software set to *H. sapiens* codon usage. GeneOptimizer software was also used to design flanking sequences that contained Gateway attachment sites (attL1 and attL2) and restriction enzyme recognition sites (5' BglII and XbaI; 3' BamHI and MfeI) to aid in sub cloning. The P450-FdxR-Fdx-P2A-HSD2 construct was then synthesized and inserted into pMK-RQ vector (GeneArt).

FIG. 96. Features of the P450-FdxR-Fdx-P2A-HSD2 nucleotide sequence. SEQ ID NO: 12

Figure 97:
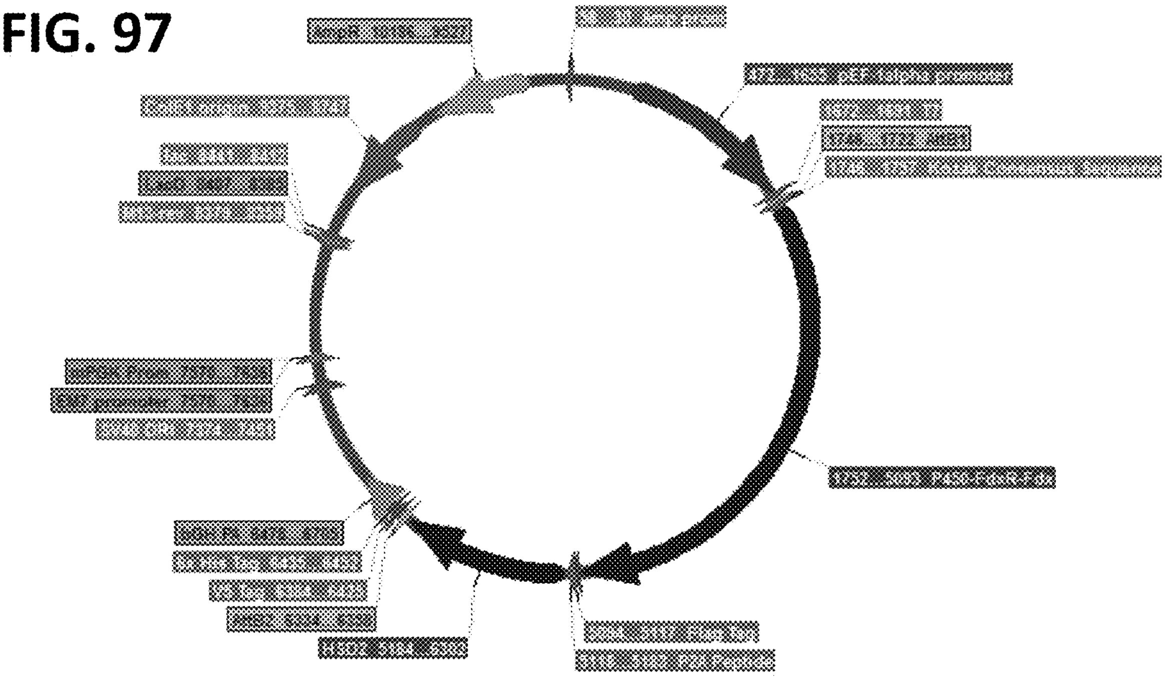

FIG. 97. Map of P450-FdxR-Fdx-P2A-HSD2 in pEF-Dest51. To generate pEF-Dest51-P450-FdxR-Fdx-P2A-HSD2, pMK-RQ-P450-FdxR-Fdx-P2A-HSD2 and pEF-Dest51 were recombined using LR Clonase II. The resulting 10,396 nt construct includes the P450-FdxR-Fdx-P2A-HSD2 construct coding sequence (1752-6302 nt), 5' Kozak consensus sequence and 3' P450-FdxR-Fdx Flag tag flanked by attB attachment sites. The pEF-Dest51 expression vector expresses P450-FdxR-Fdx-P2A-HSD2 construct under the control of an EF1α promoter and encodes for blasticidin resistance.

Figure 98:
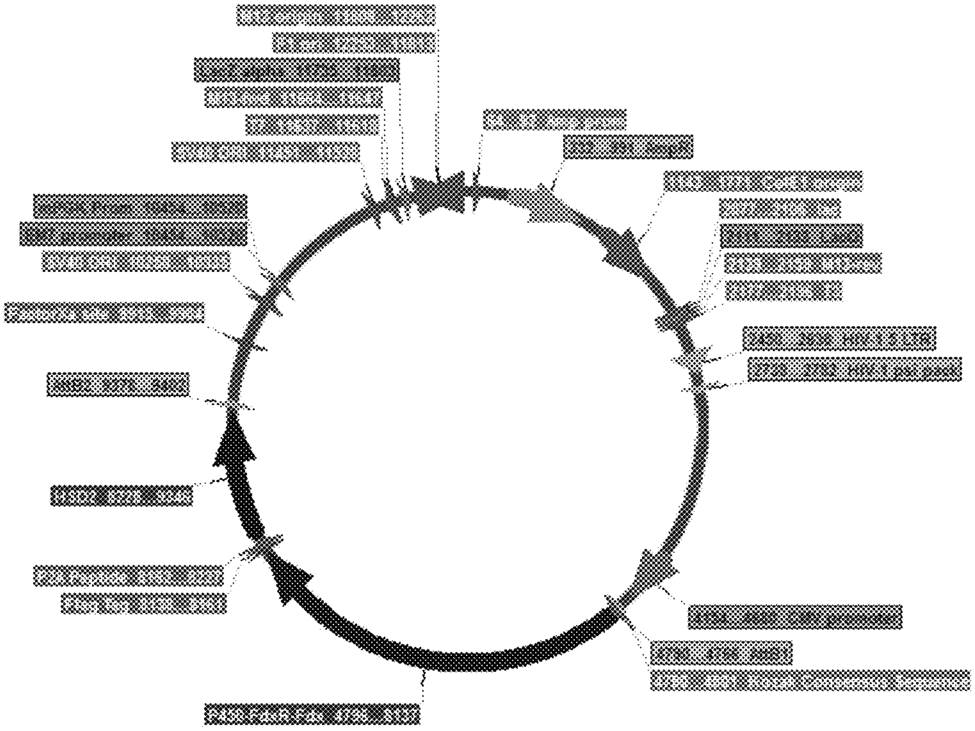

FIG. 98. Map of P450-FdxR-Fdx-P2A-HSD2 in pLenti CMV Blast DEST (706-1). To generate the pLenti CMV Blast DEST (706-1)—P450-FdxR-Fdx-P2A-HSD2 lentiviral expression vector, pMK-RQ-P450-FdxR-Fdx-P2A-HSD2 and pLenti CMV Blast DEST (706-1) were recombined using LR Clonase II. The resulting 12,263 nt construct includes the P450-FdxR-Fdx-P2A-HSD2 coding sequence (4,796-9,346 nt), 5' Kozak consensus sequence and 3' P450-FdxR-Fdx Flag tag flanked by attB attachment sites. The pLenti CMV Blast DEST (706-1) expression vector is a third generation lentiviral transfer vector that expresses the P450-FdxR-Fdx-P2A-HSD2 construct under the control of a CMV promoter and encodes for blasticidin resistance.

Figures 99, 100:
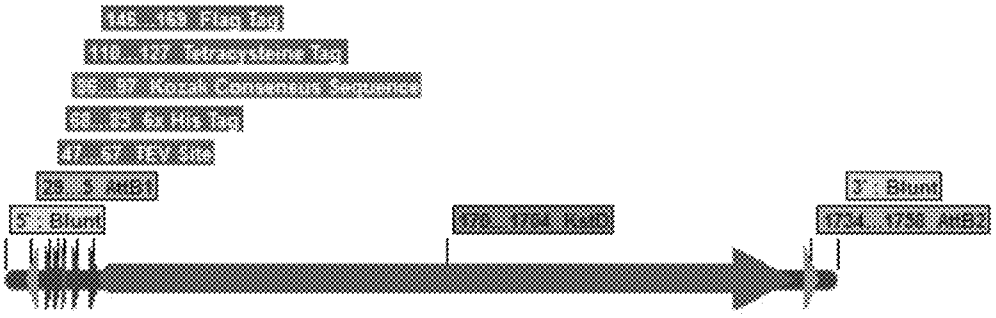

FIG. 99. Humanized 3-ketosteroid $\Delta^1$-dehydrogenase ($\Delta^1$-KstD) map. The amino acid sequence of $\Delta^1$-KstD from *Rhodococcus erythropolis* (coding region 170-1704 nt, 510 amino acids) was reverse translated using GeneOptimizer software set to *H. sapiens* codon usage. GeneOptimizer software was used to design flanking sequences that contained Gateway attachment sites (attB1 and attB2) and restriction enzyme recognition sites (5': MfeI and BamHI; 3': EcoRI, and BglII) to aid sub cloning. In addition, 5' of the $\Delta^1$-KstD sequence a TEV site, a 6×His tag, Kozak consensus sequence, tetracysteine tag, and a Flag tag were added to aid in purification and detection of the recombinant protein after expression. This humanized $\Delta^1$-KstD construct was then synthesized and inserted into the pUC57 vector (GenScript).

FIG. 100. Features of humanized 3-ketosteroid Δ1-dehydrogenase (Δ1-KstD) nucleotide sequence. SEQ ID NO: 13

Figure 101:
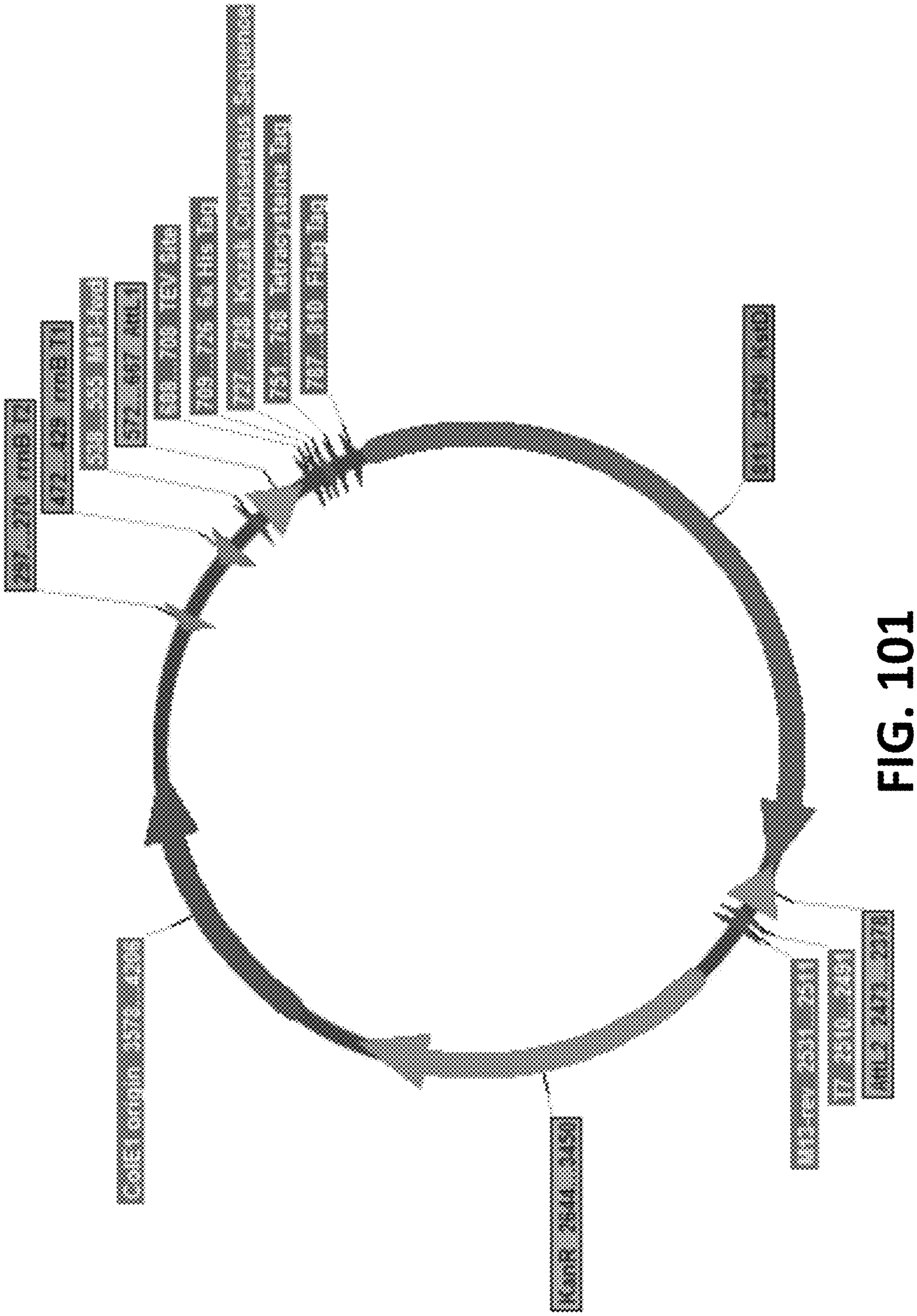

FIG. 101. Map of 3-ketosteroid $\Delta^1$-dehydrogenase ($\Delta^1$-KstD) in pEntr221. To generate the pEntr221-$\Delta^1$-KstD entry vector, pUC57-$\Delta^1$-KstD and pDonr221 were recombined using BP Clonase II. The resulting 4,247 nt construct includes the humanized $\Delta^1$-KstD coding sequence (811-2390 nt), 5' TEV site, 6×His tag, Kozak consensus sequence, tetracysteine tag, and Flag tag flanked by attL attachment sites.

Figure 102:
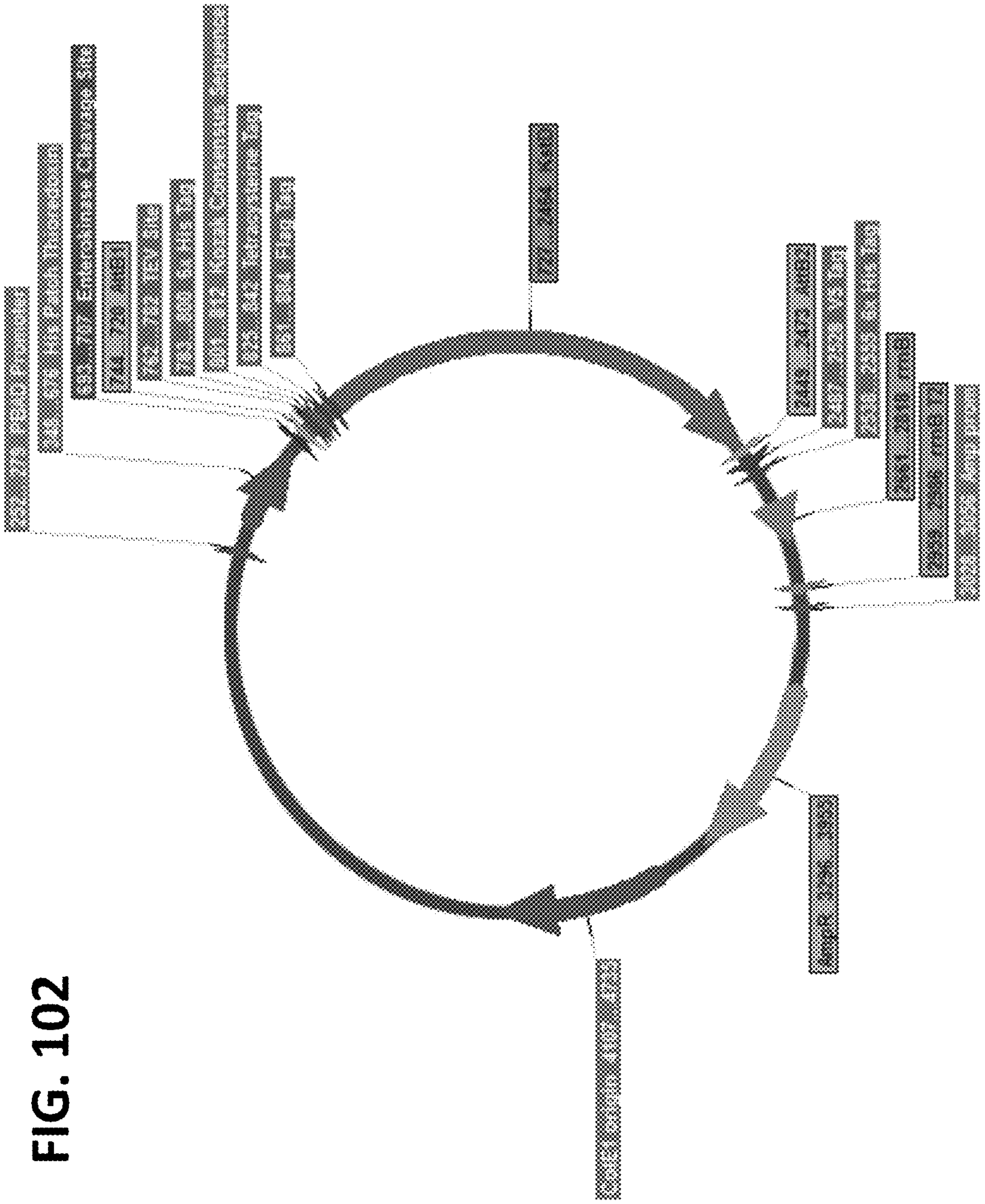

FIG. 102. Map of humanized 3-ketosteroid $\Delta^1$-dehydrogenase ($\Delta^1$-KstD) in pBAD-Dest49. To generate the pBAD-Dest49-$\Delta^1$-KstD expression vector, pEntr221-$\Delta^1$-KstD and pBAD-Dest49 were recombined using LR Clonase II. The resulting 6,209 nt construct includes the humanized $\Delta^1$-KstD coding sequence (727-2464 nt), 5' TEV site, 6×His tag, Kozak consensus sequence, tetracysteine tag, and Flag tag flanked by attB attachment sites. The pBAD-Dest49 vector expresses $\Delta^1$-KstD as an N-terminal His-Patch Thioredoxin fusion protein under the control of an arabinose inducible promoter.

FIG. 103. Map of 3-ketosteroid $\Delta^1$-dehydrogenase ($\Delta^1$-KstD) Kozak consensus sequence repair string. To repair the $\Delta^1$-KstD Kozak consensus sequence, a repair string (504 nt) was designed to insert a new attB1 site, Kozak consensus sequence, Flag tag, and the first 13 nt of $\Delta^1$-KstD's N-terminus that was removed by restriction digest. The $\Delta^1$-KstD Kozak consensus sequence was repaired in the pEF-Dest51 expression vector, and then recombined into pEntr221 for further recombinations.

FIG. 104. Features of the repair string for 3-ketosteroid $\Delta^1$-dehydrogenase ($\Delta^1$-KstD) Kozak consensus sequence repair. SEQ ID NO: 14

FIG. 105. Map of the repaired 3-ketosteroid $\Delta^1$-dehydrogenase (Repaired $\Delta^1$-KstD) in pEF-Dest51. Following repair of the $\Delta^1$-KstD Kozak consensus sequence by Gibson Assembly, the resulting 7,435 nt construct includes the repaired $\Delta^1$-KstD (1809-3388 nt), 5' Kozak consensus sequence, and Flag tag flanked by attB attachment sites. The pEF-Dest51 expression vector expresses the repaired $\Delta^1$-KstD under the control of an EF1α promoter and encodes for blasticidin resistance.

Figures 106, 107:
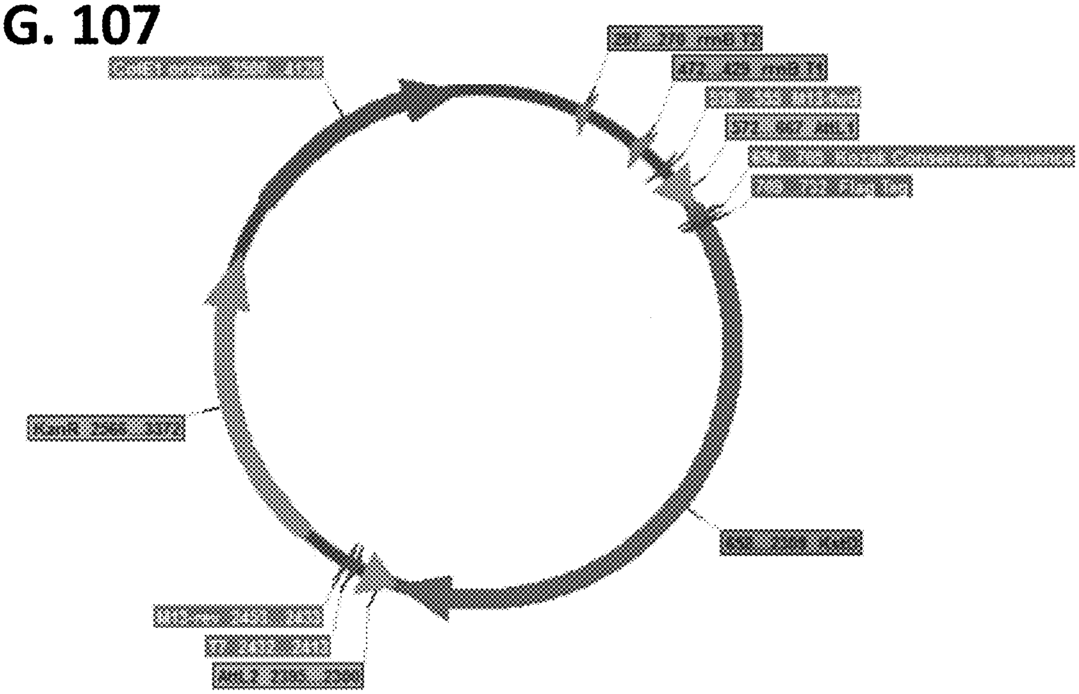

FIG. 106. Features of the nucleotide sequence for repaired 3-ketosteroid $\Delta^1$-dehydrogenase (Repaired $\Delta^1$-KstD) in pEF-Dest51 SEQ ID NO: 15

FIG. 107. Map of repaired 3-ketosteroid $\Delta^1$-dehydrogenase (Repaired $\Delta^1$-KstD) in pEntr221. To generate the pEntr221-Repaired $\Delta^1$-KstD entry vector, pEF-Dest51-$\Delta^1$-KstD and pDonr221 were recombined using BP Clonase II. The resulting 4,170 nt construct includes the Repaired $\Delta^1$-KstD coding sequence (658-2309 nt), 5' Kozak consensus sequence, and Flag tag flanked by attL attachment sites.

Figure 108:
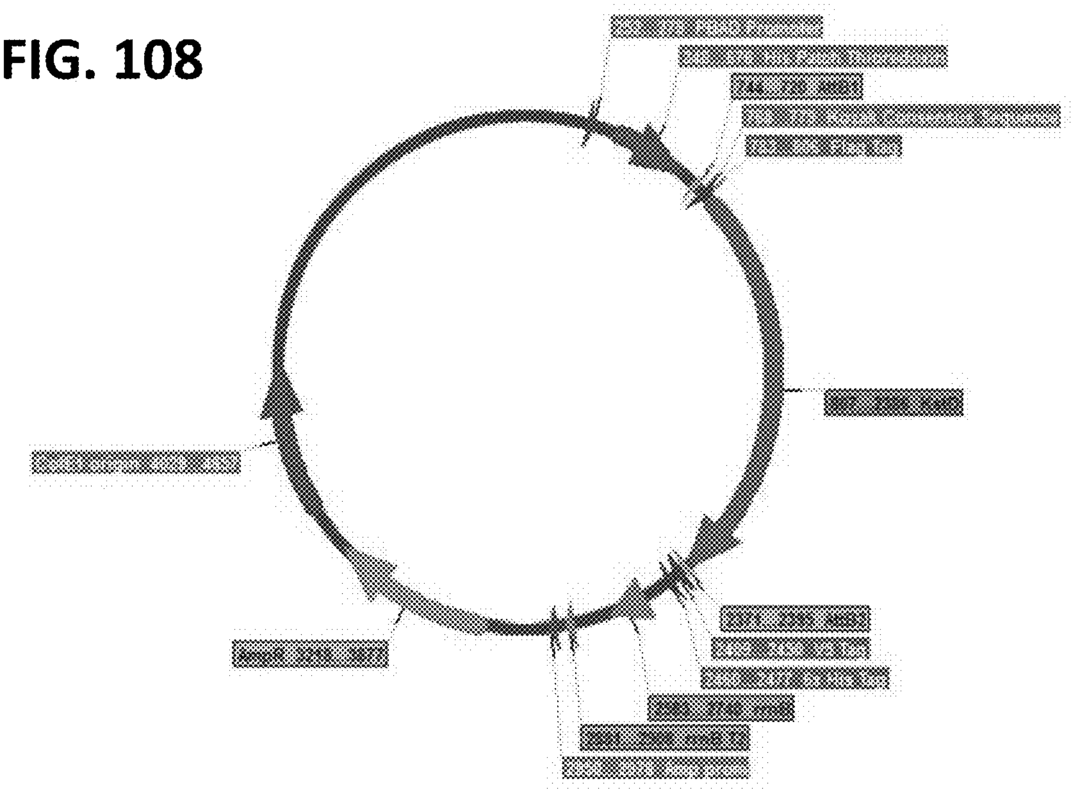

FIG. 108. Map of repaired 3-ketosteroid $\Delta^1$-dehydrogenase (Repaired $\Delta^1$-KstD) in pBAD-Dest49. To generate the pBAD-Dest49-Repaired $\Delta^1$-KstD expression vector, pEntr221-Repaired $\Delta^1$-KstD and pBAD-Dest49 were recombined using LR Clonase II. The resulting 6,131 nt construct includes the Repaired $\Delta^1$-KstD coding sequence (807-2386 nt), 5' Kozak consensus sequence, and Flag tag flanked by attB attachment sites. The pBAD-Dest49 vector expresses Repaired $\Delta^1$-KstD as an N-terminal His-Patch Thioredoxin fusion protein under the control of an arabinose inducible promoter.

Figure 109:
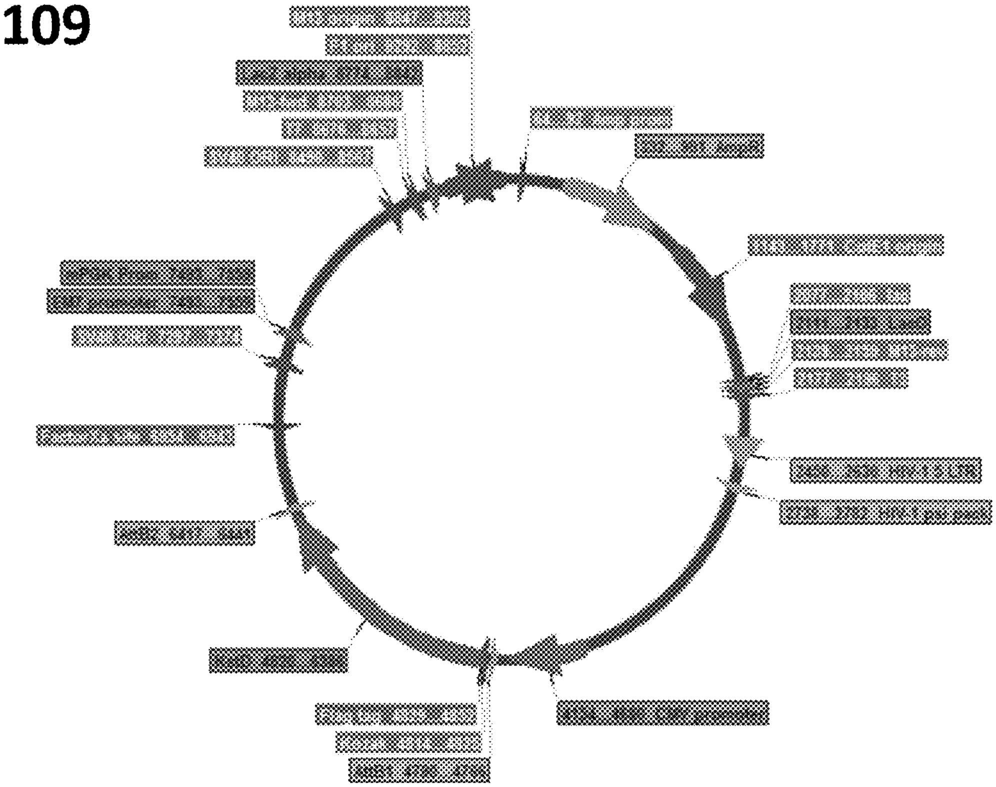

FIG. 109. Map of repaired 3-ketosteroid $\Delta^1$-dehydrogenase (Repaired $\Delta^1$-KstD) in pLenti CMV Blast DEST (706-1). To generate the pLenti CMV Blast DEST (706-1)—Repaired $\Delta^1$-KstD lentiviral expression vector, pEntr221-

Repaired $\Delta^1$-KstD and pLenti CMV Blast DEST (706-1) were recombined using LR Clonase II. The resulting 9,302 nt construct includes the Repaired $\Delta^1$-KstD coding sequence (4,820-6,386 nt), 5' Kozak consensus sequence, and Flag tag flanked by attB attachment sites. The pLenti CMV Blast DEST (706-1) expression vector is a third generation lentiviral transfer vector that expresses Repaired $\Delta^1$-KstD under the control of a CMV promoter and encodes for blasticidin resistance.

Figure 110:
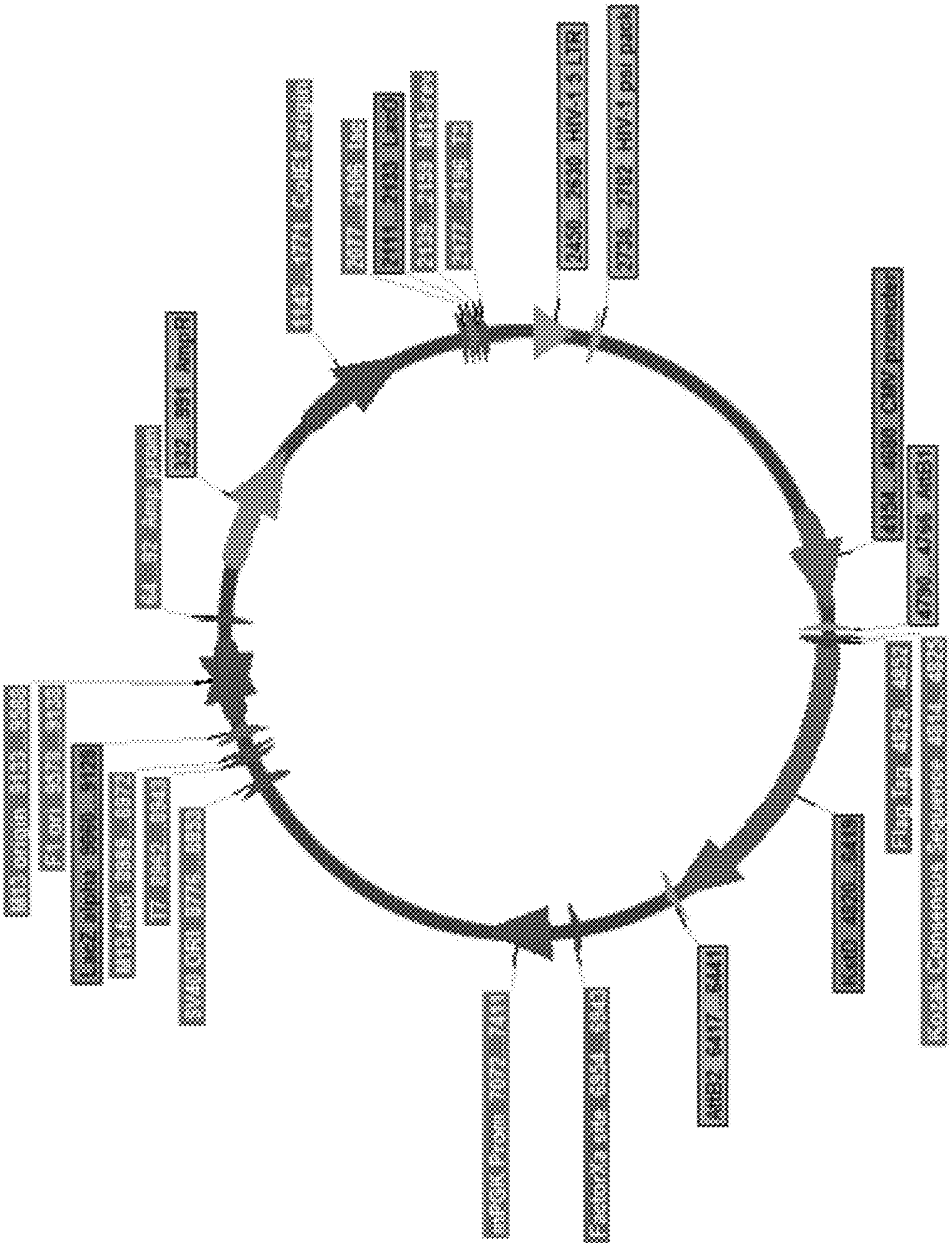

FIG. 110. Map of repaired 3-ketosteroid $\Delta^1$-dehydrogenase (Repaired $\Delta^1$-KstD) in pLenti CMV Puro DEST (w118-1). To generate the pLenti CMV Puro DEST (w118-1)—Repaired $\Delta^1$-KstD lentiviral expression vector, pEntr221-Repaired $\Delta^1$-KstD and pLenti CMV Puro DEST (w118-1) were recombined using LR ClonaseII. The resulting 9,588 nt construct includes the Repaired $\Delta^1$-KstD coding sequence (4,820-6,419 nt), 5' Kozak consensus sequence, and Flag tag flanked by attB attachment sites. The pLenti CMV Blast DEST (706-1) expression vector is a third generation lentiviral transfer vector that expresses Repaired $\Delta^1$-KstD under the control of a CMV promoter and encodes for puromycin resistance.

Figures 111, 112:
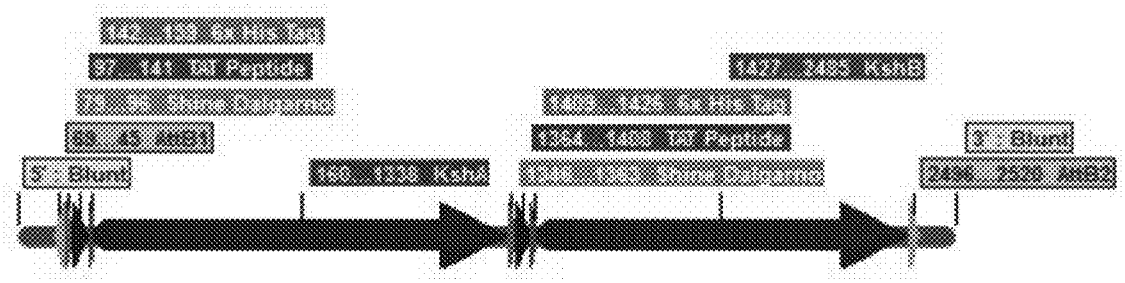

FIG. 111. Prokaryotic 3-ketosteroid 9α-hydroxylase (KshAB pro) map. The amino acid sequence of KshAB from *Rhodococcus rhodochrous*(KshA coding region 160-1338 nt, 414 amino acids; KshB coding region 1427-2485, 374 amino acids) was reverse translated using GeneOptimizersoftware set to *E. coli* codon usage. The prokaryotic KshAB vector was designed as a bicistronic construct by inserting a second shine dalgarnosequence following the 3' end of KshA. The second shine dalgarno was shifted by one nucleotide to produce a second open reading frame for coexpression of KshB. Both subunits were designed with 5' cell penetrating peptides (CPPs) from the HIV-TAT protein (MGYGRKKRRQRRR; SEQ ID NO: 9), short linker peptides (amino acids: GAS), and 6×His tags. GeneOptimizersoftware was used to design flanking sequences that contained Gateway attachment sites (attB1 and attB2) and restriction enzyme recognition sites (5' BamHI; 3' PstI and an EcoRI between the A and B subunits) to aid in sub cloning. The prokaryotic KshAB construct was synthesized and inserted into pMA-RQ (GeneArt).

FIG. 112. Features of the prokaryotic 3-ketosteroid 9α-hydroxylase (KshAB pro) nucleotide sequence. SEQ ID NO: 16

Figure 113:
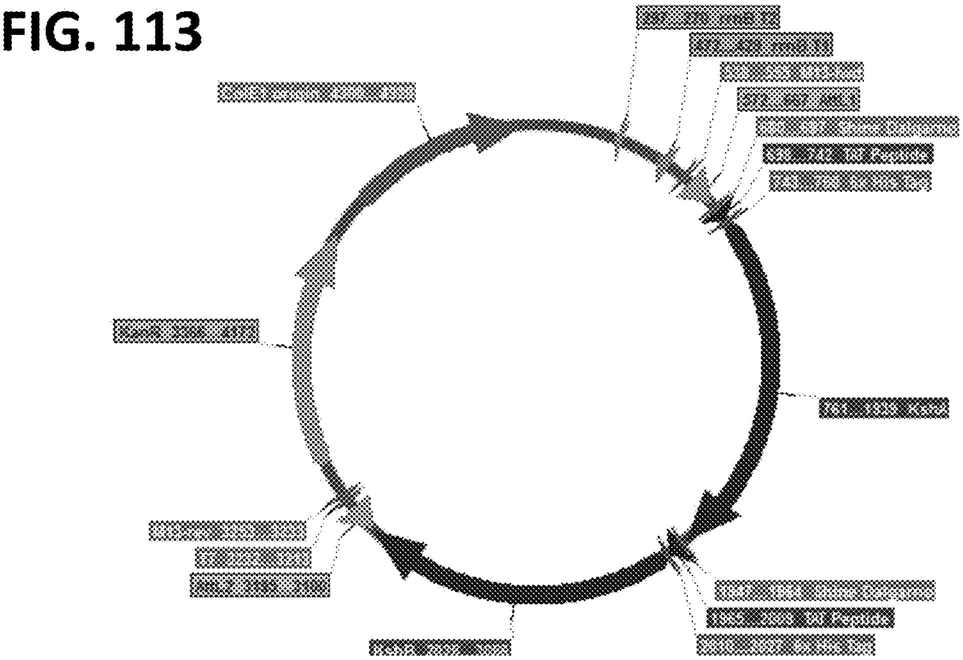

FIG. 113. Map of prokaryotic 3-ketosteroid 9α-hydroxylase (KshAB pro) in pEntr221. To generate the pEntr221-KshAB (pro) entry vector, pMA-RQ—KshAB (pro) and pDonr221 were recombined using BP ClonaseII. The resulting 4,969 nt construct includes the KshAB (pro) coding sequence (761-3086 nt), 5' KshA and KshB Shine Dalgarno sequences, cell penetrating peptides (CPPs), and 6×His tags flanked by attL attachment sites.

Figure 114:
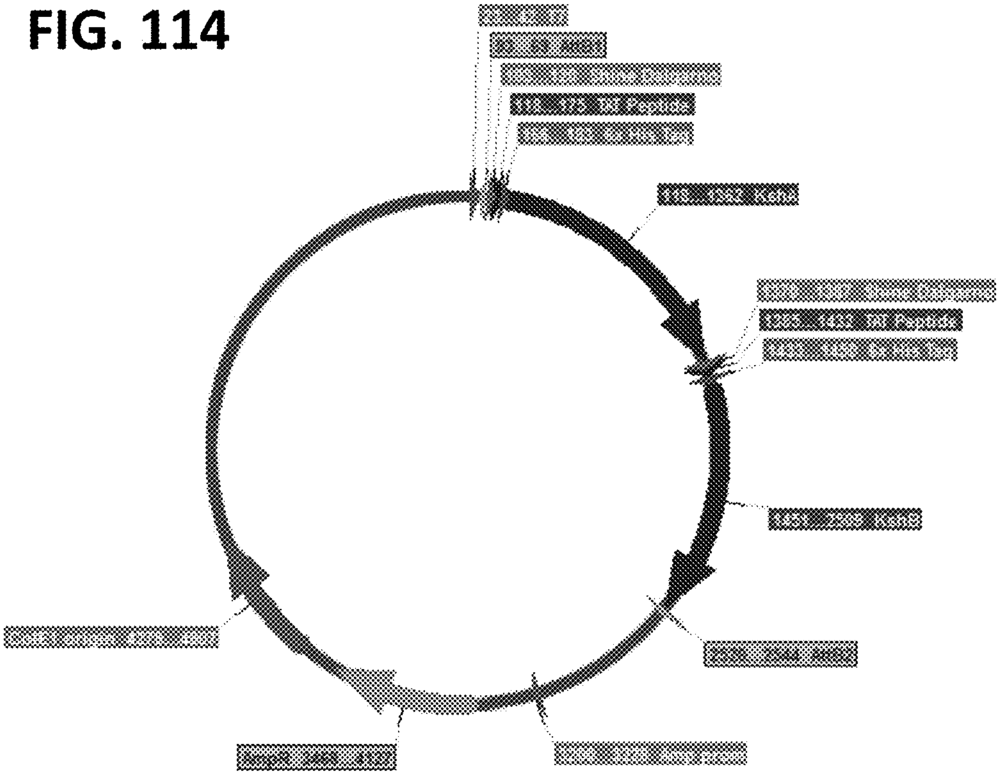

FIG. 114. Map of prokaryotic 3-ketosteroid 9α-hydroxylase (KshAB pro) in pDest14. To generate the pDest14-KshAB (pro) expression vector, pEntr221-KshAB (pro) and pDest14 were recombined using LR ClonaseII. The resulting 7,052 nt construct includes the prokaryotic KshAB coding sequence (118-2509 nt), 5' KshA and KshB Shine Dalgarno sequences, cell penetrating peptides (CPPs), and 6×His tags flanked by attB attachment sites. The pDest14 vector expresses KshAB (pro) under the control of an IPTG inducible promoter.

Figures 115, 116:
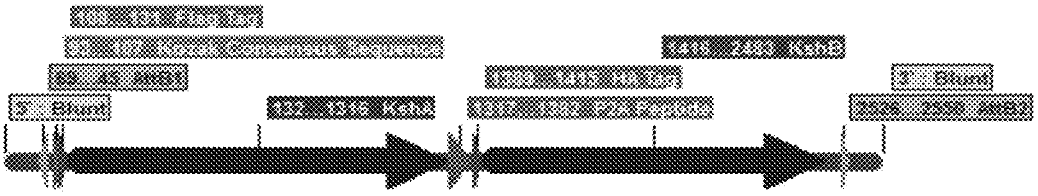

FIG. 115. Humanized 3-ketosteroid 9α-hydroxylase (KshAB euk) map. The amino acid sequence of KshAB from *Rhodococcus rhodochrous*(KshA coding region 132-1316 nt, 406 amino acids; KshB coding region 1416-2483, 367 amino acids) was reverse translated using GeneOptimizersoftware set to *H. sapiens* codon usage. The eukaryotic KshAB vector was designed as a bicistronic construct by inserting the Porcine teschovirus-12A skipping peptide (P2A) following the 3' end of KshA. In addition, a Kozak consensus sequence and Flag tag were added 5' of KshA to aid in detection of the A subunit. Similarly, an HA tag was added 5' of KshB for detection of the B subunit. GeneOptimizersoftware was used to design flanking sequences that contained Gateway attachment sites (attB1 and attB2) and restriction enzyme recognition sites (5' BglII and XbaI; 3' BamHI and MfeI) to aid in sub cloning. The eukaryotic KshAB construct was synthesized and inserted into pMA-RQ (GeneArt).

FIG. 116. Features of the humanized 3-ketosteroid 9α-hydroxylase (KshAB euk) nucleotide sequence. SEQ ID NO: 17

Figure 117:
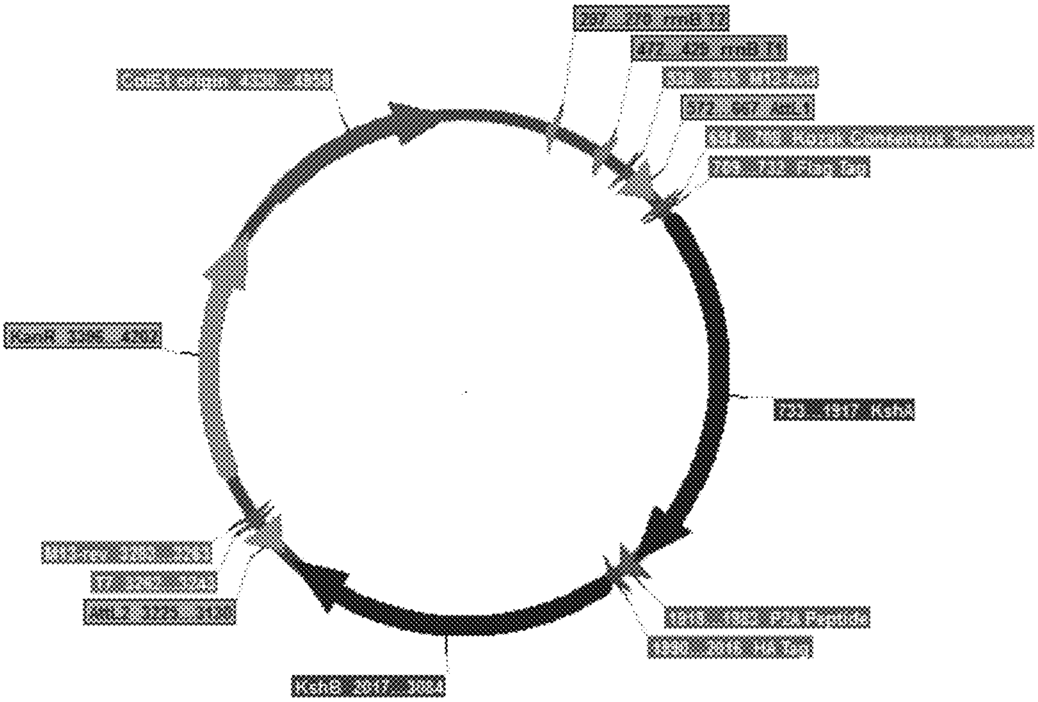

FIG. 117. Map of eukaryotic 3-ketosteroid 9α-hydroxylase (KshAB euk) in pEntr221. To generate the pEntr221-KshAB (euk) entry vector, pMA-RQ—KshAB (euk) and pDonr221 were recombined using BP Clonase II. The resulting 4,999 nt construct includes the KshAB (euk) coding sequence (733-3084 nt), 5' Kozak consensus sequence, KshA Flag tag, KshB HA tag and Porcine teschovirus-12A skipping peptide (P2A) flanked by attL attachment sites.

Figure 118:
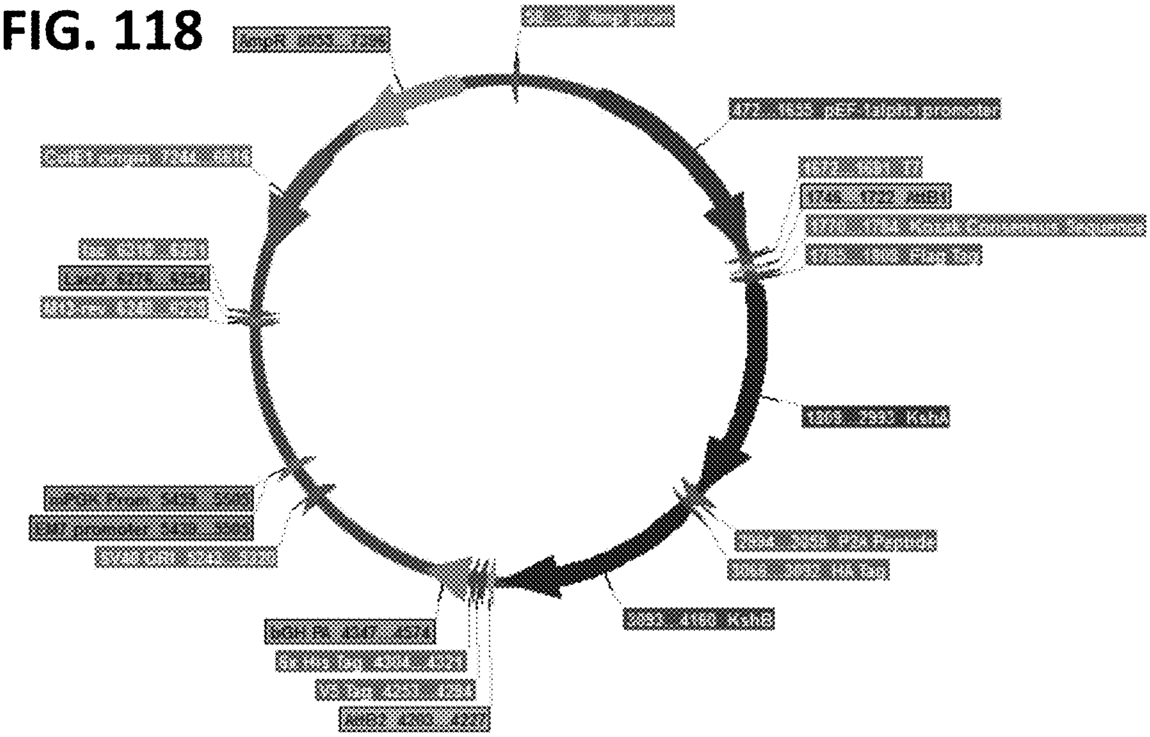

FIG. 118. Map of eukaryotic 3-ketosteroid 9α-hydroxylase (KshAB euk) in pEF-Dest51. To generate pEF-Dest51-KshAB (euk), pMA-RQ—KshAB (euk) and pEF-Dest51 were recombined using LR Clonase II. The resulting 8,265 nt construct includes the KshAB (euk) coding sequence (1809-4160 nt), 5' Kozak consensus sequence, KshA Flag tag, KshB HA tag and Porcine teschovirus-12A skipping peptide (P2A) flanked by attB attachment sites. The pEF-Dest51 expression vector expresses KshAB (euk) under the control of an EF1α promoter and encodes for blasticidin resistance.

FIG. 119. Map of the first repair string encoding the Aconitase2 mitochondrial targeting sequence addition to the KshA subunit. To fuse the Aconitase2 mitochondrial targeting sequence (MTS) to KshA, a repair string (1000 nt) was designed to insert the MTS 5' of KshA while retaining the original attL1 site, Kozak consensus sequence, and Flag tag. The KshAB MTS addition was repaired using Gibson Assembly in pEntr221 for further propagation of the mitochondrial localized KshAB into an appropriate expression vector.

FIG. 120. Features of the nucleotide sequence for the first repair string encoding the Aconitase2 mitochondrial targeting sequence addition to the KshA subunit. SEQ ID NO: 18

FIG. 121. Map of the second repair string encoding the Aconitase2 mitochondrial targeting sequence addition to the KshB subunit. To fuse the Aconitase2 mitochondrial targeting sequence (MTS) to KshB, a repair string (600 nt) was designed to insert the MTS 5' of KshB while retaining the original HA tag. The KshAB MTS addition was repaired using Gibson Assembly in pEntr221 for further propagation of the mitochondrial localized KshAB into an appropriate expression vector.

FIG. 122. Features of the nucleotide sequence for the second repair string encoding the Aconitase2 mitochondrial targeting sequence addition to the KshB subunit. SEQ ID NO: 19

Figures 123, 124:
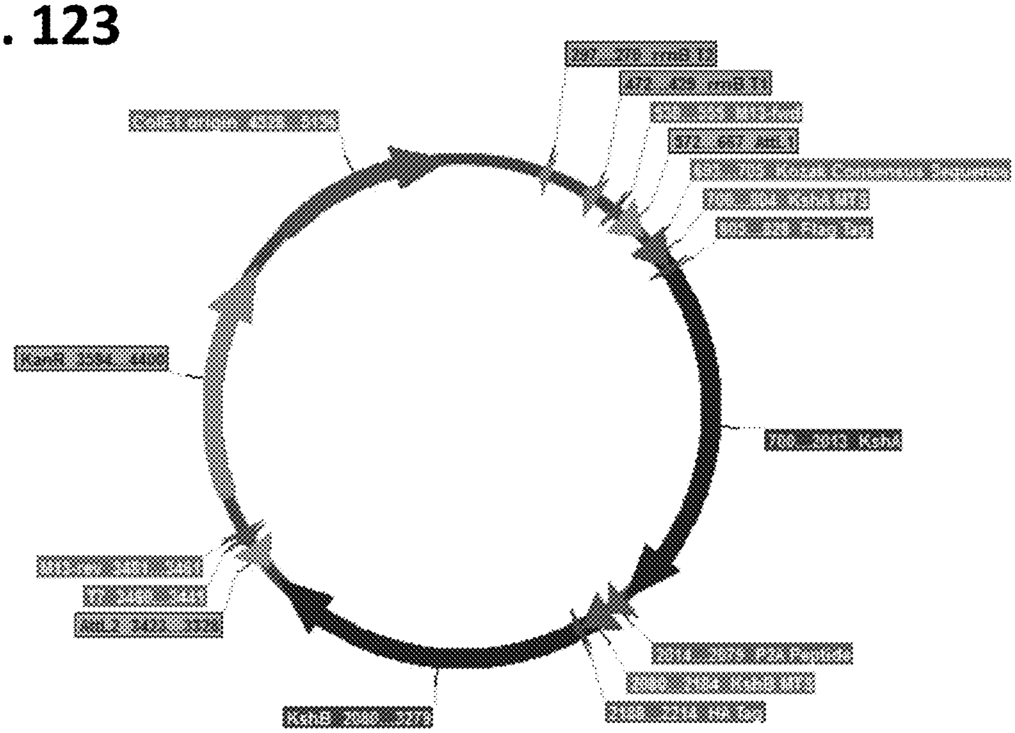

FIG. 123. Map of the mitochondrial localized 3-ketosteroid 9α-hydroxylase (MTS-KshAB) in pEntr221. Following the addition of mitochondrial targeting sequences (MTS) to the Ksh A and B subunits by Gibson Assembly, the resulting 5,197 nt construct includes the repaired MTS-KshAB construct (700-3279 nt), 5' Kozak consensus sequence, Flag tag (KshA), and HA tag (KshB) flanked by attL attachment sites.

FIG. 124. Features of the nucleotide sequence of the mitochondrial localized 3-ketosteroid 9α-hydroxylase (MTS-KshAB) in pEntr221. SEQ ID NO: 20

Figure 125:
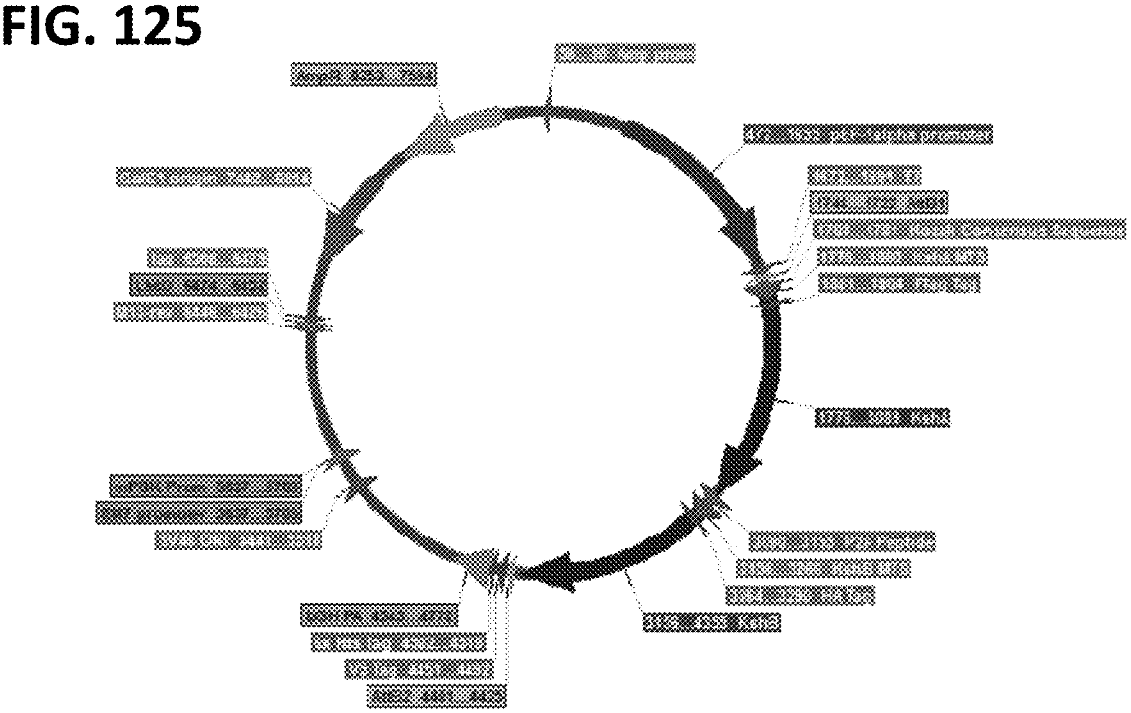

FIG. 125. Map of the mitochondrial localized 3-ketosteroid 9α-hydroxylase (MTS-KshAB) in pEF-Dest51. To generate the pEF-Dest51-MTS-KshAB expression vector, pEntr221-MTS-KshAB and pEF-Dest51 were recombined using LR Clonase II. The resulting 8,463 nt construct includes the MTS-KshAB coding sequence (1776-4355 nt), 5' Kozak consensus sequence, Flag tag (KshA), and HA tag (KshB) flanked by attB attachment sites. The pEF-Dest51 expression vector expresses MTS-KshAB under the control of an EF1α promoter and encodes for blasticidin resistance.

Figure 126:
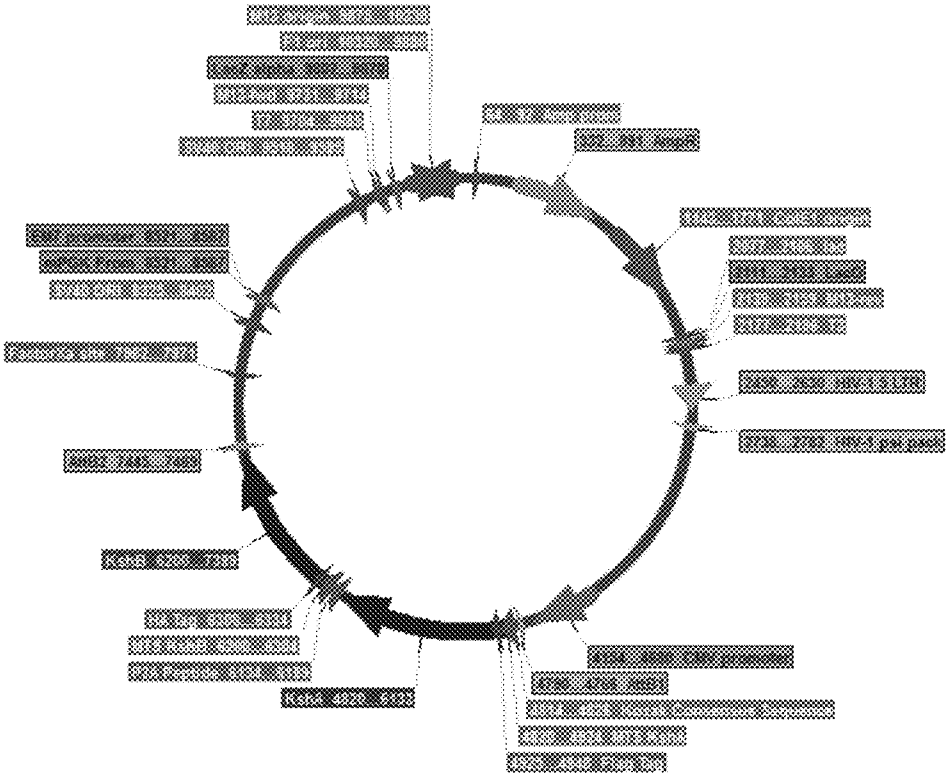

FIG. 126. Map of the mitochondrial localized 3-ketosteroid 9α-hydroxylase (MTS-KshAB) in pLenti CMV Blast DEST (706-1). To generate the pLenti CMV Blast DEST (706-1)-MTS-KshAB lentiviral expression vector, pEntr221-MTS-KshAB and pLenti CMV Blast DEST (706-1) were recombined using LR Clonase II. The resulting 10,330 nt construct includes the MTS-KshAB coding sequence (4820-7399 nt), 5' Kozak consensus sequence, Flag tag (KshA), and HA tag (KshB) flanked by attB attachment sites. The pLenti CMV Blast DEST (706-1) expression vector is a third generation lentiviral transfer vector that expresses MTS-KshAB under the control of a CMV promoter and encodes for blasticidin resistance.

FIG. 127. Map of the T2A repair string encoding the Thosea asigna 2A skipping peptide for the MTS-KshAB and $\Delta^1$-KstD tricistronic vector. To co-express MTS-KshAB and $\Delta^1$-KstD from a single vector, a repair string (656 nt) was designed to replace the native KshB stop codon with a Thosea asigna 2A skipping peptide within the MTS-KshAB $\Delta^1$-KstD ligated intermediate product. The T2A repair string was designed to encode for the C-terminal end of KshB, the T2A skipping peptide, the $\Delta^1$-KstD Flag tag, and the N-terminus of $\Delta^1$-KstD that was removed following restriction digest. The repair string included 40 bp homology arms starting from the 3' overhangs generated from the BbvCI and SpeI digest. The MTS-KshAB was repaired using Gibson Assembly in pEntr221 for further propagation of the MTS-KshAB T2A $\Delta^1$-KstD tricistronic vector into an appropriate expression vector.

FIG. 128. Features of the nucleotide sequence of the T2A repair string encoding the Thosea asigna 2A skipping peptide for the MTS-KshAB and $\Delta^1$-KstD tricistronic vector. SEQ ID NO: 21

FIG. 129. Map of the P2A repair string encoding the Porcine teschovirus-1 2A skipping peptide for the MTS-KshAB and $\Delta^1$-KstD tricistronic vector. To co-express MTS-KshAB and $\Delta^1$-KstD from a single vector, a repair string (659 nt) was designed to replace the native KshB stop codon with a Porcine teschovirus-12A skipping peptide in the MTS-KshAB $\Delta^1$-KstD ligated intermediate product. The P2A repair string was designed to encode for the C-terminal end of KshB, the P2A skipping peptide, the $\Delta^1$-KstD Flag tag, and the N-terminus of $\Delta^1$-KstD that was removed following restriction digest. The repair string included 40 bp homology arms starting from the 3' overhangs generated from the BbvCI and SpeI digest. The MTS-KshAB was repaired using Gibson Assembly in pEntr221 for further propagation of the MTS-KshAB P2A $\Delta^1$-KstD tricistronic vector into an appropriate expression vector.

FIG. 130. Features of the nucleotide sequence of the P2A repair string encoding the Porcine teschovirus-1 2A skipping peptide for the MTS-KshAB and $\Delta^1$-KstD tricistronic vector. SEQ ID NO: 22

Figures 131, 132:
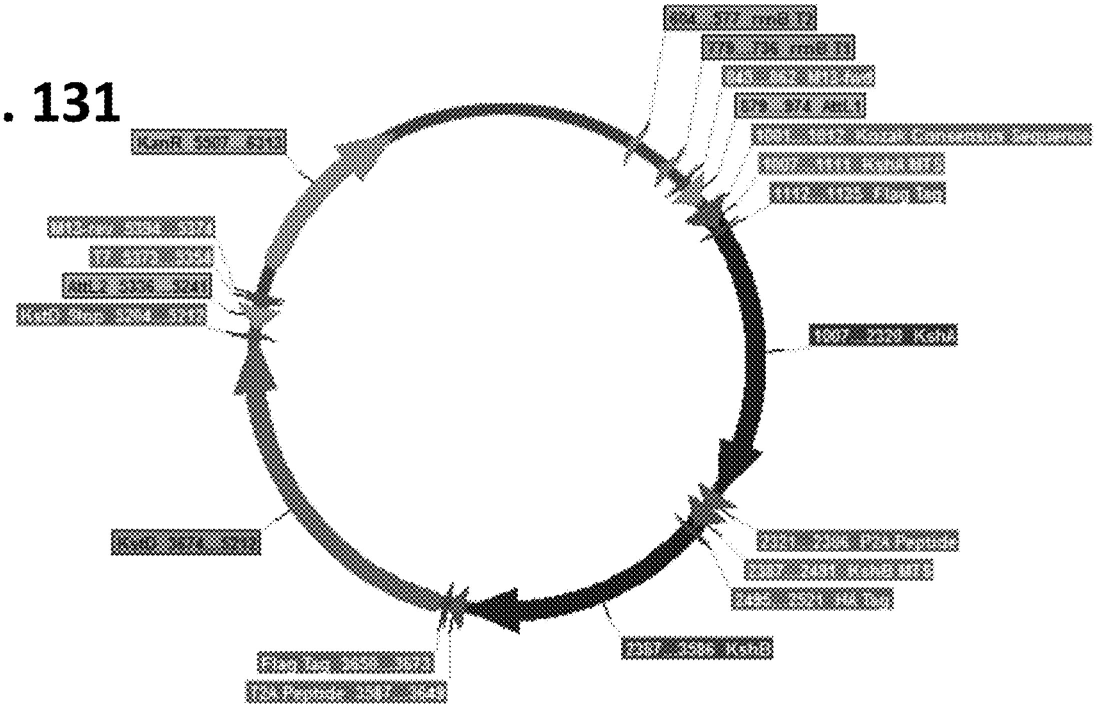

FIG. 131. Map of the MTS-KshAB-T2A-Δ1-KstD tricistronic construct in pEntr221. Following replacement of the native KshB stop codon with a Thosea asigna 2A skipping peptide (T2A) using Gibson Assembly, the resulting 6,803 nt construct includes the repaired MTS-KshAB enzyme (1,007-3,586 nt), the $\Delta^1$-KstD enzyme (3,674-5,212 nt), 5' Kozak consensus sequence, KshA Flag tag, KshB HA tag, and $\Delta^1$-KstD Flag tag flanked by attL attachment sites. The MTS-KshAB $\Delta^1$-KstD ligated intermediate product was repaired in pEntr221 for further propagation of the MTS-KshAB-T2A-$\Delta^1$-KstD tricistronic construct into an appropriate expression vector.

FIG. 132. Features of the nucleotide sequence for the MTS-KshAB-T2A-$\Delta^1$-KstD construct in pEntr221. SEQ ID NO: 23

Figure 133:
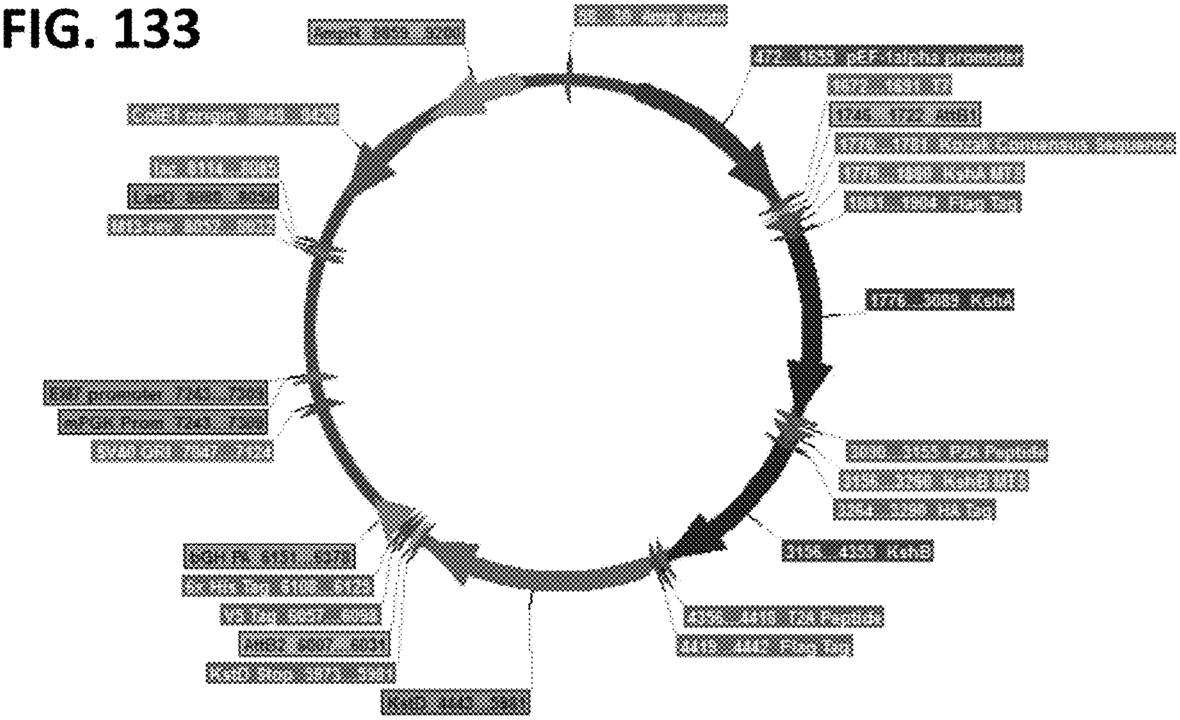

FIG. 133. Map of the MTS-KshAB-T2A-$\Delta^1$-KstD tricistronic construct in pEF-Dest51. To generate the pEF-Dest51-MTS-KshAB-T2A-$\Delta^1$-KstD expression vector, pEntr221-MTS-KshAB-T2A-$\Delta^1$-KstD and pEF-Dest51 were recombined using LR Clonase II. The resulting 10,069 nt construct includes the MTS-KshAB coding sequence (1,776-4,355 nt), $\Delta^1$-KstD (4,443-5,981 nt), 5' Kozak consensus sequence, KshA Flag tag, KshB HA tag, and $\Delta^1$-KstD Flag tag flanked by attB attachment sites. The pEF-Dest51 expression vector expresses MTS-KshAB-T2A-$\Delta^1$-KstD under the control of an EF1α promoter and encodes for blasticidin resistance.

Figure 134:
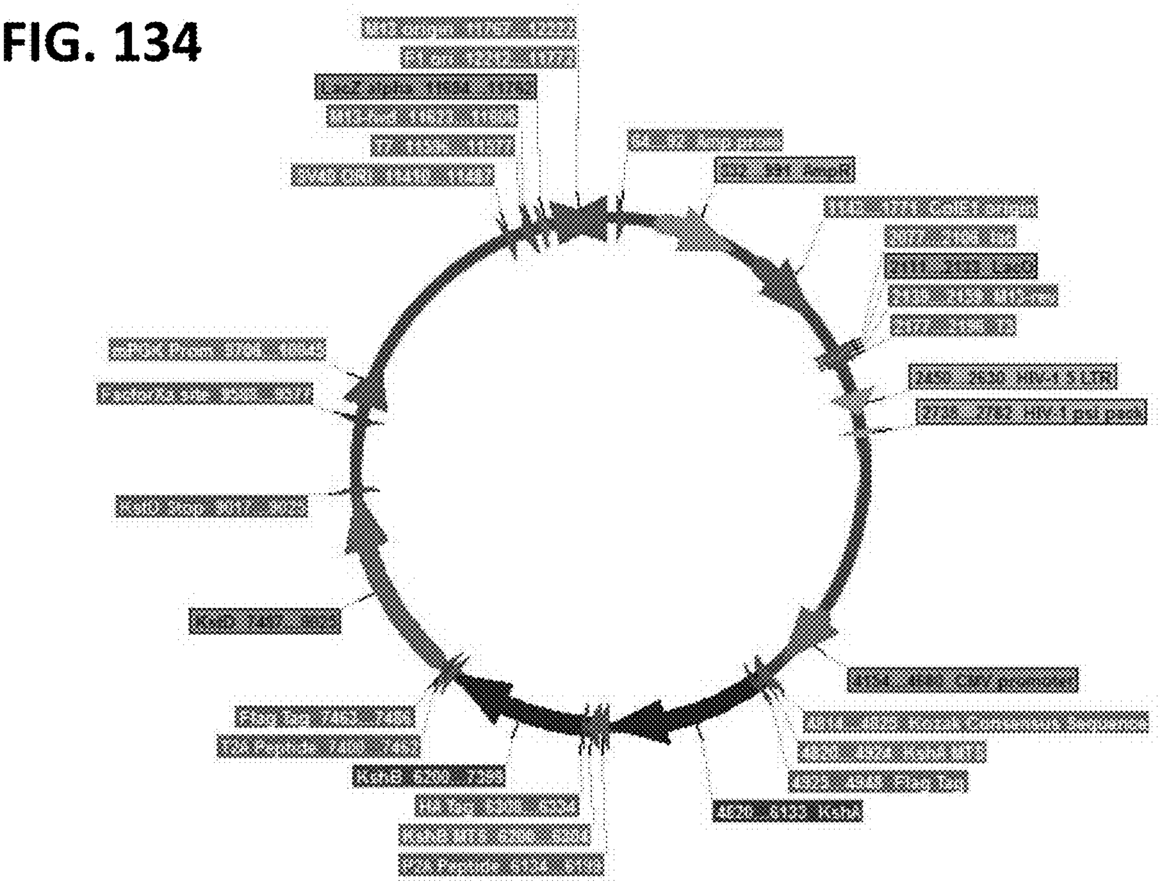

FIG. 134. Map of MTS-KshAB-T2A-$\Delta^1$-KstD in pLenti CMV Puro DEST (w118-1). To generate the pLenti CMV Puro DEST (w118-1)-MTS-KshAB-T2A-$\Delta^1$-KstD lentiviral expression vector, pEntr221-MTS-KshAB-T2A-$\Delta^1$-KstD and pLenti CMV Puro DEST (w118-1) were recombined using LR Clonase II. The resulting 12,222 nt construct includes the MTS-KshAB coding sequence (4820-7399 nt), $\Delta^1$-KstD (7487-9025 nt), 5' Kozak consensus sequence, KshA Flag tag, KshB HA tag, and $\Delta^1$-KstD Flag tag flanked by attB attachment sites. The pLenti CMV Puro DEST (w118-1) expression vector is a third generation lentiviral transfer vector that expresses MTS-KshAB-T2A-$\Delta^1$-KstD under the control of a CMV promoter and encodes for puromycin resistance.

FIG. 135. Map of the first repair string for insertion of the P450-FdxR-Fdx-P2A-HSD2 construct into the MTS-KshAB-T2A-$\Delta^1$-KstD tricistronic vector. To co-express the P450-FdxR-Fdx and HSD2 enzymes along with MTS-KshAB and $\Delta^1$-KstD, one of two repair strings (474 nt) was designed to encode for the N-terminal segment of the P450 enzyme that was lost following restriction digest. The repair string included 40 bp of homology starting from the 3' overhangs of the NcoI and ScaI restriction sites. The P450-FdxR-Fdx-P2A-HSD2 addition to the MTS-KshAB-T2A-$\Delta^1$-KstD tricistronic vector was repaired using Gibson Assembly in pEntr221 for further propagation of the pentacistronic construct into an appropriate expression vector.

FIG. 136. Features of the nucleotide sequence of the first repair string for insertion of the P450-FdxR-Fdx-P2A-HSD2 construct into the MTS-KshAB-T2A-$\Delta^1$-KstD tricistronic vector. SEQ ID NO: 24

FIG. 137. Map of the P450-FdxR-Fdx-P2A-HSD2 fragment for insertion into the MTS-KshAB-T2A-$\Delta^1$-KstD tricistronic vector. To co-express the P450-FdxR-Fdx and HSD2 enzymes along with MTS-KshAB and $\Delta^1$-KstD, the P450-FdxR-Fdx-P2A-HSD2 fragment (3221 nt) was generated by ScaI and EcoRV restriction digest of pMK-RQ—P450-FdxR-Fdx-P2A-HSD2. The P450-FdxR-Fdx-P2A-HSD2 addition to the MTS-KshAB-T2A-$\Delta^1$-KstD tricistronic vector was repaired using Gibson Assembly in pEntr221 for further propagation of the pentacistronic construct into an appropriate expression vector.

FIG. 138. Features of the nucleotide sequence of the P450-FdxR-Fdx-P2A-HSD2 fragment for insertion into the MTS-KshAB-T2A-$\Delta^1$-KstD tricistronic vector. SEQ ID NO: 25

FIG. 139. Map of the second repair string for insertion of P450-FdxR-Fdx-P2A-HSD2 construct into the MTS-KshAB-T2A-A1-KstD tricistronic vector. To co-express the P450-FdxR-Fdx and HSD2 enzymes along with MTS-KshAB and A1-KstD, a second repair string (1079nt) was designed to encode for the C-terminal segment of the HSD2 enzyme that was lost following restriction digest and a Thoseaasigna 2A skipping peptide (T2A). The repair string included 40 bp of homology starting from the 3' overhangs of the EcoRV and NcoI restriction enzyme recognition sites. The P450-FdxR-Fdx-2A-HSD2 addition to the MTS-KshAB-T2A-A1-KstD tricistronic vector was repaired using Gibson Assembly in pEntr221 for further propagation of the pentacistronic construct into an appropriate expression vector.

FIG. 140. Features of the nucleotide sequence of the second repair string for insertion of the P450-FdxR-Fdx-P2A-HSD2 fragment for insertion into the MTS-KshAB-T2A-$\Delta^1$-KstD tricistronic vector. SEQ ID NO: 26

Figures 141, 142:
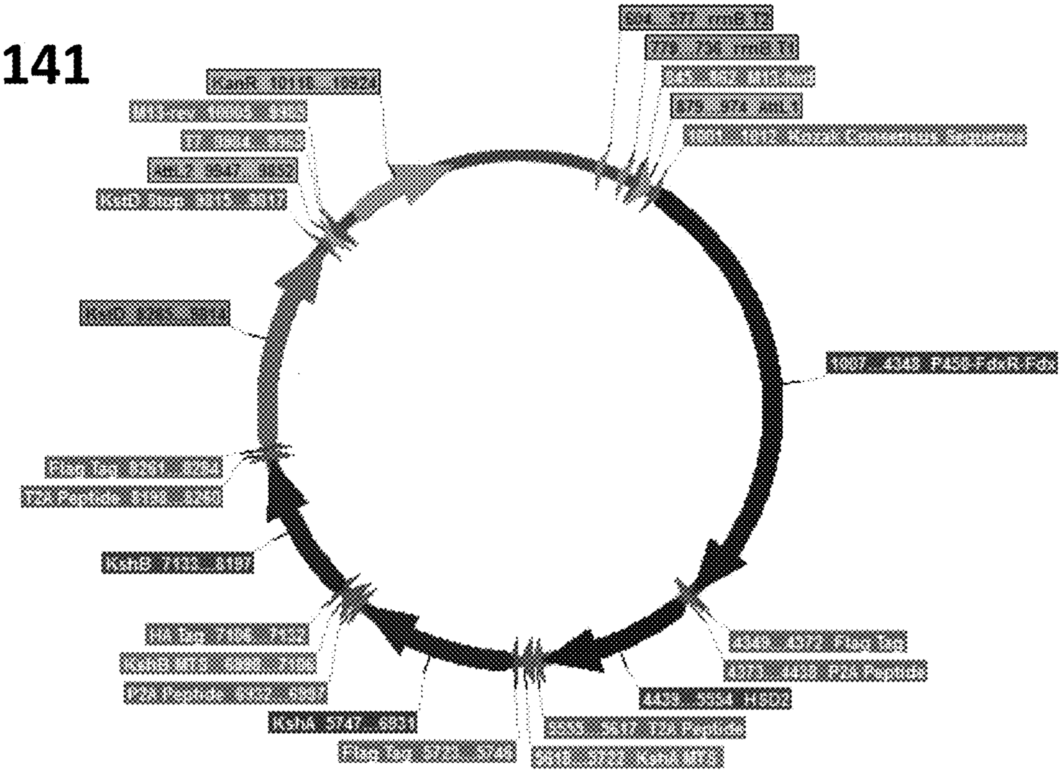

FIG. 141. Map of the P450-FdxR-Fdx-P2A-HSD2-T2A-KshA-P2A-KshB-T2A-$\Delta^1$-KstD pentacistronic construct (the cholesterol catabolizing cassette (the CCC)) in pEntr221. Following insertion of the P450-FdxR-FdxP2A-HSD2 construct into the MTS-KshAB-T2A-A1-KstD tricistronic vector using Gibson Assembly, the resulting 11,414 nt construct includes the P450-FdxR-Fdx fusion protein (1007-4,348 nt), HSD2 (4,439-5,554 nt), MTS-KshAB (5747-8197 nt), $\Delta^1$-KstD (8285-9814 nt), 5' Kozak consensus sequence, P450-FdxR-Fdx Flag tag, KshA Flag tag, KshB HA tag, and $\Delta^1$-KstD Flag tag flanked by attL attachment sites. The CCC was assembled in pEntr221 for further propagation of the pentacistronic construct into an appropriate expression vector.

FIG. 142. Features of the nucleotide sequence of the P450-FdxR-Fdx-P2A-HSD2-T2A-KshA-P2A-KshB-T2A-$\Delta^1$-KstD pentacistronic construct (the cholesterol catabolizing cassette (the CCC)) in pEntr221. SEQ ID NO: 27

Figure 143:
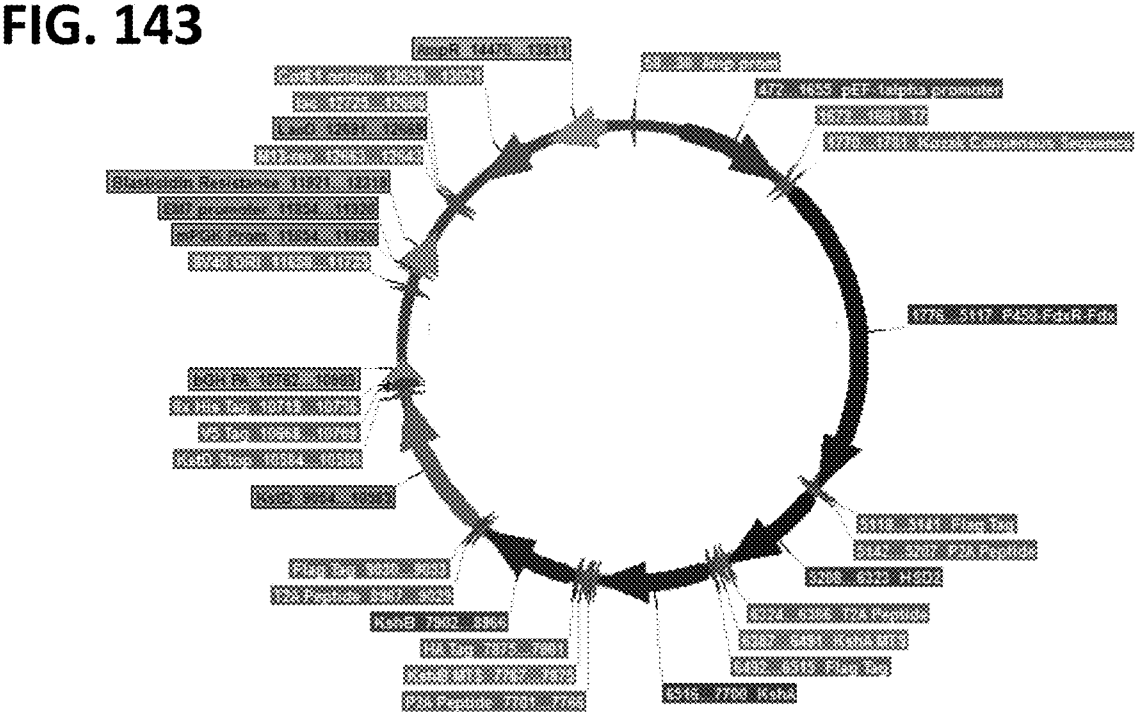

FIG. 143. Map of the P450-FdxR-Fdx-P2A-HSD2-T2A-KshA-P2A-KshB-T2A-$\Delta^1$-KstD pentacistronic construct (the cholesterol catabolizing cassette (the CCC)) in pEF-Dest51. To generate the pEF-Dest51-P450-FdxR-Fdx-P2A-HSD2-T2A-KshA-P2A-KshB-T2A-$\Delta^1$-KstD expression vector, pEntr221-P450-FdxR-Fdx-P2A-HSD2-T2A-KshA-P2A-KshB-T2A-$\Delta^1$-KstD and pEF-Dest51 were recombined using LR Clonase II. The resulting 14,680 nt construct includes the P450-FdxR-Fdx fusion protein (1,776-5,117 nt), HSD2 (5,208-6,323 nt), MTS-KshAB (6,516-8,966 nt), $\Delta^1$-KstD (9,054-10,583 nt), 5' Kozak consensus sequence, P450-FdxR-Fdx Flag tag, KshA Flag tag, KshB HA tag, and $\Delta^1$-KstD Flag tag flanked by attB attachment sites. The pEF-Dest51 expression vector expresses the P450-FdxR-Fdx-P2A-HSD2-T2A-KshA-P2A-KshB-T2A-0'-KstD construct under the control of an EF1$\alpha$ promoter and encodes for blasticidin resistance.

Figure 144:
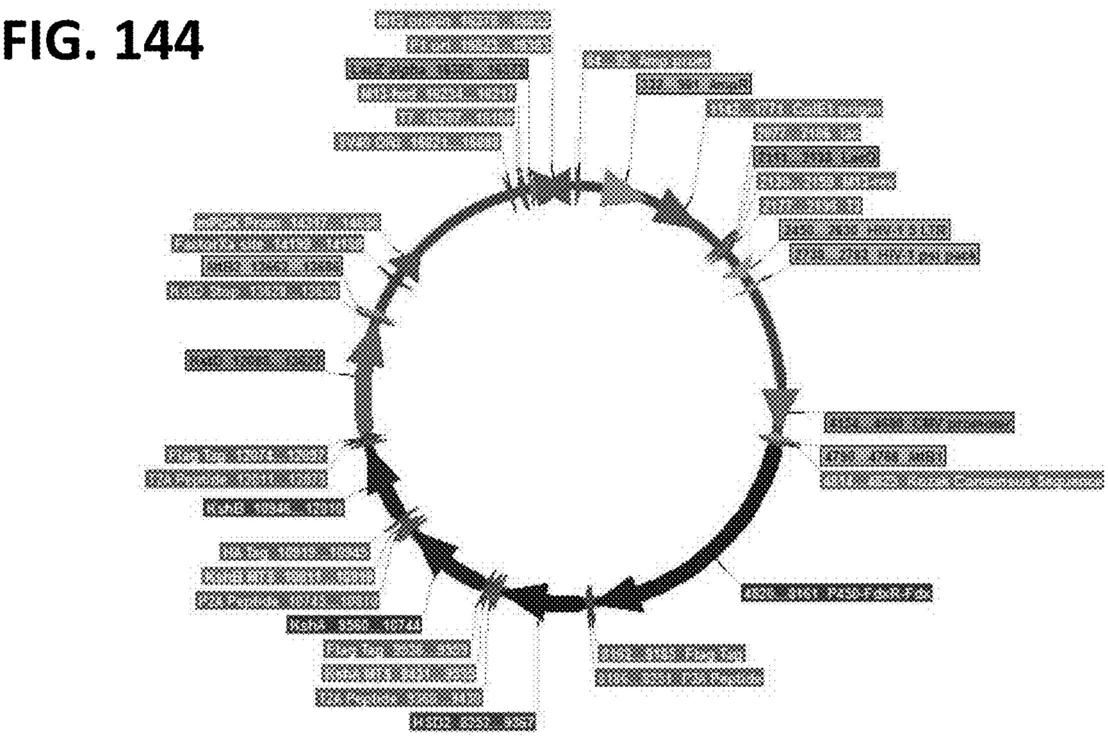

FIG. 144. Map of P450-FdxR-Fdx-P2A-HSD2-T2A-KshA-P2A-KshB-T2A-$\Delta^1$-KstD pentacistronic construct (the cholesterol catabolizing cassette (the CCC)) in pLenti CMV Puro DEST (w118-1). To generate the pLenti CMV Puro DEST (w118-1)—P450-FdxR-Fdx-P2A-HSD2-T2A-KshA-P2A-KshB-T2A-$\Delta^1$-KstD lentiviral expression vector, pEntr221-P450-FdxR-Fdx-P2A-HSD2-T2A-KshA-P2A-KshB-T2A-$\Delta^1$-KstD and pLenti CMV Puro DEST (w118-1) were recombined using LR Clonase II. The resulting 16,833 nt construct includes the P450-FdxR-Fdx fusion protein (4,820-8,161 nt), HSD2 (8,252-9,367 nt), MTS-KshAB (9,560-12,010 nt), $\Delta^1$-KstD (12,098-13,627 nt), 5' Kozak consensus sequence, P450-FdxR-Fdx Flag tag, KshA Flag tag, KshB HA tag, and $\Delta^1$-KstD Flag tag flanked by attB attachment sites. The pLenti CMV Puro DEST (w118-1) expression vector is a third generation lentiviral transfer vector that expresses MTS-KshAB under the control of a CMV promoter and encodes for puromycin resistance.

DETAILED DESCRIPTION

Disclosed herein is the development of a unique, cell-based approach to help manage homozygous familial hypercholesterolemia (FH). FH patients lack functional LDL receptors, which prevents the uptake of low density lipoproteins (LDLs) by the liver and other tissues. As a result, high levels of circulating LDLs are presented to macrophages, which express scavenger receptors (SRs) that take in LDLs. Because humans lack enzymes to degrade cholesterol and SRs are not sterol responsive, the macrophages fill with cholesterol and cholesterol esters (CE) and become foam cells. This process elicits a maladaptive immune response that place FH patients at extreme risk for having a heart attack, which usually occurs within the first two decades of life. At a biochemical level, cholesterol accumulates because human cells do not express enzymes that can open the cholestane ring. Applicants show, herein that engineering human macrophages to express cholesterol ring opening enzymes can enable cholesterol catabolism in human cells. To develop the disclosed systems, methods, and compositions, Applicants developed and characterised six enzymes involved in cholesterol catabolism (cholesterol dehydrogenase (CholD), 3-ketosteroid $\Delta^1$-dehydrogenase ($\Delta^1$-KstD), anoxic cholesterol metabolism B enzyme (acmB), 3-ketosteroid 9$\alpha$-hydroxylase (KshAB), 3$\beta$-hydroxysteroid dehydrogenase 2 (HSD2), and a P450-ferredoxin reductase-ferredoxin fusion protein (P450-FdxR-Fdx)). First, the bacterial enzymes were humanized and expressed in *E. coli*. For this effort, biochemical assays were developed to measure activity and RP-HPLC methods were developed to detect novel catabolites. Confirmation of the predicted intermediates was achieved using Liquid Chromatography-Mass Spectrometry (LC-MS). Next, lentiviral expression constructs were developed to produce stable Hep3B and U-937 cell lines that independently expressed each enzyme. Initially, KshAB was not active in human cells. This obstacle was resolved by directing expression to the mitochondria. Four enzymes were found to be sufficient to initiate cholesterol ring opening in Hep3B and U-937 cells, and both cell lines appear to have endogenous metabolic capability allowing further degradation after the cholestane ring has been opened. Once the minimal number of enzymes required to initiate cholesterol degradation was determined, human U-937 derived macrophages were engineered to express the required four enzymes from a 10 kb pentacistronic expression system that that takes advantage of multiple viral 2A skipping peptides. Macrophages engineered to express this cholesterol catabolizing cassette, or CCC, were found to retain less cholesterol following LDL loading as compared to control macrophages, and may thus have a higher resistance to foam cell formation.

Atherosclerosis is a chronic maladaptive inflammatory response initiated by the retention of cholesterol rich apoprotein-B containing lipoproteins within the arterial wall. Atherosclerosis is an underlying cause of cardiovascular disease (CVD), myocardial infarction, stroke and peripheral vascular disease, which are leading causes of death in the United States. Inherited defects in many different aspects of lipoprotein metabolism (FIG. 3), poor diet, a sedentary lifestyle, and secondary effects of other disorders (notably diabetes, hypothyroidism and kidney disease) all contribute to onset and progression of atherosclerosis.

For the medical management of CVD, physicians currently have many options (statins, niacin, bile acid binding resins, inhibitors of intestinal cholesterol absorption, fibrates, fish oils etc.). Because defects in any one of the many different proteins that control normal lipid metabolism can contribute to the progression of CVD, there is not a single treatment option that is useful for all people.

Figure 3:
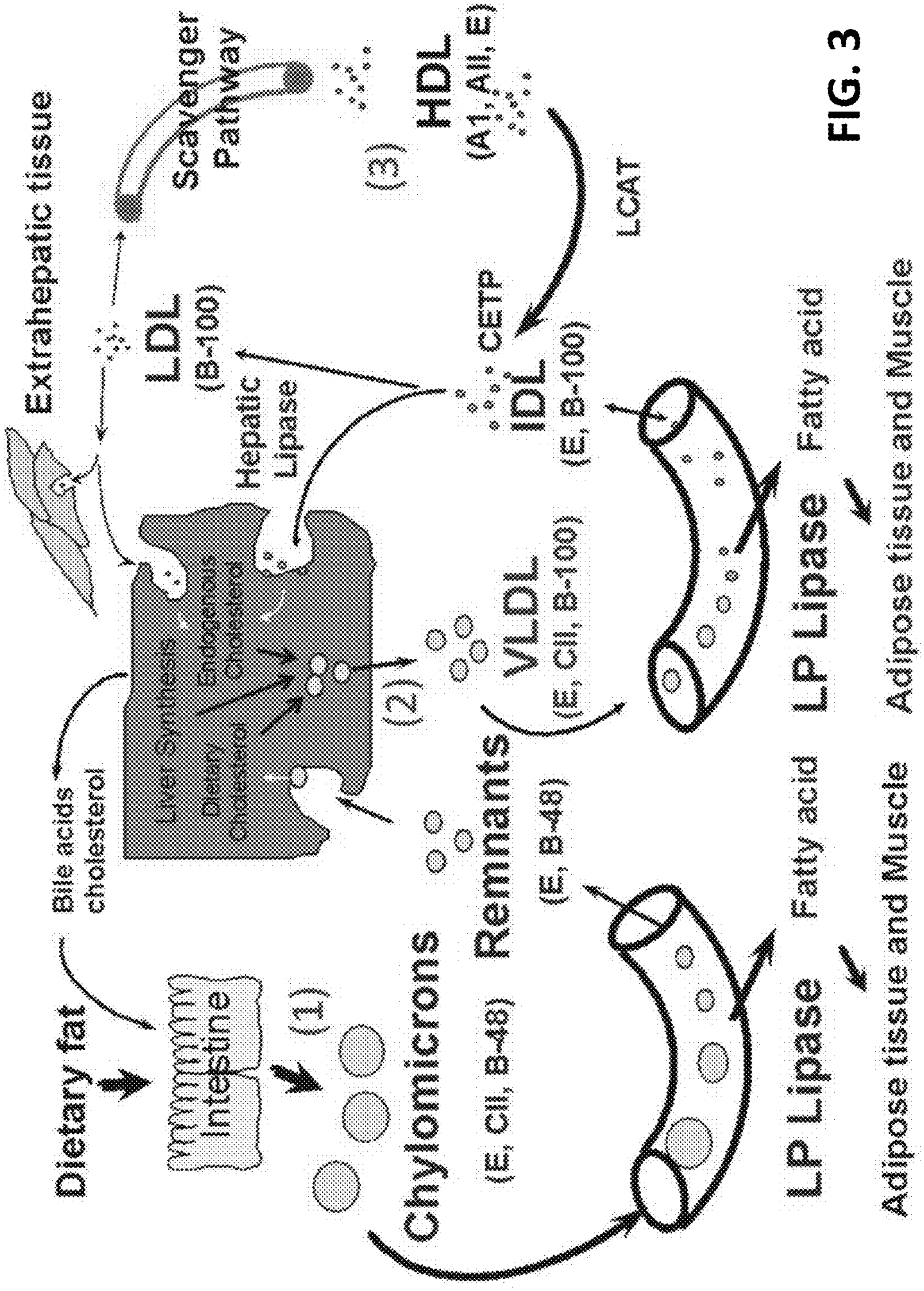
FIG. 3. Summary of lipoprotein metabolism. Lipids obtained from the diet or synthesized by the liver are packaged into and transported by lipoproteins. Dietary fats absorbed by the intestinal epithelial cells are packaged into chylomicrons which deliver fatty acids (released from TGs by lipoprotein lipase) to adipose tissue and muscle. The remnants are removed from the circulation by the liver and the contents are either utilized or repackaged into VLDLs for additional transport. As TGs are removed from VLDLs and IDLs, they become LDLs which are enriched with cholesterol esters. When elevated, LDLs contribute to cardiovascular disease. Thus, current treatment options work to lower serum LDL by targeting metabolic pathways leading to increased expression of LDL receptors that clear LDLS.

Lipid transport systems in mammals move energy rich lipids [i.e. triglycerides (TG), cholesterol, and phospholipids] from the site of intestinal absorption and hepatic synthesis through the vascular space to sites of cellular utilization (FIG. 3). As depicted in FIG. 3 at (1) Dietary fat is incorporated into the core of chylomicrons, which are transported to the liver and taken up by apoB/LDL receptor-mediated endocytosis. In the liver, cholesterol is used to make bile salts. Cholesterol, bile salts and phospholipids are then secreted back into the intestine as bile. FIG. 3 item (2) depicts when the body has a caloric surplus, the liver "repackages" dietary TG and newly synthesized TG (made from excess carbohydrate) into very low-density lipoproteins (VLDLs). Like the chylomicrons, the principle job of VLDLs is to transport TG in the blood. With the aid of lipoprotein lipase, TG in chylomicrons and VLDLs is broken down to fatty acids, which are absorbed by adipose tissue and converted back into TG for storage. Fatty acids are also absorbed by muscle and used to produce energy via beta-oxidation. At (3) is showing reverse cholesterol transport, where HDLs scavenge excess cholesterol, which is converted to cholesterol esters via the actions of lecithin cholesterol acyl-transferase (LCAT). Cholesterol ester transport proteins (CETPs) aid the movement of CEs from HDLs to VLDL remnants (IDLs). Lipoproteins containing ApoE (remnants and HDLs) are rapidly absorbed by the liver. As VLDLs lose their TG, they eventually become cholesterol ester rich LDLs. LDLs contain ApoB100, and can be cleared by LDL-receptor mediated endocytosis, which occurs mainly in the liver. Apoproteins important for the metabolism of the major lipoproteins known to be mutated in people with disease are listed below the particle (e.g. E, B-100). Genetic defects in nearly 50 ancillary proteins involved in lipid metabolism are likely to contribute to the atherosclerotic process.

Currently most medical treatments alter some aspect of normal lipoprotein metabolism to prevent the accumulation of lipoproteins (principally LDLs) in the arterial wall. Inhibitors of HMG-CoA reductase (i.e. statins) lead to an increase in LDL-receptor expression, and a large number of clinical trials indicate that statins reduce events (e.g. heart attacks and strokes) by ~25-35%. While this represents a remarkable achievement, a 35% reduction means 65% of the people with CVD still have events. Stronger statins may be developed, and combination therapy will likely further reduce the number of events. However, complete suppression of cholesterol synthesis is not a therapeutic option because cholesterol is important for normal biology. Humans need cholesterol as a precursor for the production of bile salts, and sterol hormones. In addition, cholesterol is a regulator of membrane fluidity in animals, so its production should not be eliminated entirely.

Figure 1:
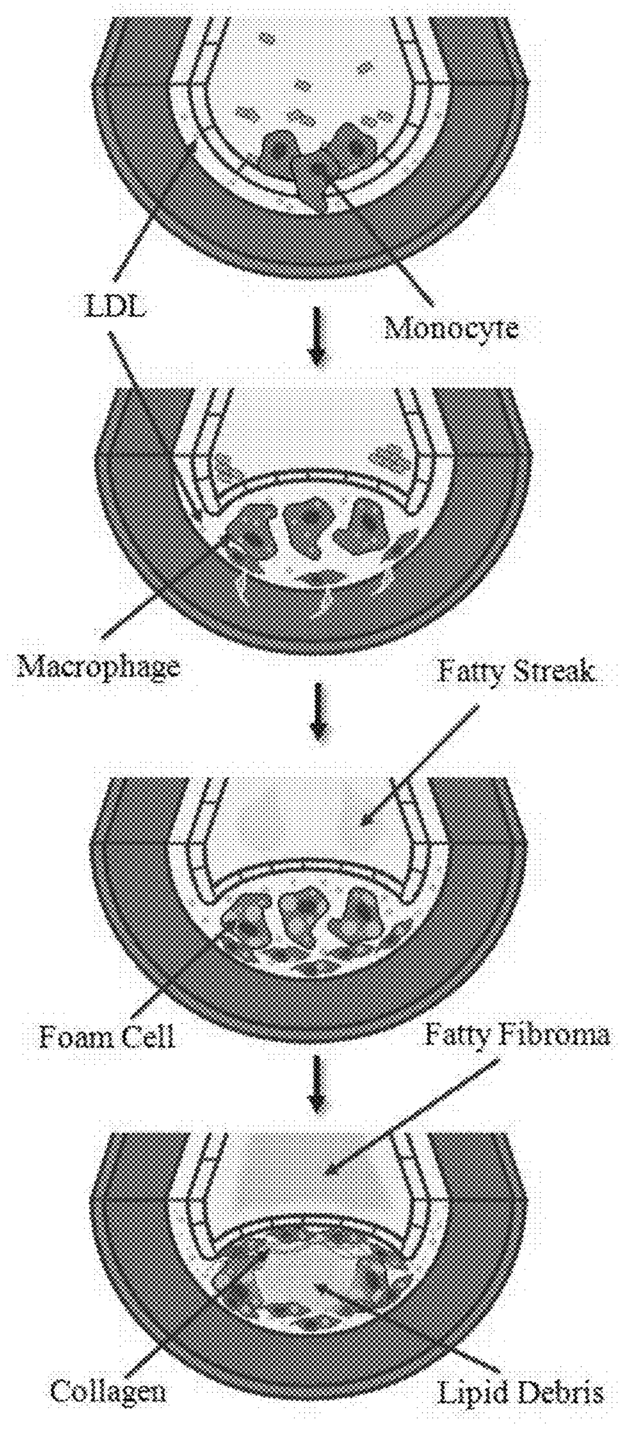
FIG. 1. Development of an atherosclerotic plaque. Upon endothelial dysfunction or damage, atherosclerotic lesions begin to develop. Interruption of the endothelial barrier allows for the infiltration and accumulation of LDLs in the intima, initiating an immune response for the recruitment of monocytes. Upon entering the subendothelialspace, monocytes differentiate into macrophages, which engulf the cholesterol/cholesterol ester (CE)-rich lipoproteins via LDL- and scavenger receptor mediated endocytosis. LDL-cholesterol accumulation in macrophages that infiltrate the intima initiates a chronic inflammatory response, resulting in the recruitment of more macrophages. With time the macrophages become engorged with CE and transform into foam cells. This maladaptive immune response leads to the accumulation of foams cells within the intima resulting in the formation of cholesterol plaques.

FIG. 1 depicts the development of CVD. In the early stages of atherosclerosis, apoB containing lipoproteins (principally LDLs) are retained in the sub-endothelial extracellular matrix of the arterial wall ($1^{st}$ diagram). Accumulation of LDLs in the intima initiates a maladaptive inflammatory response, marked by monocyte sub-endothelial infiltration and differentiation into macrophages that ingest the lipoproteins. As the macrophages "fill up" with lipids, they become foam cells ($2^{nd}$-$3^{rd}$ diagram). In advanced stages of CVD, plaques fill with inflammatory cells and lipids from dead and dying macrophages. The continual presence of dyslipidemia induces smooth muscle cells (SMC) to migrate into the intima to form a fibrous cap in an attempt to "wall off" the site of inflammation ($4^{th}$ diagram). Connective tissue is laid down, followed by calcification (hardening of the arteries). The fibrous cap can erode and eventually rupture, inducing acute thrombotic vascular events, commonly myocardial infarctions and strokes.

At a basic level, CVD is a disease of the intima. Atherogenesis starts with endothelial damage or dysfunction in the arteries, which allows the accumulation of apoB-containing lipoproteins in the intima. The half-life of LDLs in the blood is increased when the amount of circulating apoB-containing lipoproteins (principally LDLs) exceeds the rate of hepatic clearance. This aids LDL accumulation in the sub-endothelial space of arterial walls. To clear the intima of lipoproteins and lipoprotein-debris, monocytes enter the sub-endothelial space via a complex process (diapedesis) and differentiate into mononuclear phagocytes (macrophages). Macrophages ingest the cholesterol/CE-rich lipoproteins via many processes, including LDL-receptor (LDL-R) and scavenger-receptor (SR)-mediated endocytosis. As more lipoproteins enter the intima, the macrophages continue to ingest them. As a result, intracellular cholesterol starts to accumulate. To protect the cell from the membrane disruptive affects produced by excess cholesterol, acyl-CoA acyltransferase (ACAT1) is activated. ACAT1 converts cholesterol into cholesterol esters (CEs), which accumulate as less toxic cytoplasmic inclusions. Excess cholesterol also increases the expression of ATP-binding cassette-transport proteins (i.e. ABCA1 and ABCG1), allowing cholesterol efflux to apoA1 and existing HDLs. This increases reverse cholesterol transport to the liver. Intracellular cholesterol also inhibits LDL-R expression and triggers the degradation of existing LDL-Rs, preventing further uptake. However, LDL-uptake also occurs via SR-mediated mechanisms (e.g. SR-A1, SR-B1 and CD36), which continues because the SR-pathways in macrophages are not suppressed by an excess of sterols. Therefore, macrophages continue to ingest LDLs that enter the sub-endothelial space. Unless HDL levels are high, uptake is more efficient than efflux. With time the macrophages become engorged with CEs, which accumulate in intracellular droplets producing a "foamy" appearance when examined microscopically, hence the name foam cells. During this process a complex response is triggered, which elicits the "maladaptive inflammatory response" that ultimately leads to CVD. Therefore, at a fundamental level, the inability of macrophages to degrade cholesterol appears to initiate disease. Applicants hypothesized that if cholesterol could be degraded by macrophages, like fatty acids and phospholipids, they would not fill up with CEs and elicit the maladaptive immune response. Thus, by enabling cholesterol catabolism the disclosed methods and compositions may ameliorate this fundamental aspect of disease. Because CVD is the leading cause of human death, a novel method to prevent or reduce the size of existing plaques may have a huge impact on society.

The present disclosure is based on an unexpected observation. Tuberculosis (TB) is an infection caused by *Mycobacterium tuberculosis*. During the chronic stage of infection, *M. tuberculosis* resides intracellularly in macrophages, which allows the bacteria to avoid many host immune responses. When unable to eradicate infection, the host immune system encases the infected macrophages into dense granulomas structures. This restricts the growth of intracellular pathogens, in part, by depriving them of essential nutrients. How mycobacteria survive in phagosomes for extended periods of time was a key unanswered question in the field, until a surprising observation revealed *M. tuberculosis* can utilize host cholesterol as a source for carbon and energy. When sequestered into phagosomes, *M. tuberculosis* activate operons encoding many genes, some of which encode proteins that enable cholesterol catabolism. Further investigations into the molecular mechanisms of *M. tuberculosis* survival on host cholesterol identified two key enzymes [KstD and KshA/B] which catalyze reactions needed to open the cholestane ring. Mammals do not have orthologues for either enzyme. However, both were active when expressed in *E. coli.*

Figure 2A:
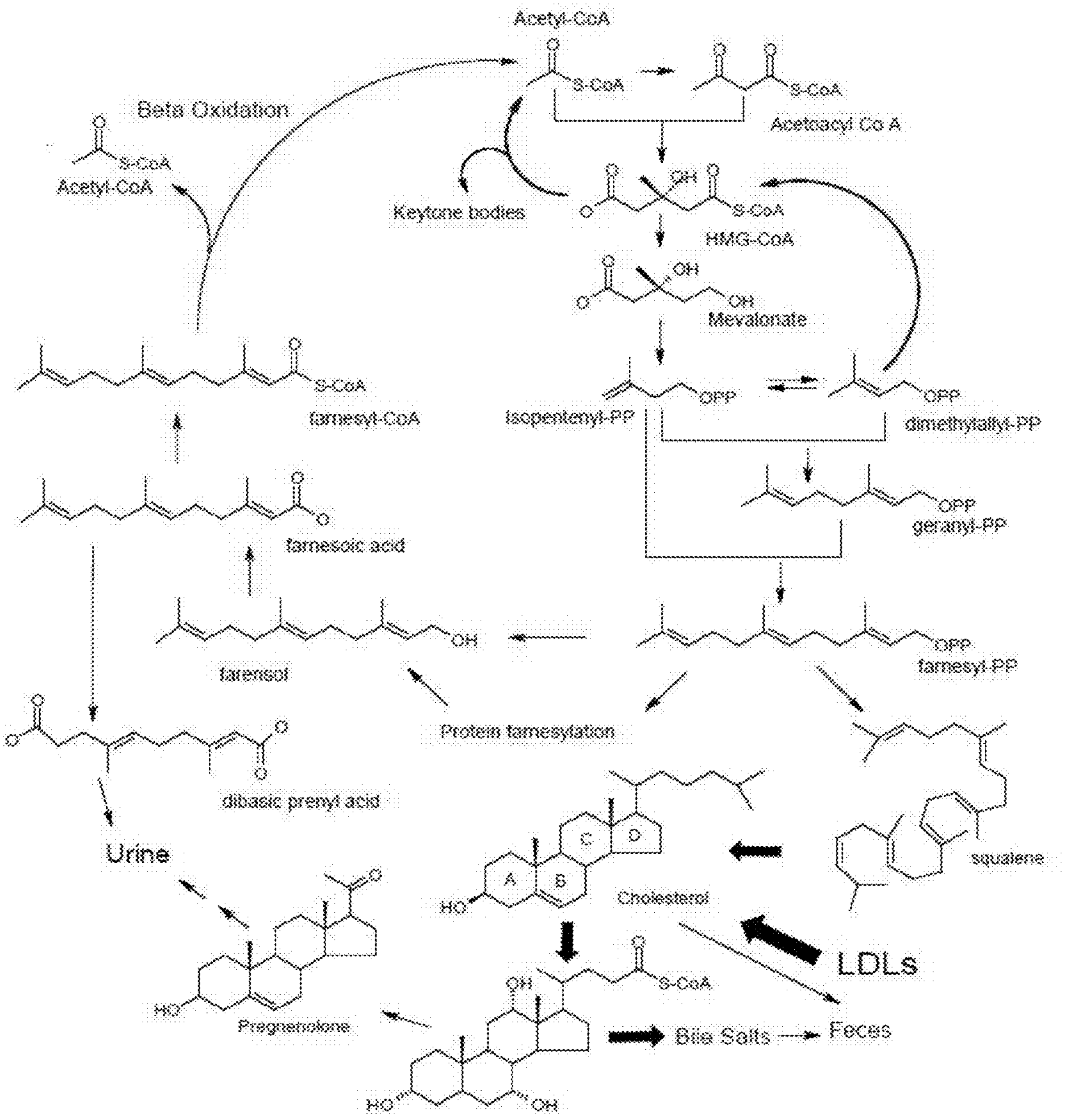
FIG. 2A. Simplified summary of human cholesterol synthesis and metabolism. All carbons of cholesterol are derived from acetyl-CoA. To synthesize cholesterol, acetyl-CoA is converted to a five carbon intermediate known as an isoprene unit. Six isoprene units are condensed to form squalene, the 30 carbon linear precursor of cholesterol. Squalene is cyclized by squalene synthase to produce lanosterol, forming the tetracyclic steroid skeleton (cholestane ring). Following an additional nineteen enzymatic steps, lanosterol is converted to cholesterol. Cholesterol is used in the production of bile salts and steroid hormones. However, one key feature of cholesterol metabolism is that once squalene is cyclized and the cholestane ring is formed, the ring cannot be opened enzymaticallyin human cells.
Figure 2B:
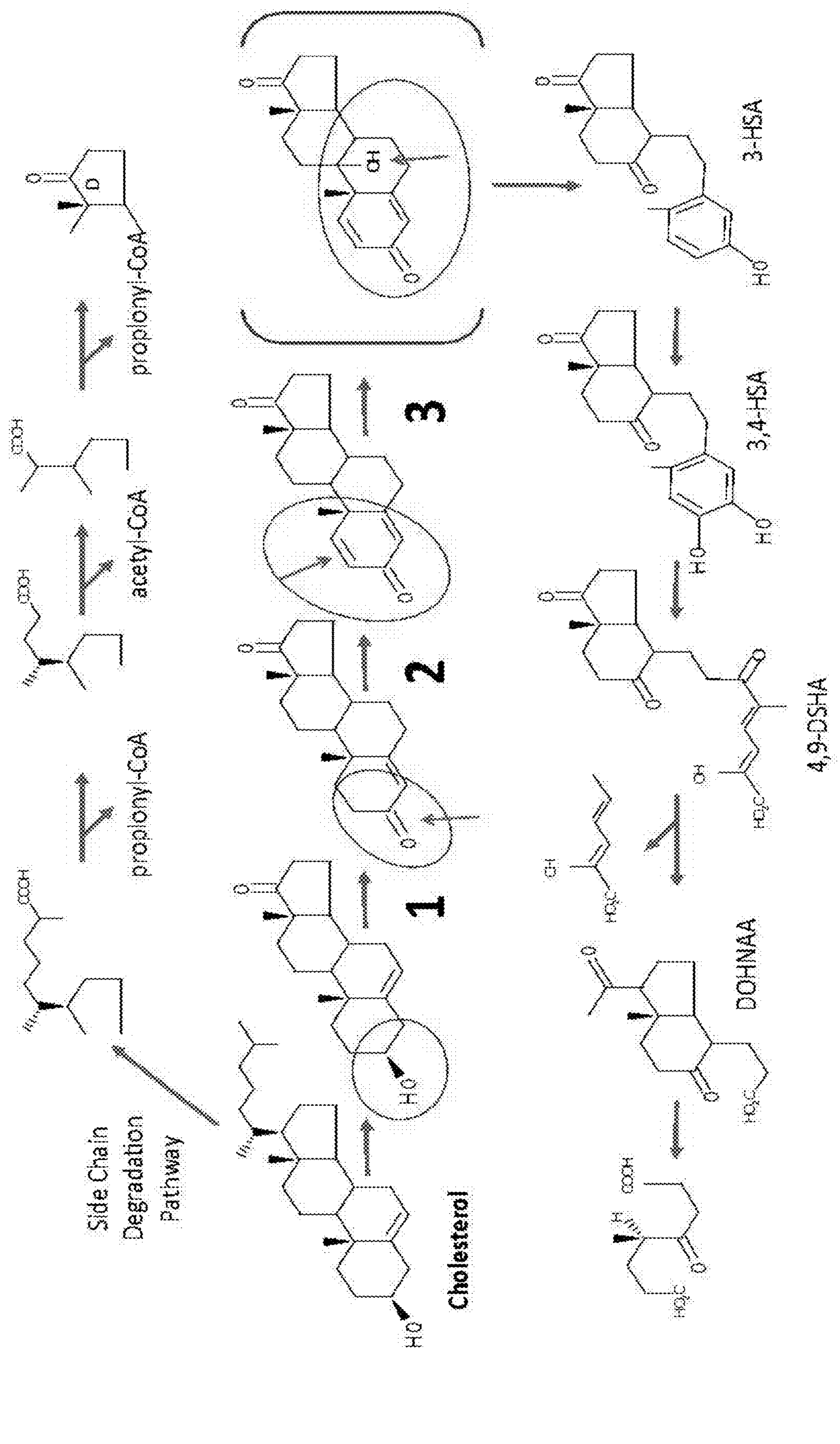
FIG. 2B. Cholesterol catabolism in *Mycobacteria*. The aliphatic side chain (C17) is removed in a process similar to beta-oxidation (side chain degradation pathway), and ring-opening is mediated by the four-ring degradation pathway. In ring degradation, ADD, 4-androstenedione is acted upon by two enzymes, 3-ketosteroid-Δ1-dehydrogenase (KstD) and 3-ketosteroid-9α-hydroxylase (KshA/B), which catalyze B-ring opening and aromatization of ring A to produce 3-HSA (3-hydroxy-9,10-seconandrost-1,3,5(10)-triene-9,17-dione). Brackets designate an intermediate compound that degrades spontaneously. This Example was adapted from Vander Geize et al.

Identification of key cholesterol catabolizing enzymes. The enzymes involved in bacterial cholesterol catabolism have been identified and characterized. Catabolism occurs via two independent pathways; the C17 chain degradation pathway, and the four-ring carbon skeleton degradation pathway (FIG. 2B). In humans cholesterol catabolism is limited. As discussed above ACATs convert cholesterol into cholesterol esters, which are readily converted back to cholesterol and fatty acids by CE-esterases. In steroidogenic cells the C-17 side chain is degraded by cytochrome p450s (e.g. CYP11A1). During both steroid hormone and bile salt synthesis the cholestane ring can be modified in many ways by a variety of p450s, hydroxylases, reductases and dehydrogenases. Studies with squalene synthase inhibitors have also revealed a number of previously unrecognized pathways that are capable of degrading the majority of the synthetic intermediates produced during cholesterol synthesis and metabolism. Still, after the ring is closed, humans do not have enzymes capable of opening the cholestane ring.

Humanization, Expression and Characterization of Cholesterol Dehydrogenase (CD) KstD and KshA/B.

Comparison of cholesterol metabolic and catabolic pathways revealed three bacterial enzymes that have no orthologues in animals: 1) cholesterol dehydrogenase (CD); 2) 3-ketosteroid-Δ1-dehydrogenase (KstD), and 3) 3-ketosteroid-9α-hydroxylase (KshA/B)]. The reactions catalyzed by these enzymes are shown in FIG. 3 (indicated as 1, 2 and 3, respectively). Together they catalyze B-ring opening and aromatization of ring A to produce 3-hydroxy-9,10-seconandrost-1,3,5(10)-triene-9,17-dione (3-HSA).

To test the disclosed hypothesis, CD, KstD, and KshA/B were humanized. Humanized enzymes were designed in silico, produced synthetically as ~200 to 2500 base pair "strings" and assembled using Gibson Assembly. Humanization included: 1) codon optimization, 2) G/C content adaptation, 3) adding components needed for eukaryotic expression (e.g. Kozak consensus sequence, etc.) 4) elimination of cryptic splice sites and RNA destabilizing sequence elements for increased RNA stability, and 5) avoidance of sequences that would yield stable RNA secondary structures. Other modifications were introduced to facilitate cloning, expression and detection. Following Gibson assembly, the constructs were subcloned into traditional expression vectors (e.g. pDest51(EF1alpha); plenti-CMV-Blast, etc.) using Gateway mediated recombination and conventional methods. For initial studies, the constructs were cloned into expression vectors driven by conventional prokaryotic or eukaryotic promoters. All constructs were sequenced in their entirety to ensure fidelity.

Expression of the disclosed humanized sequences may be through one or more control sequences. In various embodiments, the control sequences may be selected from transcriptional enhancers, promoters, and the like that allow for binding of an RNA polymerase. In most embodiments, the enhancer, promoter, or combinations thereof are eukaryotic promoters and enhancers and the polymerase is a Pol II polymerase. In most embodiments, the eukaryotic promoter or enhancer is a promoter or enhancer from a virus, plant, animal, mammal, mouse, human, fungus, yeast, or insect. In some embodiments the promoter or enhancer is selected from one or more of CMV, SV40, EF1a, PGK, Ubc, and other promoters and enhancers known to those of skill in the art.

Humanized prokaryotic nucleotide sequences of the present disclosure may be greater than about 60% identical, over at least about 200 nucleotides, to the prokaryotic sequence. In many embodiments, the disclosed humanized protein sequence may be greater than about 80% identical, over at least about 30 amino acids, to the prokaryotic amino acid sequence. In many embodiments, these humanized sequences may be greater than 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, and less than about 100%, 99%, 98%, 97%, 96%, 95%, 94%, 93%, 92%, 91%, 90%, 89%, 88%, 87%, 86%, 85%, 80%, 75%, 70%, or 65% identical to the prokaryotic sequences. In many embodiments the length of identity may be more than 30, 40, 50, 60, 70, 80, 90, 100, 120, 140, 160, 180, 200, 300, 400, 500, 600, 700, 800, 900, or 1000 amino acids or nucleotides, and less than about 1200, 1000, 900, 800, 700, 600, 500, 400, 300, 200, 180, 160, 140, 120, 100, 90, 80, 70, 60, 50, or 40 amino acids or nucleotides.

Characterization of Humanized Enzymes Expressed in E. Coll.

When expressed in *E. coli*, hCD was active. However, hKstD designed based on *Mycobacterial* KstD showed almost no activity against cholestenone (the product produced by CD). This obstacle was resolved by the identification, humanization and expression of another 3-ketosteroid-Δ1-dehydrogenase identified in *Streptomyces denitrificans* (ACMB), which can utilize cholestenone as a substrate. The expression of hKstD and hKshA/B in *E. coli* produced active enzyme.

Expression of the cholesterol catabolizing enzymes in human cells. Next activity was tested when the enzymes were expressed in human Hep3B cells. hCD was active, but the activity of both hKstD and hACMB was minimal. hKshA/B was completely inactive, and without further catabolism, the build-up of cholestenone (produced by hCD alone) killed the cells. To overcome these obstacles, focus was placed on understanding why the recombinant humanized enzymes were active when expressed in bacteria but inactive when expressed in human cells. The first insight came from the co-crystal structure of bacterial KstD in complex with ADD (FIG. 2D).

Figure 2E:
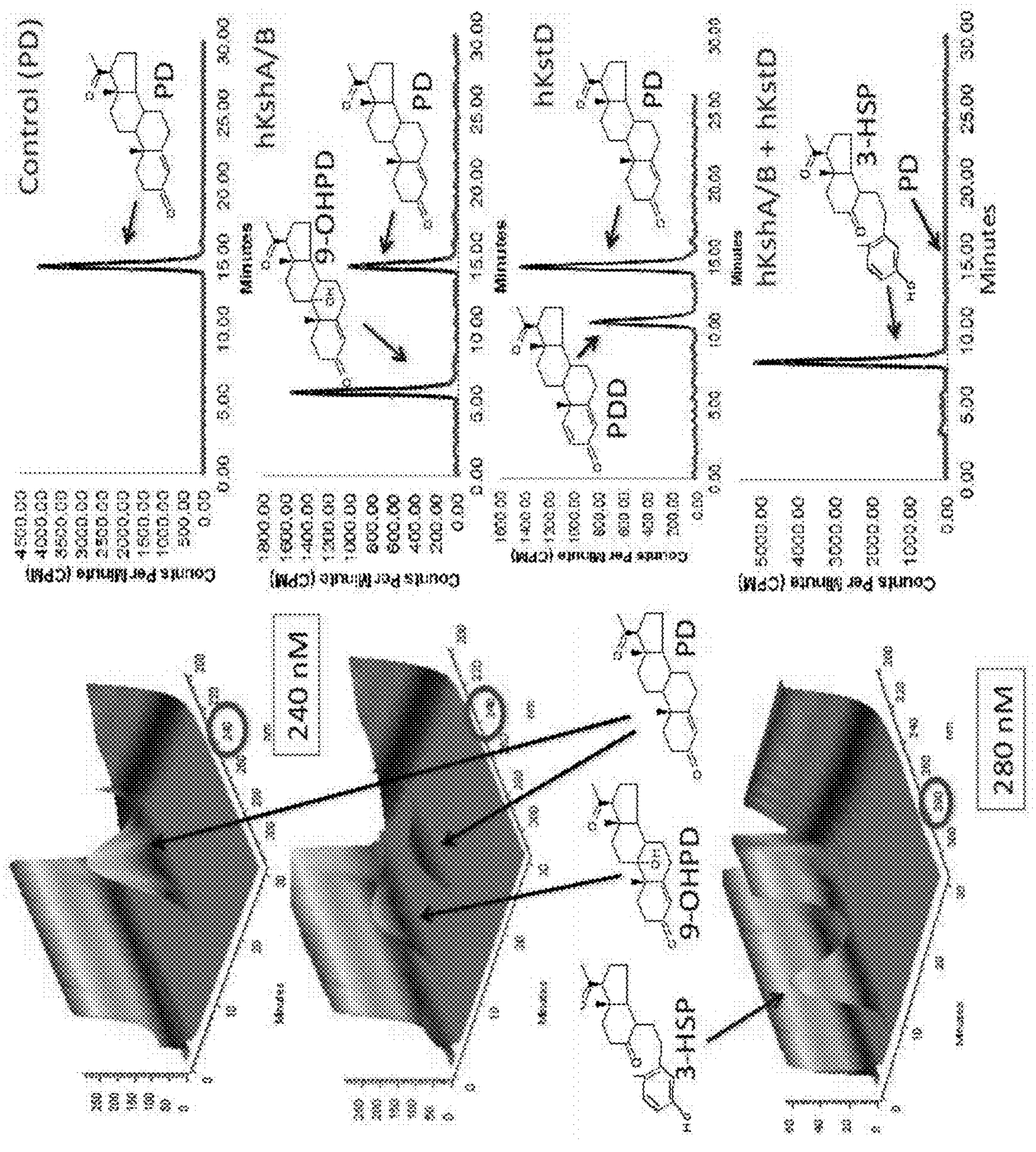
FIG. 2E Shows how the combined actions of hKstD and hKshA/B open the cholestane ring. HPLC profiles documenting the conversion of [$^{14}$C]-labeled PD to 9-OHPD, PDD, and 3-HSP by the actions of hKshA/B, hKstD, or a mixture of hKshA/B and hKstD, respectively. 10 μM PD spiked with 100 nCi [$^{14}$C]-PD was mixed with the partially purified enzymes indicated. After 24 hours the samples were extracted and analyzed by RP-HPLC above. A second spectral shift is produced with B-ring opening and aromatization of ring A (i.e. conversion of PDD or 9-OHPD to 3-HSP). PD, 9-OHPD, and PDD all have and an absorbance maximum of ~245 nM; 3-HSP absorbance maximum is 280 nm; lower left corner). This data is clean and robust, because control *E. coli* extracts do not readily catabolize or metabolize any of the compounds that retain the cholestane ring. MS data revealed an identical mass match for 3-HSP.
Figure 2F:
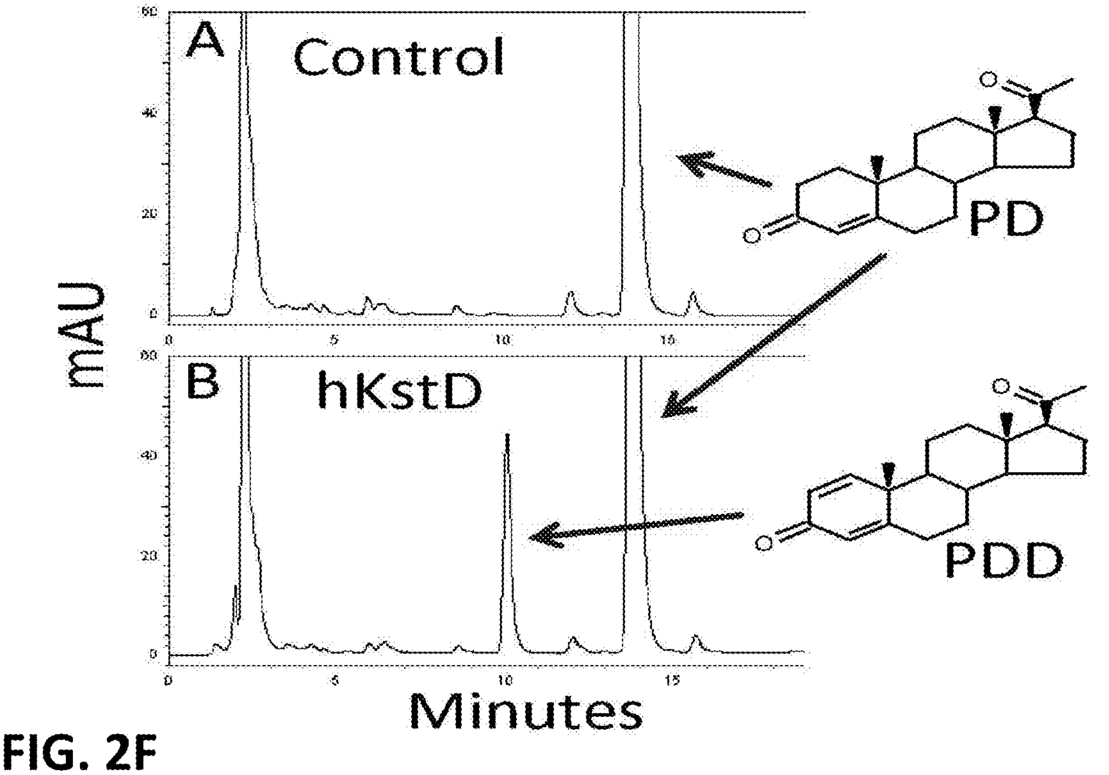
FIG. 2F is a representative HPLC elution profile showing PD is only converted to PDD by Hep3B cells that have been transfected with hKstD (Panel B).
Figure 2G:
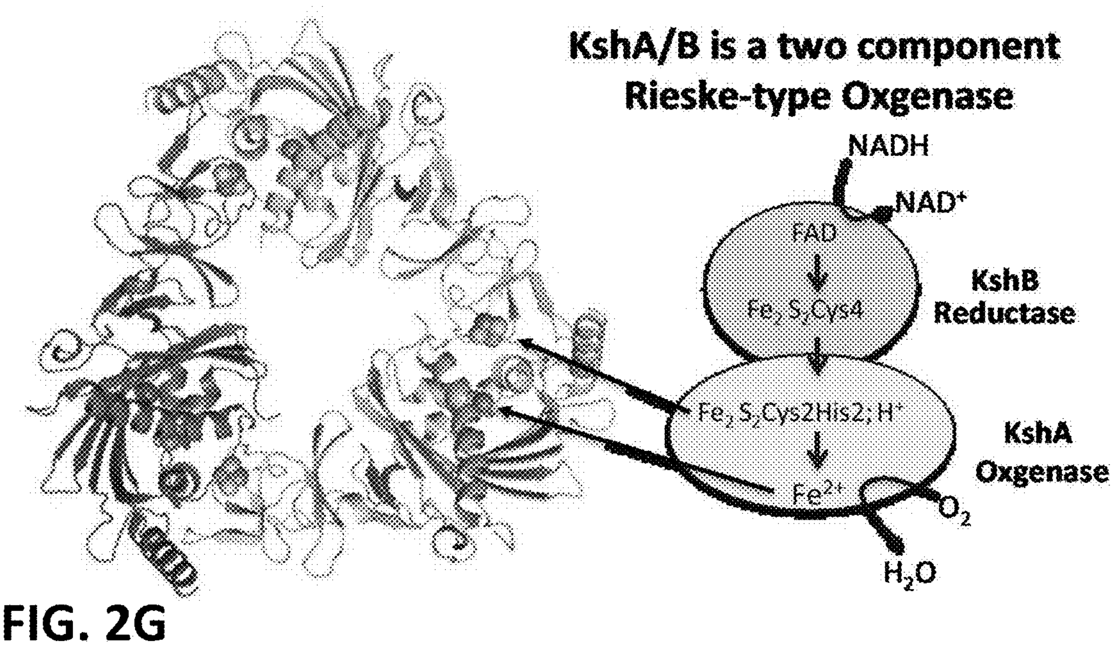
FIG. 2G shows that KshA/B (3-ketosteroid-9α-hydroxylase) is a two component oxgenase that utilizes molecular oxygen and NADH as a cofactor. The crystal structure shows that three KshA-subunits are assembled "head to tail" with electrons transferred for the iron sulfur complex in the "head" of one protein to the $Fe2_{+}$ contained in the "tail" of another. Image derived from PDB ID 2ZYL.

The structures revealed that the catalytic site of KstD is a deep pocket, with two isoleucine residues at the entrance that produce a steric clash if the C-17 side chain of cholesterol has not been removed. Although there are ongoing discussions in the literature about the need to remove the side chain prior to ring opening, the co-crystal structures provide robust evidence that the side chain is removed before hKstD can act upon the ring. Although the bacterial side chain degradation pathway produces ADD (ketone at C-17; FIG. 2B), the model predicted that 4-pregn-4-ene-3,20 dione [PD; has 2 additional side-chain carbons] could still fit in the active site. When tested experimentally, PD was efficiently catabolized by the recombinant humanized enzymes (FIG. 2E).

When hKstD was expressed in human cells (Hep3B) it was active against PD.

Expression of Active hKshA/B in Human Cells.

The next challenge was to determine why KshA/B was not functional. KshA/B is comprised of Rieske type non-heme monooxygenase comprised of an oxygenase (KshA) and a reductase KshB. Fortuitously, the crystal structure a *Rhodococcus* ortholog was solved by Capyk, J K et al.

Based in the crystal structure it became clear that KshA/B was likely a six polypeptide multi-protein complex. Therefore, to allow the complex to properly assemble it was critical to develop an expression system that would ensure an equal number of both subunits would be produced simultaneously and in close proximity.

Figure 2H:
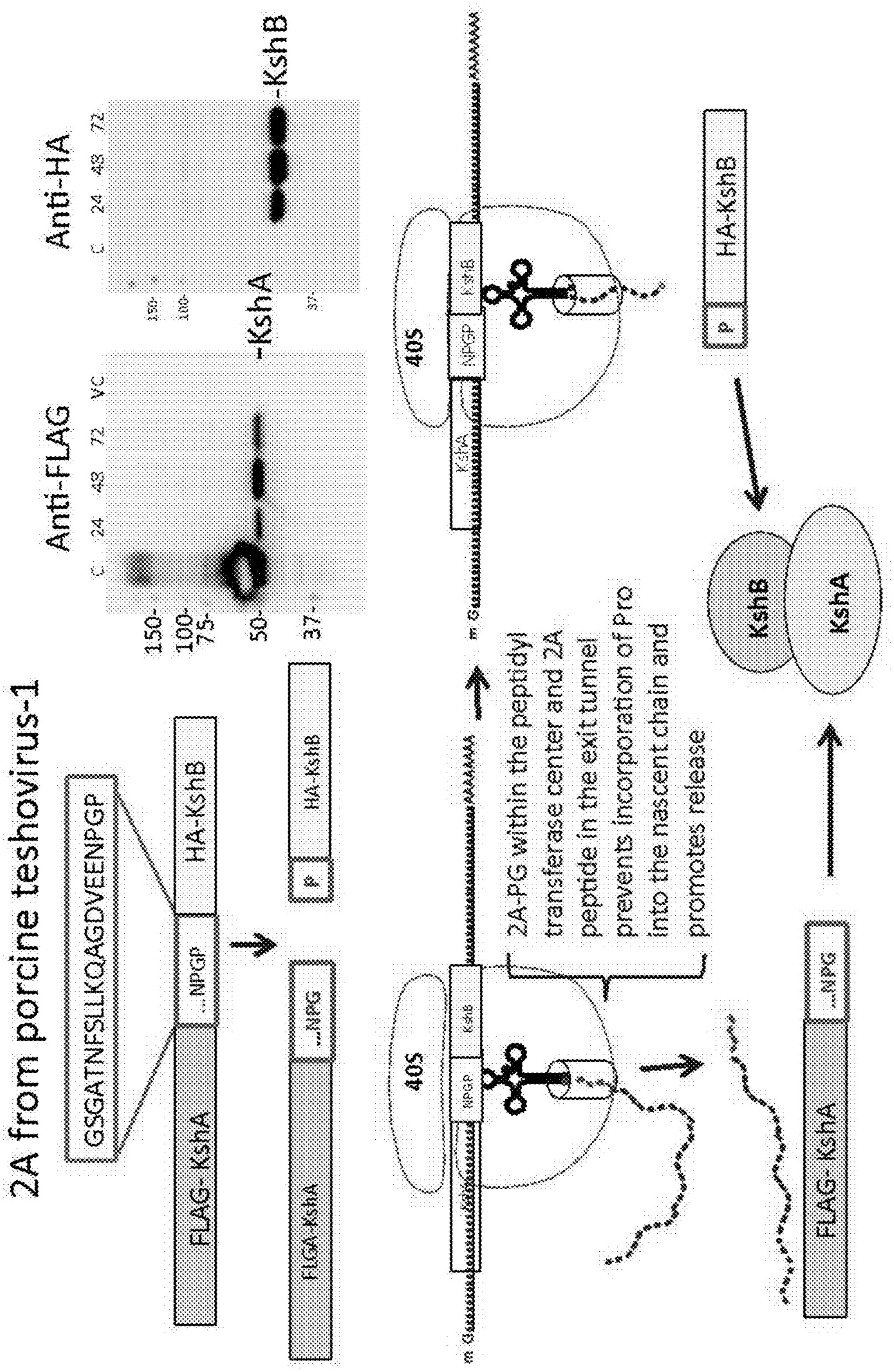
FIG. 2H is a diagram of the "2A-peptide" bicistronic expression. An expression construct was produced in which hKshA and hKshB are encoded to produce a single in-frame mRNA with the 2A peptide from porcine teshovirus-1 separating hKshA from hKshB. To help determine the efficiency of 2A-mediated release, FLAG and HA recognition sequences were added to hKshA and KshB, as illustrated. Human Hep3B cells were transfected with the construct, and levels of hKshA and hKshB were detected by western analysis using the anti-FLAG and anti-HA antibodies at 24, 48 and 72 hours after transfection. Lane C represents lysates from Hep3B transfected with PP5-FLAG as a control for detection by anti-FLAG antibody. The levels of KshA and KshB are similar. If read through of the 2A peptide had occurred, a band of ~90 kD should have been detected by both anti-FLAG and anti-HA antibodies. Based on the lack of a 90 kD band the release of the KshA appears to be extremely efficient.

Nature again provided insights needed for the expression of the active hKshA/B complex in human cells. To express equal amounts of hKshA and hKshB an expression vector was constructed with both genes in frame and separated by porcine teschovirus 2A peptide (FIG. 2H). The porcine teschovirus-1 has a single-stranded non-segmented RNA genome. It was initially believed that translation of the viral RNA produced a single polyprotein that was later proteolytically cleaved into 12 proteins. However, more recent studies revealed that the "2A" peptide expressed between proteins is not produced as a protease recognition spacer. Rather the 2A peptide has a unique action in the ribosome. 2A ends with 3 key amino acids (PGP). During translation, after the prolyl-tRNA is positioned within the peptidyltransferase center with the remainder of the 2A peptide in the exit tunnel, conformational restraints prevent the incorporation of the last proline into the nacent chain and promotes release of the growing polypeptide. Since the tRNA-(Pro) is already positioned within the ribosome before the growing polypeptide is released, translation of the next open reading frame proceeds with very high efficiency (FIG. 2H).

Figure 2I:
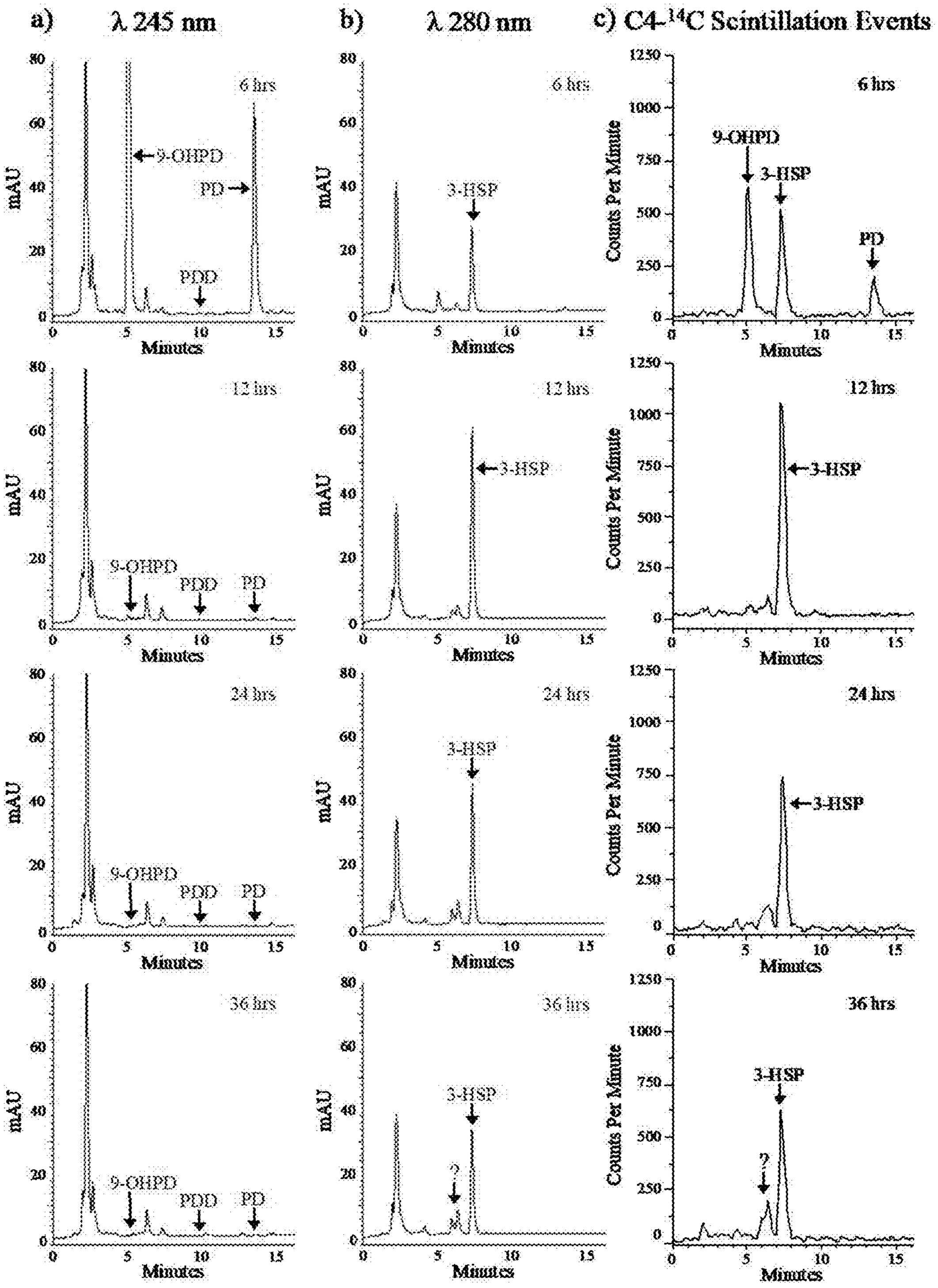
FIG. 2I shows RP-HPLC analysis of 3-hydroxy-9,10-secopregn-1,3,5(10)-triene-9,20-dione (3-HSP) product formation from progesterone (PD) by Hep3B cells transiently expressing MTS-KshAB and $\Delta^1$-KstD. Representative 2-D chromatograms at (Panel a) I 245 nm, (Panel b)(Panel b) I 280 nm, and (Panel c)(Panel c) C4-$^{14}$C scintillation events from Hep3B cells transiently expressing EF1α driven MTS-KshAB and $\Delta^1$-KstD. Cells were incubated with 15.7 mg (10 mM) progesterone spiked with 100nCi C4-$^{14}$C labeled PD ($t_r$=13.8 min) and time points taken at 6, 12, 24, and 36 hours. Analysis at (Panel a) I 245 nm reveals a large proportion of the PD substrate being converted to 9-hydroxypregn-4-ene-3,20,dione (9-OHPD, $t_r$=5.2 min) by 6 hours. Although pregn-1,4-diene-3,20-dione (PDD; $t_r$=10.0 min) is not observed at the 6 hour time point, analysis of (Panel b)(Panel b) I 280 nm and (Panel c)(Panel c) C4-$^{14}$C scintillation events reveals the formation of 3-HSP ($t_r$=7.2 min, $I_{max}$ 280 nm). By 12 hours, the PD substrate and 9-OHPD product are exhausted resulting in maximal production of 3-HSP. Interestingly, both the area and counts under the curve of 3-HSP decreases at further time points, suggesting that Hep3B cells have ability to further modify the pregnane ring once opened. Evidence of this can be observed at 24 and 36 hour time points as new C4-$^{14}$C scintillation events appear between 6.0-6.5 minutes.
Figure 2J:
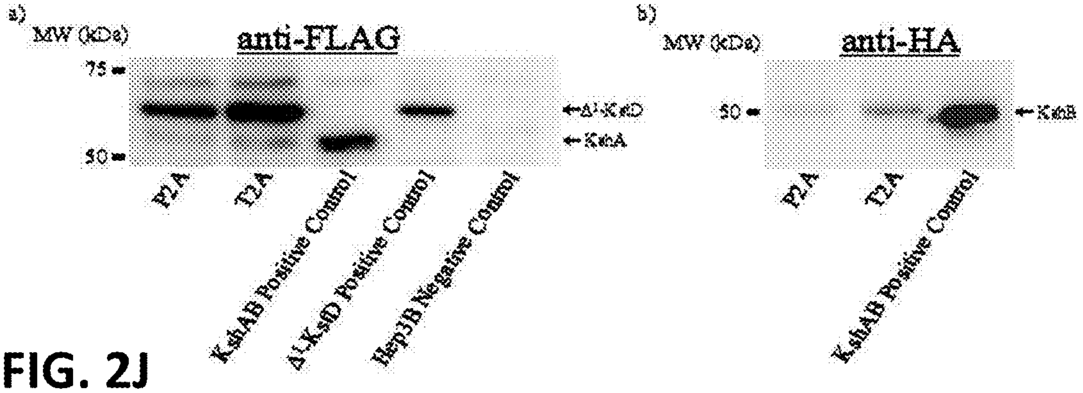
FIG. 2J is a western blot analysis of Hep3B cells expressing EF1α driven MTS-KshAB-P2A-$\Delta^1$-KstD or MTS- KshAB-T2A-$\Delta^1$-KstD constructs. Hep3B cells were transiently transfected with pDest51-KshAB-P2A-$\Delta^1$-KstD or pDest51-KshAB-T2A-$\Delta^1$-KstD plasmids in 60 mm dishes and protein expression was assessed following 48 hours incubation. Cells were collected by scraping in 500 mL RIPA buffer and mechanically lysed on ice using a syringe with a 27 gauge needle. Protein samples were mixed with an equal volume of 2× Laemmli sample buffer, boiled for 5 min, and spun at 15,000×g for 10 min at 4° C. Protein samples (25 mg) were separated using SDS-PAGE on a 10% polyacrylamide gel, transferred to PVDF membranes, and probed with anti-FLAG (1:1000) or anti-HA (1:3000). ECL anti-mouse IgG secondary antibody conjugated to HRP (1:10,000) and SuperSignal West Femto Substrate was used for detection. Samples include the P2A construct, T2A construct, Hep3B CMV-MTS KshAB cell line (positive KshA FLAG and KshB HA control), Hep3B CMV-$\Delta^1$-KstD cell line (positive $\Delta^1$-KstD FLAG control), and non-transduced Hep3B cells (negative control).
Figure 2K:
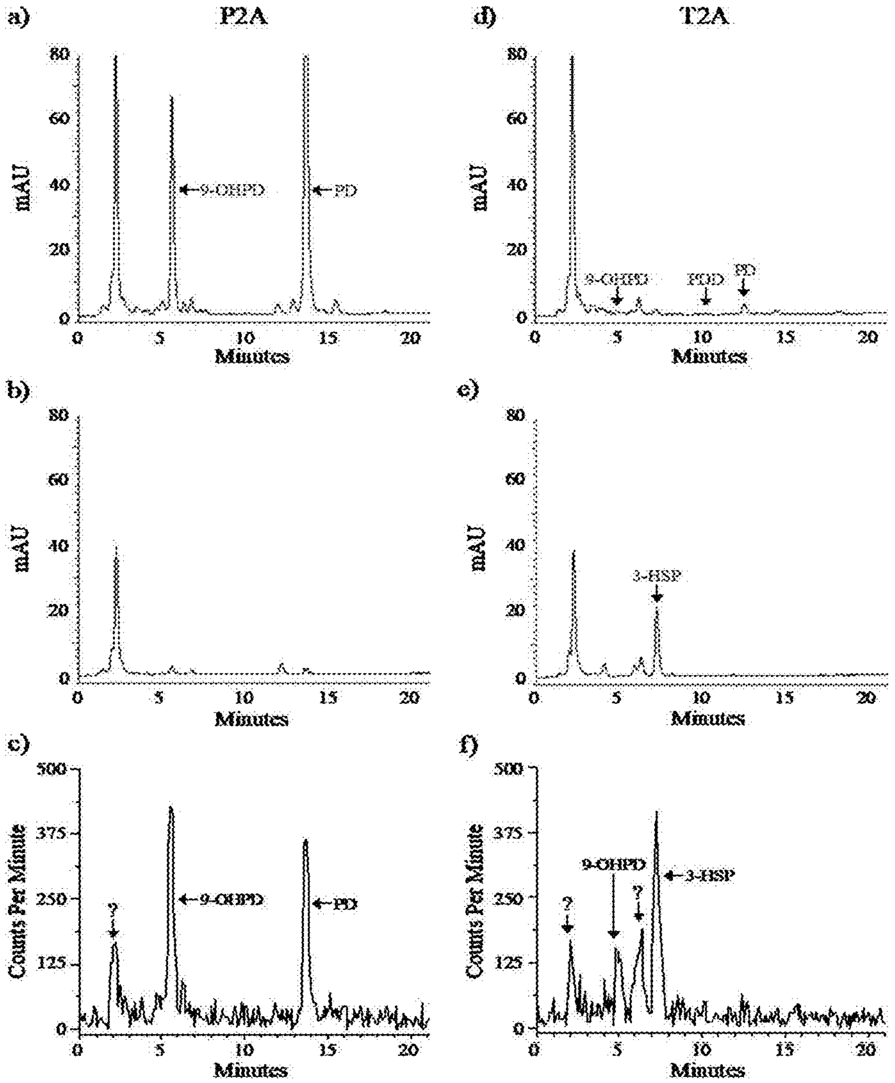
FIG. 2K shows an RP-HPLC analysis of 3-hydroxy-9,10-secopregn-1,3,5(10)-triene-9,20-dione (3-HSP) product formation from progesterone (PD) catabolism by Hep3B cells expressing EF1α driven KshAB P2A $\Delta^1$-KstD or KshAB T2A $\Delta^1$-KstD constructs. Hep3B cells were transiently transfected with pDest51-KshAB P2A $\Delta^1$-KstD or pDest51-KshAB T2A $\Delta^1$-KstD plasmids in 60 mm dishes. Following 48 hours of protein expression, cells were incubated with 15.7 mg (10 mM) PD spiked with 100nCi C4-$^{14}$C labeled PD ($t_r$=13.8 min) for 48 hours. Representative 2-D chromatograms at (Panels a & d) I 245 nm, (Panels b & e) I 280 nm, and (Panels c & f) C4-$^{14}$C scintillation events demonstrate the efficiency of the P2A and T2A constructs in producing 3-HSP ($t_r$=7.2 min, $I_{max}$ 280 nm) through PD catabolism. Analysis of the P2A construct at (Panel a) I 245 nm reveals a large proportion of the PD substrate being converted to 9-hydroxypregn-4-ene-3,20,dione (9-OHPD, $t_r$=5.2 min) by 48 hours. However, in comparison to the T2A construct at (Panel d) I 245 nm, residual 9-OHPD is observed, suggesting $\Delta^1$-KstD is the rate limiting step in 3-HSP ($t_r$=7.2 min, $I_{max}$ 280 nm) formation. Although 3-HSP is not observed at (Panel b)(Panel b) I 280 nm or in (Panel c)(Panel c) C4-$^{14}$C scintillation events, the accumulation of scintillation events from an unidentified metabolite ($t_r$=2.3 min) are detected prior to the 5.2 minute retention time of 9-OHPD. In contrast, the T2A construct at (Panel d) I 245 nm reveals complete reduction in the PD substrate, 9-OHPD, and pregn-1,4-diene-3,20-dione (PDD, $t_r$=10.0 min, $I_{max}$ 247 nm) by 48 hours. In addition, (Panel e) I 280 nm reveals the formation of 3-HSP. Furthermore, (Panel f) C4-$^{14}$C scintillation events confirm the formation of 3-HSP as well as additional scintillation events from unidentified metabolites prior to 3-HSP's 7.2 minute retention time.

Enabling Cholesterol Catabolism in Cultured Human Cells—Co-Expression of $\Delta^1$-KstD and MTS-KshAB in Hep3B Cells To determine whether Hep3B cells could co-express $\Delta^1$-KstD and MTS-KshAB to catalyze the formation of 3-hydroxy-9,10-secopregn-1,3,5(10)-triene-9,20-dione (3-HSP) from progesterone (PD), Hep3B cells were transiently transfected with equal quantities of pDest51-$\Delta^1$-KstD and MTS-KshAB. Following 48 hours for adequate protein expression, cells were incubated with 15.7 μg (10 μM) progesterone spiked with 100nCi C4-$^{14}$C labeled PD ($t_r$=13.8 min) for an additional 36 hours. RP-HPLC analysis of the 36 hour time course revealed a robust conversion of the PD substrate to 9-OHPD ($\lambda_{max}$ 245 nm; $t_r$=5.2 minutes) by 6 hours. Although PDD ($\lambda_{max}$ 247 nm; $t_r$=10.0 minutes) was not observed at 6 hours, analysis at λ280 nm reveals the formation of 3-HSP (FIG. 2I)

By 12 hours, the substrate and all intermediates had been catabolized to form 3-HSP. Interestingly, time points at 24 and 36 hours reveal that after the substrates and intermediates had been completely exhausted, 3-HSP is being further metabolized. The accumulation of C4-$^{14}$C scintillation events at 6.5 minutes confirms that once the cholestane ring has been opened it is being modified to have an increased polarity, as observed by a decrease in retention time.

Co-Expression of MTS-KshAB and $\Delta^1$-KstD from a Tricistronic Vector

Following confirmation that MTS-KshAB and $\Delta^1$-KstD could be simultaneously expressed to produce 3-hydroxy-9,10-secopregn-1,3,5(10)-triene-9,20-dione (3-HSP) from the substrate progesterone (PD), our next step was to design and assemble a tricistronic vector for co-expressing MTS-KshAB and $\Delta^1$-KstD from a single construct. Two vectors were designed to co-express MTS-KshAB and $\Delta^1$-KstD by inserting a Thosea asigna 2A skipping peptide (T2A) or a Porcine teschnovirus-1 2A skipping peptide (P2A) between the two enzymes. The T2A and P2A vectors were characterized by assessing KshAB and $\Delta^1$-KstD protein levels by Western blot and activity by RP-HPLC analysis. Hep3B cells were transiently transfected with the T2A and P2A vectors. Following 48 hours to allow for adequate protein expression, cells were analyzed by Western blot and duplicate dishes were incubated with 15.7 μg (10 μM) progesterone spiked with 100nCi C4-$^{14}$C labeled PD ($t_r$=13.8 min) for an additional 48 hours. The Western blot results reveal that co-expressing MTS-KshAB and $\Delta^1$-KstD with the T2A skipping peptide resulted in higher expression of the Flag tagged KshA subunit, the HA tagged KshB subunit, and the Flag tagged $\Delta^1$-KstD enzyme (Example 13).

In addition, RP-HPLC analysis revealed the T2A transfected cells had higher enzyme activity than the P2A transfected cells. The T2A transfected cells were able to completely catabolize the PD substrate and intermediates (FIG. 79 panel d) resulting in the formation of 3-HSP ($t_r$=7.2 min, $\lambda_{max}$ 280 nm) (FIG. 79 panel e) and additional downstream degradation products (79 panel f). The activity of the P2A construct was less, as seen by the presence of residual progesterone, 9-OHPD (FIG. 79 panel a), and a lack of 3-HSP formation (79 panel b & c). These findings reveal that the activity of $\Delta^1$-KstD is the rate limiting step in 3-HSP formation in the P2A construct.

With time 3-HSP is completely degraded, apparently by existing endogenous enzymes (i.e. 3-HSP added to non-transformed Hep3B cells is degraded). Production of downstream metabolites does not appear to affect the cultured cells.

Cholesterol is a necessary membrane lipid that is found in every cell of the body (Brown & Goldstein, 1999). Cholesterol is a planar, tetracyclic molecule consisting of a hydrophilic hydroxyl group at C3 and a hydrophobic alkyl side chain at C17. The amphipathic nature of cholesterol allows it to partition into phospholipid membranes where it acts as an important structural component that is essential for maintaining the fluidity and permeability of all animal membranes (Sinensky, 1978). A cell membrane that lacks adequate levels of cholesterol becomes highly fluid, eventually leading to lysis of the cell (Anderson, 2003; Kellner-Weibel et al., 1999; Brown & Goldstein, 1999; Sinensky, 1978). In contrast, excess membrane cholesterol decreases fluidity, adversely affecting membrane permeability (Brown & Goldstein, 1999; Cooper, 1977). As such, it is critical that all cells tightly regulate the level of free cholesterol in order to maintain cholesterol homeostasis. In addition to its contribution to the properties of membranes, cholesterol is used as a precursor for bile salts, and steroid hormones (Russell, 1992; Russell, 2009).

De Novo Synthesis of Cholesterol

Most, if not all cells have the ability to synthesize cholesterol. Cholesterol synthesis is a complex and an energy-expensive process, requiring the coordinated activity of more than fifteen enzymes. The backbone of cholesterol consists of 27 carbon atoms that are assembled by multiple enzymes, with all carbons coming from acetyl-CoA and molecular 02 to generate the C-3 hydroxyl (FIG. 2). The acetyl-CoA is derived from the catabolism of ketogenic amino acids and beta-oxidation of fatty acids. Three Acetyl-CoAs are used to produce 3-hydroxy-3-methyl glutaryl-CoA (HMG-CoA), which is subsequently converted to mevalonate by HMG-CoA reductase. Mevalonate is used as a precursor in the formation of isopentenyl pyrophosphate (IPP) and dimethylallyl-PP (DPP). In a head to tail condensation, IPP and DPP are converted to geranyl-PP (GPP). GPP and an additional IPP undergo a condensation reaction to form farnesyl-PP (FPP). In a head to head condensation reaction, two FPP molecules are used to produce squalene. Squalene is cyclized by squalene synthase to produce lanosterol, forming the tetracyclic steroid skeleton that composes the cholestane ring. Following an additional nineteen enzymatic steps, lanosterol is converted to cholesterol. One key feature of cholesterol metabolism is that once squalene is cyclized and the cholestane ring is formed, the ring cannot be opened enzymatically in human cells. Consequently, it is not possible to reduce cholesterol levels by catabolism.

Lipid Transport

In most circumstances, the cellular demand for cholesterol is fulfilled by hepatic synthesis and cholesterol obtained from the diet. To deliver lipids from the site of intestinal absorption and hepatic synthesis, hydrophobic lipids (cholesterol, cholesterol esters, triglycerides (TG), and phospholipids) are packaged into lipoproteins for transport in the aqueous environment of the blood. In the small intestine, dietary lipids are emulsified by bile, which aid the absorption of fats by intestinal epithelial cells (enterocytes) (FIG. 3). Within the enterocyte, cholesterol is converted into cholesterol esters and packaged into the core of chylomicrons. The chylomicrons are released from the enterocytes by exocytosis, and transported through the lymphatic system which drains into the left subclavian vein. As chylomicrons travel through the blood, they deliver fatty acids (released from TGs by lipoprotein lipase) to adipose tissue and muscle. Ultimately, the chylomicrons remnants reach the liver, where they are taken up by receptor-mediated endocytosis. When energy is in excess, the liver repackages dietary and newly synthesized TG into very low-density lipoproteins (VLDLs). VLDLs, like chylomicrons, transport TG to adipose tissue and muscle. As a consequence of TG removal by lipoprotein lipase, the VLDLs become intermediate density lipoproteins (IDLs). IDLs can either be taken up by the liver where the constituents can be recycled into VLDLs, or IDLs can remain in the circulation where hepatic lipase and lipoprotein lipase remove additional TGs. As VLDLs lose TGs the lipoprotein becomes enriched with cholesterol esters, and with further TG removal form low density lipoproteins (LDLs). LDLs contain ApoB100 and are primarily cleared by the liver through LDL-receptor mediated endocytosis. The cholesterol from LDLs can be used for either bile acid synthesis or repackaged into nascent VLDLS for transporting additional TGs to adipose tissue and muscle. However, elevated levels of LDL contribute to the development of cardiovascular disease (CVD). Thus, current treatment options for CVD work to lower serum LDL by targeting metabolic pathways resulting in increased expression of LDL-receptors that clear LDLs (i.e. statins).

Familial Hypercholesterolemia

Autosomal homozygous familial hypercholesterolemia (FH) is a rare genetic disease, which leads to the rapid onset of coronary heart disease due to a persistent elevation in low density lipoprotein (LDL) cholesterol concentration (Fellin et al., 2015). Heterozygous FH is more common (1 in 200 to 1 in 500 people), effecting between 14 and 34 million individuals worldwide (Nordestgaard et al., 2013). Patients with heterozygous FH demonstrate a clinical phenotype characterized by severely elevated plasma levels of total cholesterol, low density lipoprotein cholesterol, tendinous xanthomata, and have a high predisposition for cardiovascular disease (Austin et al., 2004). Most forms of familial hypercholesterolemia are genetic disorders disrupting normal lipid metabolism, often due to mutations in genes encoding the LDL receptor (LDLR), apolipoprotein B-100 (apoB), or the proprotein convertase subtilisin/kexin type 9 (PCSK9) (Robinson, 2013). Defects in any of these genes encoding proteins integral to lipoprotein metabolism result in a significant increase in levels of low density lipoprotein cholesterol (LDL-C) (Robinson, 2013). Homozygous FH is frequently associated with the loss of LDL receptor expression or function. Although FH patients lack functional LDL receptors, uptake in macrophages still occurs via scavenger receptors (SR), and lack of LDL-R in other tissues yields more LDLs for macrophages. Therefore, FH patients are at a greater risk for a myocardial infarction or stroke, which often occur within the first two decades of life (Fellin et al., 2015). Furthermore, these children do not respond to life style modification or statin therapy. Common treatment for homozygous FH currently depends on routine sessions of lipid apheresis (Lui et al., 2014). Homozygous FH is rare (~1:1,000,000) and usually leads to advanced CVD or death before the age of 20.

Figure 4:
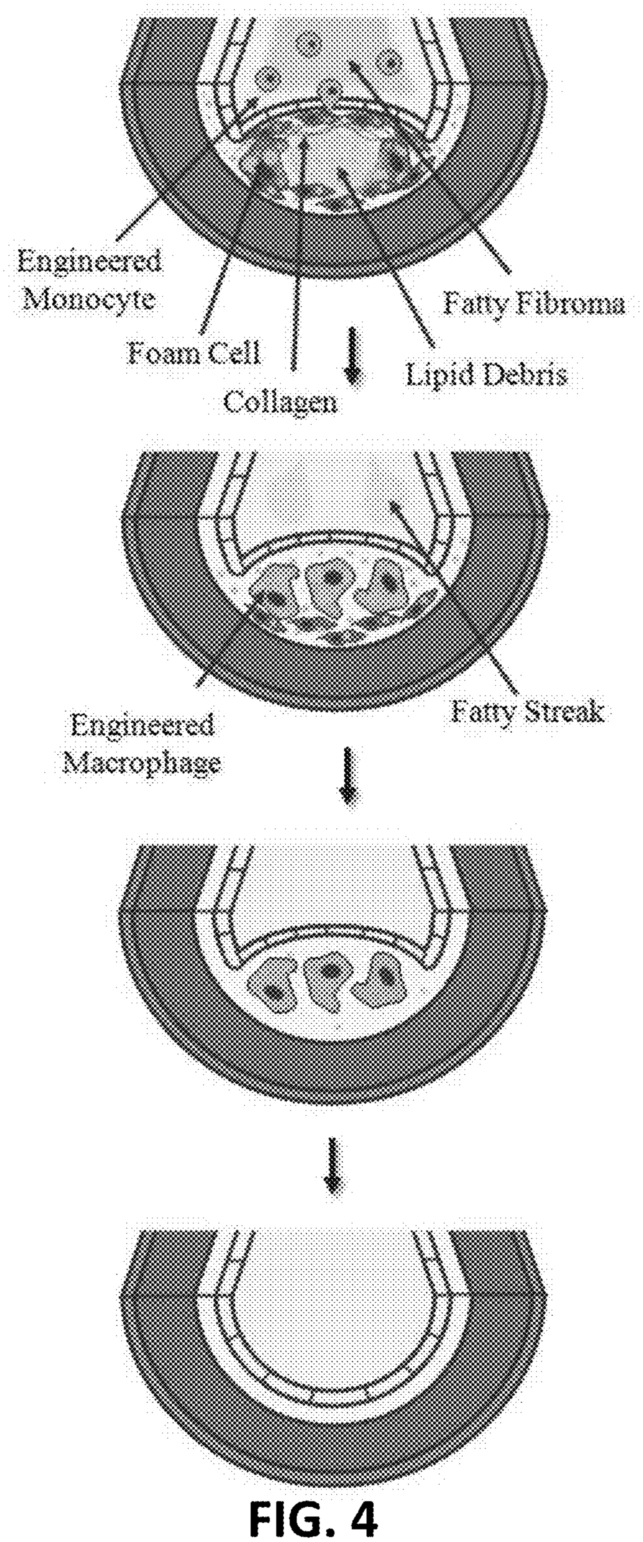
FIG. 4. Amelioration of atherosclerosis with cholesterol degrading monocyte therapy. Cholesterol degrading monocytes will be redelivered intravenously to the patient where they migrate to sites of plaque formation within the arterial intima. Once the monocytes transmigrate to the intima, they differentiate into macrophages. Macrophages will have accessibility to high levels of LDL-C which will initiate the expression of cholesterol catabolizing enzymes leading to enzymatic degradation of cholesterol.

At the fundamental biochemical level, the increased risk of cardiovascular disease is due to the inability of macrophages to clear cholesterol (Russell, 1992; Russell 2003, Russell, 2009). Interestingly, several enzymes endogenous to human cells are present that can likely degrade the intermediate metabolites produced after ring opening. For instance, macrophages are equipped with a wide range of steroidogenic enzymes that can likely act on cholesterol once the ring has been opened (cholesterol hydrolases, CoA ligases, methyacyl-CoA racemases, branched-chain oxidases and acyltransferases, and a large family of cytochrome p450s) (Enayetallah et al., 2008; Newman et al., 2005; Schiffer, 2015). This suggests that ring opening is the critical missing step in preventing cholesterol accumulation. If macrophages were equipped with the ability to rid the intima of LDL-C, the inflammatory response would be reduced or even eliminated, and the formation of atherosclerotic plaques may not occur. Our goal is to equip macrophages with the metabolic capability to catabolize cholesterol, the critical missing step needed for the reduction and prevention of plaque formation (FIG. 4).

Bacterial Enzymatic Cholesterol Catabolism

The rationale for the proposed study is based on previous findings revealing the molecular mechanisms that allow *Mycobacterium tuberculosis* survival within the phagosomes of macrophages during the choronic stage of infection (Pandey & Sassetti, 2008; Martens et al., 2008; Van der Geize et al, 2007). Tuberculosis (TB) is a chronic bacterial infection, typically affecting the lungs, caused by *M. tuberculosis*. Throughout the chronic stages of infection, *M.*

Figure 5:
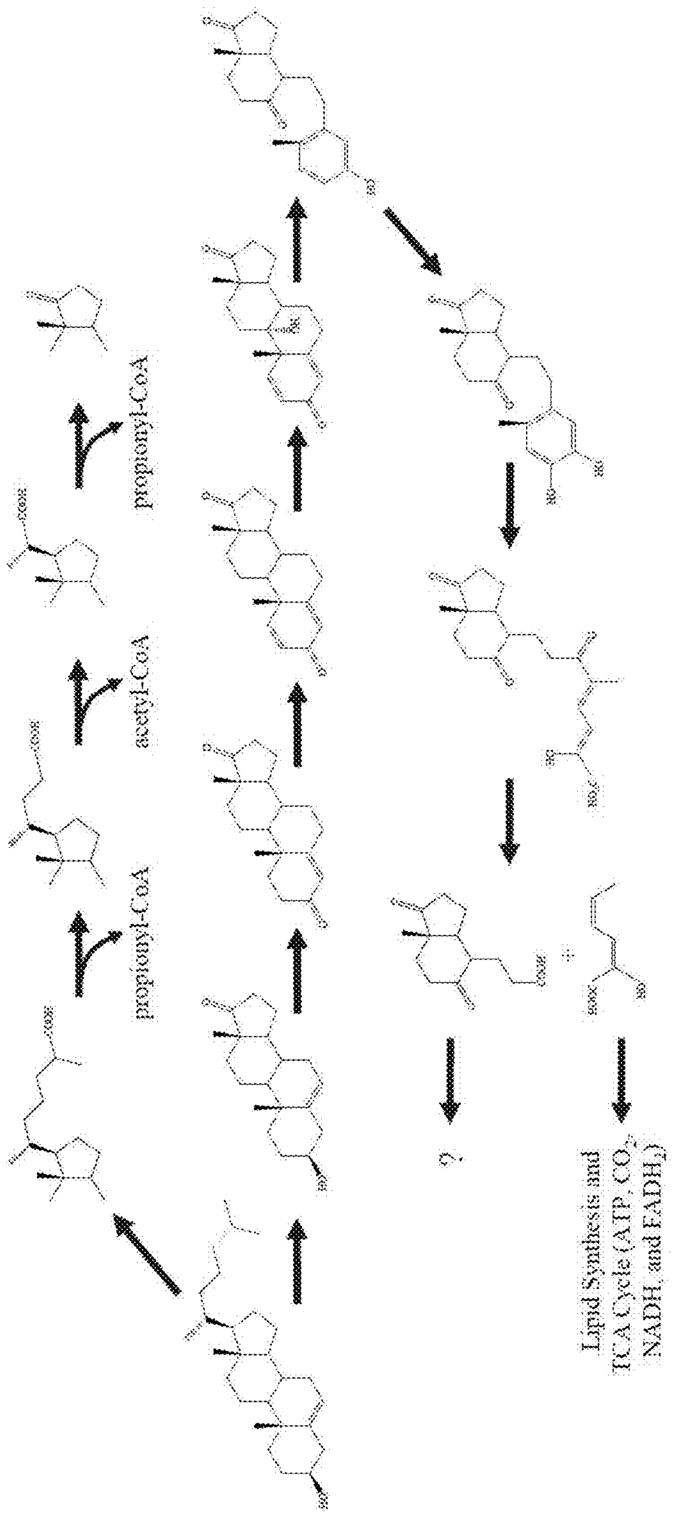
FIG. 5. Cholesterol degradation pathway utilized by *M. tuberculosis. M. tuberculosis* and many other microorganisms (e.g. *R. rhodochrous, R. erthropolis, S. denitrificans*, etc.), express enzymes that enable the bacteria to degrade cholesterol. Following an independent side chain removal pathway, enzymes sequentially modify the steroid nucleus of cholesterol resulting in B-ring cleavage. Once the ring has been opened, cholesterol is further catabolized to acetyl-CoA, which is used for metabolic processes including lipid synthesis and the TCA cycle for the production of energy.

*tuberculosis* avoids elimination by the host immune response by residing intracellulary in alveolar macrophages (Ferrari et al., 1999; Russell, 2001; Stewart et al., 2003). As the bacterial infection progresses, the host immune system encases the infected macrophages into dense granulomas structures. In many cases, the phagosomes of activated macrophages restrict the growth of intracellular pathogens by preventing access to essential nutrients. However, *M. tuberculosis* has evolved mechanisms to obtain carbon from host cholesterol in effort to survive within the confined environment (Pandey & Sassetti 2008). This is achieved by *M. tuberculosis* through the activation of several operons, some of which encode genes that enable cholesterol catabolism (Pandey & Sassetti, 2008; Van der Geize et al., 2007) (FIG. 5). The carbon obtained from host cholesterol is used in lipid synthesis and the production of energy which aid the survival of *M. tuberculosis.*

Figure 6:
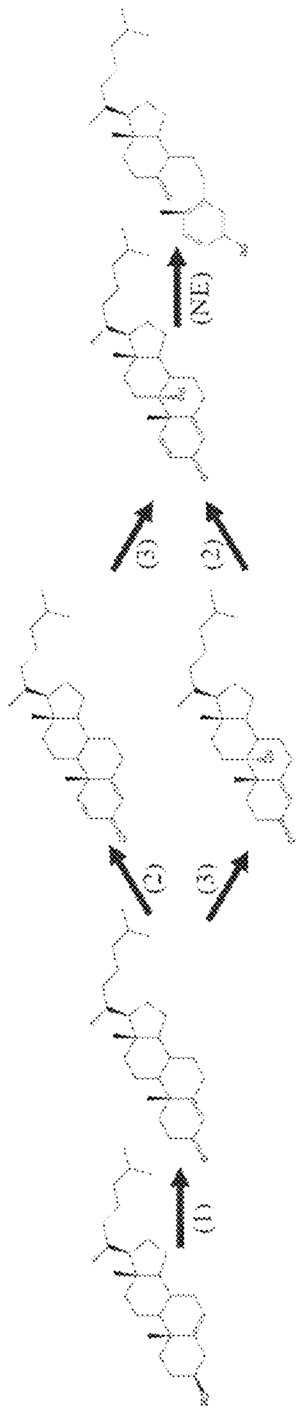
FIG. 6. Catalytic mechanism for opening the cholestane ring of cholesterol without prior side chain removal. If the cholesterol degrading enzymes do not require side chain removal, only three enzymes may be necessary to open the cholestane ring. The first enzyme, cholesterol dehydrogenase (CholD) (1), is responsible for the oxidation and isomerization of $\Delta_5$-3β-hydroxsteroids to $\Delta_4$-ketosteroids (cholesterol (CL) to cholestenone (CN)). The presence of the 3-ketone and isomerization of the double bond between C5 and C6 atoms of ring B to C4 and C5 atoms of ring A are required by the last two enzymes prior to catalyzing their respective reactions. The second enzyme, anoxic cholesterol metabolism B enzyme (acmB) (2) eliminates the 1α and 2β hydrogen atoms thereby introducing a double bond between the C1 and C2 atoms of ring A (cholestenone (CN) to choleste-1,4-diene-3-one (CDN)). The last enzyme, 3-ketosteroid 9α-hydroxylase (KshAB) (3), catalyzes the addition of a hydroxyl group on C9 of ring-B (cholestenone (CN) to 9-hydroxycholeste-4-ene-3-one (9-OHCN)). Both $\Delta_1$-KstD and KshAB are able to catalyze their respective reactions before or after the other and their combined activities lead to the formation of the unstable intermediate 9-hydroxycholeste-1,4-diene-3-one (9-OHCDN). Altogether, the presence of the 3-keto group, the isomerization of the double bond between C4 and C5, the trans-axial elimination of C1 and C2 of ring A, and the hydroxylation at C9 of ring B results in the destabilization and spontaneous opening of the cholestane ring to form the product, 3-hydroxy-9,10-secocholeste-1,3,5(10)-triene-9-one (3-HSC).

To date, our lab has identified key enzymes endogenous to *Mycobacterium tuberculosis* (Brzostek et al., 2013), *Sterolibacterium denitrificans* (Chiang et al., 2008), *Rhodococcus erythropolis* (Petrusma et al., 2011) and *Rhodococcus rhodocchrous* (Petrusma et al., 2014) that catalyze cholestane ring opening. At the time the bacterial enzymes were identified, the field was still in the early stages of development and the cholesterol catabolism pathway was not fully understood. There was controversy on whether the enzymes could catalyze cholestane ring opening with the side chain present (FIG. 6) (Penfield et al., 2014; Capyket et al., 2011; Chiang et al., 2008) or whether the enzymes required removal of the side chain prior to ring opening (FIG. 7) (Ouellet et al., 2011; Yeh et al., 2014; Petrusma et al., 2014). To initiate cholesterol degradation in human cells, it was critical for us to assess the minimal number of enzymes required to open the cholestane B-ring and how the predicted catabolites (with and without the cholesterol side chain) effected enzyme activity. We humanized four bacterial enzymes for this purpose.

The first enzyme required for ring opening is cholesterol dehydrogenase (CholD), a $NAD(P)^+$ dependent dehydrogenase. CholD oxidizes the 3p-hydroxyl at C3 of cholesterol (3β-hydroxycholest-5-ene) to yield cholestenone (cholest-4-ene-3-one). Oxidation of the 3β-hydroxyl, producing a ketone at C3, also results in the isomerization of the double bond between C5 and C6 of ring B to C4 and C5 of ring A. The next two enzymes in the cholesterol catabolism pathway the 3-keto group formed by CholD. CholD was known to have activity with steroid substrates containing the cholesterol side chain suggesting CholD was the initiating step in cholesterol catabolism (Klink et al., 2013).

For the second step in catabolism, we identified two $FAD_+$dependent 3 ketosteroid dehydrogenases (KstDs). One is 3-ketosteroid $\Delta^1$-dehydrogenase ($\Delta^1$-KstD) from *R. erythropolis*. Another is anoxic cholesterol catabolism B enzyme (acmB) from *Sterolibacterium denitrificans*. Both enzymes catalyze the desaturation of ring A by introducing a double bond between the C1 and C2 atoms of 3-ketosteroid substrates. $\Delta^1$-KstD is known to act on androstenedione (4-androstene-3,17-dione) a steroid molecule lacking the bulky side chain. However, the $\Delta^1$-KstD substrate specificity regarding the cholesterol side chain was not well established (Petrusma et al., 2011). Some reports indicated that $\Delta^1$-KstD could accommodate substrates containing the cholesterol side chain, while others suggested $\Delta^1$-KstD activity required prior side chain hydrolysis. Another report indicated the active site of the anoxic cholesterol metabolism B enzyme (acmB) from *S. denitrificans* could accommodate the cholesterol side chain (Chiang et al., 2008). If the active site of $\Delta^1$-KstD did not utilize steroid substrates with side chains, additional side chain cleavage enzymes would be necessary. Selecting an enzyme with the capacity to act upon steroid substrates with long side chains was desired to eliminate the need for additional side chain cleavage enzymes.

The last enzyme required for ring cleavage, 3-ketosteroid 9α-hydroxylase (KshAB), is an NADH dependent Rieske-type oxygenase. KshAB is a two-component iron-sulfur monooxygenase, consisting of a ferredoxin reductase (KshB) and a terminal oxygenase (KshA). KshAB catalyzes the hydroxylation of C9 on ring B of the cholesterol molecule. Previous reports suggest KshAB has subtle substrate specificity for 3-ketosteroids, and can accommodate short side chains (Petrusma et al., 2009). Additionally, KshAB is able to act either before or after the C1 and C2 dehydrogenation by 3-ketosteroid dehydrogenases.

Figure 7:
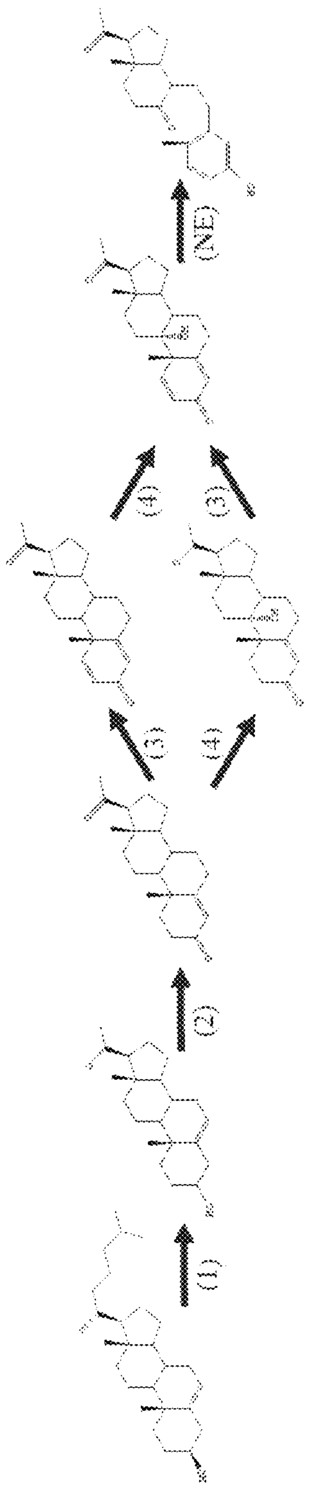
FIG. 7. Catalytic mechanism for opening the cholestane ring of cholesterol following side chain removal. Four enzymes are necessary to open the cholestane ring. The first enzyme, P450-FdxR-Fdx (1) is a fusion protein consisting of human cytochrome P450 (CYP11A1), ferrodoxinreductase, and ferrodoxin. The P450-FdxR-Fdx fusion protein removes the hydrophobic side chain of cholesterol (CL) to produce pregnenolone (PL). Side chain removal is a critical step required by the remaining enzymes prior to catalyzing their respective reactions. The second enzyme, 3β-hydroxysteroid dehydrogenase (HSD2) (2), is responsible for the oxidation and isomerization of $\Delta^5$-3β-hydroxsteroids to $\Delta^4$-ketosteroids (pregnenolone (PL) to progesterone (PD)). The presence of the 3-ketone and isomerization of the double bond between C5 and C6 atoms of ring B to C4 and C5 atoms of ring A are required by the last two enzymes prior to catalyzing their respective reactions. The third enzyme, 3-ketosteroid $\Delta^1$-dehydrogenase ($A^1$-KstD) (3) eliminates the 1α and 2β hydrogen atoms thereby introducing a double bond between the C1 and C2 atoms of ring A (progesterone (PD) to pregn-1,4-diene-3,20-dione (PDD)). The last enzyme, 3-ketosteroid 9α-hydroxylase (KshAB) (4), catalyzes the addition of a hydroxyl group on the ring-B C9 of 3-ketosteroids (progesterone (PD) to 9-hydroxypregn-4-ene-3,20-dione (9-OHPD)). Both $\Delta^1$-KstD and KshAB are able to catalyze their respective reactions before or after the other, and their combined activities lead to the formation of the unstable intermediate 9-hydroxypregn-1,4-diene-3,20-dione (9-OHPDD). The presence of the 3-keto group, the isomerization of the double bond between C4 and C5, the trans-axial elimination of C1 and C2 of ring A, and the hydroxylation at C9 of ring B results in the destabilization and spontaneous opening of the cholestane ring to form the product, 3-hydroxy-9,10-secopregnan-1,3,5(10)-triene-9,20-dione (3-HSP).

The presence of: 1) the 3-keto group, 2) the isomerization of the double bond between C4 and C5, 3) the desaturation of the C1 and C2 bond of ring A, and 4) the hydroxylation at C9 of ring B results in the destabilization and spontaneous opening of the cholestane ring (FIG. 7).

Cholesterol Side Chain Removal and 3-Ketone Production

In the event the cholesterol side chain needed to be removed, we developed a P450-FdxR-Fdx-P2A-3β-hydroxysteroid dehydrogenase (HSD2) bicistronic expression vector to produce two enzymes needed to remove the hydrophobic alkyl side chain and oxidize the 3β-hydroxy of sterol substrates. Using HSD2 to replace CholD also prevented the accumulation of cholestenone, which is toxic in high concentrations.

To produce these enzymes in human cells, we designed a fusion protein consisting of minimal structures from a human cytochrome P450 (CYP11A1) and two electron transfer proteins, ferredoxin reductase and ferredoxin. This P450 fusion protein removes the side chain of cholesterol, yielding pregnenolone. When the side chain is removed, human 3β-hydroxysteroid dehydrogenase (HSD2) can oxidize the 3β-hydroxyl of pregnenolone, yielding the 3-ketone product, progesterone. Along with the oxidation of the 3β-hydroxyl, HSD2 activity results in the isomerization of the double bond between C5 and C6 of ring B to C4 and C5 of ring A. HSD2 cannot act on substrates that retain the C-17 side chain of cholesterol. Thus, the rate-limiting step for initiating cholestane ring opening via this pathway is placed on the P450-FdxR-Fdx fusion protein. Overall we felt this was the ideal scenario, as this placed the bottleneck for degrading cholesterol on the P450 side chain cleavage enzyme, which also acts as the natural rate limiting enzyme in steroidogenesis.

In summary, we have shown that the bacterial enzymes necessary to initiate cholesterol ring opening can be humanized and functionally expressed in human cells. First, we verified the enzymes were functional by individually expressing each enzyme in *E. coli* and characterizing the activity of the clarified bacterial lysate. Using RP-HPLC analysis we showed that incubation of steroid substrates with each enzyme resulted in the formation of novel products with unique retention times and characteristic spectral properties that were not produced in the control lysates. Upon combining the bacterial lysates, we observed the formation of a new product with a unique retention time and a spectral shift that was indicative that ring opening had been achieved. The compounds produced by the clarified lysates were confirmed to be products of substrate conversion by the use of C4-$^{14}$C radiolabeled substrates. Because these compounds are not common, analytical standards of the predicted intermediates are not readily available for comparison. Therefore, the compounds produced by the bacterial lysates were used as references for characterizing the activity of the transgenic human cell lines. Each enzyme was independently expressed in Hep3B and U-937 cells and the compounds that were produced matched the retention time and spectral properties of the products that were observed in the bacterial lysates. Additionally, the use of C4-$^{14}$C radio-labeled substrates revealed that both Hep3B and U-937 cells have endogenous metabolic activity against cholesterol once the ring has been opened.

Applicants have identified four enzymes sufficient to initiate cholesterol ring opening in eukaryotic cells. Specifically, Applicants describe designed and assembly of a penta-cistronic expression vector (the cholesterol catabolizing cassette or CCC) that encodes for the enzymes needed to open the B-ring of cholesterol from a single open reading frame. We have generated U-937 cell lines that have been transduced with lentivirus encoding the CCC. However, the size of the CCC insert may be at the upper limits for some types of lentiviral packaging. Additionally, we are limited to a CMV promoter that may not be ideal for expressing the CCC. In addition to lentiviral integration, the disclosed systems, methods, and compositions may use transposon mediated integration of the disclosed cassettes, for example the CCC. Constructs may also have a responsive promoters (for example a tet-responsive promoter) to provide for modulating expression of the disclosed genes, such as the cholesterol catabolizing enzymes.

Although the prokaryotic and eukaryotic data are consistent, we need to definitively show that the predicted intermediates are being produced. We are currently working towards demonstrating the mass spectrometry fragmentation patterns of the novel products produced by the bacterial lysate and human cells are identical. Once we have developed a reference library for the predicted intermediates, our final goal will be to verify that U-937 macrophages expressing the CCC have the ability to generate cholesterol ring opening from C2,3,4-$^{13}$C3 cholesterol labeled LDLs.

LIST OF ABBREVIATIONS $\Delta^1$-KstD—3-ketosteroid $\Delta^1$-dehydrogenase
3β-HSD—3β-hydroxysteroid dehydrogenase
3-HSC—3-hydroxy-9,10-secocholestene-1,3,5(10)-triene-9-one
3-HSP—3-hydroxy-9,10-secopregn-1,3,5(10)-triene-9,20-dione
9-OHCN—9-hydroxycholeste-4-ene-3-one (9-hydroxycholestenone)
9-OHCDN—9-hydroxycholeste-1,4-diene-3-one (9-hydroxycholestedieneone)
9-OHPD—9-hydroxy-pregn-4-ene-3,20-dione (9-hydroxyprogesterone)
9-OHPDD—9-hydroxy-pregn-1,4-diene-3,20-dione (9-hydroxyprogestedienedione)
AcmB—Anoxic cholesterol metabolism B enzyme
AUC—Area under curve
Bp—Base pair
CCC—Cholesterol catabolism cassette
CholD—Cholesterol dehydrogenase
CL—3β-hydroxycholest-5-ene (cholesterol)
CDN—Choleste-1,4-diene-3-one (cholestedieneone)
CMV—Cytomegalovirus
CN—Choleste-4-ene-3-one (cholestenone)
CUC—Counts under curve
HP-THX—His patch thioredoxin
hr—hour
IMAC—Immobilized metal affinity chromatography
IPTG—Isopropyl-beta-D-thiogalactopyranoside
ISC—Iron-sulfur cluster
kD (kDa)—Kilodalton
KshAB—3-ketosteroid 9α-hydroxylase
LC-MS—Liquid Chromatography-Mass Spectrometry
mAU—Milli absorbance units
mg—Milligram
min—minute
mL—Milliliter
mM—Millimolar
nM—Nanomolar
nm—Nanometer
nt—Nucleotide
NTB—Nitrotetrazolium blue
OD600—Optical density at 600 nm
P2A—Porcine teschovirus 2A ribosomal skipping peptide
P450-FdxR-Fdx—P450 side chain cleavage enzyme-ferredoxin reductase-ferredoxin fusion protein
PAGE—Polyacrylamide gel electrophoresis
PD—Pregn-4-ene-3,20-dione (progesterone)
PDD—Pregn-1,4-diene-3,20-dione (progestedienedione)
PL—3β-hydroxypregn-5-en-20-one (pregnenolone)
PMS—Phenazine methylsulfate
PMSF—Phenylmethyulfonyl fluoride
PVDF—Polyvinylidene difluoride
RP-HPLC—Reverse phase high pressure liquid chromatography
SDS—Sodium dodecyl sulphate
T2A—Thosea asigna 2A ribosomal skipping peptide
TEV—Tobacco Etch Virus
μg—Microgram
μg—Microliter
μM—Micromolar Cardiovascular disease (CVD), the leading cause of death, is responsible for one out of every three mortalities in the United States (Go et al., 2014). CVD is complex and often associated with aberrations in normal lipid metabolism, identified by elevated levels of low density lipoproteins (LDLs) and/or reduced levels of high-density lipoproteins (HDLs) (Weverling-Rijnsburger et al., 2003). Atherosclerotic cardiovascular disease is characterized by arterial wall thickening and reduced arterial elasticity, resulting primarily from the chronic accumulation of macrophages, engorged with cholesterol from lipoproteins (i.e. LDLs), within the intima of arteries (Singh et al., 2002) (FIG. 1). For the majority of people, CVD is a progressive disease largely dependent on age and life style (Liu & Li, 2015); and can be managed by lowering low density lipoprotein cholesterol (LDL-C) with currently available treatment options (Franklin et al., 2014). In contrast, children affected by homozygous familial hypercholesterolemia (FH) are unresponsive to identical regimens. Familial hypercholesterolemia is a genetic disorder in which mutations in genes encoding LDL-receptors prevent the expression of functional LDL receptors. LDL-receptors are integral to lipoprotein metabolism and their loss result in a marked increase in levels of LDL-C(Robinson, 2013). Elevations in serum LDL-C place FH patients at great risk for both myocardial infarction and stroke, which often occur within the first two decades of life (Fellin et al., 2015). To date, effective treatment options for patients suffering from homozygous familial hypercholesterolemia have not been developed.

Analysis has revealed that humans lack enzymes required to degrade the cholestane ring of cholesterol (Pandey & Sassetti, 2008; Martens et al., 2008; Van der Geize et al, 2007). Because humans lack enzymes needed to initiate degradation, cholesterol accumulates when cellular uptake exceeds efflux to passing high density lipoproteins. Ata biochemical level this represents a critical component in the initiation of the maladaptive immune response that is responsible for the induction and progression of atherosclerotic cardiovascular disease.

Recent studies have shown that *M. tuberculosis* is equipped with the metabolic capability to degrade cholesterol, which is used as a primary energy source in the phagosomes of macrophages (Russell, 1992; Russell 2003, Russell, 2009). This observation raised the fundamental question on whether macrophages could be engineered to degrade cholesterol by expressing humanized bacterial cholesterol catabolizing enzymes.

In theory enabling cholesterol degradation in human macrophages would transform the treatment of FH patients. The large number of variations in genetic defects which culminate into the FH phenotype makes treatment difficult. Engineering human cells with the ability to degrade cholesterol using methods reliant on recombinant gene expression represents a novel approach in the management of both familial hypercholesterolemia and atherosclerotic cardiovascular disease. Developing such a therapy would circumvent the need for personalized pharmacotherapies, and may serve as an entirely new treatment for all patients suffering from atherosclerosis.

EXAMPLES

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

Results and Discussion

Humanization and Cloning of CholD, acmB, $\Delta^1$-KstD, and KshAB (Pro)

To characterize the cholesterol catabolizing enzymes, the genes encoding cholesterol dehydrogenase (CholD), anoxic cholesterol metabolism B enzyme (acmB), 3-ketosteroid-$\Delta^1$-dehydrogenase ($\Delta^1$-KstD), and 3-ketosteroid 9α-hydroxylase (KshAB) were humanized. Humanization was achieved by reverse translation of the bacterial amino acid sequence with GeneOptimization (GeneArt) software, which predicts optimal codon usage, GC content, and adds a Kozak consensus sequence for *H. sapiens*. To aid cloning, "Gateway attachment sites" and restriction enzyme recognition sites were added, with the aid of GeneOptimization software. The cDNA of each humanized enzyme was then synthesized (GeneArt; Waltham, Mass. USA) and subcloned into standard commercial vectors as discussed in methods. To determine if the humanized enzymes were active, the enzymes were subcloned into Gateway expression vectors using standard Gateway cloning techniques. Humanized CholD, acmB, and $\Delta^1$-KstD were subcloned into pBAD-Dest49 and heterologously expressed in Rosetta2 *E. coli*, which contain plasmids that express tRNA that recognize codon usage that are common in humans but rare in *E. coli*. Two constructs for KshAB were designed to express this multi subunit enzyme in either prokaryotic or eukaryotic cells. The eukaryotic KshAB construct utilizes a Porcine teschnovirus-1 2A skipping peptide that allows for equimolar expression of each subunit. Due to the bacterial ribosome being unaffected by the viral 2A skipping peptide, a prokaryotic KshAB vector was designed as a bicistronic system that utilized two ShineDalgarno sequences positioned 5' of both the A and B subunits. The prokaryotic KshAB construct was subcloned into pDest14 and heterologously expressed in C41 *E. coli*. Additionally, Rosetta2 and C41 *E. coli* were transformed with the pUC19 vector to act as empty vector transformed controls.

CholD, acmB, $\Delta^1$-KstD, and KshAB (Pro) are Functional in *E. coli*

Figure 8:
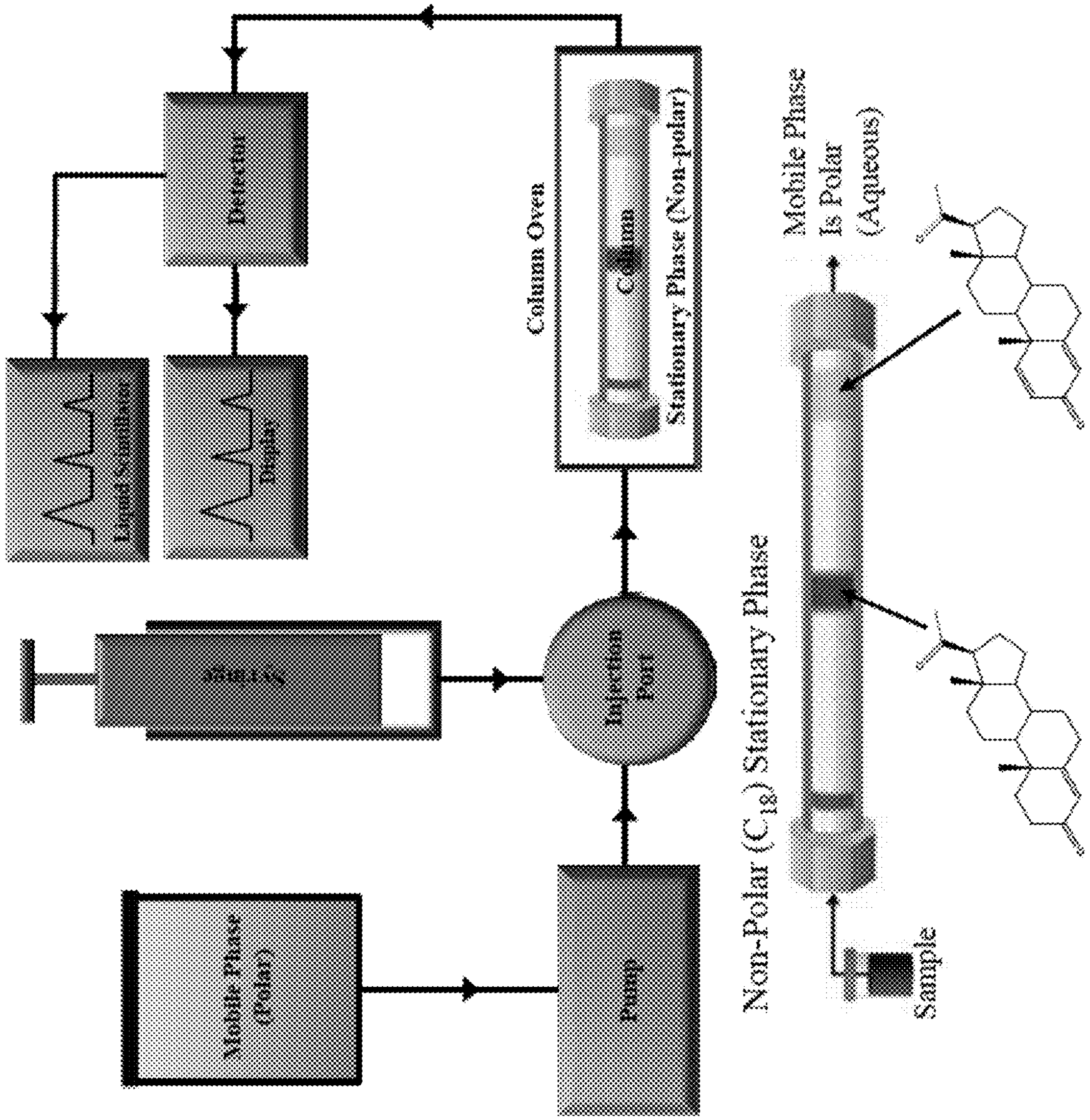
FIG. 8. Overview of Reverse Phase High Pressure Liquid Chromatography (RP-HPLC). RP-HPLC is an analytical technique used for separating, characterizing, and quantifying analytes within a mixture. RP-HPLC relies on an aqueous polar phase that is pressurized and pumped through a column filled with a non-polar stationary phase composed of octadecylcarbon chain (C18)-bonded silica. The mobile polar phase carries the sample to the column where the analytes adsorb to the non-polar stationary phase through hydrophobic interactions. Depending on the relative affinity of the analyte between the stationary and mobile phases dictates the amount of time required for the analyte to elute from the column. Analytes with higher polarities will interact with the column less, and therefore elute from the column faster. As the analytes exit the column they can be detected by their UV absorbance, or if radiolabeled, by the in-line liquid scintillation analyzer.

To characterize the products of steroid catabolism and verify the humanized enzymes were indeed functional, reverse phase high pressure liquid chromatography (RP-HPLC) (FIGS. 8 and 9) methods were developed. As cholesterol is degraded, the resulting intermediates have increased polarity in comparison to the starting substrates. To effectively separate and identify the downstream catabolites, we developed RP-HPLC methods to increase the retention time of progesterone ($t_r$=13.8 min) and cholesterol ($t_r$=38.9 min) to an analytical C18 (octadecyl carbon chain bonded silica) column for sufficient lengths of time. This allowed us to separate the steroid bioconversion analytes, characterize the intermediates of cholesterol catabolism (identify retention times and spectral absorbance), and verify the enzymes were active.

Additionally, we needed to determine the substrate specificity of the cholesterol catabolizing enzymes in regards to the cholesterol side chain. At the time there were conflicting reports in the literature. The studies of Penfield et al., Capyk et al., and Chiang et al., have suggested that the enzymes within the cholesterol catabolism pathway have the ability to catabolize substrates with the hydrophobic side chain (Chiang et al., 2008; Capyk et al., 2011; Penfield et al., 2014). Other reports indicated the ring opening enzymes required substrates without the hydrophobic side chain, suggesting side chain hydrolysis occurred first (Ouellet et al., 2011; Petrusma et al., 2014; Yeh et al., 2014). To resolve this apparent conflict, we tested the substrate specificity of our humanized enzymes, using substrates with (cholesterol and cholestenone) and without (pregnenolone and progesterone) the C-17 side chain.

Figure 10:
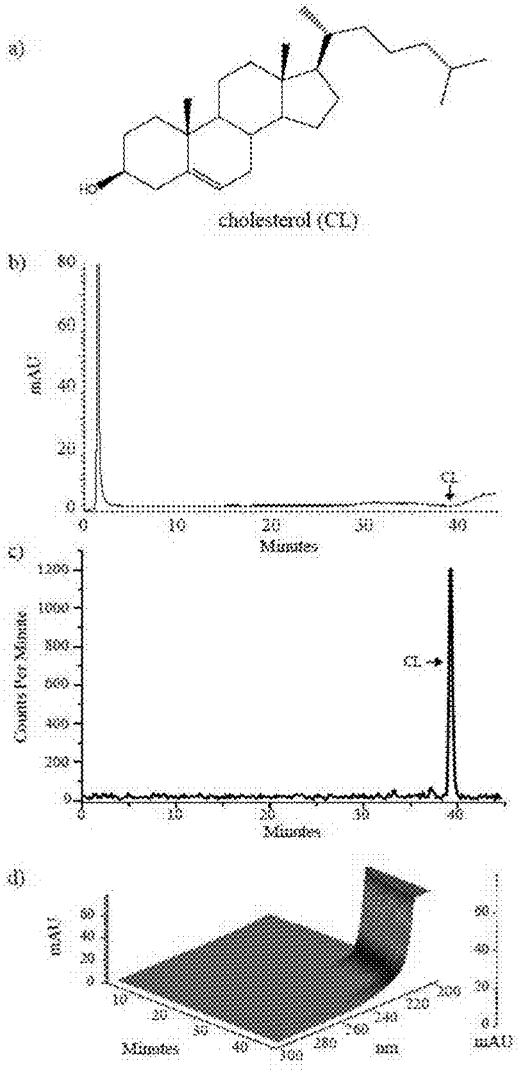
FIG. 10. RP-HPLC analysis of pUC19 transformed *E. coli* clarified lysate incubated with cholesterol (CL). (Panel a) Molecular structure of CL. Representative (Panel b)(Panel b) 2-D chromatogram (λ239 nm), (Panel c) C4-$^{14}$C scintillation events, and (Panel d)(Panel d) 3-D chromatogram from pUC19 transformed bacterial lysate following incubation with 3.87 μg (100 μM) cholesterol spiked with 20 nCi C4-$^{14}$C labeled CL ($\lambda_{max}$: <200 nm; $t_r$=38.9 min) for 24 hours. (Panel b)(Panel b) Analysis of the clarified lysate reveals *E. coli* lack the ability to metabolize CL into new UV absorbing products within 24 hours. (Panel c) Analysis of C4-$^{14}$C scintillation events confirms this inability as the reduction of C4-$^{14}$C CL into downstream radiolabeled intermediates is not observed. Lastly, (Panel d)(Panel d) the 3-D chromatogram reinforces that while CL lacks UV absorbance within 200-300 nm, the clarified bacterial lysate is unable to metabolize CL into products that produce a UV absorbance between the 200-300 nm range following 24 hours of incubation. Together, the chromatograms demonstrate why *E. coli* are ideal for characterizing the humanized cholesterol catabolizing enzymes in the presence of CL as a substrate.
Figure 11:
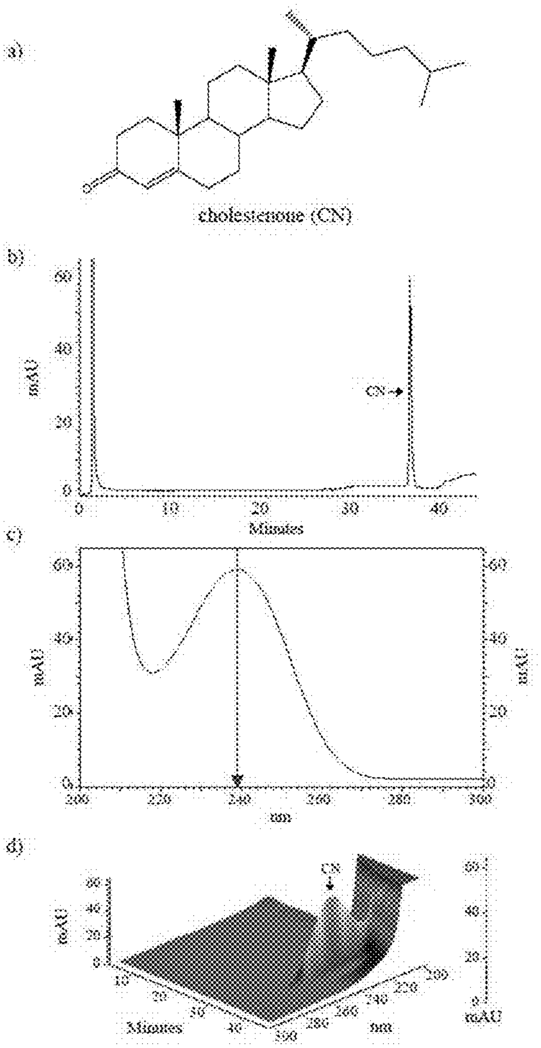
FIG. 11. RP-HPLC analysis of pUC19 transformed *E. coli* clarified lysate incubated with cholestenone (CN). (Panel a) Molecular structure of CN. Representative (Panel b)(Panel b) 2-D chromatogram (λ239 nm), (Panel c) CN UV absorbance spectrum, and (Panel d)(Panel d) 3-D chromatogram from pUC19 transformed bacterial lysate following incubation with 3.85 μg (100 μM) cholestenone ($\lambda_{max}$: 239 nm; $t_r$=36.9 min) for 24 hours. (Panel b)(Panel b) Analysis of the clarified lysate reveals *E. coli* lack the ability to metabolize CN into new UV absorbing products within 24 hours. (Panel c) Analysis of the CN UV absorbance shows the 36.9 min peak has a $\lambda_{max}$ of 239 nm, matching the CN analytical standard. Lastly, (Panel d)(Panel d) the 3-D chromatogram reinforces the empty vector transformed bacterial lysate lacks the ability to metabolize CN into products that produce a UV absorbance between the 200-300 nm range following 24 hours of incubation. Together, the chromatograms demonstrate why *E. coli* are ideal for characterizing the humanized cholesterol catabolizing enzymes in the presence of CN as a substrate.
Figure 12:
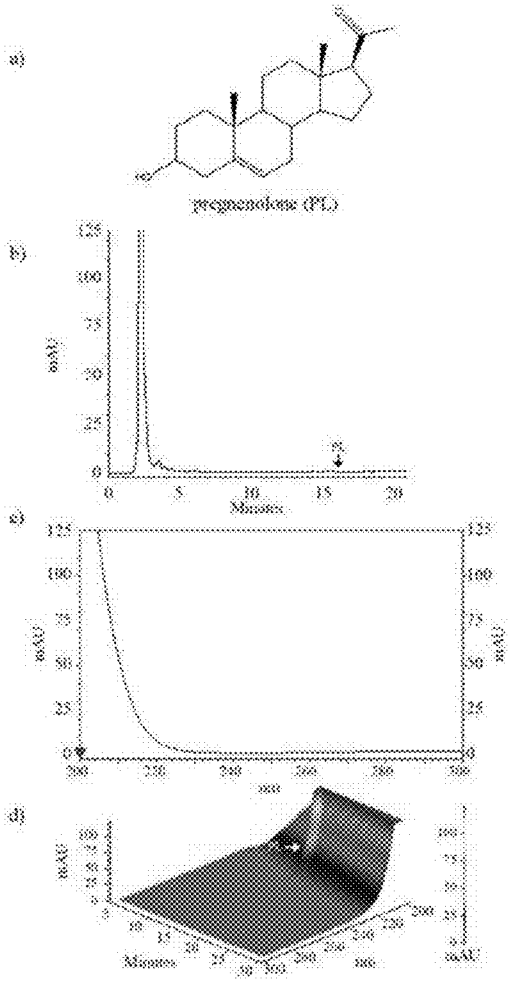
FIG. 12. RP-HPLC analysis of pUC19 transformed *E. coli* clarified lysate incubated with pregnenolone (PL). (Panel a) Molecular structure of PL. Representative (Panel b)(Panel b) 2-D chromatogram (λ245 nm), (Panel c) PL UV absorbance spectrum, and (Panel d) 3-D chromatogram from pUC19 transformed bacterial lysate following incubation with 3.16 μg (100 μM) pregnenolone ($\lambda_{max}$: <200 nm; $t_r$=15.5 min) for 24 hours. (Panel b)(Panel b) Analysis of the clarified lysate reveals *E. coli* lack the ability to metabolize PL into new UV absorbing products within 24 hours. (Panel c) Analysis of the PL UV absorbance reveals the substrates maximal UV absorbance is found below the 200 nm wavelength range. Lastly, (Panel d) the 3-D chromatogram reinforces the empty vector transformed bacterial lysate lacks the ability to metabolize PL into products that produce a UV absorbance between the 200-300 nm range following 24 hours of incubation. Together, the chromatograms demonstrate why *E. coli* are ideal for characterizing the humanized cholesterol catabolizing enzymes in the presence of PL as a substrate.
Figure 13:
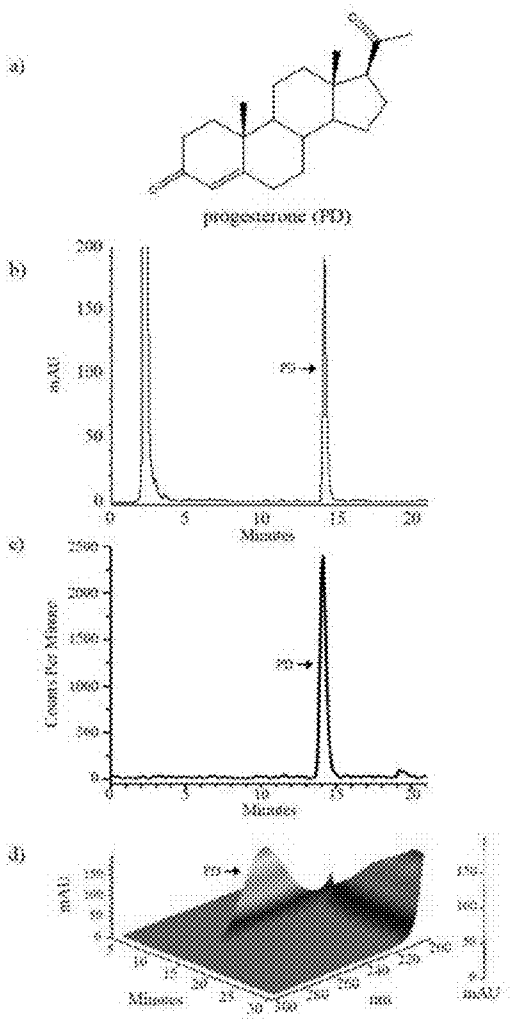
FIG. 13. RP-HPLC analysis of pUC19 transformed *E. coli* clarified lysate incubated with progesterone (PD). (Panel a) Molecular structure of PD. Representative (Panel b)(Panel b) 2-D chromatogram (λ245 nm), (Panel c) C4-$^{14}$C scintillation events, and (Panel d) 3-D chromatogram from pUC19 transformed bacterial lysate following incubation with 3.14 μg (100 μM) progesterone spiked with 20 nCi C4-$^{14}$C labeled PD ($\lambda_{max}$: 245 nm; $t_r$=13.8 min) for 24 hours. (Panel b)(Panel b) Analysis of the clarified lysate reveals E. co/clack the ability to metabolize PD into new UV absorbing products within 24 hours. (Panel c) Analysis of C4-$^{14}$C scintillation events confirms this inability as the reduction of the C4-$^{14}$C PD substrates into downstream radiolabeled intermediates is not observed. Lastly, (Panel d) the 3-D chromatogram reinforces the empty vector transformed bacterial lysate lacks the ability to metabolize PD into products that produce a UV absorbance between the 200-300 nm range following 24 hours of incubation. Together, the chromatograms demonstrate why *E. coli* are ideal for characterizing the humanized cholesterol catabolizing enzymes in the presence of PD as a substrate.

Following transformation, bacterial cultures were grown, mechanically lysed, and the crude protein was clarified by centrifugation. The enzymatic activity of the clarified lysates was assessed by incubation with the steroid substrates cholesterol (CL, 30 hydroxycholest-5-ene), cholestenone (CN, choleste-4-ene-3-one), pregnenolone (PL, 30 hydroxy-pregn-5-en-20-one) or progesterone (PD, pregn-4-ene-3,20-dione). Reactions were stopped by extracting with ethyl acetate and the steroid bioconversion analytes were analyzed by RP-HPLC. In agreement with the literature, *E. coli* were found to be ideal organisms for steroid bioconversion analysis due to their lack of metabolic activity against steroid substrates, as observed with pUC19 transformed *E. coli* incubated with 100 μM cholesterol (FIG. 10), cholestenone (FIG. 11), pregnenolone (FIG. 12), or progesterone (FIG. 13) for 24 hours. The use of *E. coli* facilitated the identification of novel metabolites generated by the humanized cholesterol catabolizing enzymes through observation of new absorbances/peaks with unique retention times following incubation of the substrates with the enzyme expressing bacterial lysates. Additionally, novel metabolites were confirmed as products of enzymatic steroid bioconversions by C4-$^{14}$C scintillation events when cholesterol (CL) or progesterone (PD) were used.

Figure 14:
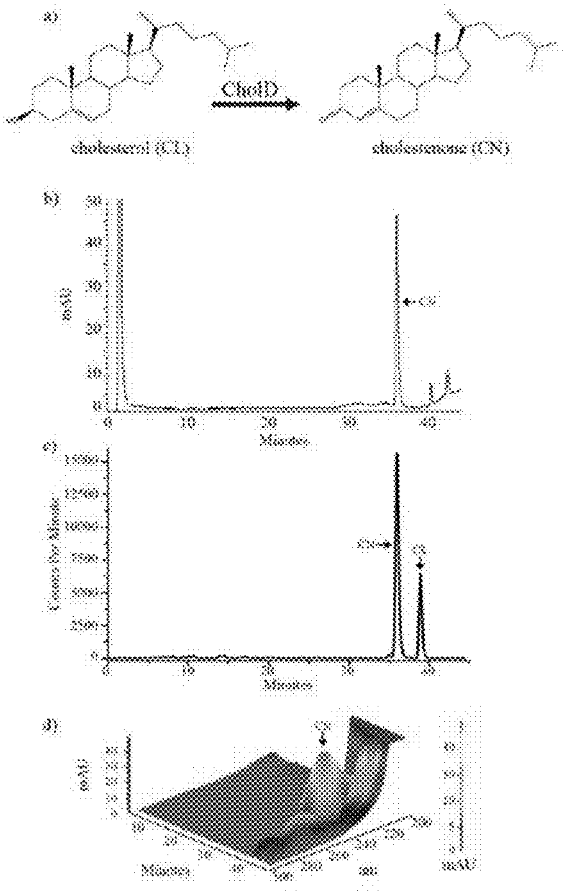
FIG. 14. RP-HPLC analysis of cholestenone(CN) formation from cholesterol(CL) utilization by *E. coli* clarified lysate expressing humanized cholesterol dehydrogenase (CholD). (Panel a) Reaction overview of CN formation from CLring-A3β-hydroxyloxidation by CholD. Representative (Panel b)(Panel b) 2-Dchromatogram (λ239 nm), (Panel c) C4-$^{14}$C scintillation events, and (Panel d) 3-Dchromatogram from CholD bacterial lysate following incubation with 3.87 μg (100 μM) cholesterol spiked with 60 nCiC4-$^{14}$C labeled CL ($\lambda_{max}$: <200 nm; $t_r$=38.9 min) for 24 hours. (Panel b)(Panel b) Analysis of the CholD lysates hows reduction in CL and formation of CN($\lambda_{max}$:239 nm; $t_r$=36.9 min) within 24 hours. (Panel c) Analysis of C4-$^{14}$C scintillation events confirms that production of radiolabeled CN is concomitant to the reduction of C4-$^{14}$CCL. Lastly, (Panel d) the 3-Dchromatogram reinforces that while CL lacks UV absorbance within 200-300 nm, the 3β-oxidation of CL produces a new peak with the same characteristic $\lambda_{max}$ and $t_r$ of CN that is not observed in the control pUC19 lysate.
Figure 15:
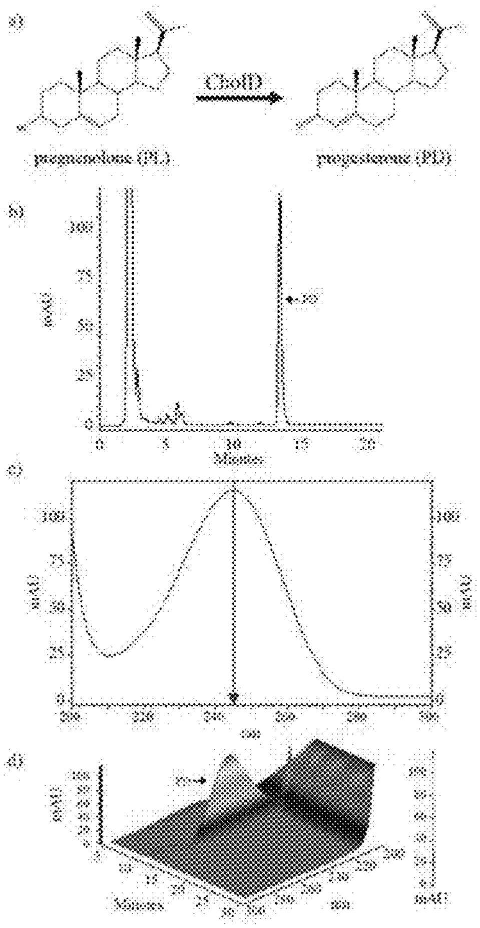
FIG. 15. RP-HPLC analysis of progesterone (PD) formation from pregnenolone (PL) utilization by *E. coli* clarified lysate expressing humanized cholesterol dehydrogenase (CholD). (Panel a) Reaction overview of PD formation from PL ring-A 3β-hydroxyl oxidation by CholD. Representative (Panel b)(Panel b) 2-D chromatogram (λ245 nm), (Panel c) PD UV absorbance spectrum, and (Panel d) 3-D chromatogram from CholD bacterial lysate following incubation with 3.16 μg (100 μM) pregnenolone ($\lambda_{max}$: <200 nm; $t_r$=15.5 min) for 24 hours. (Panel b)(Panel b) Analysis of the CholD lysate shows formation of PD ($\lambda_{max}$: 245 nm; $t_r$=13.8 min) within 24 hours. (Panel c) Analysis of the PD UV absorbance spectrum shows the λmax of the 13.8 min peak is 245 nm. Lastly, (Panel d) the 3-D chromatogram reinforces that while PL lacks UV absorbance within 200-300 nm, the 3β-oxidation of PL produces a new peak with the same characteristic $\lambda_{max}$ and $t_r$ of PD that is not observed in the control pUC19 lysate.

The CholD enzyme was determined to be active by incubating the bacterial lysate with two 30-hydroxy steroid substrates in independent reactions containing 100 μM C4-$^{14}$C labeled cholesterol (CL) (FIG. 14) or 100 μM pregnenolone (PL) (FIG. 15) for 24 hours. Both cholesterol and pregnenolone lack an observable UV absorbance within the 200-300 nm range, a feature that results from a lack of conjugation in the A-ring of the cholestane ring. However, following oxidation of the 3β-hydroxy to a 3-ketone with concomitant isomerization of the C5-C6 double bond to C4-05, the resulting conjugated 3-ketosteroids (cholestenone and progesterone) possess a detectable UV absorbance. Although a lack in UV absorbance prevents the determination of the substrates retention time, we used radiolabeled cholesterol and an in-line flow scintillation analyzer to determine the retention time of the substrate. Analysis of the CholD bacterial lysate incubated with 100 μNA C4-$^{14}$C labeled cholesterol (CL) showed reduction in CL ($\lambda_{max}$: <200 nm; $t_r$=38.9 min) and formation of a new peak corresponding to cholestenone (CN) ($\lambda_{max}$: 239 nm; $t_r$=36.9 min) within 24 hours (FIG. 14 panels b & c). Cholestenone (CN) demonstrated a unique retention time of 36.9 minutes and a lambda max of 239 nm that was not observed in the control pUC19 bacterial lysate incubated with 100 WI cholesterol (CL) for 24 hours. Analysis of the cholestenone (CN) UV absorbance spectrum shows the $\lambda_{max}$ of the 36.9 minute peak is 239 nm (FIG. 14 panel d), matching the UV absorbance and retention time of the cholestenone (CN) analytical standard. Analysis of 04-$^{14}$C scintillation events confirmed that production of radiolabeled cholestenone (CN) is concomitant to the reduction of C4-$^{14}$C cholesterol (CL) (FIG. 14 panel c). In addition, incubating the CholD bacterial lysate with 100 μM pregnenolone (PL) ($\lambda_{max}$: <200 nm; $t_r$=15.5 min) resulted in the formation of progesterone (PD) ($\lambda_{max}$: 245 nm; $t_r$=13.8 min) within 24 hours (FIG. 15). Progesterone (PD) demonstrated a unique retention time of 13.8 minutes and a lambda max of 245 nm that was not observed in the control pUC19 bacterial lysate incubated with 100 μM pregnenolone (PL) for 24 hours (FIG. 15 panels b). Analysis of the progesterone (PD) UV absorbance spectrum shows the $\lambda_{max}$ of the 13.8 minute peak is 245 nm (FIG. 15 panels c & d), matching the UV absorbance and retention time of the progesterone (PD) analytical standard. This data confirms that humanized CholD can be heterologously expressed in *E. coli* as an active enzyme, and its activity is not hindered by the presence or the absence of the cholesterol side chain.

Figure 16:
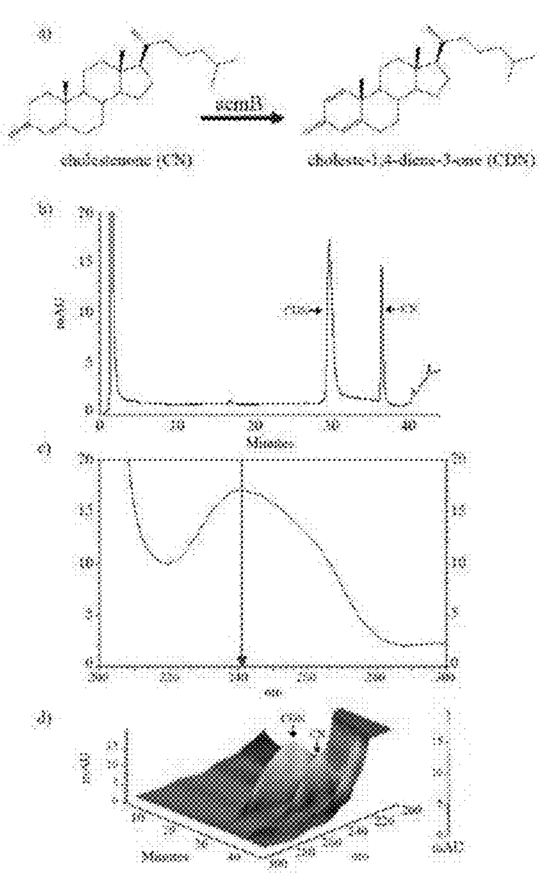
FIG. 16. RP-HPLC analysis of choleste-1,4-diene-3-one (CDN) formation from cholestenone (CN) utilization by *E. coli* clarified lysate expressing humanized anoxic cholesterol metabolism B enzyme (acmB). (Panel a) Reaction overview of CDN formation from CN ring-A C1-C2 desaturation by acmB. Representative (Panel b)(Panel b) 2-D chromatogram (λ241 nm), (Panel c) CDN UV absorbance spectrum, and (Panel d) 3-D chromatogram from acmB bacterial lysate following incubation with 3.85 μg (100 μM) cholestenone ($\lambda_{max}$: 239 nm; $t_r$=36.9 min) for 24 hours. (Panel b)(Panel b) Analysis of the acmB lysate shows formation of CDN ($\lambda_{max}$: 241 nm; $t_r$=29.8 min) within 24 hours. (Panel c) Analysis of the CDN UV absorbance spectrum shows the $\lambda_{max}$ of the 36.9 min peak is 241 nm. Lastly, (Panel d) the 3-D chromatogram reinforces that acmB has the ability to desaturate the C1-C2 bond of CN by the formation of a new peak with a unique $\lambda_{max}$ and $t_r$ that is not observed in the control pUC19 lysate.
Figure 17:
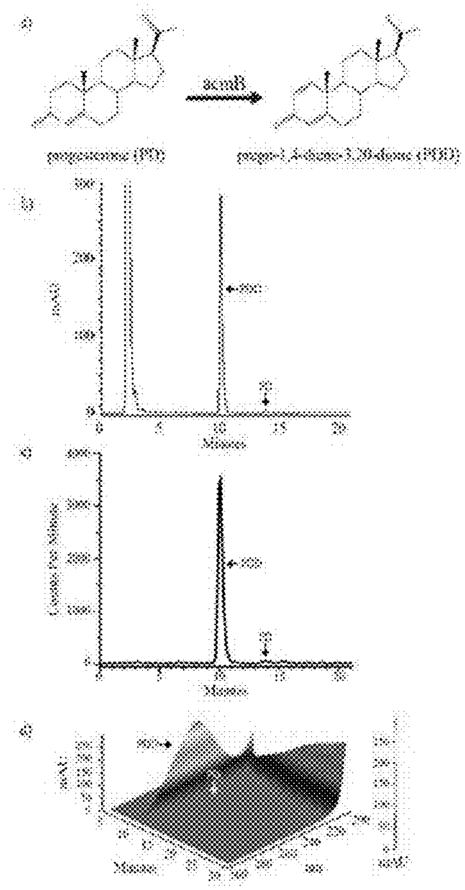
FIG. 17. RP-HPLC analysis of pregn-1,4-diene-3,20-dione (PDD) formation from progesterone (PD) utilization by *E. coli* clarified lysate expressing humanized anoxic cholesterol metabolism B enzyme (acmB). (Panel a) Reaction overview of PDD formation from PD ring-A C1-C2 desaturation by acmB. Representative (Panel b) 2-D chromatogram (λ245 nm), (Panel c) C4-$^{14}$C scintillation events, and (Panel d) 3-D chromatogram from acmB bacterial lysate following incubation with 3.14 μg (100 μM) progesterone spiked with 20 nCi C4-$^{14}$C labeled PD ($\lambda_{max}$: 245 nm; $t_r$=13.8 min) for 24 hours. (Panel b) Analysis of acmB lysate shows reduction in PD and formation of PDD ($\lambda_{max}$: 247 nm; $t_r$=10.0 min) within 24 hours. (Panel c) Analysis of C4-$^{14}$C scintillation events confirms that production of radiolabeled PDD is concomitant to the reduction of C4-$^{14}$C PD. Lastly, (Panel d) the 3-D chromatogram reinforces that acmB has the ability to desaturate the ring-A C1-02 bond of PD to produce a new peak with a unique $\lambda_{max}$ and $t_r$ that is not observed in the control pUC19 lysate.

The acmB enzyme was determined to be active by incubating the bacterial lysate with two 3-ketosteroid substrates in independent reactions containing 100 μM cholestenone (CN) (FIG. 16) and 100 μM progesterone (PD) (FIG. 17) for 24 hours. Both the substrates and their respective products demonstrate an observable UV absorbance, facilitating the determination of their retention times. AcmB is a dehydrogenase that catalyzes the ring-A C1-C2 desaturation of 3-ketosteroid substrates. Analysis of the acmB bacterial lysate following incubation with 100 μM cholestenone (CN) ($\lambda_{max}$: 239 nm; $t_r$=36.9 min) for 24 hours reveals the formation of choleste-1,4-diene-3-one (CDN) ($\Delta_{max}$: 241 nm; $t_r$=29.8 min) (FIG. 16). Choleste-1,4-diene-3-one (CDN) demonstrated a unique retention time of 29.8 minutes (FIG. 16 panel b) and a lambda max of 241 nm (FIG. 16 panel c) that was not observed in the control pUC19 bacterial lysate incubated with 100 μM cholestenone (CN) for 24 hours. In addition, incubating the acmB bacterial lysate with 100 μM C4-$^{14}$C labeled progesterone (PD) ($\lambda_{max}$: 245 nm; $t_r$=13.8 min) resulted in the formation of C4-$^{14}$C labeled pregn-1,4-diene-3,20-dione (PDD) ($\lambda_{max}$: 247 nm; $t_r$=10.0 min) (FIG. 17). Pregn-1,4-diene-3,20-dione (PDD) demonstrated a unique retention time of 10.0 minutes (FIG. 17 panel b) and a lambda max of 247 nm (FIG. 17 panel d) that was not observed in the control pUC19 bacterial lysate incubated with 100 μM C4-$^{14}$C labeled progesterone (PD) for 24 hours. Analysis of C4-$^{14}$C scintillation events confirmed that production of radiolabeled pregn-1,4-diene-3,20-dione (PDD) is concomitant to the reduction of C4-$^{14}$C progesterone (PD) (FIG. 17 panel c). This data confirms that humanized acmB can be heterologously expressed in *E. coli* as an active enzyme, and its activity is not hindered by the presence or absence of the cholesterol side chain.

Figure 18:
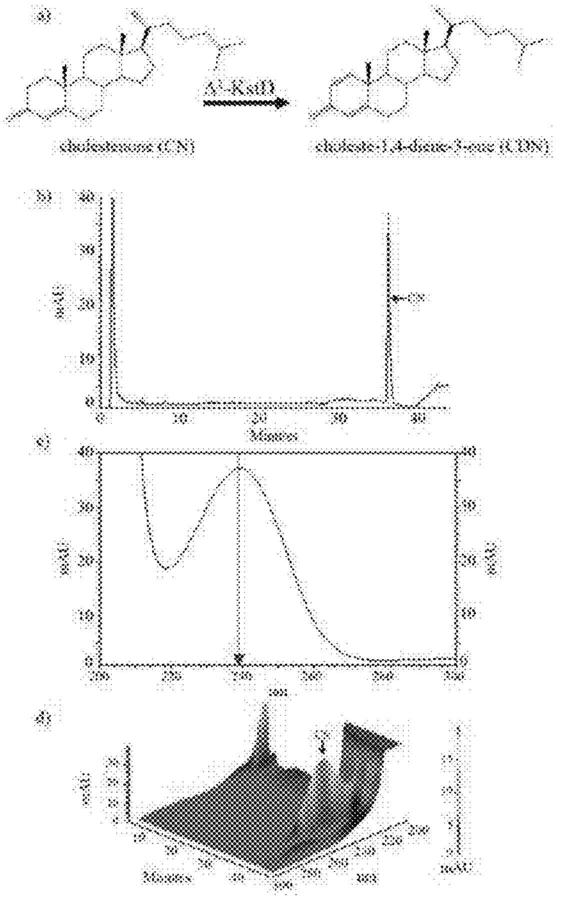
FIG. 18. RP-HPLC analysis of the clarified lysate from *E. coli* expressing humanized 3-ketosteroid $\Delta^1$-dehydrogenase ($\Delta^1$-KstD) demonstrating a lack in the ability to form choleste-1,4-diene-3-one (CDN) from cholestenone (CN). (Panel a) Reaction overview of CDN formation from CN ring-A C1-C2 desaturation by $\Delta^1$-KstD. Representative (Panel b) 2-D chromatogram (λ239 nm), (Panel c) CN UV absorbance spectrum, and (Panel d) 3-D chromatogram from $\Delta^1$-KstD bacterial lysate following incubation with 3.85 μg (100 μM) cholestenone ($\lambda_{max}$: 239 nm; $t_r$=36.9 min) for 24 hours. (Panel a) Analysis of the 2-D chromatogram reveals $\Delta^1$-KstD is unable to form CDN ($\lambda_{max}$: 241 nm; $t_r$=29.8 min) from CN within 24 hours. (Panel b) Analysis of the CN UV absorbance spectrum shows a detectable peak within 200-300 nm has a $t_r$ of 36.9 and a $\lambda_{max}$ of 239 nm, matching the CN analytical standard. Lastly, (Panel c) the 3-D chromatogram reinforces that $\Delta^1$-KstD lacks the ability to desaturate the C1-C2 bond of CN as the chromatogram matches the control pUC19 lysate.
Figure 19:
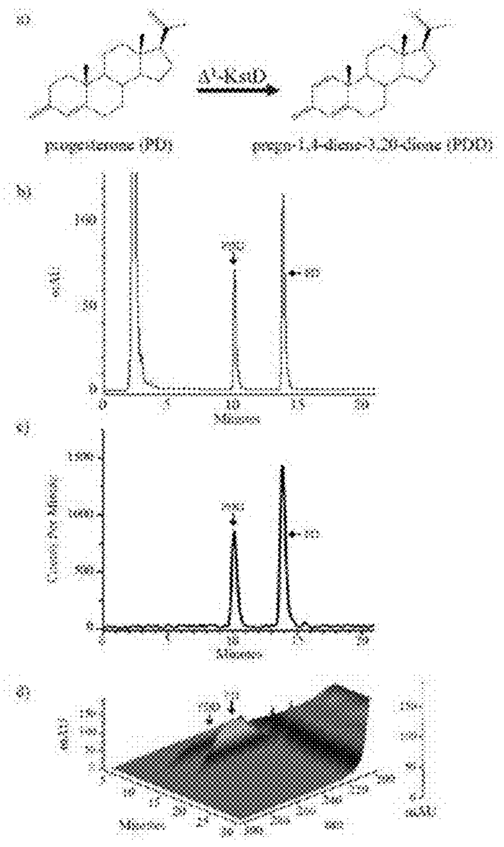
FIG. 19. RP-HPLC analysis of pregn-1,4-diene-3,20-dione (PDD) formation from progesterone (PD) utilization by *E. coli* clarified lysate expressing humanized 3-ketosteroid $\Delta^1$-dehydrogenase ($\Delta^1$-KstD). (Panel a) Reaction overview of PDD formation from PD ring-A C1-C2 desaturation by $\Delta^1$-KstD. Representative (Panel b) 2-D chromatogram (λ245 nm), (Panel c) C4-14C scintillation events, and (Panel d) 3-D chromatogram from $\Delta^1$-KstD bacterial lysate following incubation with 3.14 μg (100 μM) progesterone spiked with 20 nCi C4-14C labeled PD ($\lambda_{max}$: 245 nm; $t_r$=13.8 min) for 24 hours. (Panel b) Analysis of $\Delta^1$-KstD lysate shows reduction in PD and formation of PDD ($\lambda_{max}$: 247 nm; $t_r$=10.0 min) within 24 hours. (Panel c) Analysis of C4-$^{14}$C scintillation events confirms that production of radiolabeled PDD is concomitant to the reduction of C4-$^{14}$C PD. Lastly, (Panel d) the 3-D chromatogram reinforces that $\Delta^1$-KstD has the ability to desaturate the ring-A C1-C2 of PD to produce a new peak with a unique $\lambda_{max}$ and $t_r$ that is not observed in the control pUC19 lysate.

The $\Delta^1$-KstD enzyme, a second 3-ketosteroid dehydrogenase that catalyzes the same reaction as acmB, was determined to be active by incubating the bacterial lysate with the 3-ketosteroid substrates, 100 μM cholestenone (CN) (FIG. 18) and 100 μM C4 $^{14}$C labeled progesterone (PD) (FIG. 19) for 24 hours. Analysis of the $\Delta^1$-KstD bacterial lysate following incubation with 100 μM cholestenone (CN) ($\lambda_{max}$: 239 nm; $t_r$=36.9 min) for 24 hours reveals an inability to produce choleste-1,4-diene-3-one (CDN) ($\lambda_{max}$: 241 nm; $t_r$=29.8 min) (FIG. 18) as observed with the acmB bacterial lysate. A lack in activity with cholestenone (CN) suggests that Δ1-KstD may not accommodate the cholesterol side chain. However, incubating the $\Delta^1$-KstD bacterial lysate with 100 μM C4-$^{14}$C labeled progesterone (PD) ($\lambda_{max}$: 245 nm; $t_r$=13.8 min) resulted in the formation of C4-$^{14}$C labeled pregn-1,4-diene-3,20-dione (PDD) ($\lambda_{max}$: 247 nm; $t_r$=10.0 min) (FIG. 19). The pregn-1,4-diene-3,20-dione (PDD) product demonstrated the same retention time of 10 minutes (FIG. 19 panel b) and lambda max of 247 nm (FIG. 19 panel d) as seen with the pregn-1,4-diene-3,20-dione (PDD) formation with the acmB lysate. Analysis of C4-$^{14}$C scintillation events confirmed that production of radiolabeled pregn-1,4 diene-3,20-dione (PDD) is concomitant to the reduction of C4-$^{14}$C progesterone (PD) (FIG. 19 panel c). This data confirms that humanized $\Delta^1$-KstD can be heterologously expressed in *E. coli* as an active enzyme, but its activity is hindered by the presence of the cholesterol side chain.

Figure 20:
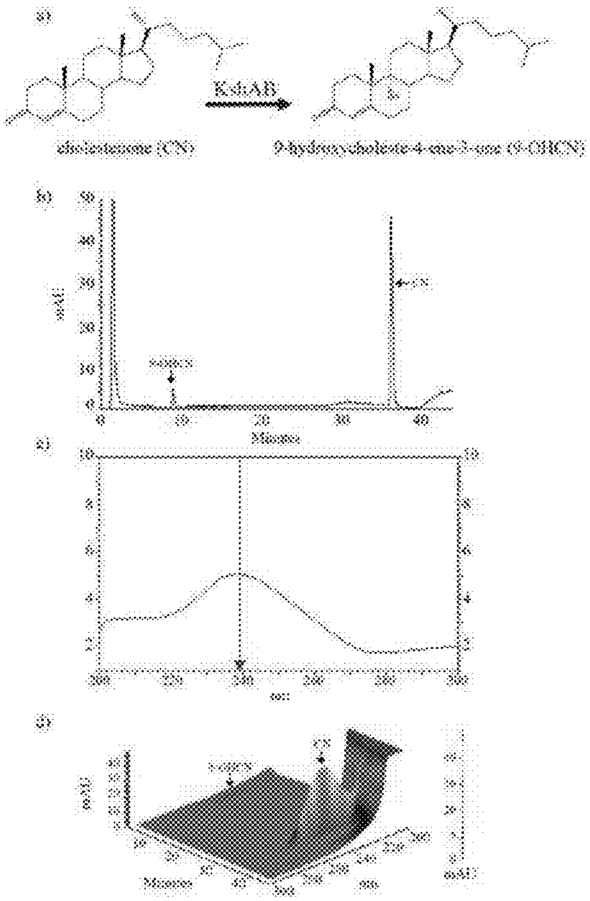
FIG. 20. RP-HPLC analysis of 9-hydroxycholeste-4-ene-3-one (9-OHCN) formation from cholestenone (CN) utilization by *E. coli* clarified lysate expressing humanized 3-ketosteroid 9α-hydroxylase (KshAB). (Panel a) Reaction overview of 9-OHCN formation from CN ring-B C9 hydroxylation by KshAB. Representative (Panel b) 2-D chromatogram (λ239 nm), (Panel c) 9-OHCN UV absorbance spectrum, and (Panel d) 3-D chromatogram from KshAB bacterial lysate following incubation with 3.85 μg (100 μM) cholestenone ($\lambda_{max}$: 239 nm; $t_r$=36.9 min) for 24 hours. (Panel b) Analysis of KshAB lysate shows a slight reduction in CN and small formation of 9-OHCN ($\lambda_{max}$: 239 nm; $t_r$=8.9 min) within 24 hours. (Panel c) Analysis of the 9-OHCN UV absorbance spectrum shows the $\lambda_{max}$ of the 8.9 min peak is 239 nm. Lastly, (Panel d) the 3-D chromatogram reinforces that KshAB has the ability to hydroxylate C9 of the CN ring-B to produce a new peak with a unique $t_r$ that is not observed in the control pUC19 lysate.
Figure 21:
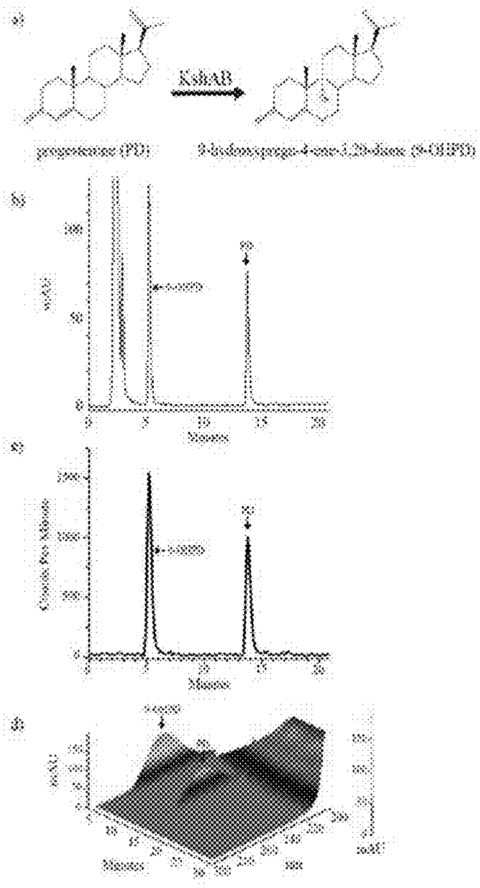
FIG. 21. RP-HPLC analysis of 9-hydroxypregn-4-ene-3,20-dione (9-OHPD) formation from progesterone (PD) utilization by *E. coli* clarified lysate expressing humanized 3-ketosteroid 9α-hydroxylase (KshAB). (Panel a) Reaction overview of 9-OHPD formation from PD ring-B C9 hydroxylation by KshAB. Representative (Panel b) 2-D chromatogram (λ245 nm), (Panel c) C4-$^{14}$C scintillation events, and (Panel d) 3-D chromatogram from KshAB bacterial lysate following incubation with 3.14 μg (100 μM) progesterone spiked with 20 nCi C4-$^{14}$C labeled PD ($\lambda_{max}$: 245 nm; $t_r$=13.8 min) for 24 hours. (Panel b) Analysis of KshAB lysate shows reduction in PD and formation of 9-OHPD ($\lambda_{max}$: 245 nm; $t_r$=5.2 min) within 24 hours. (Panel c) Analysis of C4-$^{14}$C scintillation events confirms that production of radiolabeled 9-OHPD is concomitant to the reduction of C4-$^{14}$C PD. Lastly, (Panel d) the 3-D chromatogram reinforces that KshAB has the ability to hydroxylate C9 of the PD ring-B to produce a new peak with a unique $t_r$ that is not observed in the control pUC19 lysate.

The KshAB enzyme was determined to be active by incubating the bacterial lysate with 100 μM cholestenone (CN) (FIG. 20) and 100 μM C4-$^{14}$C labeled progesterone (PD) (FIG. 21) for 24 hours. KshAB is a hydroxylase that catalyzes the addition of a hydroxyl group to the ring-B C9 of 3-ketosteroids. Analysis of the KshAB bacterial lysate following incubation with 100 μM cholestenone (CN) ($\lambda_{max}$: 239 nm; $t_r$=36.9 min) for 24 hours reveals a small formation of 9-hydroxycholeste-4-ene-3-one (9 OHCDN) ($\lambda_{max}$: 239 nm; $t_r$=8.9 min) (FIG. 20). The 9-hydroxycholeste-4-ene-3-one (9 OHCDN) product demonstrated a unique retention time of 8.9 minutes (FIG. 20 panel b) and a lambda max of 239 nm (FIG. 20 panel c) that was not observed in the control pUC19 bacterial lysate incubated with 100 μM cholestenone (CN) for 24 hours. Incubation of the KshAB bacterial lysate with 100 μM C4-$^{14}$C labeled progesterone (PD) ($\lambda_{max}$: 245 nm; $t_r$=13.8 min) resulted in the formation of C4-$^{14}$C labeled 9-hydroxypregn-4-ene-3,20-dione (9-OHPD) ($\lambda_{max}$: 245 nm; $t_r$=5.2 min) (FIG. 21). The 9-hydroxypregn-4-ene-3,20-dione (9-OHPD) product demonstrated a unique retention time of 5.2 minutes (FIG. 21 panel b) and a lambda max of 245 nm (FIG. 21 panel d) that was not observed in the control pUC19 bacterial lysate incubated with 100 μM C4-14C labeled progesterone (PD) for 24 hours. Analysis of C4-$^{14}$C scintillation events confirmed that production of radiolabeled 9-hydroxypregn4-ene-3,20-dione (9-OHPD) is concomitant to the reduction of C4-$^{14}$C progesterone (PD) (FIG. 21 panel c). This data confirms that humanized KshAB can be heterologously expressed in *E. coli* as an active enzyme, but its activity is moderately affected by the presence of the cholesterol side chain.

Figure 22:
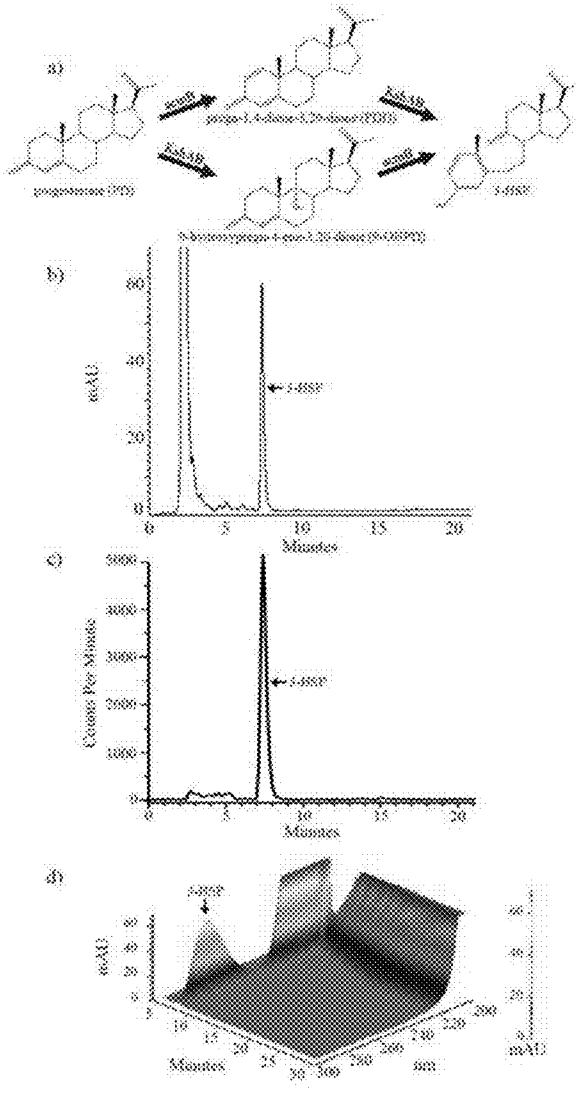
FIG. 22. RP-HPLC analysis of 3-hydroxy-9,10-seco-pregn-1,3,5(10)-triene-9,20-dione (3-HSP) formation from progesterone (PD) utilization by *E. coli* clarified lysates expressing humanized anoxic cholesterol metabolism B enzyme (acmB) and 3-ketosteroid 9α-hydroxylase (KshAB). (Panel a) Reaction overview of 3-HSP formation from PD ring-A C1-C2 desaturation and ring-B C9 hydroxylation by acmB and KshAB, respectively. Representative (Panel b) 2-D chromatogram (λ280 nm), (Panel c) C4-$^{14}$C scintillation events, and (Panel d) 3-D chromatogram from acmB and KshAB bacterial lysates following incubation with 6.28 μg (100 μM) progesterone spiked with 40 nCi C4-$^{14}$C labeled PD ($\lambda_{max}$: 245 nm; $t_r$=13.8 min) for 24 hours. (Panel b) Analysis of acmB and KshAB lysates shows complete reduction in PD and formation of 3-HSP ($\lambda_{max}$: 280 nm; $t_r$=7.2 min) within 24 hours. (Panel c) Analysis of C4-$^{14}$C scintillation events confirms that production of radiolabeled 3-HSP is concomitant to the reduction of C4-$^{14}$C PD. Lastly, (Panel d) the 3-D chromatogram reinforces that together, acmB and KshAB have the ability to desaturate the ring-A C1-C2 bond and hydroxylate the ring-B C9 of PD to produce a new peak with a unique $\lambda_{max}$ and $t_r$ that is not observed in the control pUC19 lysate.
Figure 23:
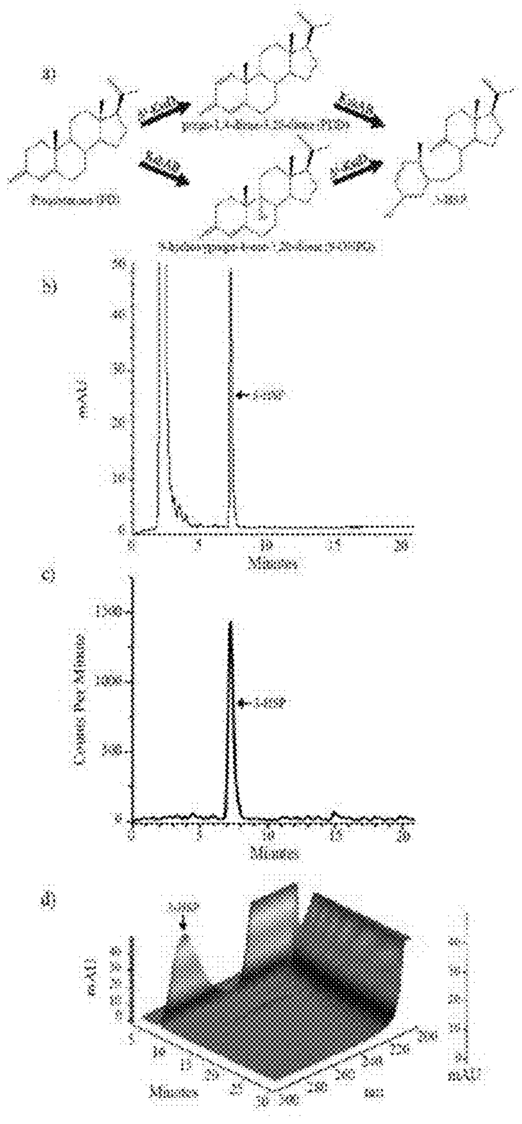
FIG. 23. RP-HPLC analysis of 3-hydroxy-9,10-seco-pregn-1,3,5(10)-triene-9,20-dione (3-HSP) formation from progesterone (PD) utilization by *E. coli* clarified lysates expressing humanized 3-ketosteroid $\Delta^1$-dehydrogenase ($\Delta^1$-KstD) and 3-ketosteroid 9α-hydroxylase (KshAB). (Panel a) Reaction overview 3-HSP formation from PD ring-A C1-C2 desaturation and ring-B C9 hydroxylation by $\Delta^1$-KstD and KshAB, respectively. Representative (Panel b) 2-D chromatogram (λ280 nm), (Panel c) C4-$^{14}$C scintillation events, and (Panel d) 3-D chromatogram from $\Delta^1$-KstD and KshAB bacterial lysates following incubation with 6.28 μg (100 μM) progesterone spiked with 40 nCi C4-$^{14}$C labeled PD ($\lambda_{max}$: 245 nm; $t_r$=13.8 min) for 24 hours. (Panel b) Analysis of $\Delta^1$-KstD and KshAB lysates shows complete reduction in PD and formation of 3-HSP ($\lambda_{max}$: 280 nm; $t_r$=7.2 min) within 24 hours. (Panel c) Analysis of C4-$^{14}$C scintillation events confirms that production of radiolabeled 3-HSP is concomitant to the reduction of C4-$^{14}$C PD. Lastly, (Panel d) the 3-D chromatogram reinforces that together, $\Delta^1$-KstD and KshAB have the ability to desaturate the ring-A C1-C2 bond as well as hydroxylate the ring-B C9 of PD to produce a new peak with a unique $\lambda_{max}$ and $t_r$ that is not observed in the control pUC19 lysate.

To characterize the production of 3-hydroxy-9,10-seco-pregn-1,3,5(10)-triene9,20-dione (3-HSP), the bacterial lysates expressing acmB (FIG. 22) or $\Delta^1$-KstD (FIG. 23) were combined with KshAB and incubated with 100 μM C4-14C labeled progesterone (PD) ($\Delta_{max}$: 245 nm; $t_r$=13.8 min) for 24 hours. Reactions containing acmB and KshAB (FIG. 22) or $4^1$-KstD and KshAB (FIG. 23) resulted in exhaustion of the progesterone (PD) substrate with concomitant formation of a new product with a unique retention time of 7.2 minutes and a lambda max of 280 nm that was not observed in the control pUC19 bacterial lysate following incubation with 100 μM C4-$^{14}$C labeled progesterone (PD) for 24 hours. Analysis of C4-$^{14}$C scintillation events confirms that production of radiolabeled 3-HSP is concomitant to the reduction of C4-$^{14}$C progesterone (PD) (FIG. 22 panel c and 23 panel c). This data confirms that the combined activities of humanized acmB and KshAB or $\Delta^1$-KstD and KshAB lead to the formation of the novel metabolite, 3-HSP.

Figure 24:
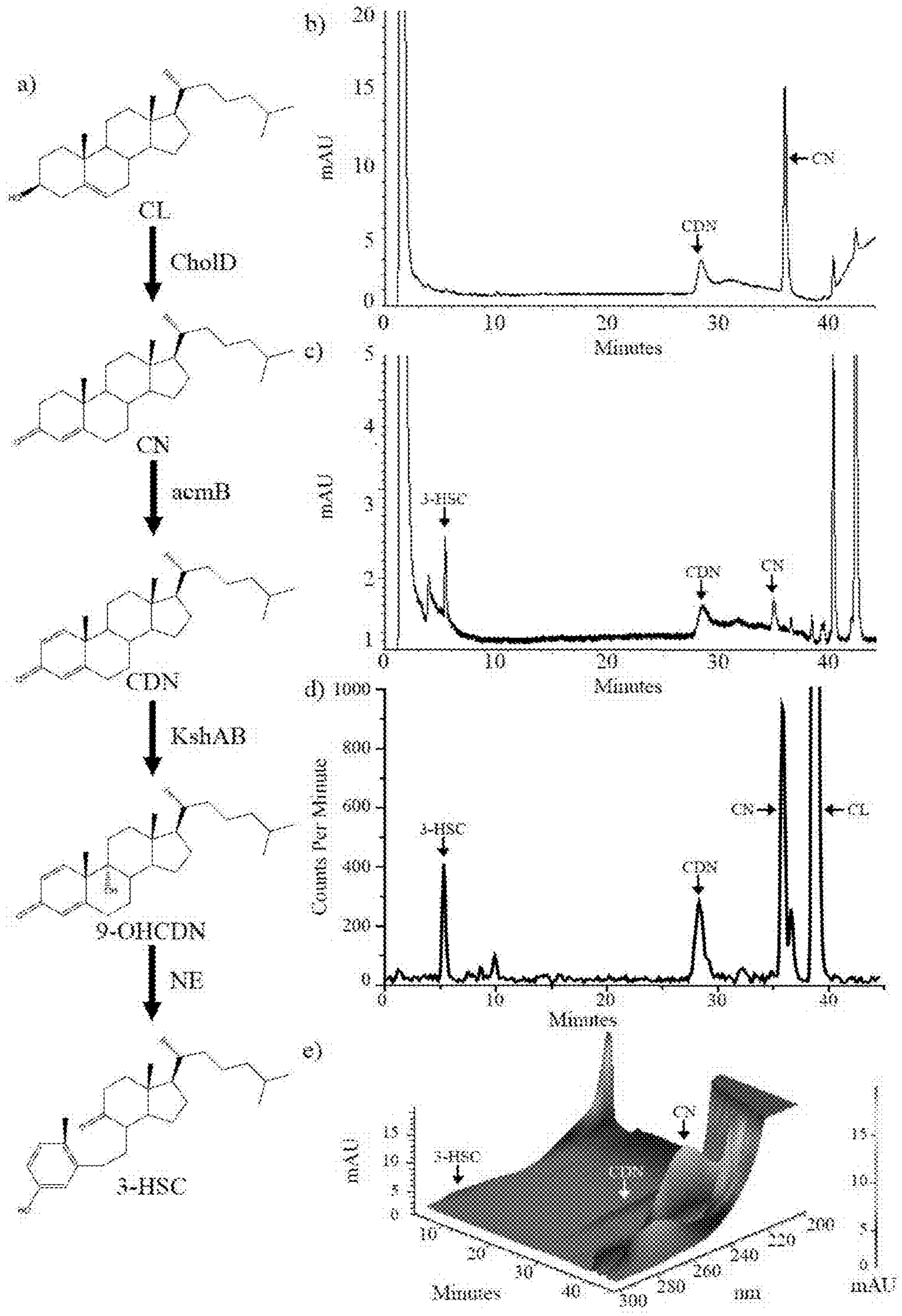
FIG. 24. RP-HPLC analysis of 3-hydroxy-9,10-secocholestene-1,3,5(10)-triene-9-one (3-HSC) formation from cholesterol (CL) utilization by *E. coli* clarified lysates independently expressing humanized cholesterol dehydrogenase (CholD), anoxic cholesterol metabolism B enzyme (acmB) and 3-ketosteroid 9α-hydroxylase (KshAB). (Panel a) Reaction overview 3-HSC formation from CL ring-A 3p-hydroxyl oxidation, ring-A C1-C2 desaturation, and ring-B C9 hydroxylation by CholD, acmB, and KshAB, respectively. Representative (Panel b) 2-D chromatogram (λ239 nm), (Panel c) 2-D chromatogram (λ280 nm), (Panel d) C4-$^{14}$C scintillation events, and (Panel d) 3-D chromatogram from a mixed reaction of CholD, acmB, and KshAB bacterial lysates incubated with 11.60 μg (100 μM) cholesterol spiked with 100 nCi C4-$^{14}$C labeled CL ($\lambda_{max}$: <200 nm; $t_r$=38.9 min) for 24 hours. (Panels b & c) Analysis of CholD, acmB, and KshAB lysates shows formation of cholestenone (CN) ($\lambda_{max}$: 239 nm; $t_r$=36.0 min), choleste-1,4-diene-3-one (CDN) ($\lambda_{max}$: 241 nm; $t_r$=29.5 min), and 3-hydroxy-9,10-secocholestene-1,3,5(10)-triene-9-one (3-HSC) ($\lambda_{max}$: 280 nm; $t_r$=5.3 min) within 24 hours. (Panel d) Analysis of C4-$^{14}$C scintillation events confirms production of radiolabeled 3-HSC is concomitant to the reduction of C4-$^{14}$C CL. Lastly, (Panel e) the 3-D chromatogram reinforces that when combined, CholD, acmB, and KshAB equip the bacterial lysates with the ability to oxidize the 3β-hydroxyl to a 3-ketone, desaturate the C1-C2 bond of ring-A, and hydroxylate the ring-B C9 of CL, respectively. The presence of all three humanized enzymes equip the bacterial lysates with the ability to produce 3-HSC, a novel compound having a unique $\lambda_{max}$ and $t_r$ that is not observed in the control pUC19 lysate incubated with CL.
Figure 25:
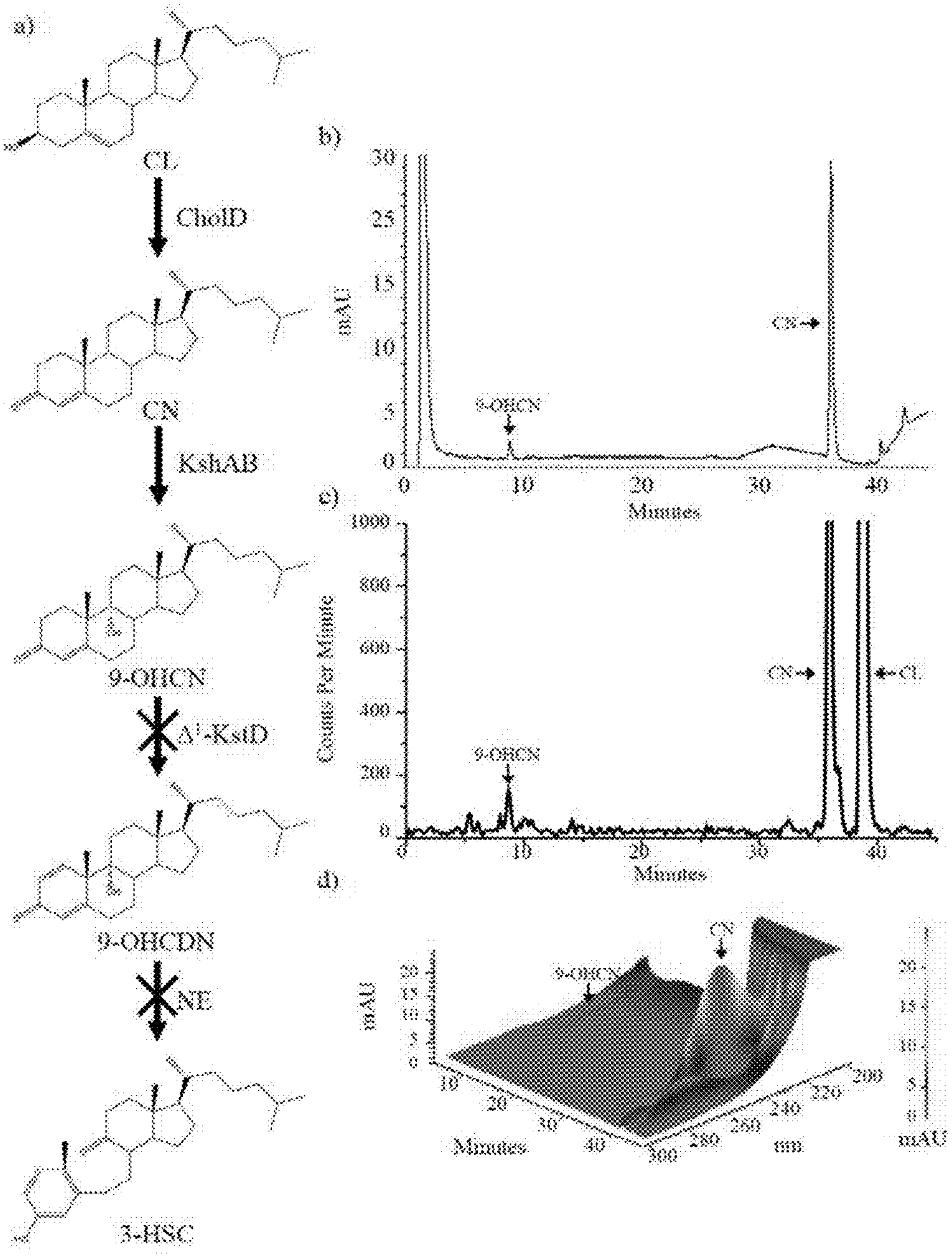
FIG. 25. RP-HPLC analysis of *E. coli* clarified lysates independently expressing humanized cholesterol dehydrogenase (CholD), 3-ketosteroid $\Delta^1$-dehydrogenase ($\Delta^1$-KstD) and 3-ketosteroid 9α-hydroxylase (KshAB) are unable to produce 3-hydroxy-9,10-secocholestene-1,3,5(10)-triene-9-one (3-HSC) from cholesterol (CL). (Panel a) Reaction overview 3-HSC formation from CL ring-A 3p-hydroxyl oxidation, ring-A C1-C2 desaturation, and ring-B C9 hydroxylation by CholD, $\Delta^1$-KstD, and KshAB, respectively. Representative (Panel b) 2-D chromatogram (λ239 nm), (Panel c) C4-$^{14}$C scintillation events, and (Panel d) 3-D chromatogram from a mixed reaction of CholD, $\Delta^1$-KstD, and KshAB bacterial lysates incubated with 11.60 μg (100 μM) cholesterol spiked with 100 nCi C4-$^{14}$C labeled CL ($\lambda_{max}$: <200 nm; $t_r$=38.9 min) for 24 hours. (Panel b) Analysis of CholD, $\Delta^1$-KstD, and KshAB lysates shows formation of cholestenone (CN) ($\lambda_{max}$: 239 nm; $t_r$=36.0 min) and 9-hydroxycholeste-4-ene-3-one (9-OHCN) ($\lambda_{max}$: 239 nm; $t_r$=8.9 min),but not choleste-1,4-diene-3-one (CDN) ($\lambda_{max}$: 241 nm; $t_r$=29.5 min) or 3-hydroxy-9,10-secocholestene-1,3,5(10)-triene-9-one (3-HSC) ($\lambda_{max}$: 280 nm; $t_r$=5.3 min) within 24 hours. (Panel c) Analysis of C4-$^{14}$C scintillation events confirms $\Delta^1$-KstD lacks the ability to desaturate CN due to the presences of the side chain. Lastly, (Panel d) the 3-D chromatogram reinforces that when combined, CholD and KshAB equip the bacterial lysates with the ability to oxidize the 3β-hydroxyl to a 3-ketone and hydroxylate the ring-B C9 of CL, respectively. However, due to the presence of the C17 sidechain, $\Delta^1$-KstD is unable to desaturate the C1-C2 bond of ring-A and thus, the combined bacterial lysates lack the ability to form 3-HSC.

Next, we wanted to determine whether the combined activities of CholD, acmB, $\Delta^1$-KstD, and KshAB could facilitate ring opening starting from the substrate cholesterol. In two separate reactions, CholD, acmB, and KshAB (FIG. 24) or CholD, $\Delta^1$-KstD, and KshAB (FIG. 25) were combined and incubated with 100 μM C4-$^{14}$C labeled cholesterol (CL) ($\lambda_{max}$: <200 nm; $t_r$=38.9 min) for 24 hours. Analysis of the combined CholD, acmB, and KshAB lysates (FIG. 24) shows formation of cholestenone (CN) ($\lambda_{max}$: 239 nm; $t_r$=36.0 min), choleste-1,4-diene-3-one (CDN) ($\lambda_{max}$: 241 nm; $t_r$=29.5 min), and 3-hydroxy-9,10-secocholestene-1,3,5(10)-triene-9-one (3-HSC) ($\lambda_{max}$: 280 nm; $t_r$=5.3 min) within 24 hours. Analysis of C4-$^{14}$C scintillation events confirms production of radiolabeled 3-HSC is concomitant to the reduction of 04-$^{14}$C labeled cholesterol (CL) (FIG. 24 panel c). In contrast, analysis of the CholD, $\Delta^1$-KstD, and KshAB lysates (FIG. 25) shows formation of cholestenone (CN) ($\lambda_{max}$: 239 nm; $t_r$=36.0 min) and 9-hydroxycholeste-4-ene-3-one (9-OHCN) ($\lambda_{max}$: 239 nm; $t_r$=8.9 min), but not choleste1,4-diene-3-one (CDN) ($\lambda_{max}$: 241 nm; $t_r$=29.5 min) or 3-hydroxy-9,10-secocholestene1,3,5(10)-triene-9-one (3-HSC) ($\lambda_{max}$: 280 nm; $t_r$=5.3 min) within 24 hours. Additionally, analysis of C4-$^{14}$C scintillation events confirms Δ1-KstD lacks the ability to desaturate cholestenone (CN), as previously demonstrated (side chain issues), and thus 3 HSC cannot be generated (FIG. 25 panel c). From this data, we have determined that CholD, acmB, and KshAB equip the bacterial lysates with the ability to oxidize the 30-hydroxyl to a 3-ketone, desaturate the C1-C2 bond of ring-A, and hydroxylate the ring-B C9 of CL, respectively. The presence of all three humanized enzymes equip the bacterial lysates with the ability to produce 3-HSC, a novel compound having a unique $\lambda_{max}$ and $t_r$ that is not observed in the control pUC19 lysate incubated with cholesterol (CL) for 24 hours. If $\Delta^1$-KstD is to be used to generate ring opening, removal of the cholesterol side chain may be required.

Cholestenone is Toxic to Cells

Figure 26:
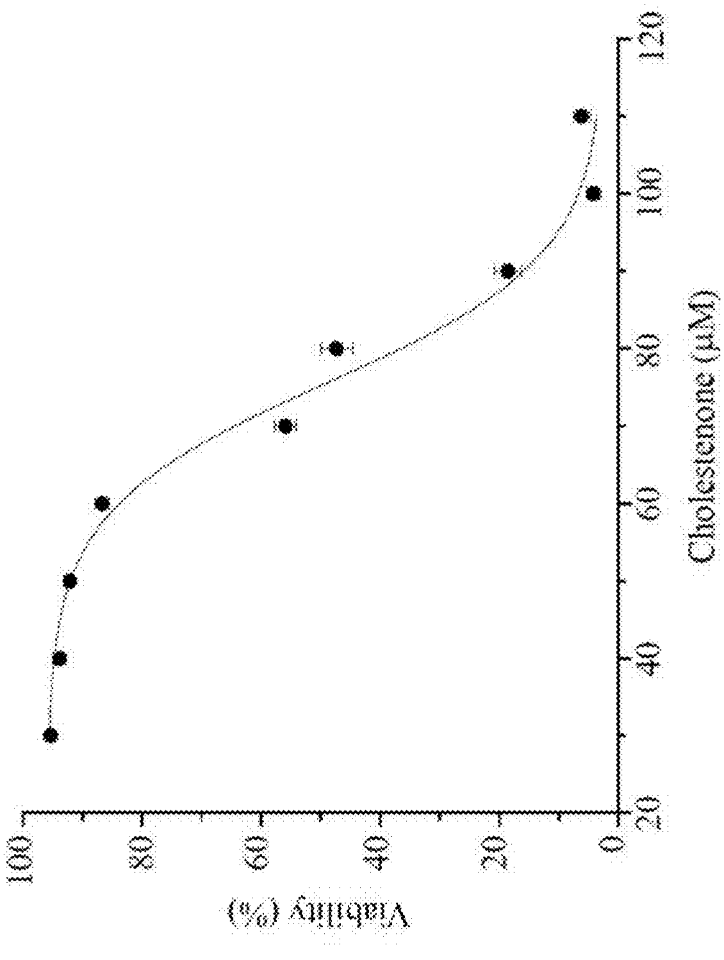
FIG. 26. Cholestenone dose response curve with Hep3B cells. Hep3B cells were seeded ($6\times10^4$ cells/well) to reach 90% confluency on day of treatment. Cells were incubated in 200 μL media A containing 30-110 μM cholestenone for 72 hours. After 48 hours of cholestenone treatment, 120 μM of resazurin was added to each well for an additional 24 hours. Following incubation, the fluorescent intensity of each well was measured at 540±25 ex and 620±40 em with a BioTeKSynergy 2 plate reader. The mean fluorescent intensity from each concentration of cholestenone was graphed as a percent of the maximum fluorescent intensity. Data represents an N of 1 with 8 replicates. Error bars indicate the standard error of the mean.

A key step in developing the enzyme cassette was to determine which enzymes were sufficient in activity to avoid creating bottlenecks that led to the accumulation of toxic intermediates. Cholesterol ring opening may require the 3β-hydroxyl of cholesterol to be oxidized to a 3-ketone by CholD, forming the product cholestenone. Cholestenone, an intermediate degradation product in 3-HSC formation, is known to partition into the plasma membrane and disrupt normal function. To determine the level of toxicity associated with cholestenone, the compound resazurin was used to construct a cell viability curve with Hep3B cells in the presence of increasing concentrations of cholestenone (FIG. 26). The results demonstrate that cholestenone concentrations above 60 μM become detrimental to cell viability. Thus, it is important that cholestenone does not accumulate. To maintain low levels of cholestenone, it is pertinent for the downstream enzymes to be highly efficient in catalyzing their respective reactions. Unfortunately, we found that the activities of acmB and KshAB expressed in eukaryotic cells were not sufficient to maintain low levels of cholestenone, likely due to substrate accessibility issues (data not shown). The toxicity associated with cholestenone is due to the presence of the ring-A 3-ketone and the hydrophobic cholesterol side chain. The 3 ketone is required by the remaining bacterial enzymes to catalyze ring opening and is therefore a necessary catalytic step. However, as demonstrated in the bacterial lysates, the presence of the cholesterol side chain is not required to produce ring opening. Therefore, to reduce the toxicity associated with generating intermediates of cholesterol degradation, we decided to explore side chain removal options using the human P450 FdxR-Fdx fusion protein.

P450-FdxR-Fdx-P2A-HSD2 Expression in U-937-Derived Macrophages

Figure 27:
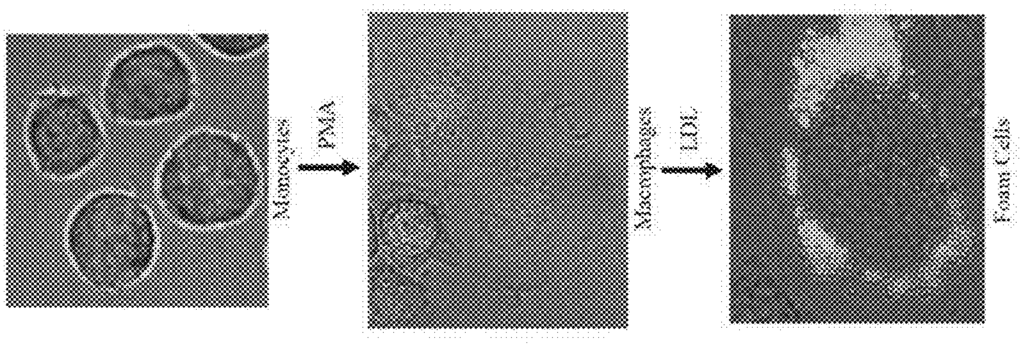
FIG. 27. BODIPY 493/503 stained U-937 derived macrophages and foam cells. U-937 Monocytes were differentiated with 200 nM PMA for 48 hours. PMA was removed and cells were allowed to continue differentiating for three additional days. Five day old macrophages were incubated with 50 μg acLDL for 24 hours. Cells were stained with 1 μg/mL BODIPY 493/503 for 30 min at 37° C. for 30 min and imaged with a Nikon A1 confocal microscope.

The P450-FdxR-Fdx-P2A-HSD2 construct encodes for two separate enzymes. The first enzyme, P450-FdxR-Fdx is a fusion protein consisting of the P450 cholesterol side chain cleavage enzyme (CYP11A), ferredoxin reductase, and ferredoxin. The P450-FdxR-Fdx was modeled after the P450 F2 system designed by the Miller lab (Huang & Miller, 2001). Following the P450-FdxR-Fdx is a Porcine teschovirus-1 2A skipping peptide for co-expression of the second enzyme, 30-hydroxysteroid dehydrogenase 2 (HSD2). The P450-FdxR-Fdx fusion protein catalyzes the conversion of cholesterol into pregnenolone by removal of the cholesterol side chain through three monooxygenase reactions. Once the side chain has been removed, HSD2 can oxidize the 30-hydroxyl of pregnenolone to a 3-ketone to form progesterone. This enzyme construct replaces the need for the bacterial enzyme CholD, and solves the issues of toxicity associated with cholestenone by removing the hydrophobic side chain. To verify the enzyme construct was functional, stable U-937 cell lines were generated using lentivirus as described in methods. U-937 cells are a human leukemic monocyte lymphoma cell line that can be stimulated to differentiate into macrophages. Macrophages express low density lipoprotein receptors (LDL-R) and scavenger receptors (SR), and therefore have the ability to take up extracellular cholesterol in a physiological manner (FIG. 27). Additionally, macrophages are the target cell line we plan to engineer with the cholesterol catabolizing cassette to act as a cellular vehicle for the amelioration of atherosclerotic plaques.

Figure 28:
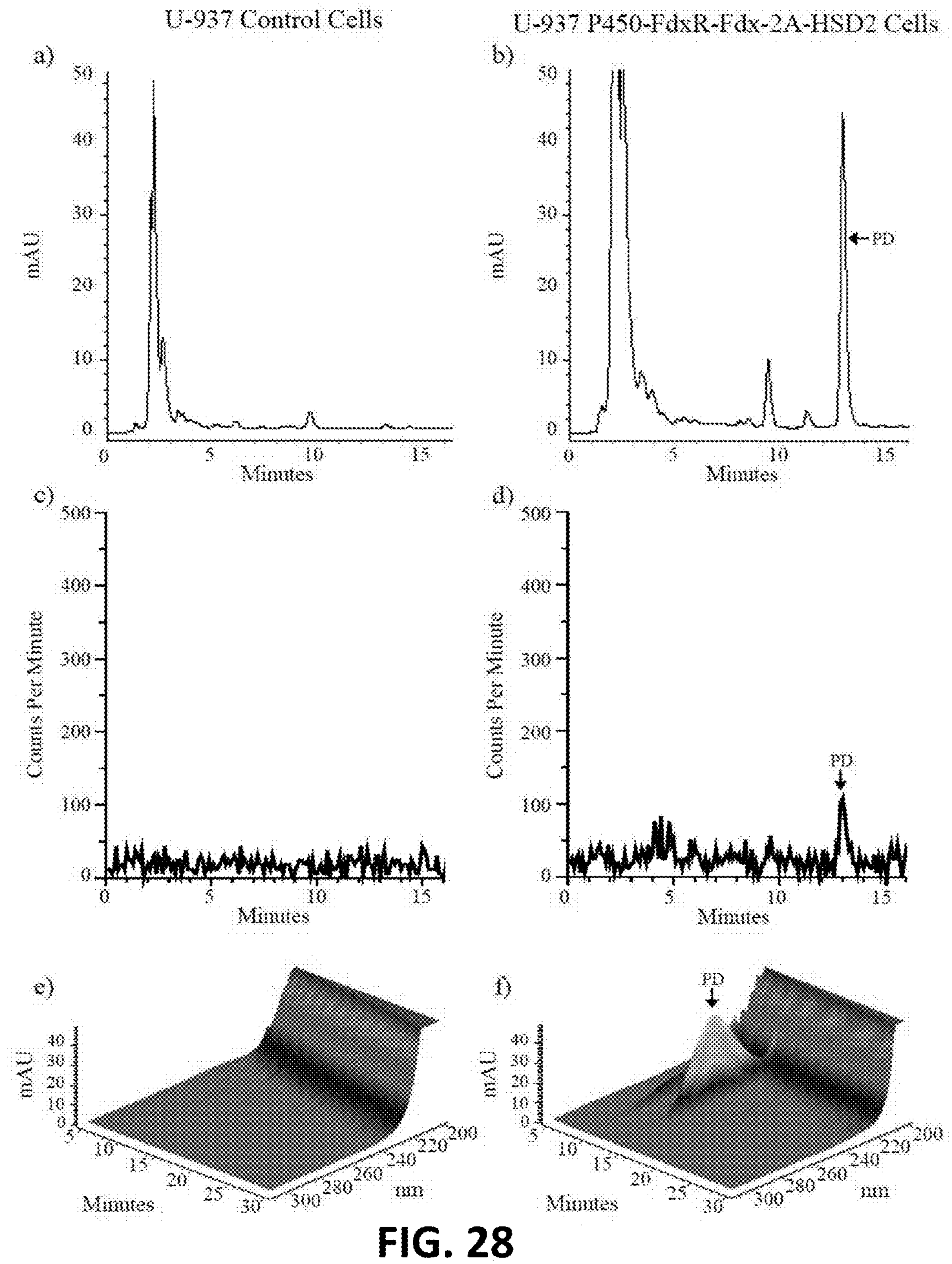
FIG. 28. RP-HPLC analysis of progesterone (PD) product formation from C4-$^{14}$C cholesterol labeled LDLs by P450-FdxR-Fdx-P2A-HSD2 expressing U-937-derived macrophages. Representative 2-D chromatograms of (Panels a & b) λ245 nm, (Panels c & d) C4-$^{14}$C scintillation events, and (Panels e & f) 3-D spectral data from (Panels a, c, & e) control macrophages and (Panels b, d, & f) P450-FdxR-Fdx-2A-HSD2 expressing macrophages incubated with 50 μg C4-$^{14}$C cholesterol labeled LDLs (163 nCi C4-14C cholesterol) for 72 hours. Analysis at (Panel b) λ245 nm reveals P450-FdxR-Fdx-2A-HSD2 macrophages are equipped with the ability to hydrolyze the cholesterol side chain and oxidize the 3β-hydroxyl to a 3-ketone forming PD ($t_r$=13.8 min, $λ_{max}$245 nm) following 72 hours incubation. In contrast, (Panel a) control macrophages lack the ability to convert cholesterol to progesterone at an appreciable amount.

The two enzymes in the P450-FdxR-Fdx-P2A-HSD2 construct were determined to be active by incubating the transgenic U-937-derived macrophages with 50 μg C4-$^{14}$C cholesterol labeled LDLs (163 nCi C4-$^{14}$C cholesterol) for 72 hours (FIG. 28). RP-HPLC analysis reveals the P450-FdxR-Fdx-P2A-HSD2 macrophages are equipped with the ability to hydrolyze the cholesterol side chain and oxidize the 30-hydroxyl to a 3-ketone forming progesterone (PD) ($t_r$=13.8 min, $\lambda_{max}$ 245 nm) following 72 hours incubation (FIG. 28 panels b, d, & f). In contrast, control macrophages lacked the ability to convert cholesterol to progesterone (FIG. 28 panels a, c, & e).

Figure 29:
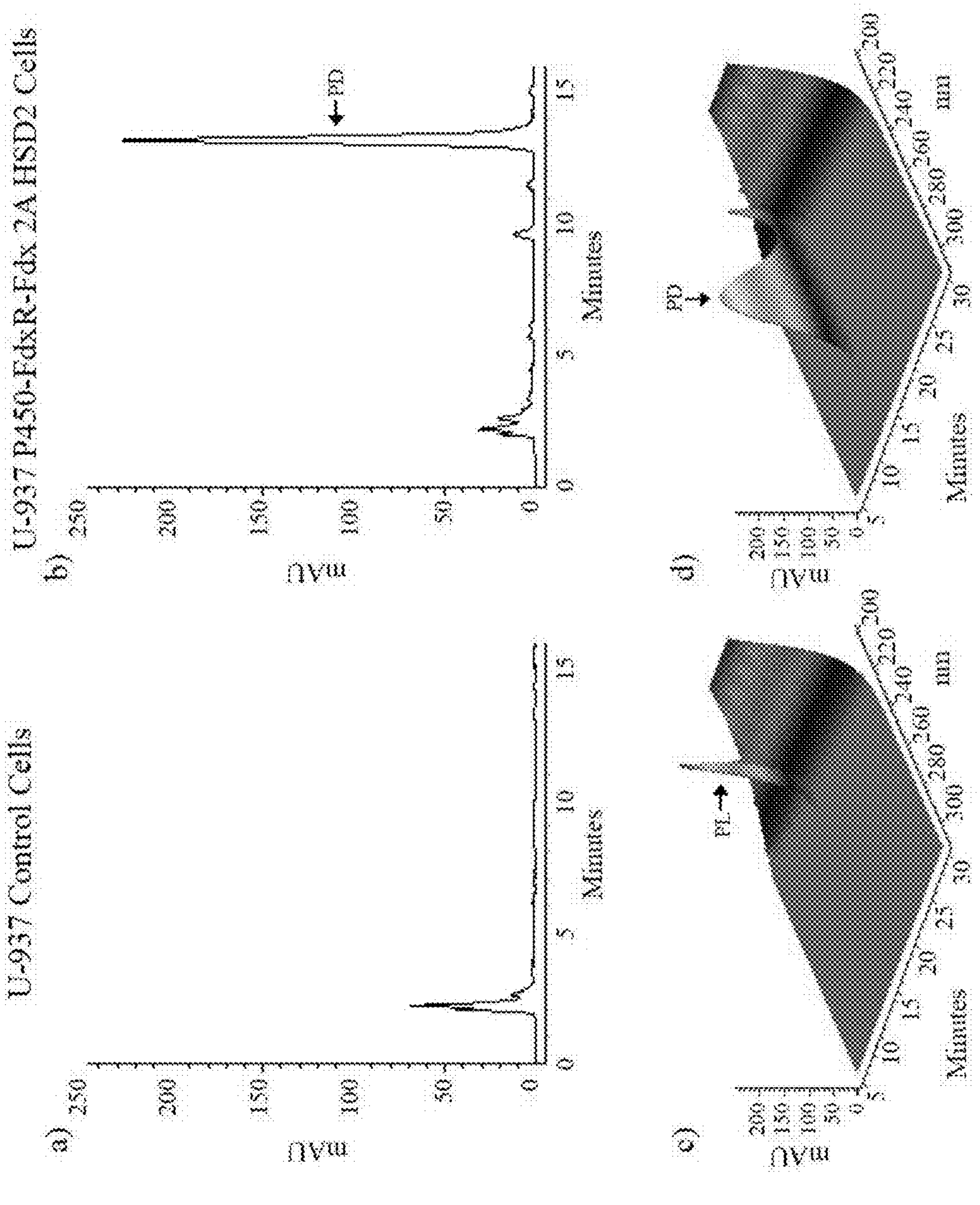
FIG. 29. RP-HPLC analysis of progesterone (PD) product formation from pregnenolone (PL) by P450-FdxR-Fdx 2A HSD2 expressing U-937-derived macrophages. Representative 2-D chromatograms of (Panels a & b) λ245 nm, and (Panels c & d) 3-D spectral data from (Panels a & c) control macrophages and (Panels b & d) P450-FdxR-Fdx-2A-HSD2 expressing macrophages incubated with 15.8 μg pregnenolone (PL) ($λ_{max}$: <200 nm; $t_r$=15.5 min) for 72 hours. Analysis at (Panels b & d) λ245 nm reveals P450-FdxR-Fdx-2A-HSD2 macrophages are equipped with the ability to oxidize the 3p-hydroxyl to a 3-ketone forming PD ($t_r$=13.8 min, $λ_{max}$245 nm) following 72 hours incubation. In contrast, (Panels a & c) control macrophages lack the ability to convert PL to PD.

To determine whether the P450-FdxR-Fdx or HSD2 was the rate limiting enzyme in the conversion of cholesterol to progesterone, the P450-FdxR-Fdx-P2A-HSD2 macrophages were incubated with 15.8 μg (10 μM) pregnenolone (PL) ($\lambda_{max}$: <200 nm; $t_r$=15.5 min) for 72 hours (FIG. 29). Analysis revealed a robust conversion of pregnenolone (PL) to progesterone (PD) ($t_r$=13.8 min, $\lambda_{max}$ 245 nm) by the P450-FdxRFdx-P2A-HSD2 expressing macrophages following the 72 hours incubation (FIG. 29 panels b & d). In contrast, control macrophages lacked the ability to convert pregnenolone (PL) to progesterone (PD) (FIG. 29 panels a & c).

These results suggest that the rate limiting enzyme in the conversion of cholesterol to progesterone is the P450-FdxR-Fdx fusion protein. All subsequent catalytic steps may require side chain removal prior to opening the cholesterol ring. This may place a bottleneck for degrading cholesterol at the first enzymatic step, the removal of the cholesterol side chain by the P450-FdxR-Fdx fusion protein, and thus regulates the remaining enzymes ability to participate in generating cholesterol ring opening.

Purification of $\Delta^1$-KstD

Figure 30:
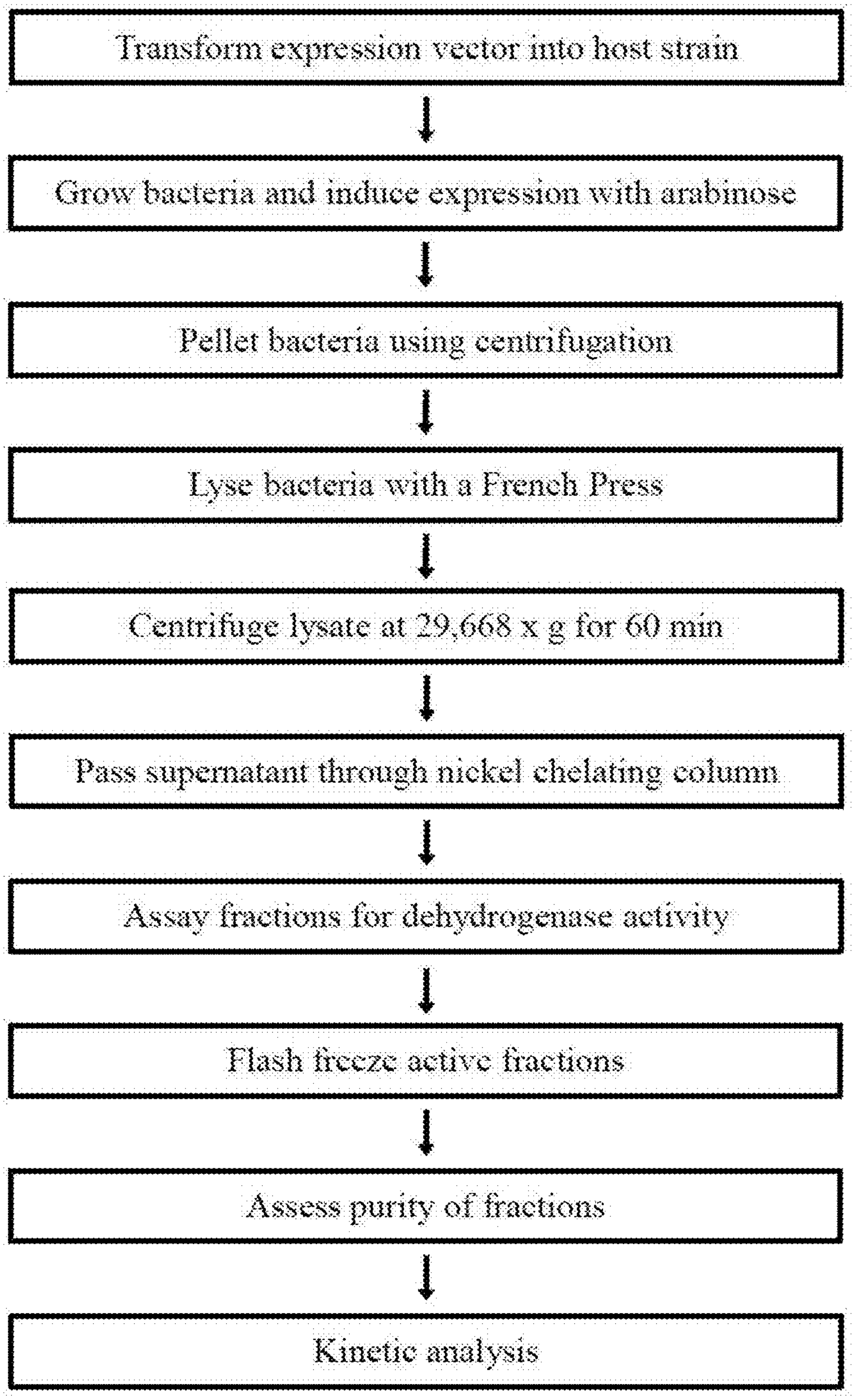
FIG. 30. Purification outline for £$^1$-KstD. The details are described in the section of Materials and Methods, below.
Figure 31:
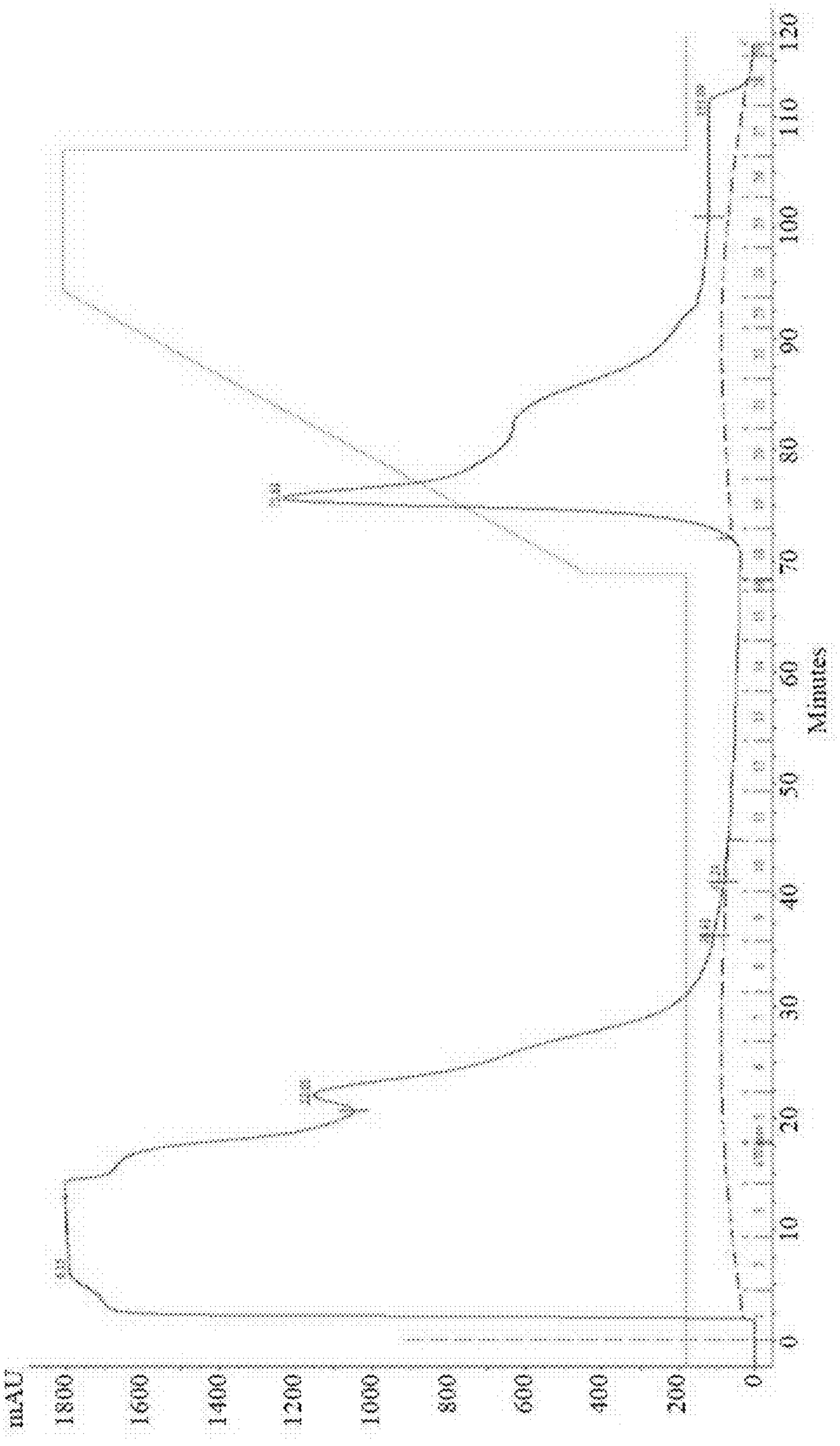
FIG. 31. Chromatogram from Δ$^1$-KstD isolation using immobilized metal affinity chromatography (IMAC). Representative 2-D chromatogram showing the elution profile of the clarified lysate from *E. coli* expressing the HP-Thioredoxin (HP-THX) Δ$^1$-KstD fusion protein. The lysate was loaded onto a 5 mL G.E. HiTrap nickel chelating column using a 50 mL super loop. Protein elution was monitored at λ280 nm and is represented by the blue line. A linear gradient of imidazole, represented by the gold line, was used to elute HP-THX Δ$^1$-KstD. The run begins with a 20 mM imidazole isocratic wash for 150 mL. The first 50 mLs of eluate contained the flow through, and was followed by 100 mL wash. The gradient begins with a 50 mM imidazole step into a 50 mL linear gradient to 200 mM imidazole. The column was washed with 200 mM imidazole for an additional 50 mL before returning to 20 mM imidazole for 20 mL.
Figure 32:
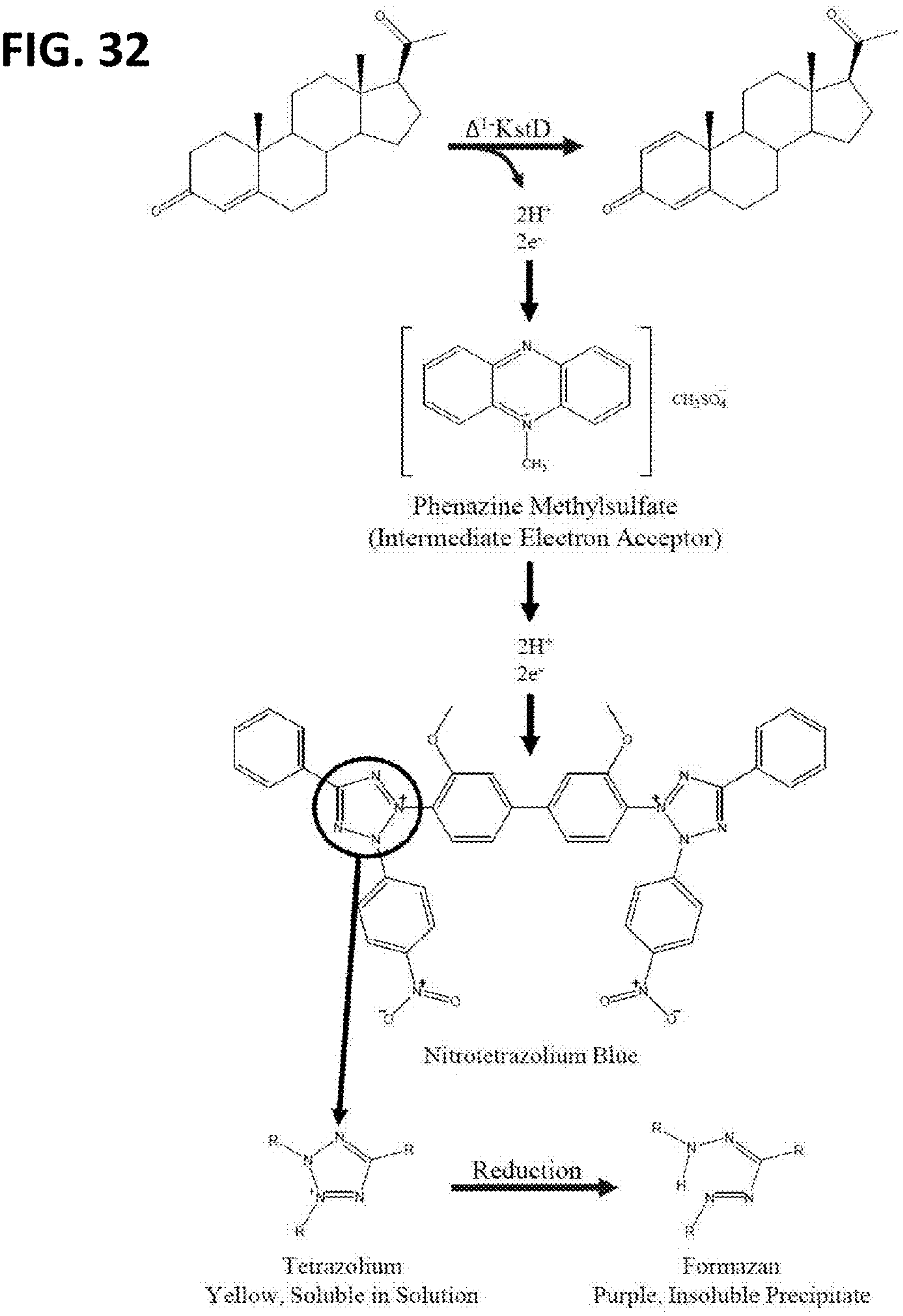
FIG. 32. Nitrotetrazolium blue (NTB) reaction mechanism. The NTB assay is an indirectly coupled redox reaction that allows the assessment of the relative dehydrogenase activity found in each IMAC fraction. The reaction proceeds with the removal of two high energy electrons from progesterone (PD) by Δ$^1$-KstD to form pregn-1,4-diene-3,20-dione (PDD). The electrons are passed from the FADH of Δ$^1$-KstD to the intermediate electron acceptor, phenazine methylsulfate (PMS). PMS relays the electrons to NTB where the center tetrazolium ring is reduced to formazan. The reaction causes NTB, which in the oxidized state forms a soluble yellow solution, to transition into an insoluble purple precipitate at sites where dehydrogenation is occurring. The assay was adapted to be used in a Native-PAGE format to assess the relative dehydrogenase activity of each IMAC fraction.
Figure 33:
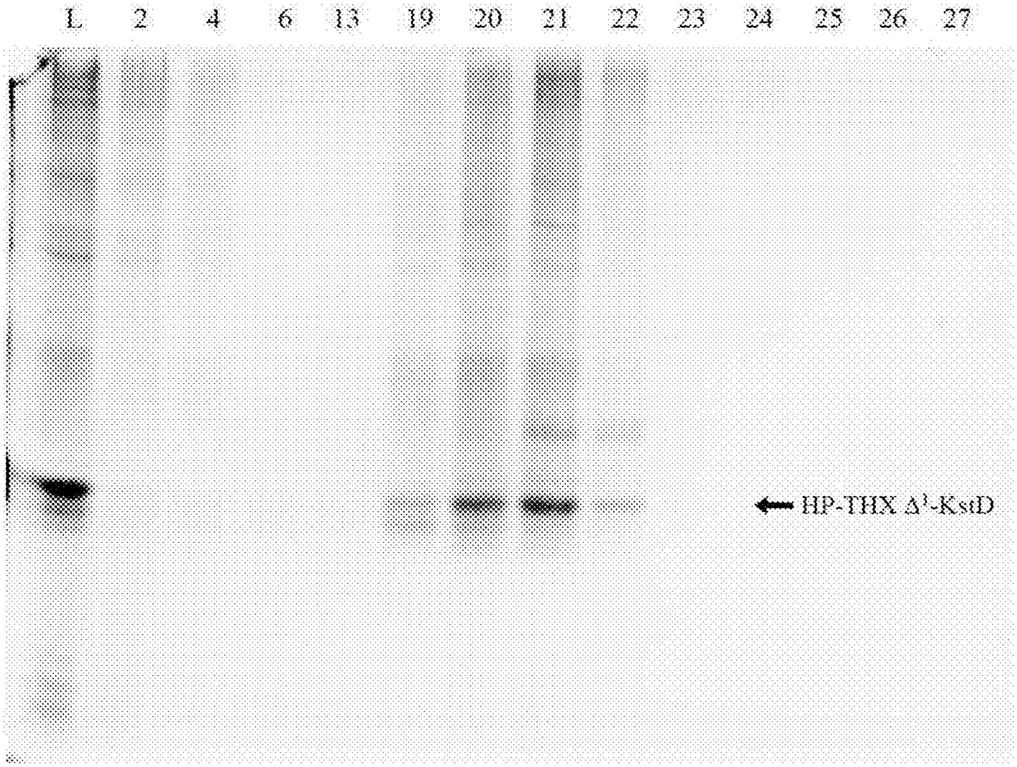
FIG. 33. In-gel nitrotetrazolium blue (NTB) activity assay of fractions collected from the Δ$^1$-KstD isolation by immobilized metal affinity chromatography. Protein samples of the fractions collected from the HiTrap nickel chelating column were mixed with an equal volume of 2× native sample buffer. Equivalent volumes of each fraction were separated using Native-PAGE on a 10% polyacrylamide gel. Δ$^1$-KstD activity was visualized by NTB staining for 5 min. NTB staining buffer consists of 160 nM PMS, 80 nM NTB, 1.5 nM progesterone (PD) in 66.7 mM Tris. Equivalent volumes (5 μL) from the lysate (L), fractions 2, 4, 6, 13, 19, 20, 21, 22, 23, 24, 25, 26, and 27 are shown.

To better characterize one of the downstream enzymes in 3-HSP production, $\Delta^1$-KstD was isolated and its kinetic parameters were determined (Outline of isolation to kinetic analysis of $\Delta^1$-KstD FIG. 30). As previously described, $\Delta^1$-KstD was heterologously expressed in Rosetta2 *E. coli* as an N-terminal His-Patch thioredoxin fusion protein. Following verification $\Delta^1$-KstD could be functionally expressed in *E. coli*, the His-Patch thioredoxin fusion protein (HP-THX) was partially purified by immobilized metal affinity chromatography (IMAC) using an imidazole linear gradient (FIG. 31). The chromatogram, monitoring protein absorption at 280 nm, shows the majority of endogenous *E. coli* proteins eluting in the flow through fractions and a single elongated peak eluting in the linear gradient between 60 and 170 mM imidazole. Relative dehydrogenation activities of the major fractions collected from IMAC were assessed using an in-gel nitrotetrazolium blue assay (NTB) (FIG. 32). The in-gel nitrotetrazolium blue activity assay revealed high amounts of $\Delta^1$-KstD activity in the lysate and elution fractions 19, 20, 21, and 22 (FIG. 33).

Figure 34:
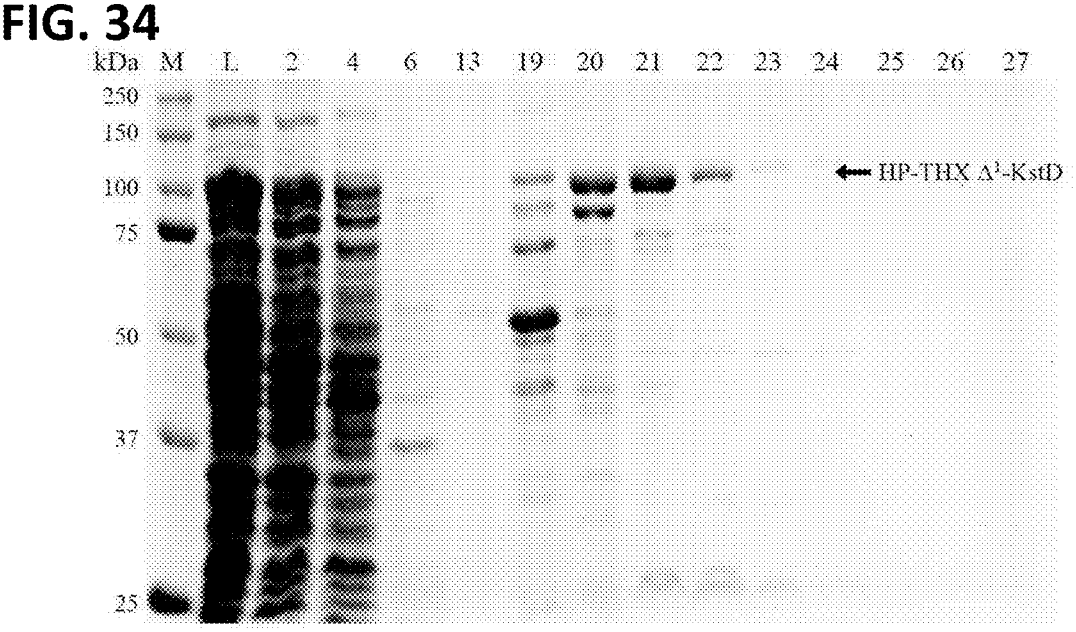
FIG. 34. Coomassie blue stained SDS-PAGE of fractions collected from Δ$^1$-KstD isolation by immobilized metal affinity chromatography. Protein samples of the fractions collected from the HiTrap nickel chelating column were mixed with an equal volume of 2× Laemmli sample buffer, boiled for 5 min, and spun at 15,000×g for 10 min at 4° C. Equivalent volumes of each fraction were separated using SDS-PAGE on a 10% polyacrylamide gel and visualized by Coomassie blue staining. Separated proteins from the lysate (L), fractions 2, 4, 6, 13, 19, 20, 21, 22, 23, 24, 25, 26, and 27 are shown. Elution fraction 21 was selected for further characterization.
Figure 35:
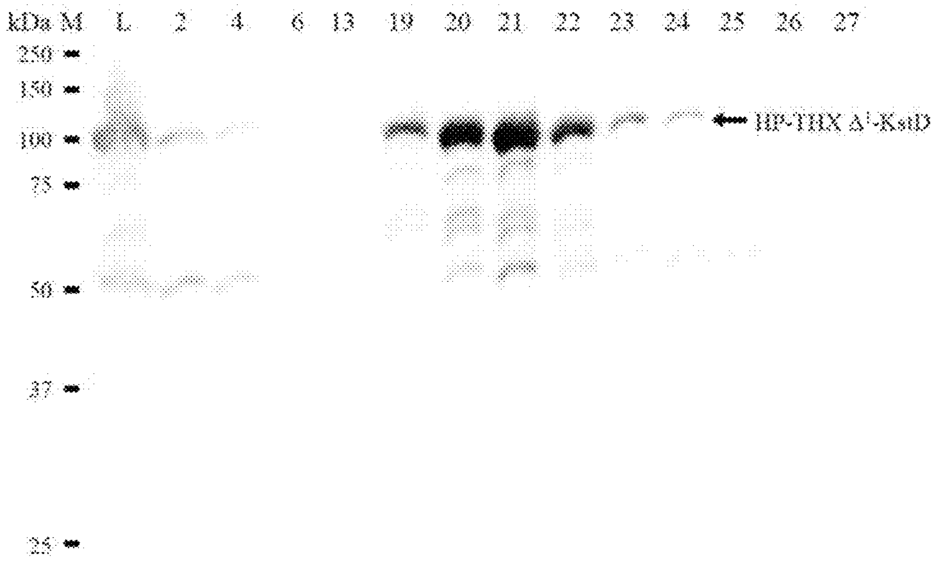
FIG. 35. Western blot analysis of Δ$^1$-KstD isolation from fractions collected by immobilized metal affinity chromatography. Protein samples of the fractions collected from the HiTrap nickel chelating column were mixed with an equal volume of 2×SDS sample buffer, boiled for 5 min, and spun at 15,000×g for 10 min at 4° C. Equivalent volumes of each fraction were separated using SDS-PAGE on a 10% polyacrylamide gel, transferred to a PVDF membrane, and probed with anti-FLAG (1:1000). ECL anti-mouse IgG secondary antibody conjugated to HRP (1:10,000) and SuperSignalWest FemtoSubstrate was used for detection. Separated proteins from the lysate (L), fractions 2, 4, 6, 13, 19, 20, 21, 22, 23, 24, 25, 26, and 27 are shown. Elution fraction 21 was selected for further characterization.
Figure 36:
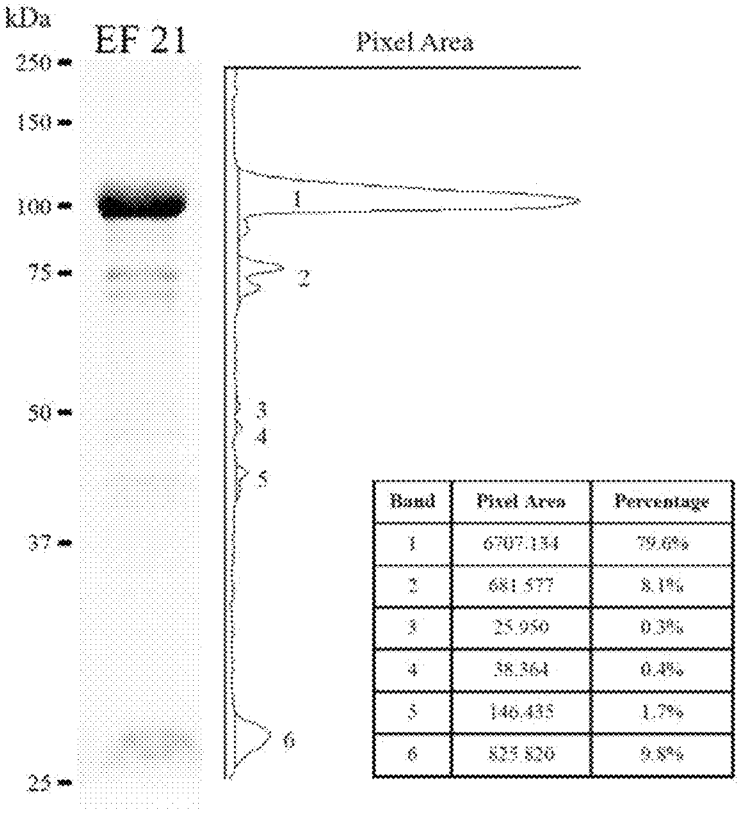
FIG. 36. Yield and purity of isolated Δ$^1$-KstD. Concentration of partially purified Δ$^1$-KstD was determined to be 0.385 mg/mL with 79.6% purity determined by densitometry (ImageJ) of elution fraction (EF) 21 from the coomassie stained SDS-PAGE.

A coomassie stained SDS-PAGE of the lysate, flow through, washes, and elution fractions was made to assess the purity of the collected fractions from IMAC (FIG. 34). The lane containing the clarified lysate shows the total cellular protein. As seen in the chromatogram, a majority of the endogenous *E. coli* protein was unable to bind to the $Ni^{2+}$ chelating column and eluted in the flow through fractions (FT fractions 1-4). The wash fractions demonstrate that the non-bound protein was removed prior to the protein with highest affinity eluted in the linear gradient between 60-170 mM imidazole (elution fractions 19-27). The coomassie stained SDS-PAGE shows the 100 kDa HP-THX-$\Delta^1$-KstD fusion protein eluting over several fractions of the imidazole gradient. $\Delta^1$-KstD was engineered with an N-terminal FLAG tag to identify the enzyme. The anti-FLAG western blot recognized the 100 kDa protein band as the FLAG tagged HP-THX-$\Delta^1$-KstD fusion protein. In addition, a number of lower molecular weight proteins were identified, likely resulting from C-terminal degradation products of $\Delta^1$-KstD (FIG. 35). Elution fraction 21 was assessed to contain a high yield of $\Delta^1$-KstD, relatively low contaminating proteins, and had sufficient activity for further characterization. The concentration of $\Delta^1$-KstD captured in elution fraction 21 was estimated to contain 0.385 mg/mL of $\Delta^1$-KstD with 79.6% purity determined by densitometry from the Coomassie stained SDS-PAGE (FIG. 36). The HP-THX-$\Delta^1$-KstD captured in elution fraction 21 was eluted in 25 mM Tris-HCl, pH 7.5, containing 500 mM NaCl and 120 mM imidazole.

Figure 37:
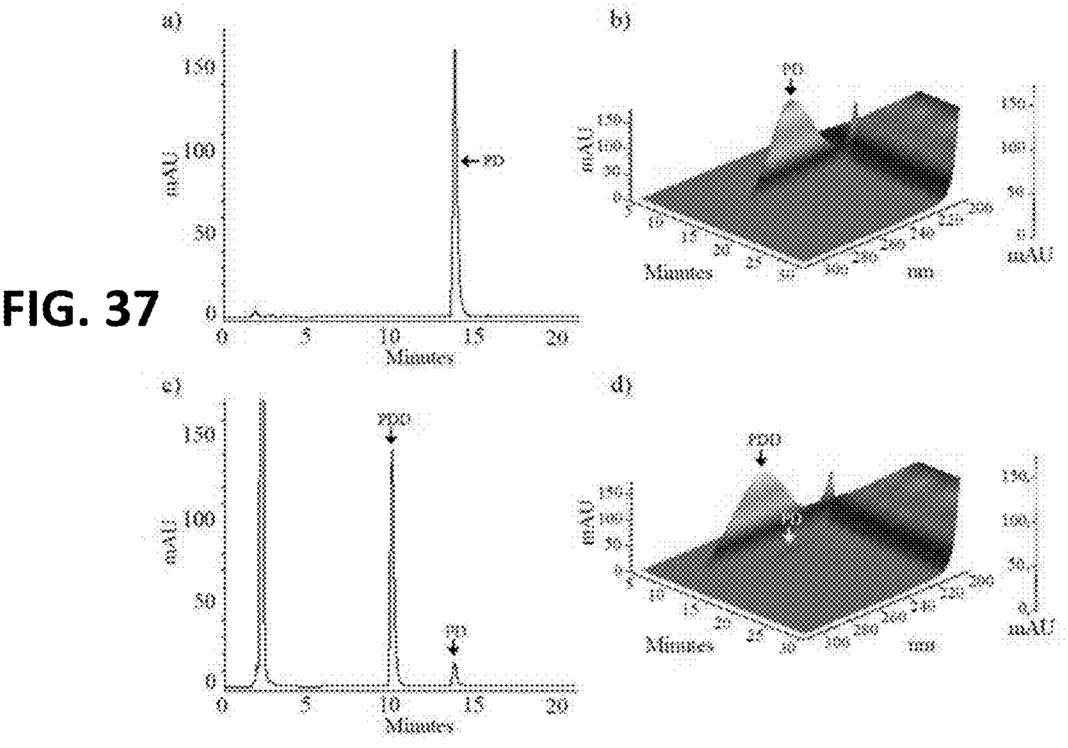
FIG. 37. RP-HPLC analysis of pregn-1,4-diene-3,20-dione (PDD) formation from progesterone (PD) desaturation by isolated Δ$^1$-KstD. Representative 2-D chromatograms and 3-D spectral data from (Panels a & b) 6.29 μg PD analytical standard and (Panels c & d) an isolated Δ$^1$-KstD reaction containing 770 ng of enzyme incubated with 6.29 μg PD for four hours at 37° C. (Panels c & d) Results reveal a diminished absorbance maximum at the retention time typical of the substrate PD ($λ_{max}$: 245 nm, $t_r$=13.8 min) and formation of the product PDD ($λ_{max}$: 247 nm, $t_r$=10.0 min) by RP-HPLC-based analysis. Within four hours, Δ$^1$-KstD converted 90% of the substrate PD to PDD. This data demonstrates that the enzyme isolated from IMAC is in fact Δ$^1$-KstD and is highly active.

To validate $\Delta^1$-KstD was responsible for the activity observed in the NTB assay, 0.77 μg of the partially purified protein was incubated for four hours at 37° C. with the substrate progesterone (PD). Following incubation, the reaction was extracted and analyzed by RP-HPLC (FIG. 37). The RP-HPLC analysis revealed a diminished absorbance maximum at the retention time typical of the substrate progesterone (PD) ($\lambda_{max}$: 245 nm, $t_r$=13.8 min) and formation of the product pregn-1,4-diene-3,20-dione (PDD) ($\lambda_{max}$: 247 nm, $t_r$=10.0 min). Within four hours, $\Delta^1$-KstD converted approximately 90% of the progesterone (PD) substrate to pregn-1,4-diene-3,20-dione (PDD). This data demonstrates that the enzyme isolated from IMAC is in fact $\Delta^1$-KstD and is highly active.

Measurement of $\Delta^1$-KstD Activity Using Progesterone (PD) and Resazurin

Figure 38:
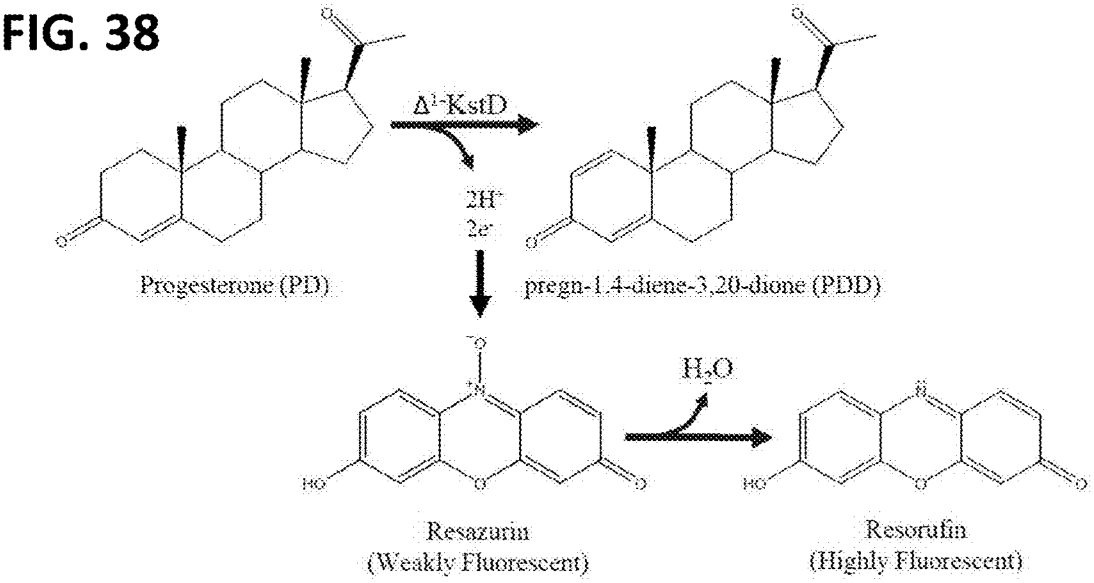
FIG. 38. Resazurin reaction mechanism. Resazurin, a weakly fluorescent redox dye, is irreversibly reduced upon accepting electrons removed from the desaturation of progesterone's (PD) ring-A C1-C2 bond by Δ$^1$-KstD. Resazurin's center ring has an electronegative oxygen pulling the lone pair electrons from nitrogen, forming a zwitterion. Once the oxygen is reduced by the electrons released from the desaturation of progesterone (PD), water acts as a leaving group freeing the lone pair electrons of nitrogen to form the highly fluorescent compound, resorufin. Unlike indirectly coupled assays that use $NAD_+$, diaphorase, or other intermediate electron acceptors to relay electrons to the redox dye, resazurin is a directly coupled reaction. This assay is unique in that resazurin is able to directly accept the liberated protons, allowing one to measure the rate of substrate desaturation by $\Delta^1$-KstD through the formation of the fluorescent product, resorufin.
Figure 39:
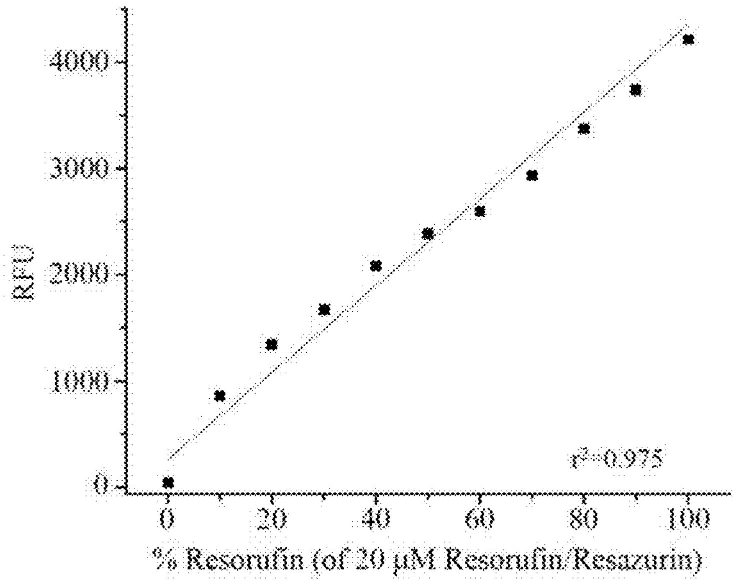
FIG. 39. Resorufin/resazurin standard curve. To best represent the reaction that occurs in the resazurin assay during the desaturation of progesterone (PD) by $\Delta^1$-KstD, several concentrations of resorufin were added to inversely proportional concentrations of resazurin. These values were expressed as a percent of resorufin, totaling to 20 μM resorufin and resazurin. The data shows a linear increase in fluorescence with increasing concentration of resorufin in the presence of decreasing concentrations of resazurin.

To determine $\Delta^1$-KstD's kinetic parameters, I developed a directly coupled fluorometric assay using the compound resazurin. Resazurin, a weakly fluorescent redox dye, is irreversibly reduced upon accepting protons released from a donor molecule. Reduction of resazurin results in the formation of the highly fluorescent product resorufin. In this assay, protons are removed from the 3-ketosteroid substrates ring-A C1-C2 bond by $\Delta^1$-KstD. The $\Delta^1$-KstD FADH cofactor donates the protons to resazurin resulting in the formation of resorufin (FIG. 38). This reduction can be measured by monitoring the increase in fluorescence intensity with time, allowing the assessment of the initial rates of $\Delta^1$-KstD substrate conversion. To demonstrate the linearity of this assay, a standard curve was made by adding several concentrations of resorufin to inversely proportional concentrations of resazurin (FIG. 39).

Figure 40:
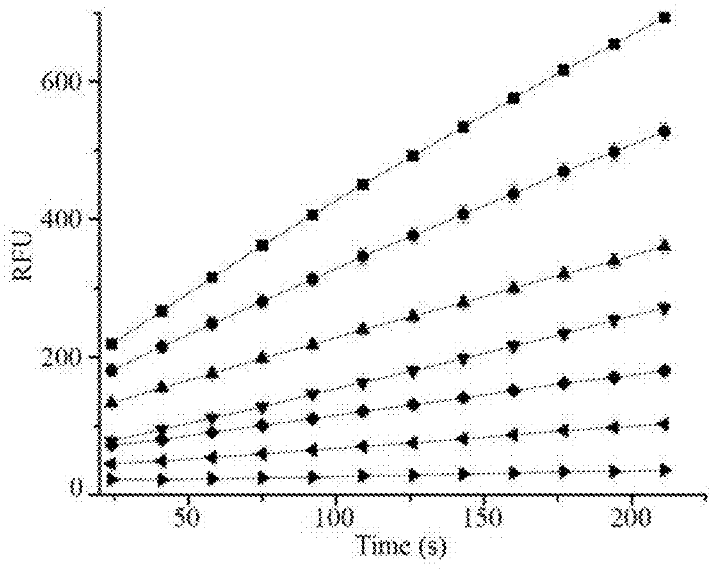
FIG. 40. $\Delta^1$-KstD enzyme titration curves. Effect of $\Delta^1$-KstD enzyme concentration (2.1 nM; square, 1.6 nM; circle, 1.1 nM; upward facing triangle, 0.55 nM; downward facing triangle, 0.37 nM; diamond, 0.19 nM; left facing triangle, and 0.05 nM; right facing triangle) on fluorescent signal (RFU) with respect to time using fixed concentrations of progesterone (20 μM) as substrate and resazurin (20 μM) as the fluorescent electron acceptor. Resorufin fluorescence was measured at 17 sec intervals for 3.5 min. All seven concentrations of $\Delta^1$-KstD demonstrate a linear increase in fluorescence over 3.5 min in the presence of 20 μM progesterone and 20 μM resazurin. Each enzyme titration curve was made with an N of 1 in triplicate.
Figure 41:
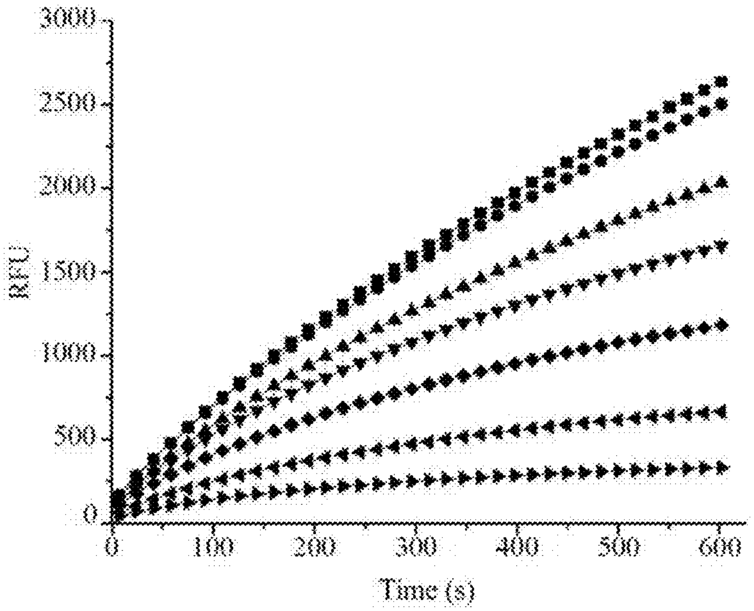
FIG. 41. 1.6 nM $\Delta^1$-KstD enzyme progress curves. Reaction progress curves at fixed concentrations of $\Delta^1$-KstD (1.6 nM), fixed concentrations of resazurin (20 μM), and varying concentrations of progesterone (40 μM; square, 30 μM; circle, 20 μM; upward facing triangle, 10 μM; downward facing triangle, 5 μM; diamond, 2.5 μM; left facing triangle, and 1 μM; right facing triangle). Resorufin fluorescence was measured at 17 sec intervals for 10 minutes. Of the three enzyme progress curves, 1.6 nM $\Delta^1$-KstD demonstrated the lowest linear increase in fluorescence over 10 min in the presence of varying concentrations of progesterone. Each enzyme titration curve was made with an N of 1 with 8 replicates. Error bars indicate the standard error of the mean.
Figure 42:
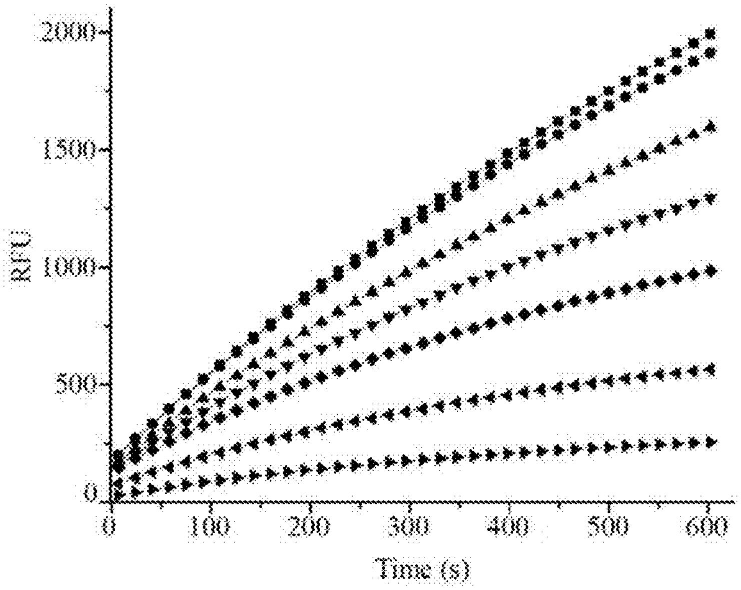
FIG. 42. 1.1 nM $\Delta^1$-KstD enzyme progress curves. Reaction progress curves at fixed concentrations of $\Delta^1$-KstD (1.1 nM), fixed concentrations of resazurin (20 μM), and varying concentrations of progesterone (40 μM; square, 30 μM; circle, 20 μM; upward facing triangle, 10 μM; downward facing triangle, 5 μM; diamond, 2.5 μM; left facing triangle, and 1 μM; right facing triangle). Resorufin fluorescence was measured at 17 sec intervals for 10 minutes. The 1.1 nM $\Delta^1$-KstD enzyme progress curves demonstrated an improvement in fluorescent linearity, as compared to the 1.6 nM $\Delta^1$-KstD enzyme progress curves. Each enzyme titration curve was made with an N of 1 with 8 replicates. Error bars indicate the standard error of the mean.
Figure 43:
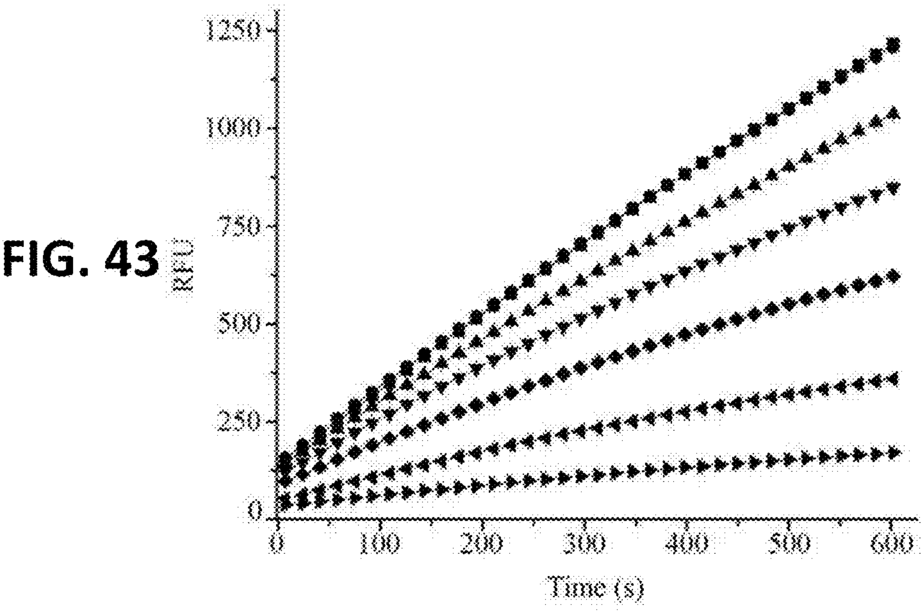
FIG. 43. 0.55 nM $\Delta^1$-KstD enzyme progress curves. Reaction progress curves at fixed concentrations of $\Delta^1$-KstD (0.55 nM), fixed concentrations of resazurin (20 μM), and varying concentrations of progesterone (40 μM; square, 30 μM; circle, 20 μM; upward facing triangle, 10 μM; downward facing triangle, 5 μM; diamond, 2.5 μM; left facing triangle, and 1 μM; right facing triangle). Resorufin fluorescence was measured at 17 sec intervals for 10 minutes. Of the three enzyme progress curves, 0.55 nM $\Delta^1$-KstD demonstrated the highest linearity in fluorescence over the 10 min measurement. Each enzyme titration curve was made with an N of 1 with 8 replicates. Error bars indicate the standard error of the mean.
Figure 44:
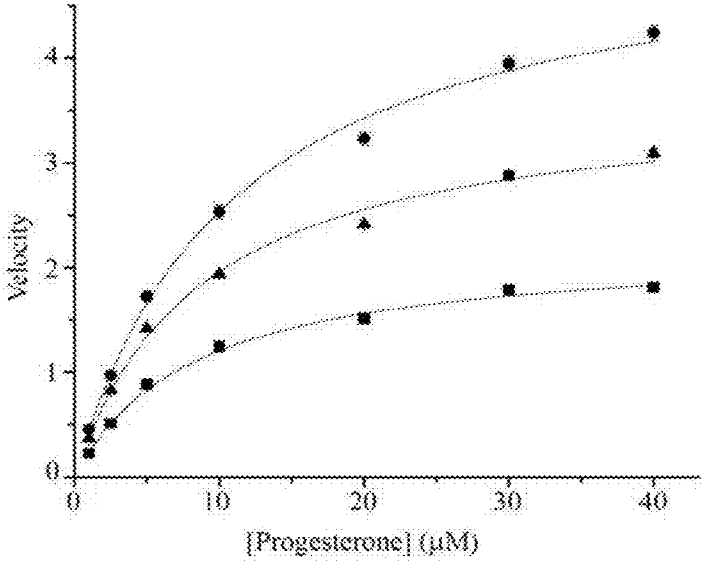
FIG. 44. Kinetic analysis of progesterone C1-C2 A-ring desaturation by $\Delta^1$-KstD. Resorufin fluorescence was measured for each reaction at 17 second intervals for 10 min. Initial velocities of the reactions were determined from the linear portion of the 0.55 nM $\Delta^1$-KstD progress curves by least squares analysis and plotted against the substrate concentration. Data are shown for all $\Delta^1$-KstD progress curves (1.6 nM; circle, 1.1 nM; triangle, and 0.55 nM; square) which were made with 8 replicates at each indicated concentration of progesterone and fixed concentrations of resazurin (20 μM). Error bars indicate the standard error of the mean. $K_m$(8.3+/−0.5 μM) and $V_{max}$(2.2+/−0.05 RFU/sec) were determined by fitting the data to the Michaelis-Menten equation.

Several concentrations of Δ1-KstD (0.05, 0.19, 0.37, 0.55, 1.1, 1.6, 2.12 nM) were assayed to determine the optimal concentration of enzyme required to measure the linear phase of the reaction (FIG. 40). The results show a linear increase in fluorescence with all tested concentrations over 3.5 minutes. Extending the analysis further than 3.5 minutes resulted in a decrease in linearity as enzyme concentration was increased. Enzyme progress curves were made by incubating 1.6 nM (FIG. 41), 1.1 nM (FIG. 42), and 0.55 nM (FIG. 43) $\Delta^1$-KstD with increasing concentrations of progesterone (1, 2.5, 5, 10, 20, 30, 40 μM). The enzyme progress curves using 0.55 nM $\Delta^1$-KstD demonstrated the highest linearity and were used for further analysis. The slopes of each curve were fit to a hyperbola using nonlinear regression (FIG. 44). $\Delta^1$-KstD's $K_m$ (8.3+/−0.5 mM) and $V_{max}$ (2.2+/−0.05 RFU/sec) were determined by fitting the data to the Michaelis-Menten equation. Steady-state kinetics demonstrate $\Delta^1$-KstD is sufficiently active in terms of physiological conditions with progesterone; the expected metabolic intermediate within the cholesterol catabolism pathway.

Figure 45:
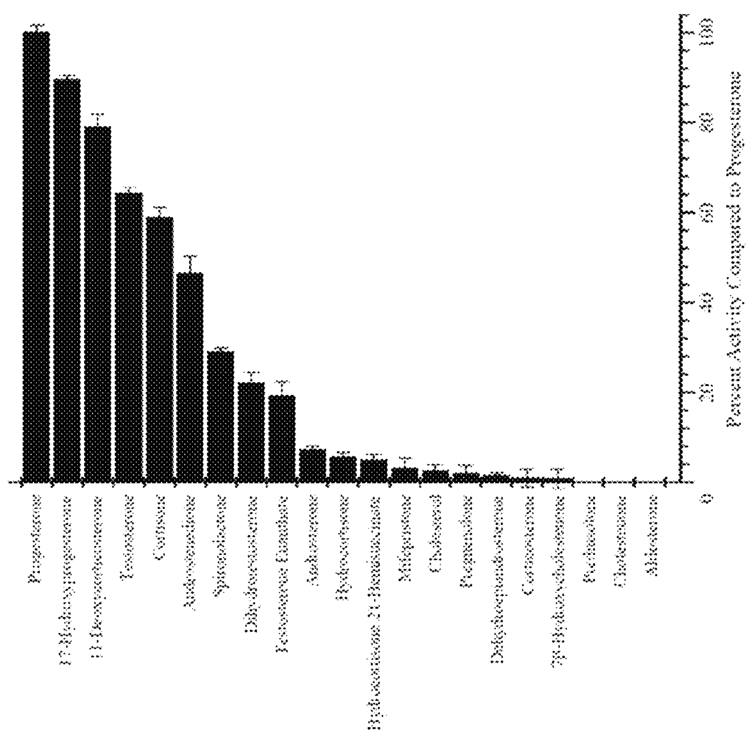
FIG. 45. $\Delta^1$-KstD substrate specificity screen. Substrate preference of $\Delta^1$-KstD was assessed with 21 cholesterol derivatives (pregnane-, adrostane-, and cholestane-based derivatives). Reaction mixtures containing 5.35 nM Δ1-KstD and 0.1 mg/mL BSA (dispensed with a PD syringe) were equilibrated for 30 sec before the reaction was initiated by adding 20 μM resazurin and 20 μM of the steroid substrate. Of the twenty-one substrates screened, eight were found to substrates for $\Delta^1$-KstD. Data reveals $\Delta^1$-KstD requires a 3-ketone on ring-A; $\Delta^1$-KstD specificity exceeds that of the previously established substrate, androstenedione; however, $\Delta^1$-KstD lacks the capability to utilize substrates with long, alkyl C17 side chains. Assay was performed with an N of 1 in quadruplicate.
Figure 46:
FIG. 46. $\Delta^1$-KstD preferred substrates. (Panels a-i) Representative structures of eight substrates $\Delta^1$-KstD demonstrated high activity with from the substrate specificity screen. (Panel a) pregn-4-ene-3,20-dione (progesterone), (Panel b) 4-pregnen-17-ol-3,20-dione (17-hydroxyprogesterone), (Panel c) 4-pregnen-21-ol-3,20-dione (11-deoxy-cortico-sterone), (Panel d) 4-androsten-17β-ol-3-one (testosterone), (Panel e) 4-pregnen-17α,21-diol-3,11,20-trione (cortisone), (Panel f) 4-androsten-3,17-dione (androstenedione), (Panel g) 7α-acetylthio-3-oxo-17α-pregn-4-ene-21, 17-carbolactone (spironolactone), (Panel h) 5α-androstan-17β-ol-3-one (dihydrotestosterone), (Panel i) 17β-hydroxy-4-androsten-3-one 17-enanthate (testosterone enanthate).
Figure 47:
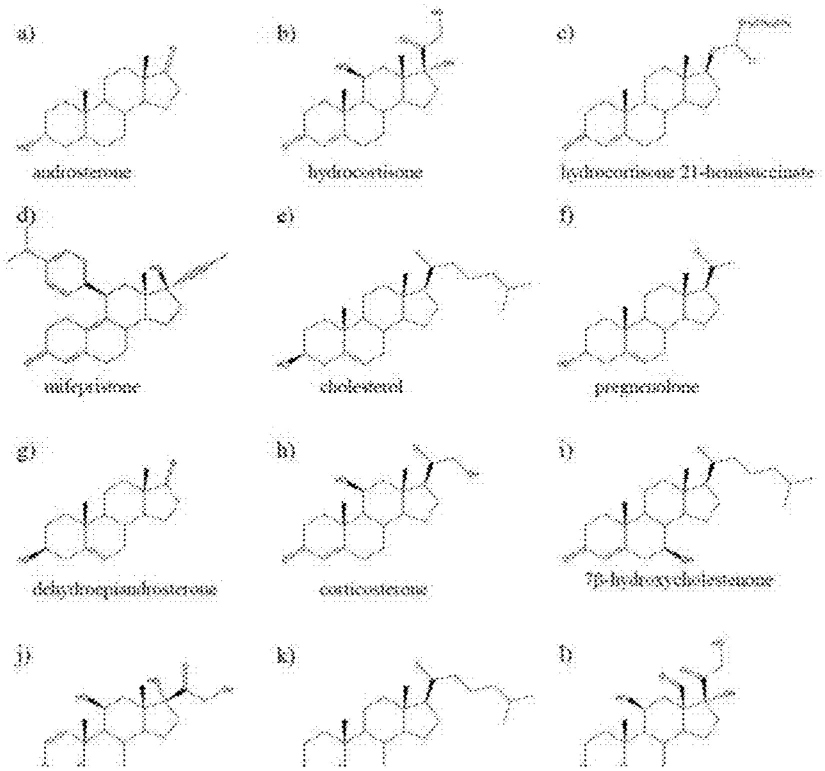
FIG. 47. Poor substrates for $\Delta^1$-KstD. (Panels a-i) Representative structures of twelve substrates from the substrate specificity screen $\Delta^1$-KstD demonstrated little to no activity against. (Panel a) 5α-androstan-3α-ol-17-one (androsterone), (Panel b) (11β)-11,17,21-trihydroxypregn-4-ene-3,20-dione (hydrocortisone), (Panel c) 11β,17α,21-trihydroxy pregnene-3,20-dione 21-hemisuccinate sodium salt (hydrocortisone 21-hemisuccinate), (Panel d) 11β-(4-dimethyl-amino)phenyl-17β-hydroxy-17-(1-propynyl)estra-4,9-dien-3-one (mifepristone), (Panel e) 3β-hydroxy-5-cholestene (cholesterol), (Panel f) 3β-hydroxypregn en-20-one (pregnenolone), (Panel g) 5-androsten-3β-ol-17-one (dehydroepiandrosterone), (Panel h) (11β)-11,21-dihydroxypregn-4-ene-3, 20-dione(corticosterone), (Panel i) 4-Cholesten-7b-ol-3-one (7β-hydroxycholestenone), (Panel j) (11β)-11,17, 21-trihydroxypregna-1,4-diene-3,20-dione (prednisolone), (Panel k) choleste-4-ene-3-one (cholestenone), (Panel I) 11β,21-dihydroxy-3,20-dioxopregn-4-en-18-al (aldosterone).

In addition to determining the kinetic parameters of $\Delta^1$-KstD with the substrate progesterone, the resazurin assay was used to screen an additional 20 cholesterol derivatives. The $\Delta^1$-KstD substrate screen provided insight on the enzymes substrate specificity in regards to variations to the steroid nucleus and side chain. The cholesterol derivatives included a number of pregnane-, androstane-, and cholestane-based compounds. Data shows the percent activity of the 20 screened substrates compared to progesterone (FIG. 45). Of the 21 compounds tested, $\Delta^1$-KstD demonstrated activity with nine substrates (ranked highest to lowest in activity) (FIG. 46): progesterone, 17-hydroxyprogesterone, 11-deoxycorticosterone, testosterone, cortisone, androstenedione, spironolactone, dihydrotestosterone, and testosterone enanthate. Substrates resulting in less than 10% activity compared to $\Delta^1$-KstD's activity with progesterone were considered poor substrates (FIG. 47). Results demonstrate that $\Delta^1$-KstD requires the 3-ketone on ring-A; $\Delta^1$-KstD specificity exceeds that of the previously established substrate, androstenedione (i.e. progesterone); however, $\Delta^1$-KstD lacks the capability to utilize substrates with long alkyl C17 side chains (i.e. cholestenone).

$\Delta^1$-KstD Expression in Hep3B and U-937 Cells

Figure 48:
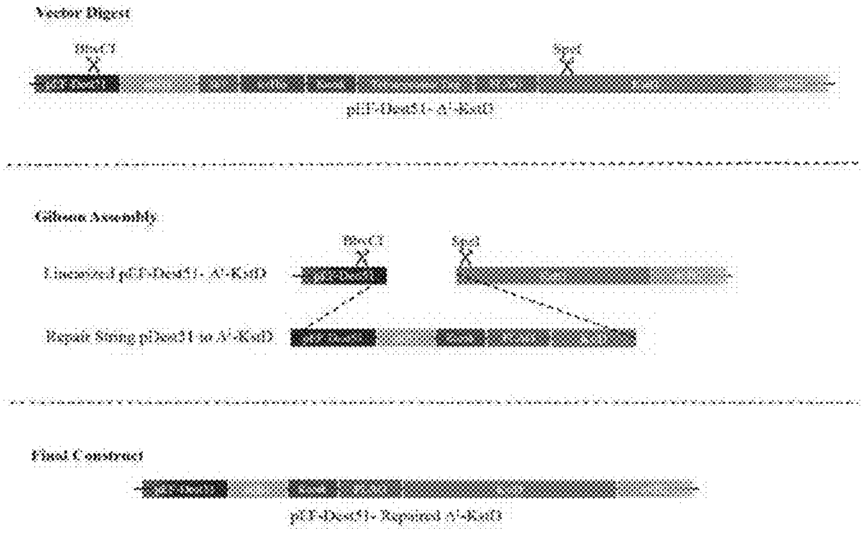
FIG. 48. $\Delta^1$-KstD Kozak Repair using Gibson Assembly. $\Delta^1$-KstD's Kozak consensus sequence was repaired using Gibson Assembly and synthetic DNA. The starting vector was linearized by double restriction enzyme digest to remove the attB1 site, TEV site, 6× His tag, Kozak consensus sequence, tetracysteine tag, and Flag tag. The nucleotide sequence was replaced using synthetic DNA encoding the attB1 site, a new Kozak consensus sequence, and a Flag tag flanked by 40 bp of homology to the backbone vector. The vector was reassembled using Gibson assembly as described in methods.
Figure 50:
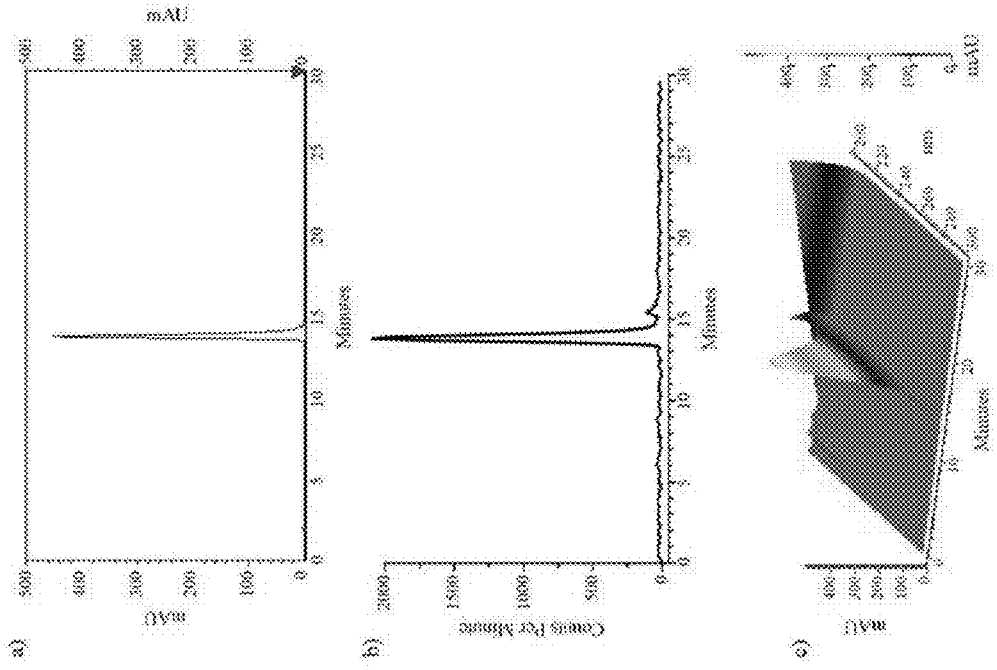
FIG. 50. RP-HPLC analysis of progesterone (PD) spiked with 100 nCi C4-$^{14}$C labeled PD analytical standard. Representative (Panel a) 2-D chromatogram at λ245 nm, (Panel b) C4-$^{14}$C scintillation events, and (Panel c) 3-D spectral data of an 80 μL injection of 15.7 μg PD spiked with 100 nCi C4-$^{14}$C labeled PD in 500 μL HPLC running buffer 2. RP-HPLC analysis reveals the PD substrate has a $\lambda_{max}$ of 245 nm and a 13.8 min retention time ($t_r$).
Figure 49:
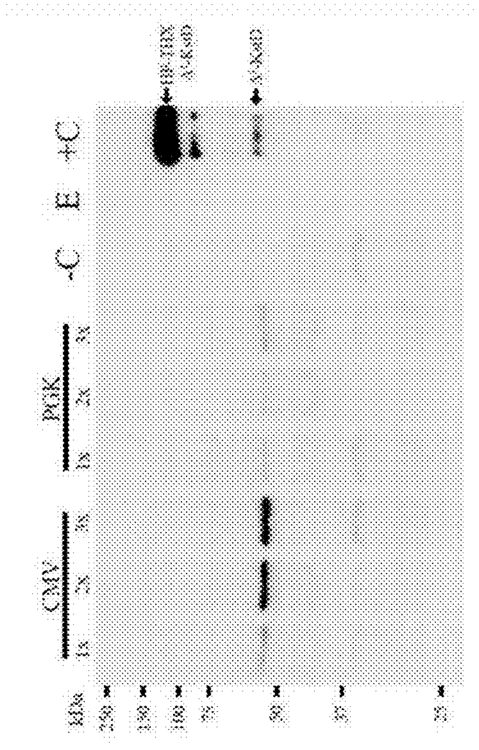
FIG. 49. Western blot analysis of Hep3B cells expressing CMV or PGK driven $\Delta^1$-KstD. Cells were transduced with increasing titers of lentiviral particles encoding $\Delta^1$-KstD. Cells expressing $\Delta^1$-KstD were selected for using blasticidin (CMV) or hygromycin(PGK) antibiotic. Cells were passed into 60 mm dishes, grown to confluency, and collected by scraping in 500 μL RIPA buffer. Cells were mechanically lysedon ice using a syringe with a 27 gauge needle. Protein samples were mixed with an equal volume of 2× Laemmlisample buffer, boiled for 5 min, and spun at 15,000×g for 10 min at 4° C. Protein samples (25 μg) were separated using SDS-PAGE on a 10% polyacrylamide gel, transferred to a PVDF membrane, and probed with anti-FLAG (1:1000). ECL anti-mouse IgG secondary antibody conjugated to HRP (1:10,000) and SuperSignalWest FemtoSubstrate was used for detection. Samples include three representative titers from both CMV and PGK driven $\Delta^1$-KstD Hep3B cells, negative control Hep3B lysate (−C), empty lane (Panel E), and the isolated HP-THX $\Delta^1$-KstD as a positive control (+C).
Figure 52:
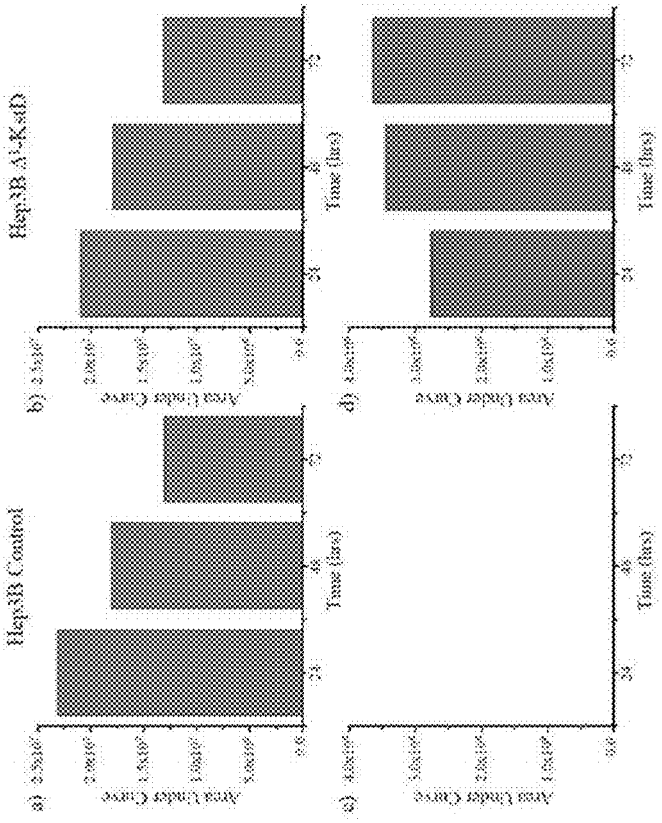
FIG. 52. Quantitative analysis of pregn-1,4-diene-3,20-dione (PDD) product formation from progesterone (PD) C1-C2 ring A desaturation by Hep3B $\Delta^1$-KstD cells. Bar graphs representing the measured area under the curve (AUC) of (Panels a & c) Hep3B control and (Panels b & d) Hep3B $\Delta^1$-KstD cells incubated with 15.7 μg (10 μM) progesterone spiked with 100 nCi C4-$^{14}$C labeled PD. The AUC of PD (Panels a & b) and PDD (Panels c & d) were measured at λ245 nm from 2-D chromatograms at time points: 24, 48, and 72 hours. Quantitative analysis of PDD AUC reveals Hep3B $\Delta^1$-KstD cells are equipped with the ability to desaturate the ring-A C1-C2 bond of PD to form the product PDD. However, Hep3B control cells lack this metabolic capability.
Figure 51:
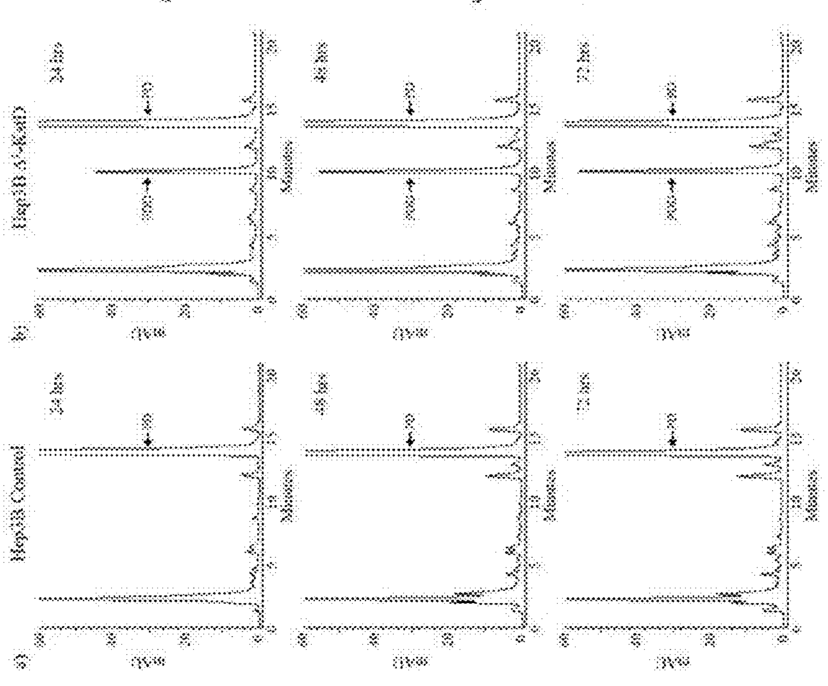
FIG. 51. RP-HPLC analysis of pregn-1,4-diene-3,20-dione (PDD) formation from progesterone (PD) C1-02 ring-A desaturation by Hep3B $\Delta^1$-KstD cells. Representative 2-D chromatograms (λ245 nm; time points: 24, 48, and 72 hours) from (Panel a) Hep3B control and (Panel b) Hep3B $\Delta^1$-KstD cells incubated with 15.7 μg (10 μM) progesterone spiked with 100 nCi C4-$^{14}$C labeled PD (6=13.8 min). Analysis of Hep3B $\Delta^1$-KstD cells shows formation of PDD ($t_r$=10.0 min, $\lambda_{max}$ 247 nm) throughout the 72 hour time course. In contrast, control Hep3B cells lack the ability to desaturate the C1-C2 bond of the pregnane A-ring, as no 10.0 min peak is observed.
Figure 53:
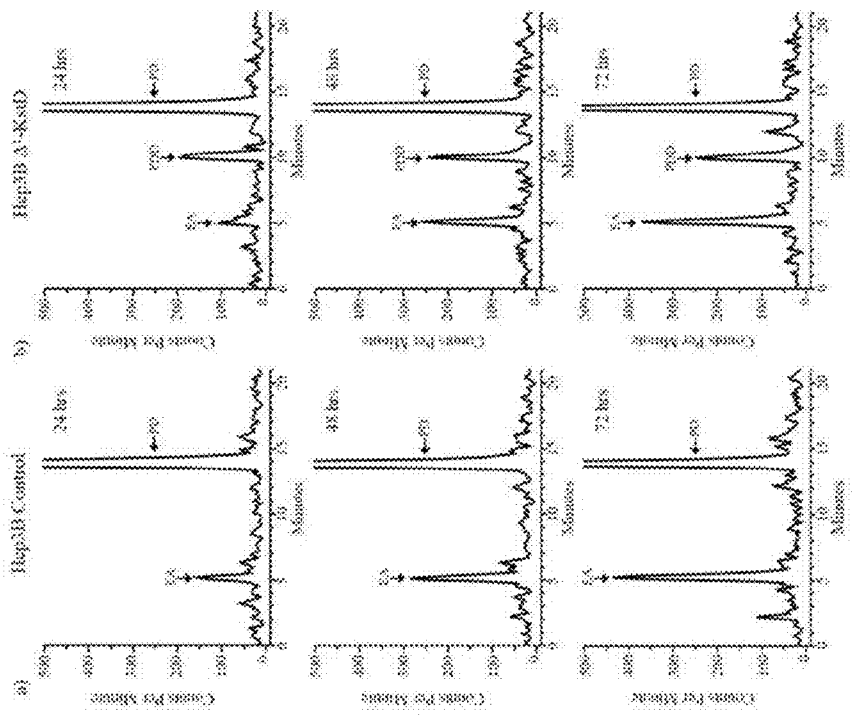
FIG. 53. RP-HPLC analysis of pregn-1,4-diene-3,20-dione (PDD) formation from progesterone (PD) utilization by Hep3B $\Delta^1$-KstD cells. Representative 2-D chromatograms of C4-$^{14}$C scintillation events at 24, 48, and 72 hour time points from (Panel a) Hep3B control and (Panel b) Hep3B $\Delta^1$-KstD cells incubated with 15.7 μg (10 μM) progesterone spiked with 100 nCi C4-$^{14}$C labeled PD ($t_r$=13.8 min). Analysis of Hep3B control and $\Delta^1$-KstD cells reveal reduction in C4-$^{14}$C PD scintillation events over the 72 hour time course for both group of cells. Reduction in the amount of PD in both groups is partially due to unidentified endogenous activity (EA) resulting in the accumulation of a new product peak identified by C4-$^{14}$C scintillation events ($t_r$=5.2 min). However, this new peak lacks an observable absorbance between 200-300 nm. More importantly, concomitant to PD catabolism in Hep3B $\Delta^1$-KstD cells, PDD ($t_r$=10.0 min)accumulates over the 72 hour time course as observed by a new peak forming with a $\lambda_{max}$ of 247 nm and containing C4-$^{14}$C scintillation events. Hep3B control cells lack the ability to catabolize PD to PDD, as seen by the absence of a peak with a 10.0 min retention time.

The original $\Delta^1$-KstD construct expressed poorly in eukaryotic cells due to the Kozak consensus sequence being positioned between a 6×His tag and tetracysteine tag (FIG. 99). For optimal expression of $\Delta^1$-KstD in eukaryotic cells, we modified the original construct by removing the TEV site, 6×His tag, and tetracysteine tag. Using Gibson assembly and a repair string encoding a new Kozak consensus sequence, the $\Delta^1$-KstD construct was repaired (FIG. 48). The repaired $\Delta^1$-KstD construct was subcloned into two lentiviral expression vectors which were used to generate several stable PGK and CMV driven $\Delta^1$-KstD Hep3B cells lines. Expression levels of the PGK and CMV driven $\Delta^1$-KstD were assessed by western blot (FIG. 49). A high level of expression was observed in the 3×CMV $\Delta^1$-KstD cell line, and was subsequently used to assess enzyme activity. $\Delta^1$-KstD expressing Hep3B cells and control non-transduced Hep3B cells were grown to confluency in 60 mm dishes and incubated with 15.7 μg (10 μM) progesterone (PD) spiked with 100 nCi C4-$^{14}$C radiolabeled PD (FIG. 50). Following 24, 48, and 72 hours incubation, the cells and media were extracted with ethyl acetate, and the lipid profiles were analyzed by RP-HPLC. Spectral data from the RP-HPLC analysis of $\Delta^1$-KstD Hep3B cells revealed pregn-1,4-diene-3,20-dione (PDD; $t_r$=10.0 minutes; $\lambda_{max}$ 247 nm) accumulated over the 72 hour time course (FIG. 51 panel b). The retention time and lambda max of the 10.0 minute peak matches the PDD peak identified in the $\Delta^1$-KstD bacterial lysate and partially purified $\Delta^1$-KstD incubated with PD. As expected, Hep3B control cells lacked the metabolic activity to produce PDD, as observed by the absence of a 10.0 minute peak (FIG. 51 panel a). Quantitative analysis of the area under the curve shows that as PD is utilized by $\Delta^1$-KstD Hep3B cells (FIG. 52*b*), a concomitant formation of PDD is observed (FIG. 52 panel d). The decrease in the PD substrate with Hep3B control cells (FIG. 52 panel a) can be explained by analysis of the $^{14}$C scintillation events (FIG. 53 panel a).

Figure 54:
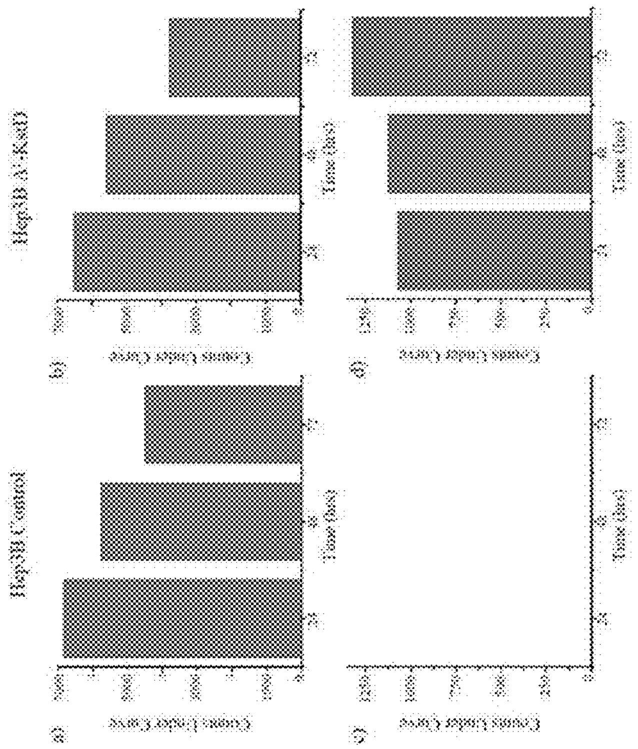
FIG. 54. Quantitative analysis of C4-$^{14}$C scintillation events of pregn-1,4-diene-3,20-dione (PDD) product formation from progesterone (PD) C1-C2 ring A desaturation by Hep3B $\Delta^1$-KstD cells. Bar graphs representing the measured counts under the curve (CUC) of Hep3B control (Panels a & c) and Hep3B $\Delta^1$-KstD (Panels b & d) cells incubated with 15.7 μg (10 μM) progesterone spiked with 100nCi C4-$^{14}$C labeled PD. The CUC of PD (Panels a & b) and PDD (Panels c & d) were measured at 24, 48, and 72 hour time points. Quantitative analysis of PDD CUC reveals Hep3B $\Delta^1$-KstD cells are equipped with the ability to desaturate the PD A-ring C1-C2 bond to form the product PDD, whereas, Hep3B control cells lack this metabolic capability.

Unsurprisingly, Hep3B cells have endogenous metabolic capability to metabolize PD (i.e. bile acid formation, etc). More importantly, the C4-$^{14}$C PDD peak identified with the $\Delta^1$-KstD Hep3B cells (FIG. 53 panel b) did not appear in the Hep3B control samples (FIG. 53 panel a). Quantitative analysis of the counts under the curve shows that as the radiolabeled PD substrate is utilized by Hep3B cells expressing $\Delta^1$-KstD, the radiolabeled PDD product forms with time (FIG. 54).

Figure 55:
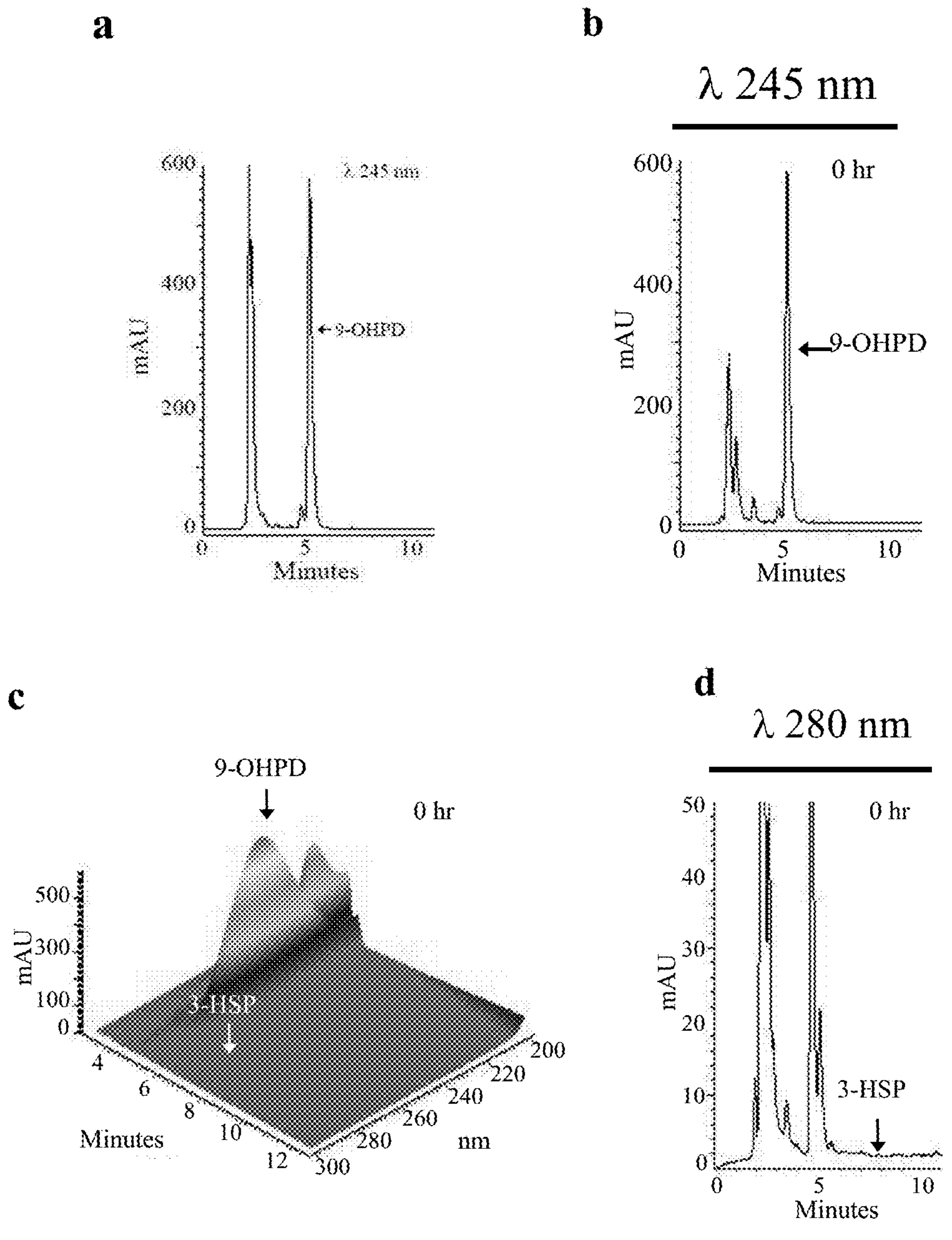
FIG. 55. RP-HPLC analysis of 9-hydroxypregn-4-ene-3,20-dione (9-OHPD) substrate. (Panel a) Representative 2-D chromatogram at λ245 nm from an 80 μL injection of 17 μg 9-OHPD in 500 μL HPLC running buffer 2. 9-OHPD was produced and isolated from bacterial KshAB lysate and used as substrate for Hep3B $\Delta^1$-KstD cells to determine whether cells equipped with the ability to desaturate C1 and C2 of the pregnaneA-ring can produce the ring opened compound, 3-hydroxy-9,10-secopregn-1,3,5(10)-triene-9,20-dione (3-HSP). The 9-OHPD substrate standard in has a $\lambda_{max}$ of 245 nm and a 5.2 min retention time ($t_r$). (Panel b) Representative HPLC chromatogram showing 9-OHPD ($\lambda_{max}$: 245 nm; $t_r$=5.2 min) utilization in control cell lysates at hour 0. (Panel c) 3-D chromatogram showing the spectral data ($\lambda_{300\text{-}200\ nm}$) plotted against time and absorption (mAU) of the sample run shown in (Panel b). (Panel d) Representative HPLC chromatogram showing the lack of 3-HSP ($\lambda_{max}$: 280 nm; $t_r$=7.2 min) at 0 hours in control cell lysates.
Figure 56:
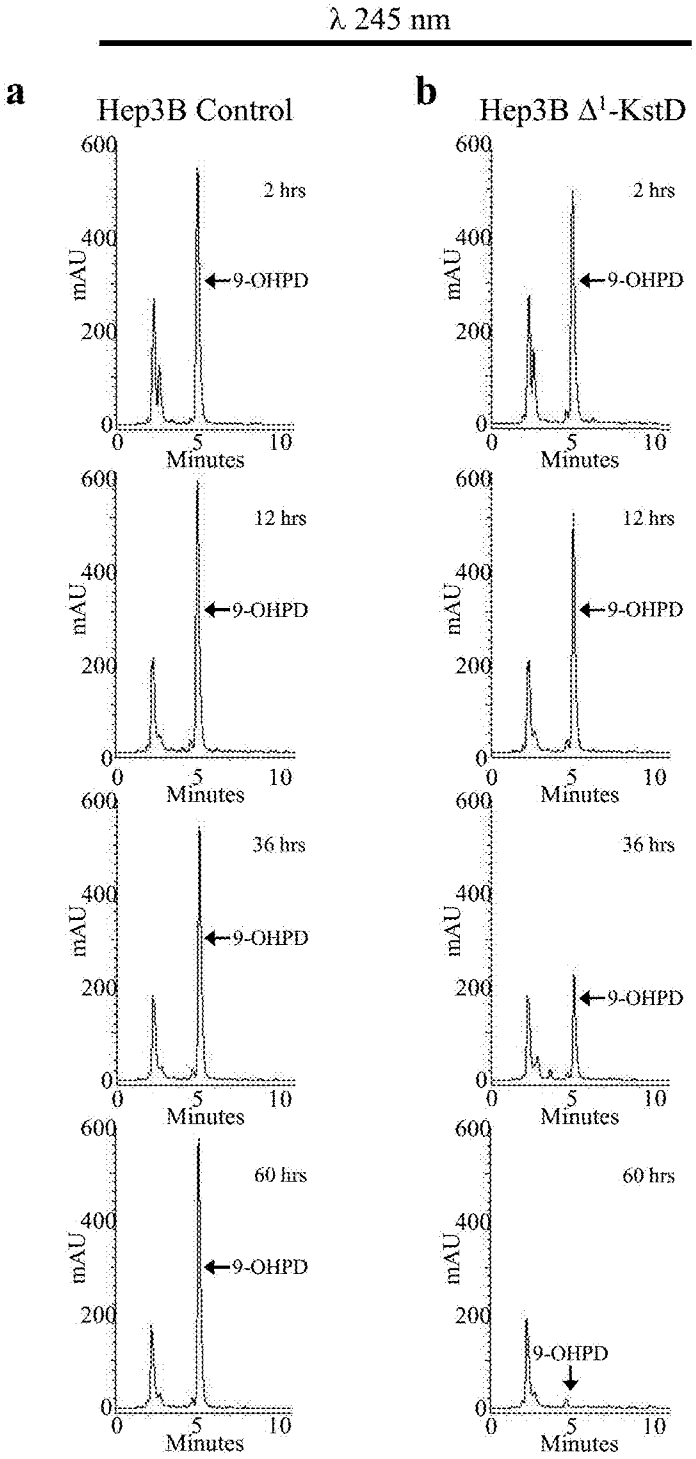
FIG. 56. Cholestane ring opening in human cells. In Hep3B M-KstD cells, catabolism of 9-hydroxypregn-4-ene-3,20-dione (9-OHPD) forms 3-hydroxy-9,10-secopregn-1,3,5(10)-triene-9,20-dione (3-HSP). Representative 2-D chromatograms (λ245 nm; time points: 2, 12, 36, and 60 hours) from (Panel a) Hep3B control and (Panel b) Hep3B $\Delta^1$-KstD cells incubated with 17 μg (10 μM) 9-hydroxypregn-4-ene-3,20-dione (9-OHPD; $t_r$=5.2 min)produced and isolated from bacterial KshAB lysate. Analysis of Hep3B $\Delta^1$-KstD cells shows reduction in 9-OHPD over the 72 hour time course. In contrast, Hep3B control cells lack the metabolic capability to catabolize 9-OHPD resulting in the substrates retention over the time course.
Figure 57:
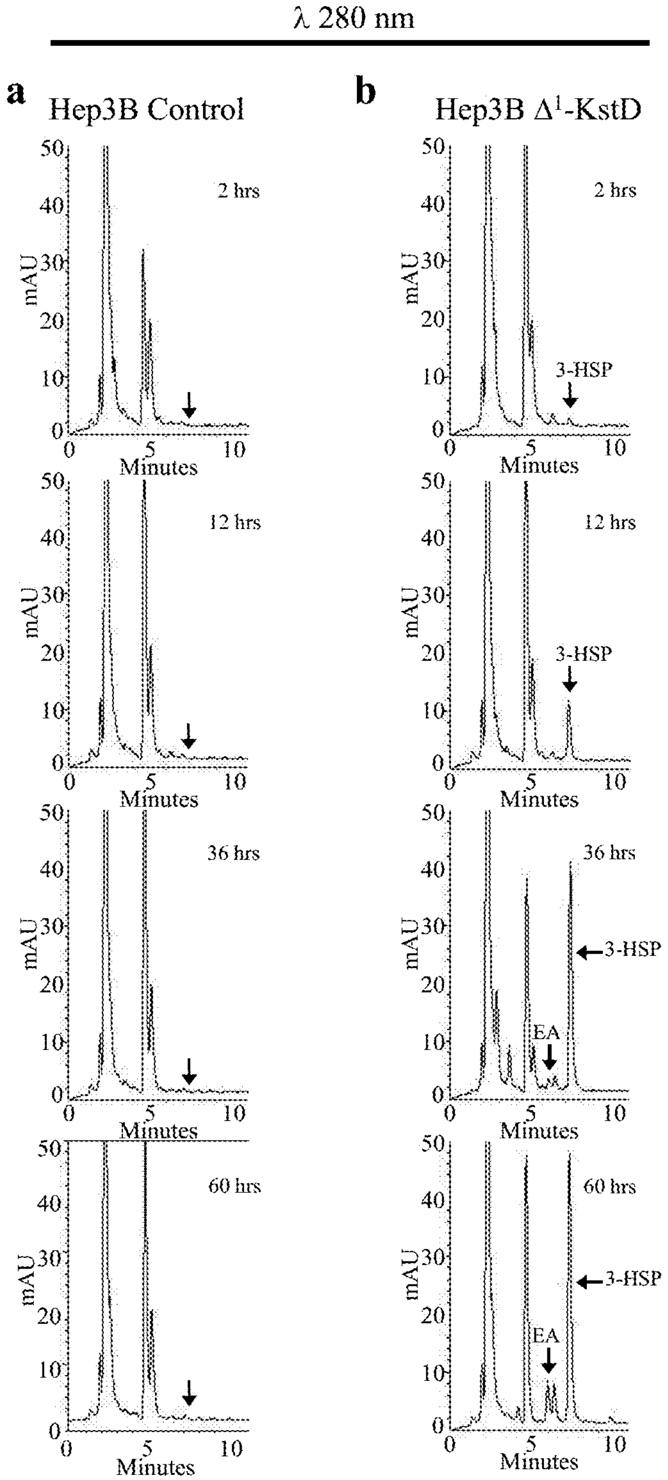
FIG. 57. Cholestane ring opening in human cells. In Hep3B Δ1-KstD cells, catabolism of 9-hydroxypregn-4-ene-3,20-dione (9-OHPD) forms 3-hydroxy-9,10-secopregn-1,3,5(10)-triene-9,20-dione (3-HSP). RP-HPLC analysis of 3-hydroxy-9,10-secopregn-1,3,5(10)-triene-9,20-dione (3-HSP) formation by Hep3B $\Delta^1$-KstD cells. Representative 2-D chromatograms (λ280 nm; time points: 2, 12, 36, and 60 hours) from (Panel a) Hep3B control and (Panel b) Hep3B $\Delta^1$-KstD cells incubated with 17 μg (10 μM) 9-hydroxy-pregn-4-ene-3,20-dione (9-OHPD; $t_r$=5.2 min)produced and isolated from bacterial KshAB lysate. Analysis of Hep3B $\Delta^1$-KstD cells shows the formation of 3-HSP ($t_r$=7.2 min) concomitant to the reduction of 9-OHPD throughout the 72 hour time course. In contrast, control Hep3B cells lack the metabolic capability to catabolize 9-OHPD, and thus are unable to produce 3-HSP.

We next set out to characterize the activity of our $\Delta^1$-KstD expressing Hep3B cells against the primed ring opening substrate, 9-hydroxypregn-4-ene-3,20-dione (9- OHPD). The 9-OHPD substrate ($\lambda_{max}$ 245 nm; $t_r$=5.2 min) was enzymatically produced by incubation of progesterone (PD) with the KshAB bacterial lysate (FIG. 55). Following hydroxylation of PD by KshAB, this 3-ketosteroid product requires the desaturation of the C1-C2 bond of ring-A by $\Delta^1$-KstD to form the unstable product, 9-hydroxypregn-1,4-diene-3,20-dione (9-OHPDD). The B-ring of 9-OHPDD is then subject to spontaneous non-enzymatic cleavage with concomitant aromatization of ring-A to form the product 3 hydroxy-9,10-secopregn-1,3,5(10)-triene-9,17-dione (3-HSP). As a consequence of ring-A aromatization, 3-HSP demonstrates a characteristic lambda max of 280 nm and is an indicator that ring opening has been achieved. To study whether the $\Delta^1$-KstD Hep3B cells could catalyze this reaction if presented with the appropriate intermediate, cells were incubated with 17 μg (10 μM) of 9-OHPD for 72 hours. RP-HPLC analysis of the $\Delta^1$-KstD Hep3B cells at λ245 nm shows 9-OHPD decrease over the time course, whereas Hep3B control cells retain the 9-OHPD substrate (FIG. 56). RP-HPLC analysis at λ280 nm shows that as 9-OHPD is catabolized by the $\Delta^1$-KstD Hep3B cells, a new peak with a retention time of 7.2 minutes and a lambda max of 280 nm appears with time (FIG. 57 panel b). An identical peak, corresponding to 3-HSP, was observed with pregnane ring opening by $\Delta^1$-KstD and KshAB clarified bacterial lysates following incubation with progesterone (PD). In contrast, non-transduced Hep3B cells did not demonstrate the ability to produce the same 7.2 minute peak when incubated with 9-OHPD (FIG. 57 panel a). Quantitative analysis of the 9-OHPD area under the curve shows that Hep3B control cells lack the metabolic activity to metabolize 9-OHPD, as revealed by the retention of the substrate over the 72 hour time course. In comparison, $\Delta^1$-KstD Hep3B cells catabolized the 9-OHPD substrate leading to the production of 3-HSP. Maximal production of 3 HSP was observed at 48 hours. At later time points, 3-HSP peak area was found to decrease. Reduction in 3-HSP suggest that Hep3B cells have endogenous metabolic capability to further modify the cholestane ring once opened (FIG. 58).

We have also verified that $\Delta^1$-KstD can be independently expressed in U-937 cells (FIG. 59). As described in methods, stable $\Delta^1$-KstD expressing monocytes were generated. The $\Delta^1$-KstD U-937-derived macrophages were incubated with 15.7 μg (10 μM) progesterone (PD) spiked with 100 nCi C4-$^{14}$C labeled PD ($t_r$=13.8 min; $\lambda_{max}$ 245 nm) for 72 hours. Analysis of U-937 $\Delta^1$-KstD cells shows formation of a new peak with a retention time of 10.0 minutes, a $\lambda_{max}$ of 247 nm, and containing C4-14C scintillation events corresponding to pregn-1,4-diene-3,20-dione (PDD; $t_r$=10.0 min; $\lambda_{max}$ 247 nm) following 72 hours incubation with PD (FIG. 59 panels b, d, & f). In contrast, U-937 control cells lack the ability to catabolize PD to PDD, as seen by the absence of a peak with a 10.0 minute retention time (FIG. 59 panels a, c, & e).

To confirm these cells could generate 3-HSP when provided the appropriate intermediate substrate, the $\Delta^1$-KstD U-937-derived macrophages were incubated with 17 μg (10 μM) 9-hydroxypregn-4-ene-3,20-dione (9-OHPD, $t_r$=5.2 min; $\lambda_{max}$ 245 nm) produced and isolated from bacterial KshAB lysate. Analysis of Hep3B $\Delta^1$-KstD cells following 72 hours incubation shows the formation of the ring opened product, 3-HSP ($t_r$=7.2 min; $\lambda_{max}$ 280 nm) (FIG. 60 panels b & d). In contrast, control Hep3B cells lack the metabolic capability to produce 3-HSP (FIG. 60 panels a & c).

KshAB Expression in Hep3B and U-937 Cells

As previously described in methods, two KshAB vectors were designed for prokaryotic and eukaryotic expression. The prokaryotic KshAB expression vector was designed using conventional methods to coexpress the A and B subunits using two Shine-Dalgarno sequences. To coexpress KshAB in eukaryotic cells, we designed a bicistronic expression vector by inserting DNA encoding the Porcine teschovirus-1 2A skipping peptide between the A and the B subunit genes. The 2A skipping peptide consists of 22 amino acids that facilitate equimolar expression of two or more genes from one expression vector. The C-terminus of the 2A skipping peptide contains two proline residues separated by a glycine. This motif adopts a confirmation in the ribosomal exit tunnel that interferes with the ability of the ribosome to synthesize the nascent polypeptide string. In efforts to continue polypeptide synthesis, the ribosome skips formation of the peptide bond leaving twenty-one amino acid residues on the C-terminus of the KshA subunit and a proline on the N-terminus of the KshB subunit. As a result, translation of the 2A skipping peptide generates two individual peptides from one open reading frame.

The original eukaryotic KshAB construct was subcloned into the CMV lentiviral expression vector to generate stable Hep3B cells lines. KshAB was expressed as a cytosolic enzyme whose expression levels were adequate for identification by anti-FLAG and anti-HA western blot (FIG. 62), however, RP-HPLC analysis revealed the enzyme lacked the hydroxylase activity identified with the KshAB bacterial lysate (FIG. 63 panels a & c). Recently, the crystal structure of the KshA subunit has shown the enzyme is dependent on iron-sulfur prosthetic groups for 9α-hydroxylase activity. Iron-sulfur clusters are responsible for mediating the transfer of electrons in redox reactions between the subunit and substrate. The mitochondria of eukaryotic cells are known to be a major contributor in iron-sulfur cluster (ISC) biogenesis. Thus, we reasoned that a loss in enzyme activity was potentially a consequence of the bacterial Fe—S clusters failing to assemble at the active site. We resolved this obstacle by redirecting expression of the KshAB subunits to the mitochondria. This was accomplished by modifying the KshAB DNA construct with N-terminal aconitase2 mitochondrial targeting sequences (MTS) onto both A and B subunits using Gibson assembly and synthetic DNA repair strings (FIG. 61). Modifying the A and B subunit with mitochondrial targeting sequences ensured the colocalization of KshAB in an environment rich in cofactors (NADH, iron-sulfur clusters) and a more evolutionarily conserved iron-sulfur cluster (ISC) assembly machinery. The aconitase2 MTS is a polypeptide sequence (35 amino acids) that adopts the amphiphilic a-helical secondary structure responsible for directing proteins to the mitochondria. The aconitase2 MTS contains a native protease cleavage signal 31 residues within the sequence. Removal of the MTS sequence ensures the MTS residues will not interfere with the maturated enzyme once localized within the mitochondrial matrix.

We found that targeting KshAB expression to the mitochondria restored hydroxylase activity. As proof of concept, Hep3B cells were transiently transfected with pDest51-MTS KshAB for 48 hours and incubated with 15.7 μg (10 μM) progesterone (PD) spiked with 100nCi C4-$^{14}$C labeled PD ($t_r$=13.8 min) for an additional 48 hours. RP-HPLC analysis revealed the PD substrate was completely utilized to produce a new peak with a 5.2 minute retention and a lambda max of 245 nm (FIG. 63 panels b & d). This 5.2 minute peak matched the lambda max and retention time of the 9-OH PD identified in the bacterial lysate. Additionally, the 9-OHPD product peak contained C4-$^{14}$C scintillation events, confirming the 5.2 minute peak was a product of PD catabolism. In contrast, the Hep3B cells expressing the cytosolic form of KshAB lacked 9α-hydroxylase activity as observed by the inability to form a 5.2 minute peak with a lambda max of 245 nm (FIG. 63 panels a & c).

To determine whether the addition of the aconitase2 MTS resulted in localization of the subunits to the mitochondria, we transiently transfected Hep3B cells with the mitochondrial targeted KshAB and cytosolic KshAB constructs for 48 hours. Cells were immunostained with fluorescent antibodies against the HA tag of the KshB subunit, co-stained with Mito Tracker Far-red, and then analyzed by confocal microscopy (FIG. 64). The merged channel show greater signal colocalization (white) between the mitochondrial targeted KshAB and mitotracker than between cytosolic targeted KshAB and mitotracker.

With verification that the activity of KshAB was restored, MTS-KshAB was subcloned into the plenti-CMV-Blast lentiviral expression vector to generate stable Hep3B MTS-KshAB expressing cells lines. Stable Hep3B MTS-KshAB cells were grown to confluency in 60 mm dishes and incubated with 15.7 μg (10 μM) progesterone spiked with 100 nCi C4-$^{14}$C PD. At the indicated time points (1, 2, 4, 6, 8, 12, 24, 36, and 48 hours), cells and media were extracted with ethyl acetate, and the lipid profiles were analyzed by RP-HPLC. Spectral data and C4-$^{14}$C scintillation events from the RPHPLC analysis of MTS-KshAB Hep3B cells revealed the 9-hydroxypregn-4-ene-3,20-dione (9-OHPD; $t_r$=5.2 minutes; $\Delta_{max}$ 245 nm) product accumulated over the 48 hour time course (FIG. 65). The retention time and lambda max of the 5.2 minute peak matches the 9-OHPD peak produced with the KshAB bacterial lysate. Quantitative analysis of both the area under the curve (AUC) and counts under the curve (CUC) reinforces that as PD is catabolized by Hep3B MTS-KshAB cells, a concomitant formation of 9-OHPD is observed (FIG. 66).

We next set out to characterize the activity of our MTS-KshAB expressing Hep3B cells against the primed ring opening substrate, pregn-1,4-diene-3,20-dione (PDD). The PDD substrate ($\lambda_{max}$ 247 nm; $t_r$=10.0 minutes) was enzymatically produced by incubation of progesterone (PD) with an aliquot of $\Delta^1$-KstD from the IMAC partial purification (FIG. 67). Following desaturation of PD by $\Delta^1$-KstD, this 3-ketosteroid product requires the hydroxylation of the C9 bond of ring-B by KshAB to form the unstable product, 9-hydroxypregn-1,4-diene-3,20-dione (9-OHPDD). The B-ring of 9 OHPDD is then subject to spontaneous non-enzymatic cleavage with concomitant aromatization of ring-A to form the product 3-hydroxy-9,10-secopregn-1,3,5(10)-triene9,17-dione (3-HSP) which demonstrates a characteristic lambda max of 280 nm and is an indicator that ring opening has been achieved. We first confirmed that Hep3B control cells lacked the ability to form 3-HSP by incubating non-transduced cells with 15.6 μg (10 μM) of PDD for 72 hours. Following 24, 48, and 72 hours incubation, cells and media were extracted with ethyl acetate, and the lipid profiles were analyzed by RPHPLC. Analysis shows that Hep3B control cells lack the ability to produce 3-HSP, or any additional peaks with a retention time of 7.2 minutes and lambda max of 280 nm (FIG. 68). To determine whether the MTS-KshAB Hep3B cells could produce 3-HSP from the appropriate intermediate, cells were incubated with 7.85 μg (5 μM) of PDD for 72 hours. We used half the amount of the PDD substrate for this experiment to observe the formation and degradation of 3-HSP as observed with the $\Delta^1$-KstD Hep3B incubated with 9-OHPD. RP-HPLC analysis (FIG.

69 panel a) and the quantitative analysis of the area under the curve at λ245 nm (FIG. 70 panel a) of the MTS-KshAB Hep3B cells shows the PDD substrate decrease with time. By 36 hours, the PDD substrate has been depleted. Analysis at λ280 nm reveals that as PDD is utilized, a peak with a 7.2 minute retention time and a lambda max of 280 nm accumulates (FIGS. 69 panel b & 70 panel b). An identical peak, corresponding to 3-HSP, was observed with pregnane ring opening by $\Delta^1$-KstD and KshAB clarified bacterial lysates following incubation with progesterone (PD) and with $\Delta^1$-KstD Hep3B cells incubated with 9-hydroxypregn-4-ene-3,20-dione (9-OHPD). Interestingly, time points following 36 hours shows 3-HSP decrease over the remaining 72 hours (FIGS. 71 panels b & 72*b*). As previously observed with $\Delta^1$-KstD Hep3B cells incubated with 9-OHPD, the reduction in 3-HSP suggest that Hep3B cells have endogenous metabolic capability to further modify the pregnane ring once opened. Quantitative analysis of the 3-HSP area under the curve shows that Hep3B cells expressing MTS-KshAB not only catabolized the PDD substrate, but once exhausted, can also catabolize the 3-HSP that was produced. An overview of quantitative analysis of PDD catabolism and formation and degradation of 3 HSP over the 72 hour time course has been provided (FIG. 73).

Next, we verified MTS-KshAB could be independently expressed in U-937 cells (FIG. 74). Stable MTS-KshAB expressing monocytes were generated using lentiviral transduction. The MTS-KshAB U-937-derived macrophages were incubated with 15.7 μg (10 μM) progesterone (PD) spiked with 100 nCi C4-$^{14}$C labeled PD ($t_r$=13.8 min) for 72 hours. Analysis of U-937 MTS-KshAB macrophages reveal the PD substrate was exhausted by 72 hours. Concomitant to PD catabolism, 9-hydroxypregn-4-ene-3,20 dione ($t_r$=5.2 min) is observed by the formation of a new peak with a retention time of 5.2 minutes, a $\lambda_{max}$ of 245 nm, and confirmed by C4-$^{14}$C scintillation events (FIG. 74 panels b & d). In contrast, U-937 control cells lack the ability to catabolize PD to 9-OHPD, as seen by the absence of a peak with a 5.2 minute retention time (FIG. 74 panels a & c).

To confirm these cells could generate 3-HSP when provided the appropriate intermediate, the MTS-KshAB U-937-derived macrophages were incubated with 15.6 μg (10 μM) pregn-1,4-diene-3,20-dione (PDD, $t_r$=10.0 min) produced and isolated from partially purified $\Delta^1$-KstD. Analysis of U-937 MTS-KshAB cells following 72 hours incubation show formation of 3-HSP ($t_r$=7.2 min) (FIG. 75 panels b & d). In contrast, control U937 cells lack the metabolic capability to produce 3-HSP due to lacking the ability to hydroxylate C9 of ring-B (FIG. 75 panels a & c).

Co-Expression of $\Delta^1$-KstD and MTS-KshAB in Hep3B Cells

To determine whether Hep3B cells could co-express $\Delta^1$-KstD and MTS-KshAB to catalyze the formation of 3-hydroxy-9,10-secopregn-1,3,5(10)-triene-9,20-dione (3-HSP) from progesterone (PD), Hep3B cells were transiently transfected with equal quantities of pDest51-$\Delta^1$-KstD and MTS-KshAB. Following 48 hours for adequate protein expression, cells were incubated with 15.7 μg (10 μM) progesterone spiked with 100nCi C4-$^{14}$C labeled PD= ($t_r$=13.8 min) for an additional 36 hours. RP-HPLC analysis of the 36 hour time course revealed a robust conversion of the PD substrate to 9-OHPD ($\lambda_{max}$ 245 nm; $t_r$=5.2 minutes) by 6 hours. Although PDD ($\lambda_{max}$ 247 nm; $t_r$=10.0 minutes) was not observed at 6 hours, analysis at λ280 nm reveals the formation of 3-HSP (FIG. 76). By 12 hours, the substrate and all intermediates had been catabolized to form 3 HSP. Interestingly, time points at 24 and 36 hours reveal that after the substrates and intermediates had been completely exhausted, 3-HSP is being further metabolized. The accumulation of C4-$^{14}$C scintillation events at 6.5 minutes confirms that once the cholestane ring has been opened it is being modified to have an increased polarity, as observed by a decrease in retention time.

Co-Expression of MTS-KshAB and $\Delta^1$-KstD from a Tricistronic Vector

Following confirmation that MTS-KshAB and $\Delta^1$-KstD could be simultaneously expressed to produce 3-hydroxy-9,10-secopregn-1,3,5(10)-triene-9,20-dione (3-HSP) from the substrate progesterone (PD), our next step was to design and assemble a tricistronic vector for co-expressing MTS-KshAB and $\Delta^1$-KstD from a single construct. Two vectors were designed to co-express MTS-KshAB and $\Delta^1$-KstD by inserting a Thosea asigna 2A skipping peptide (T2A) or a Porcine teschnovirus-1 2A skipping peptide (P2A) between the two enzymes (FIG. 77). The T2A and P2A vectors were characterized by assessing KshAB and $\Delta^1$-KstD protein levels by Western blot and activity by RP-HPLC analysis. Hep3B cells were transiently transfected with the T2A and P2A vectors. Following 48 hours to allow for adequate protein expression, cells were analyzed by Western blot and duplicate dishes were incubated with 15.7 μg (10 μM) progesterone spiked with 100nCi C4-$^{14}$C labeled PD ($t_r$=13.8 min) for an additional 48 hours. The Western blot results reveal that co-expressing MTS-KshAB and $\Delta^1$-KstD with the T2A skipping peptide resulted in higher expression of the Flag tagged KshA subunit, the HA tagged KshB subunit, and the Flag tagged $\Delta^1$-KstD enzyme (FIG. 78). In addition, RP-HPLC analysis revealed the T2A transfected cells had higher enzyme activity than the P2A transfected cells. The T2A transfected cells were able to completely catabolize the PD substrate and intermediates (FIG. 79 panel d) resulting in the formation of 3-HSP ($t_r$=7.2 min, $\lambda_{max}$ 280 nm) (FIG. 79 panel e) and additional downstream degradation products (FIG. 79 panel f). The activity of the P2A construct was less, as seen by the presence of residual progesterone, 9-OHPD (FIG. 79 panel a), and a lack of 3-HSP formation (FIG. 79 panels b & c). These findings suggest that the activity of $\Delta^1$-KstD is the rate limiting step in 3-HSP formation in the P2A construct. Thus, the T2A construct was used as the standard tricistronic vector for subsequent experiments.

Co-Expression of P450-FdxR-Fdx, HSD2, MTS-KshAB, and $\Delta^1$-KstD from a Pentacistronic Vector (The Cholesterol Catabolism Cassette or CCC)

Lastly, to express enzymes required to catabolize cholesterol to 3-HSP, we modified the MTS-KshAB-T2A-$\Delta^1$-KstD vector to co-express the P450-FdxR-Fdx fusion protein and HSD2 enzymes using repair strings, DNA fragments obtained from restriction digest, and Gibson assembly (FIG. 80). Due to the increased activity observed with the T2A skipping peptide used for co-expressing MTS-KshAB and $\Delta^1$-KstD; we designed a repair sting to include a second T2A peptide between the HSD2 enzyme and MTS-KshA subunit. In total, this vector includes two P2A and two T2A ribosomal skipping peptides which alternate between the enzymes. The final pentacistronic construct expresses all enzymes in this order: P450-FdxR-Fdx-P2A-HSD2-T2A-KshA-P2A-KshB-T2A-$\Delta^1$-KstD. To characterize the pentacistronic cassette and to confirm the enzymes were expressed and functional, Hep3B cells were transiently transfected with the cholesterol catabolizing cassette (CCC). Following 48 hours of incubation, protein levels of the enzymes were assessed (FIG. 81) and duplicate dishes were incubated with 15.7 μg (10 μM) progesterone (PD) spiked with 100nCi C4-$^{14}$C labeled PD ($t_r$=13.8 min) for an additional 24 and 72 hours (FIG. 82). Anti-Flag Western blot analysis confirmed the Flag tagged KshA and $\Delta^1$-KstD enzymes were expressed. Additionally, the anti-HA Western blot identified the HA tagged KshB enzyme. Although the Flag tagged P450-FdxR-Fdx fusion protein and HSD2 enzyme (primary antibody only) were not identified in these western blots, the identification of KshAB and $\Delta^1$-KstD supports that the enzymes are being expressed from the correct open reading frame (FIG. 81). RP HPLC analysis revealed the majority of the progesterone (PD) substrate was catabolized into downstream degradation products (FIG. 82). Interestingly, scintillation events accumulated in the solvent front (2-3 minutes), suggesting that 3-HSP was further modified once formed. Similar results were observed in the MTS-KshAB-T2A-$\Delta^1$-KstD transfected Hep3B cells after incubation with PD for 48 hours.

Following verification that the cholesterol catabolizing cassette (CCC) was functional, U-937 cells stably expressing the CCC were generated using lentiviral transduction. U-937 cells (CCC and control) were plated in 60 mm dishes and differentiated into macrophages (as described in methods). Five day old macrophages were loaded with 5 μg C4-$^{14}$C labeled LDLs (18 nCi C4-$^{14}$C—cholesterol) for 24 hours. Following incubation, the media containing the radiolabeled LDLs was removed and the cells were washed with PBS. The cells were provided with new media and cholesterol retention was monitored by measuring C4-$^{14}$C scintillation events in the cells at timed intervals for 48 hours. The data from two independent experiments with four replicates revealed more C4-$^{14}$C labeled cholesterol in the control cells as compared to the CCC cell line (FIG. 83). The decrease in C4-$^{14}$C scintillation events in control macrophages can likely be attributed to cholesterol efflux via the ABCA1 lipid transporter. In theory, when cholesterol levels become low, ABCA1 mediated cholesterol efflux is suppressed. However, the experimental design for these experiments measure retention and at this time it is not clear how much cholesterol leaves via ABCA1 mediated export and how much is degraded via catabolism in the CCC cell line.

Materials and Methods

Codon Optimization and cDNA Synthesis of the Bacterial Enzymes

1. Cholesterol Dehydrogenase (CholD)

To obtain DNA encoding humanized CholD, the amino acid sequence of cholesterol dehydrogenase, gene: 1917_07855 from *Mycobacterium tuberculosis* (strain Haarlem/NITR202), accession number: R4M4B2 was reverse translated using GeneOptimizer software (Gene Art; Waltham, Mass. USA) set to *Homo sapiens* codon usage. GeneOptimizer software was also used to design flanking sequences that contained Gateway attachment sites (attB1 and attB2) and restriction enzyme recognition sites (5': MfeI and BamHI; 3': SmaI, EcoRI, and BglII) which were added to aid sub cloning. In addition, 5' of the CholD sequence a tobacco etch protease recognition site (TEV site) for cleaving upstream fusion proteins, a 6×His tag, Kozak consensus sequence, a tetracysteine tag, and a Flag tag were added to aid purification and detection of the recombinant protein after expression. This humanized CholD (FIG. 85) construct was then synthesized and inserted into the pMK-RQ vector (GeneArt). Upon arrival the lyophilized DNA was resuspended in $H_2O$ at a concentration of 100 ng/μL. The concentration of the DNA was measured using a BioRad Smartspec 3000 spectrophotometer.

2. Anoxic Cholesterol Metabolism Enzyme B (acmB)

To obtain DNA encoding humanized acmB, the amino acid sequence of anoxic cholesterol metabolism enzyme B (Cholest-4-en-3-one-delta1-dehydrogenase), gene: acmB from *Sterolibacterium denitrificans* (strain Chol-1st), accession number: A9XWD7 was reverse translated using GeneOptimizer software set to *H. sapiens* codon usage. GeneOptimizer software was used to design flanking sequences that contained Gateway attachment sites (attB1 and attB2) and restriction enzyme recognition sites (5': MfeI and BamHI; 3': NaeI, SmaI, EcoRI, and BglII), which were added to aid sub cloning. In addition, 5' of the acmB sequence a TEV site, Kozak consensus sequence and 3' HA tag were added to aid in purification and detection of the recombinant protein after expression. This humanized acmB construct (FIG. 89) was then synthesized and inserted into the pMA-RQ vector (GeneArt). Upon arrival, the lyophilized DNA was resuspended in $H_2O$ at a concentration of 100 ng/μL.

3. 3-Ketosteroid $\Delta^1$-Dehydrogenase ($\Delta^1$-KstD)

To obtain DNA encoding humanized $\Delta^1$-KstD, the amino acid sequence of 3-ketosteroid $\Delta^1$-dehydrogenase, gene: KstD1 from *Rhodococcus erythropolis* (strain PR4/NBRC 100887), accession number: COZQP5 was reverse translated using GeneOptimizer software set to *H. sapiens* codon usage. GeneOptimizer software was used to design flanking sequences that contained Gateway attachment sites (attB1 and attB2) and restriction enzyme recognition sites (5': MfeI and BamHI; 3': EcoRI, and BglII), which were added to aid sub cloning. In addition, 5' of the $\Delta^1$-KstD sequence a TEV site, a 6×His tag, Kozak consensus sequence, tetracysteine tag, and a Flag tag were added as discussed above. The humanized $\Delta^1$-KstD construct (FIG. 99) was then synthesized and inserted into the pUC57 vector (GenScript). Before use, the DNA was resuspended in $H_2O$ at a concentration of 200 ng/μL.

4. 3-Ketosteroid 9α-Hydroxylase (KshAB)

Two different 3-ketosteroid 9α-hydroxylase (KshAB) bicistronic vectors were synthesized, one for prokaryotic and the other for eukaryotic expression. The genes used to design the two constructs were: kshA5B from *Rhodococcus rhodochrous* (strain DSM 43269), KshA5 gene: kshA5, accession number: F1CMY8; and KshB gene: kshB, accession number: F1CMX3. The amino acid sequence of KshAB was reverse translated using GeneOptimizer software for *Escherichia coli* and *Homo sapiens* codon usage.

The prokaryotic KshAB vector was designed as a bicistronic construct by inserting a second Shine-Dalgarno sequence following the 3' end of KshA. The second Shine-Dalgarno was shifted by one nucleotide to produce a second open reading frame for coexpression of KshB. Both subunits were designed with 5' cell penetrating peptides (CPPs) from the HIV-TAT protein (MGYGRKKRRQRRR; SEQ ID NO:9), short linker peptides (amino acids: GAS), and 6×His tags. GeneOptimizer software was used to design flanking sequences that contained Gateway attachment sites (attB1 and attB2) and restriction enzyme recognition sites (5' BamHI; 3' PstI and an EcoRI between the A and B subunits) which were added to aid sub cloning. The open reading frame was also optimized for expression in *E. coli.*

The eukaryotic KshAB vector was designed as a bicistronic construct by inserting the Porcine teschovirus-1 2A skipping peptide following the 3' end of KshA. In addition, a Kozak consensus sequence and Flag tag were added 5' of KshA to aid in detection of the A subunit. Similarly, an HA tag was added 5' of KshB for detection of the B subunit. Gateway attachment sites (attB1 and attB2) and restriction enzyme recognition sites (5' BglII and XbaI; 3' BamHI and MfeI) which were added to aid sub cloning. The open reading frame was also optimized for expression in *H. sapiens*.

The prokaryotic (FIG. 111) and eukaryotic (FIG. 115) constructs were synthesized and inserted into pMA-RQ (GeneArt). Before use, the DNA was resuspended in $H_2O$ at a concentration of 100 ng/μL.

Codon Optimization and cDNA Synthesis of the Human Enzymes

P450 Side Chain Cleavage Enzyme-Ferredoxin Reductase-Ferredoxin-P2A-30-Hydroxysteroid Dehydrogenase 2 Construct (P450-FdxR-Fdx-P2A-HSD2 Construct)

The P450-FdxR-Fdx-P2A-HSD2 construct is a bicistronic expression vector encoded the P450-FdxR-Fdx fusion protein and 30-hydroxysteroid dehydrogenase 2 enzyme (HSD2), separated by the 2a "ribosomal-skipping peptide". The three genes used in the design of the P450 fusion protein are listed from 5' to 3': a P450 side chain cleavage enzyme, CYP11A, from *H. sapiens*, accession number: P05108; ferredoxin reductase, FDXR, from *H. sapiens*, accession number: P22570; and ferredoxin FDX1, from *H. sapiens*, accession number: P10109. Truncated versions of P450 side chain cleavage enzyme, ferredoxin reductase (FdxR), and ferredoxin (Fdx) enzymes were fused using short linkers: amino acid sequence TDGTS between P450 and FdxR; and amino acid sequence TDGAS between FdxR and Fdx (FIG. 94). The native P450 mitochondrial targeting sequence (MTS) was retained to direct the fusion protein to the mitochondria; however, the MTS for FdxR and Fdx were omitted. A Flag tag was added to the 3' end of Fdx protein to aid identification. The P450-FdxR-Fdx-P2A-HSD2 construct was designed with a Porcine teschovirus-1 2A skipping peptide following the 3' Fdx Flag tag for co-expressing the HSD2 enzyme. The HSD2 gene used for this construct is 3β-hydroxysteroid dehydrogenase ($\Delta^{5-4}$-isomerase) from *H. sapiens*, gene: HSD3B2, accession number: P26439. To obtain DNA encoding the P450-FdxR-Fdx-P2A-HSD2 construct, the amino acid sequence was reverse translated using GeneOptimizer software set to *H. sapiens* codon usage. GeneOptimizer software was also used to design flanking sequences that contained Gateway attachment sites (attL1 and attL2) and restriction enzyme recognition sites (5' BglII and XbaI; 3' BamHI and MfeI), which were added to aid sub cloning. The P450-FdxR-Fdx-P2A-HSD2 construct (FIG. 95) was then synthesized and inserted into pMK-RQ vector (GeneArt). Before use, the DNA was resuspended in $H_2O$ at a concentration of 100 ng/μL.

Amplification of Initial Vectors

Aliquots of omnimax $2T1^R$ cells (50 μL) were transformed with pMK-RQ-CholD, pMA-RQ-acmB, pUC57-$\Delta^1$-KstD, pMA-RQ-KshAB (pro), pMA-RQ-KshAB (euk), or pMK-RQ-P450-FdxR-Fdx-P2A-HSD2 vectors, respectively, by incubating bacterial cells with 1 μL of the indicated plasmid DNA (on ice for 30 minutes). Following incubation, cells were heat shocked for 30 seconds in a 42° C. water bath. Transformants were placed back on ice for 2 minutes. Then 250 μL of SOC media was added. Transformants were placed in a shaking incubator at 37° C. at 250 RPM for 1 hour. Following incubation, 30 μL and 70 μL of transformants were plated onto two LB agar plates containing 100 μg/mL ampicillin (pMA-RQ and pUC57) or 50 μg/mL kanamycin (pMK-RQ) and grown for 14 hours at 37° C.

Isolation of Initial Vector DNA

To isolate initial vectors, twenty colonies of each were selected and plated on one 100 μg/mL ampicillin (pMA-RQ and pUC57) or 50 μg/mL kanamycin (pMK-RQ) LB agar plate and grown for 14 hours at 37° C. Three to nine clones were selected and streaked onto additional LB agar plates containing the same concentration of antibiotic and grown for 14 hours at 37° C. The clones were used to inoculate 5 mL LB broth starter cultures containing 100 μg/mL ampicillin (pMA-RQ and pUC57) or 50 mg/mL kanamycin (pMK-RQ). Starter cultures were grown at 250 RPM for 14 hours at 37° C. Initial vector DNA (pMK-RQ-CholD, pMA-RQ-acmB, pUC57-$\Delta^1$-KstD, pMA-RQKshAB (pro), pMA-RQ-KshAB (euk), or pMK-RQ-P450-FdxR-Fdx-P2A-HSD2) was isolated using the Qiagen mini kit, screened by restriction enzyme digest, and verified by DNA sequence analysis.

BP Reaction and Transformation of Omnimax 2T1 R Cells with pEntr221-CholD, acmB, $\Delta^1$-KstD, KshAB (pro), or KshAB (euk) vectors BP reactions were assembled using equimolar concentrations (50 fmols) of each initial vector and pDonr221. BP Clonase II (2 μL) was added to the DNA, and the final volume was adjusted to 10 μL with TE buffer. Reactions were incubated at 25° C. for one hour. To terminate the BP reaction, 1 μL of Proteinase K was added and incubated at 37° C. for 10 minutes. Omnimax $2T1^R$ cells (50 μL) were transformed with the entry vector product by incubating cells with 1 μL DNA on ice for 30 minutes. Following incubation, the cells were heat shocked for 30 seconds in a 42° C. water bath. Transformants were placed back on ice for 2 minutes and 250 μL of SOC media was added. Transformants were placed in a shaking incubator at 37° C. for 1 hour at 250 RPM. Following incubation, 30 μL and 70 μL of transformants were plated onto two LB agar plates containing 50 μg/mL kanamycin and grown for 14 hours at 37° C.

Isolation of pEntr221-CholD, acmB, $\Delta^1$-KstD, KshAB (pro), and KshAB (euk) DNA To isolate pEntr221-CholD (FIG. 87), acmB (FIG. 91), $\Delta^1$-KstD (FIG. 101), KshAB (pro) (FIG. 113) and KshAB (euk) (FIG. 117), twenty colonies of each entry clone were selected and plated on one 50 μg/mL kanamycin LB agar plate and grown for 14 hours at 37° C. Three to nine clones of each pEntr221 vector were selected from the plate and streaked onto an additional LB agar plate containing 50 μg/mL kanamycin and grown for 14 hours at 37° C. The clones were used to inoculate 5 mL LB broth starter cultures containing 50 μg/mL kanamycin and grown at 250 RPM for 14 hours at 37° C. Entry clone vectors were isolated using the Qiagen mini kit, screened by restriction enzyme digest, and verified by DNA sequence analysis.

LR Reaction and Transformation of Omnimax 2T1 R Cells with Expression Constructs LR reactions were assembled using equimolar concentrations (50 fmols) of each pEntr221 clone and the desired expression vector. Prokaryotic expression vectors included pBAD-Dest49 (CholD (FIG. 88), acmB (FIG. 92), $\Delta^1$-KstD (FIG. 102)) and pDest14 (KshAB (pro) (FIG. 114)). Eukaryotic expression vectors included pEF-Dest51 ($\Delta^1$-KstD (FIG. 105), KshAB (euk) (FIG. 118), and P450-FdxR-Fdx (FIG. 97)); pLenti-CMV-Blast (w706-1) (acmB (FIG. 93), $\Delta^1$-KstD (FIG. 109), KshAB (euk) (FIG. 125), and P450-FdxR-Fdx (FIG. 98)); and pLenti-CMV-Puro (W118-1) ($\Delta^1$-KstD (FIG. 110)). LR Clonase II (2 μL) was added to the DNA and the final volume was brought to 10 μL with TE buffer. Reactions were incubated at 25° C. for one hour. To terminate the LR reaction, 1 μL of Proteinase K was added, and the reaction was incubated at 37° C. for 10 minutes. Omnimax $2T1^R$ cells (50 μL) were transformed with the expression vector product by incubating cells with DNA (1

μL) on ice for 30 minutes. Following incubation, the cells were placed in a 42° C. water bath (heat shocked) for 30 seconds. Transformants were placed back on ice for 2 minutes and 250 μL of SOC media was added. Transformants were placed in a shaking incubator (250 RPM) at 37° C. After 1 hour, 30 μL or 70 μL aliquots were plated onto LB agar plates containing 100 μg/mL ampicillin, and the bacteria were allowed to grow for 14 hours at 37° C.

Isolation of Expression Vectors

To isolate each of the expression vectors, twenty colonies were selected and plated on one 100 μg/mL ampicillin LB agar plate and grown for 14 hours at 37° C. Three to nine clones were selected from this plate and streaked onto an additional LB agar plate containing 100 μg/mL ampicillin. After 14 hours at 37° C., each of the clones were used to inoculate 5 mL LB broth starter cultures containing 100 μg/mL ampicillin and grown at 250 RPM for 14 hours at 37° C. Expression vectors were isolated using the Qiagen mini kit, and the fidelity of each construct was verified by restriction enzyme digest and activity screening (described below).

Transformation of Rosetta2 & C41 Expression Strains

Rosetta2 (pBAD-Dest49 vectors) or C41 (pDest14 vectors) *E. coli* cells (50 μL) were transformed with the expression vector (1 μL) by incubating on ice for 30 minutes and heat shocking for 30 seconds in a 42° C. water bath. Transformants were placed back on ice for 2 minutes and 250 μL of SOC media was added. Transformants were placed in a shaking incubator at 37° C. for 1 hour at 250 RPM before 30 μL or 70 μL aliquots were plated onto two LB agar plates containing 100 μg/mL ampicillin and 34 μg/mL chloramphenicol (Rosetta2 cells) or 100 μg/mL ampicillin only (C41 cells) and grown for 14 hours at 37° C.

Rosetta2 and C41 Expression Strain Culture Preparation

Twenty colonies of each clone were selected and plated onto one LB agar plate containing 100 μg/mL ampicillin and 34 μg/mL chloramphenicol for Rosetta2 cells or 100 μg/mL ampicillin for C41 cells. After 14 hours at 37° C., one colony was selected from this plate, streaked onto an additional LB agar plate containing the same concentration of antibiotic and grown for 14 hours at 37° C. A single colony from each clone was selected and used to inoculate 5 mL LB broth starter cultures containing 100 μg/mL ampicillin and 34 μg/mL chloramphenicol (Rosetta2 cells) or 100 μg/mL ampicillin only (C41 cells). Cultures were grown for 14 hours at 37° C. shaking at 250 RPM. A 1:250 dilution of the starter culture was used to initiate a 500 mL LB broth liquid culture containing 100 μg/mL ampicillin and 34 μg/mL chloramphenicol (Rosetta2 cells) or 100 μg/mL ampicillin only (C41 cells). Cultures were incubated at 37° C. for six hours shaking at 250 rpm. Once the culture reached an $OD_{600}$ of 0.4, 0.10% arabinose (pBAD-Dest49 vectors) or 300 μM IPTG (pDest14 vector) was added to induce heterologous expression. Cultures were grown at 25° C. for 24 hours shaking at 250 rpm until reaching an $OD_{600}$ of 4.0.

Bacterial Lysis

The bacterial culture was subjected to centrifugation at 4,000×g for 20 minutes at 4° C. in a Sorvall Instruments RC5C using a GSA rotor. The bacterial pellet was weighed and suspended in four volumes of chilled lysis buffer (1:4; w/v). Lysis buffer consisted of 25 mM Tris-HCl, pH 7.5, 500 mM NaCl, 1 mM $MgCl_2$, 1 mM PMSF, 1× Calbiochem Protease Inhibitor Cocktail Set 1, and 525U of Pierce Universal Nuclease. For protein purification by IMAC, 20 mM imidazole was added to this buffer. Cells were lysed using a chilled French press with a high pressure setting of 18,000 psi with a Thermo IEC French Press Cell Disruptor. The bacterial pellet was placed on ice and then run through the French press a second time for adequate lysis of bacteria. The crude lysate was subjected to centrifugation at 28,500×g for 1 hr at 4° C., to separate the soluble and insoluble fractions, in a Sorvall Instruments RC5C with an SS34 rotor.

Clarified Lysate Activity Assessment by RP-HPLC

Independent assays were conducted with clarified lysate from CholD, acmB, $\Delta^1$-KstD, KshAB, or empty vector transformed *E. coli*. For each assay, 100 μL of clarified lysate was mixed with 100 μM substrate (3.87 μg cholesterol (CL) spiked with 20 nCi $^{14}C$ radiolabeled CL, 3.87 μg cholestenone (CN), 3.16 μg pregnenolone (PL), or 3.14 μg progesterone (PD) spiked with 20 nCi $^{14}C$ radiolabeled PD) in an 2 mL glass HPLC vial for 24 hours on a rotator. Following incubation, steroids were isolated and analyzed by RP-HPLC as described below.

$\Delta^1$-KstD Partial Purification by Immobilized Metal Affinity Chromatography Clarified lysate (23.75 mL) containing $\Delta^1$-KstD was loaded onto a nickleSepharose column (GE HiTrap Chelating HP columns, 1.6×2.5 cm). Isolation was performed by washing out unbound protein with twenty-two column volumes 98:2 buffer A:B; (buffer A; 25 mM Tris-HCl, pH 7.5, and 500 mM NaCl; buffer B; 25 mM Tris-HCl, pH 7.5, 500 mM NaCl, and 1 M imidazole). $\Delta^1$-KstD was then eluted with a 2 mL/min imidazole linear gradient, collected in 9 mL fractions at 4° C. using an AKTA FPLC System (GE Healthcare). Elution occurred in two steps. Step one was 95:5 solvent A:B and was followed by a linear gradient to 80:20 solvent A:B over ten column volumes. The 80:20 solvent A:B was held for five column volumes before returning to 98:2 solvent A:B for two column volumes. The N-terminal HP-Thioredoxin $\Delta^1$-KstD fusion protein was eluted in 25 mM Tris-HCl, pH 7.5, containing 500 mM NaCl and 120 mM imidazole. Elution fraction 21 was assessed to contain a high yield of $\Delta^1$-KstD with relatively low contaminating proteins. Protein concentration was determined using the Bio-Rad Protein assay using bovine serum albumin as a standard. The SDS-PAGE of elution fraction 21 was coomassie stained was analyzed with ImageJ and estimated to contain 0.385 mg/mL of $\Delta^1$-KstD at 79.6% purity by densitometry.

Nitrotetrazolium Blue $\Delta^1$-KstD Activity Assay

Equal volumes (5 μL) of representative fractions from the $\Delta^1$-KstD IMAC purification were loaded onto a native gel (10% acrylamide) and ran at 50 v for 5 hours at 4° C. Following electrophoresis, the gel was incubated in 10 mL of nitrotetrazolium blue solution (160 nM phenazine methylsulfate, 80 nM nitrotetrazolium blue, and 1.5 nM progesterone in 66.7 mM Tris) for 5 minutes at 25° C.

Partially Purified $\Delta^1$-KstD SDS-PAGE and Western Blot

To assess the purity and yield of $\Delta^1$-KstD from the IMAC purification, aliquots of each fraction were diluted (1:1; v/v) in laemmli sample buffer. Equal volumes (5 μL) from each fraction were separated using SDS-PAGE on a 10% polyacrylamide gel at 50 v for 0.5 hours followed by 125 v for 1.4 hours at 4° C. Protein was transferred to a PVDF membrane using 300 mA for 2.3 hours, and probed with anti-FLAG (1:1000; Sigma F3163, from mouse). ECL anti-mouse IgG secondary antibody conjugated to horseradish peroxidase (HRP) linked whole antibody (1:10,000, GE Healthcare NA931VS, from sheep) and SuperSignal West Femto Substrate was used for detection of the N-terminal FLAG tag of $\Delta^1$-KstD. Duplicate SDS-PAGE gels were coomassie stained to assess purity and yield.

$\Delta^1$-KstD Enzyme Titration Curves

Fluorometric assays using resazurin were performed in 25 mM Tris-HCl, pH 7.5 at 37° C. in a 96-well format using a BioTek Synergy 2 plate reader with excitation 540±25 nm and emission 620±40 nm. Several concentrations of $\Delta^1$-KstD (0.05, 0.19, 0.37, 0.55, 1.1, 1.6, 2.12 nM) and 0.1 mg/mL BSA were dispensed with a PD syringe. Reactions were initiated by the addition of 20 μM resazurin and 20 μM progesterone. Measurements were made with an N of 1 with three replicates and three blanks for baseline subtraction by measuring the fluorescence of each well every 17 seconds for a total of 3.5 minutes.

$\Delta^1$-KstD Steady State Kinetic Analysis with Resazurin Assay

Initial velocities were measured by monitoring the reduction of resazurin at 37° C. Reaction mixtures containing 0.55 nM, 1.1 nM, or 1.6 nM $\Delta^1$-KstD and 0.1 mg/mL BSA were dispensed with a PD syringe prior to initiating the reaction by the addition of increasing concentrations of progesterone (1, 2.5, 5, 10, 20, 30, and 40 μM) and 20 μM resazurin in 25 mM Tris-HCl, pH 7.5. Measurements were made with an N of 1 with eight replicates and four blanks for baseline subtraction by measuring the fluorescence of each well every 17 seconds for a total of 10 minutes.

$\Delta^1$-KstD Substrate Specificity with Resazurin Assay

Substrate specificity assays were performed in 300 μL 25 mM Tris-HCl, pH 7.5. Relative fluorescent intensity was measured following 10 minutes of incubation with several steroid substrates at 37° C. Reaction mixtures containing 5.35 nM $\Delta^1$-KstD and 0.1 mg/mL BSA (dispensed with a PD syringe) were equilibrated for 30 sec before the reaction was initiated by adding 20 μM resazurin and 20 μM of the steroid substrate. Screened steroid substrates include: 3β-hydroxy-pregn-5-en-20-one (Pregnenolone) (Sigma), Pregn-4-ene-3,20-dione (Progesterone) (Sigma), (11β)-11,17,21- trihydroxypregna-1,4-diene-3,20-dione (Prednisolone) (Sigma), 4-pregnen-17-ol-3,20-dione (17-hydroxyprogesterone) (Steraloids Q3360), 4-pregnen-21-ol-3,20-dione (11- deoxycorticosterone) (Steraloids Q3460), (11φ-11,21-dihydroxy-pregn-4-ene-3,20-dione (Corticosterone) (Sigma C-2505), (11p)-11,17,21-trihydroxypregn-4-ene-3,20-dione (Hydrocortisone) (Sigma No. H-4001), 17α,21-dihydroxy-4-pregnene-3,11,20-trione (Cortisone) (Sigma C-2755) 11β,21-dihydroxy-3,20-dioxopregn-4-en-18-al (Aldosterone) (Acros Organics 215360050), 11β,17α,21-trihydroxy-4-pregnene-3,20-dione 21-hemisuccinate sodium salt (Hydrocortisone 21-hemisuccinate) (Sigma), 5α-androstan-3α-ol-17-one (Androsterone) (Steraloids A2420), 5-androsten-3β-ol-17-one (DH EA/Dehydroepiandrosterone) (Steraloids A8500), 5α-androstan-17β-ol-3-one (5α-DHT) (Steraloids A2570), 4-androsten-17β-ol-3-one (Testosterone) (Steraloids A6950), 4-androsten-3,17-dione (Androstenedione) (Steraloids A6030), 17β-hydroxy-4-androsten-3-one 17-enanthate (Testosterone enanthate or Delatestryl) (Sigma), 3β-hydroxy-5-cholestene (Cholesterol) (Sigma), 5-Cholesten-3-one (Cholestenone) (Sigma), 11β-(4-dimethylamino) phenyl-170-hydroxy-17-(1-propynyl)estra-4,9-dien-3-one (Mifepristone) (Roussel UCLAF 7A 4087 RU 38486), 7α-acetylthio-3-oxo-17α-pregn-4- ene-21,17-carbolactone (Spironolactone) (Sigma), and 4-Cholesten-7β-ol-3-one (7β-hydroxycholestenone) (Steraloids C6230-000). Measurements were made with an N of 1 with four replicates and four blanks for baseline subtraction.

Partially Purified $\Delta^1$-KstD Reactions

Reactions containing 770 ng isolated $\Delta^1$-KstD in 25 mM Tris-HCl, pH 7.5, 200 μM resazurin, and 0.1 mg/mL BSA were incubated with 6.29 μg (100 μM) progesterone for 4 hours in a 37° C. water bath. Steroid isolation and analysis are described below.

Gibson Assemblies $\Delta^1$-KstD Kozak Consensus Sequence Repair

The $\Delta^1$-KstD construct's Kozak consensus sequence was repaired by digesting pDest51-$\Delta^1$-KstD with BbvCI and SpeI. The BbvCI and SpeI digest removed the TEV site, 6×His tag, Kozak consensus sequence, tetracysteine tag, Flag tag, and the first 13 nt of $\Delta^1$-KstD's N-terminus. The pDest51-Δ1-KstD backbone was isolated by agarose gel electrophoresis (0.8%), extracted from the gel using a Qiagen gel extraction kit, and the concentration of DNA was determined using a nanodrop spectrophotometer. The repair string (FIG. 103) (504 nt) was designed to insert a new attB1 site, Kozak consensus sequence, Flag tag, and the first 13 nt of $\Delta^1$-KstD's N-terminus that was removed from the BbvCI and SpeI digest. The repair string was synthesized by GeneArt. The repair string included 40 bp homology arms starting from the 3' overhang of the BbvCI restriction site in pDest51-$\Delta^1$-KstD (left homology arm) and 40 bp homology starting from the 3' overhang of the SpeI restriction site (right homology arm). The repair string (150 ng) and the linearized pDest51-$\Delta^1$-KstD backbone (50 ng) were assembled using Gibson Assembly (following standard procedures). The assembled vector (2 μL) was diluted with water (4 μL) and propagated by transforming (2 μL DNA) Omnimax $2T1^R$ *E. coli*. Plasmid DNA from six bacterial colonies was isolated using the Qiagen mini kit, screened by restriction enzyme digest, and verified by DNA sequence analysis. The pDest51-Repaired $\Delta^1$-KstD construct (FIG. 105) was subcloned back into the pEntr221 (FIG. 107) entry vector and the further subcloned into pBAD-Dest49 (FIG. 108), pLentiCMV-puro (w118-1) (FIG. 109) and pLenti-CMV-Blast (w706-1) (FIG. 110) expression vectors using Gateway recombination as described previously.

Aconitase2 Mitochondrial Targeting Sequence Addition to KshAB (MTS-KshAB)

The KshA and KshB subunits were modified by the addition of N-terminal mitochondrial targeting sequences (MTS) from the *H. sapiens* Aconitase2 enzyme. KshAB was modified by first linearizing pEntr221-KshAB (euk) (FIG. 117) with NaeI, a restriction enzyme with two recognition sites. The pEntr221-KshAB backbone was isolated by agarose gel electrophoresis (0.8%), extracted from the gel using a Qiagen gel extraction kit, and the concentration of DNA was determined using a nanodrop spectrophotometer. For repair string synthesis, the 35 amino acid Aconitase2 protein sequence (MAPYSLLVTR LQKALGVRQY HVASVLCQRA KVAMS) was codon optimized for *H. sapiens* expression by GeneArts codon optimization software and then fused to the 5' ends of both the KshA and KshB subunits. Due to synthesis problems of a single repair string encoding the entire repair (likely due to the highly similar MTSs), two repair strings were synthesized by GeneArt. The first repair string (FIG. 119) (1000 nt) encoded the Kozak consensus sequence, Aconitase2 MTS, Flag tag, and first 835 nt of KshA. The second repair string (FIG. 121) (600 nt) encoded the remaining 347 nt of KshA, the Porcine Teschovirus 2A skipping peptide, and the N-terminal segment of KshB that was removed by restriction digest. The first repair string included 40 bp homology arms starting from the 3' overhang of the upstream NaeI restriction site in pEntr221-KshAB (left homology arm) and 40 bp homology starting from the 3' overhang of the second repair string (right homology arm). The second repair string included 40 bp homology starting from the 3' overhang of the first repair string (left homology arm) and 40 bp homology starting from the 3' overhang of the downstream NaeI restriction site in pEntr221-KshAB (right homology arm). The repair strings (150 ng) and the linearized pEntr221-KshAB backbone (50 ng) were assembled using Gibson Assembly (following standard procedures). The assembled vectors (2 μL each) were diluted with water (4 μL) and propagated by transforming (2 μL DNA) Onimax 2T1$^R$ *E. coli*. Plasmid DNA from six bacterial colonies was isolated using the Qiagen mini kit, screened by restriction enzyme digest, and verified by DNA sequence analysis. The pEntr221-MTS-KshAB (FIG. 122) construct was subcloned into the pDest51 (FIG. 124) and pLenti-CMV-Blast (w706-1) (FIG. 125) expression vectors using Gateway recombination as described previously.

KshAB-T2A-$\Delta^1$-KstD and KshAB-P2A-$\Delta^1$-KstD Tricistronic Vectors

The KshAB-T2A-$\Delta^1$-KstD and KshAB-P2A-$\Delta^1$-KstD construct were assembled by first linearizing pEntr221-MTS-KshAB (FIG. 122) with MfeI. Second, the $\Delta^1$-KstD fragment was generated by digesting pEntr221-Repaired $\Delta^1$-KstD (FIG. 107) with EcoRI, a restriction enzyme with two recognition sites flanking $\Delta^1$-KstD. Both the pEntr221-MTS-KshAB backbone and the $\Delta^1$-KstD insert were isolated by agarose gel electrophoresis (0.8%), extracted from the gel using a Qiagen gel extraction kit, and the concentration of DNA was determined using a nanodrop spectrophotometer. The isolated $\Delta^1$-KstD fragment was ligated into the linearized pEntr221-KshAB backbone vector using standard ligation with NEB T4 ligase. Following ligation and transformation of the construct into Omnimax 2T1$^R$ *E. coli* cells, the vector was sequence verified for proper insertion and orientation of the $\Delta^1$-KstD insert. The ligated pEntr221-MTS-KshAB $\Delta^1$-KstD vector was linearized by digesting with BbvCI and SpeI to remove the KshB C-terminal stop codon and $\Delta^1$-KstD kozak sequence. The linearized pEntr221 MTS-KshAB $\Delta^1$-KstD backbone was isolated by agarose gel electrophoresis (0.8%), extracted from the gel using a Qiagen gel extraction kit, and the concentration of DNA was determined using a nanodrop spectrophotometer. Two repair strings were designed with 40 bp homology arms starting from the 3' overhangs generated from the BbvCI and SpeI digest. The repair strings were synthesized by GeneArt to encode for the KshB C-terminus (excluding the native KshB stop codon), one of two viral 2A ribosomal skipping peptides, and the N-terminus of $\Delta^1$-KstD that was removed from the BbvCI and SpeI digest. For co-expressing $\Delta^1$-KstD along with KshAB, the first repair string (FIG. 126) (656 nt) was synthesized with a Thosea asigna 2A skipping peptide (T2A peptide) and the second repair string (FIG. 128) (659 nt) was synthesized with a Porcine teschovirus 2A skipping peptide (P2A peptide). Following the P2A and T2A skipping peptide sequences are the $\Delta^1$-KstD Flag tag and the remaining $\Delta^1$-KstD coding sequence removed by the BbvCI and SpeI digest. The repair strings (150 ng) and the linearized pEntr221 MTS-KshAB $\Delta^1$-KstD ligated product (50 ng) were assembled using Gibson Assembly (following standard procedure) to produce a circularized tricistronic vector. The assembled vectors (2 μL each) were diluted with water (4 μL) and propagated by transforming (2 μL DNA each) Onimax 2T1R *E. coli*. Plasmid DNA from six bacterial colonies was isolated using the Qiagen mini kit, screened by restriction enzyme digest, and verified by DNA sequence analysis. The pEntr221-KshAB-T2A-A1-KstD (FIG. 130) and pEntr221-KshAB-P2A-$\Delta^1$-KstD constructs were subcloned into the pDest51 (FIG. 132) and pLenti-CMV-puro (w118-1) (FIG. 133) expression vectors using Gateway recombination as described previously.

P450-FdxR-Fdx-P2A-HSD2-T2A-KshA-P2A-KshB-T2A-$\Delta^1$-KstD Pentacistronic Vector (Cholesterol Catabolizing Cassette or the CCC)

The P450-FdxR-Fdx-P2A-HSD2-T2A-KshAB-T2A-$\Delta^1$-KstD (the CCC) (FIG. 140) construct was assembled by linearizing pEntr221-KshAB-T2A-$\Delta^1$-KstD with NcoI. The P450-FdxR-Fdx-P2A-HSD2 fragment (FIG. 136) (3221 nt) was generated by digesting pMK-RQ-P450-FdxR-Fdx-P2A-HSD2 (FIG. 95) with ScaI and EcoRV. The linearized pEntr221-KshAB-T2A-$\Delta^1$-KstD (FIG. 130) backbone and P450-FdxR-FdxP2A-HSD2 fragment (FIG. 136) were isolated by agarose gel electrophoresis (0.8%), extracted from the gel using a Qiagen gel extraction kit, and the concentration of DNA was determined using a nanodrop spectrophotometer. Two repair strings were designed with 40 bp homology arms starting from the 3' overhangs of the pEntr221-KshAB-T2A$\Delta^1$-KstD vector backbone and the P450-FdxR-Fdx-P2A-HSD2 fragment. The first repair string (FIG. 134) included 40 bp of homology starting from the 3' overhangs of the NcoI restriction site in pEntr221-KshAB-T2A-$\Delta^1$-KstD (left homology arm) and the ScaI restriction site of the P450-FdxR-Fdx-P2A-HSD2 fragment (right homology arm). The second repair string (FIG. 138) included 40 bp of homology starting from the 3' overhangs of the EcoRV restriction site of the P450-FdxR-Fdx-P2A-HSD2 fragment (left homology arm) and the NcoI restriction site in pEntr221-KshAB-T2A-$\Delta^1$-KstD (right homology arm). The first repair string (474 nt) includes the KshAB Kozak consensus sequence and the P450 sequence that was lost after generating the P450-FdxR-Fdx fragment. The second repair string (1079 nt) included the C-terminal end of HSD2 excluding the native stop codon and a Thosea asigna 2A skipping peptide (T2A peptide). The two repair strings (150 ng each), the P450-FdxR-Fdx-P2A-HSD2 digested fragment (50 ng), and the linearized pEntr221-KshAB-T2A-$\Delta^1$-KstD backbone (50 ng) were assembled using Gibson Assembly (following standard procedure) to produce a circularized pentacistronic vector. The assembled vector (2 μL) was diluted with water (4 μL) and propagated by transforming (2 μL DNA) Onimax 2T1$^R$ *E. coli*. Plasmid DNA from six bacterial colonies was isolated using the Qiagen mini kit, screened by restriction enzyme digest, and verified by DNA sequence analysis. The pEntr221-P450-FdxR-FdxP2A-HSD2-T2A-KshA-P2A-KshB-T2A-$\Delta^1$-KstD construct (FIG. 140) was subcloned into the pDest51 (FIG. 142) and pLenti-CMV-puro (w118-1) (FIG. 143) expression vectors using Gateway recombination as described previously.

Mammalian Cell Culture

Hep3B (ATCC HB-8064) and HEK293FT (Thermo Fisher R70007) cells were cultured in media A: DMEM containing 1 mM sodium pyruvate, 0.5×NEAA, and 10% fetal bovine serum. For experiments, Hep3B cells were maintained in media B: DMEM containing 1 mM sodium pyruvate, 0.5×NEAA, and 0% fetal bovine serum. U-937 monocytes (ATCC CRL-1593.2) were cultured in media C: RPMI-1640 media supplemented with 1×NEAA, 100 units/mL penicillin, 100 μg streptomycin, and 10% fetal bovine serum. For experiments, U-937 derived macrophages were maintained in media D: RPMI-1640 media supplemented with 1×NEAA, 100 units/mL penicillin, 100 μg streptomycin, and 2% fetal bovine serum. Mammalian cells were cultured in corning T75 flasks at 37° C. and 5% $CO_2$.

U-937 Derived Macrophages

U-937 monocytes were differentiated into macrophages by incubation with phorbol 12-myristate 13-acetate (PMA P1585 Sigma) in media C. PMA was prepared by diluting 100 μg PMA with 1 mL DMSO. U-937 monocytes were seeded into 35 mm ($5\times10^6$ cells), 60 mm ($1.5\times10^6$ cells), or 100 mm dishes ($6\times10^6$ cells) coated with 0.1% gelatin. PMA was added to a final concentration of 200 nM (120 ng/mL of media) for 48 hours. Following PMA treatment, media was removed, cells rinsed with PBS (2×), and cells were allowed to continue differentiating in media C for 72 hours.

Transient Expression Experiments in Hep3B Cells

Plasmid DNA (2.5 μg of pDest51-MTS-KshAB or pDest51-$\Delta^1$-KstD) was diluted with 250 μL (2.5 μg DNA for single enzyme expression) or 500 μL (5.0 μg DNA for dual enzyme expression) Opti-MEM in a glass vial (1 μg plasmid DNA/100 μL OptiMEM). DNA was mixed gently by tapping bottom of vial 30 times. A 3:1 ratio of XtremeGene 9 (XG9) to DNA (7.5 μL XG9 for 2.5 μg DNA and 15.0 μL XG9 for 5.0 μg DNA) was added to the glass vial and mixed gently by tapping 30 times. The DNA and transfection reagent mix were allowed to incubate at room temperature for 30 minutes. Following incubation, the DNA/transfection reagent was added drop wise to Hep3B cells that were pre-seeded ($2.3\times10^6$ cells) and grown to 90% confluency in 60 mm dishes. Cells were allowed to incubate with transfection reagent for 48 hours prior to analysis. For western blot analysis, cells were washed twice with PBS and scrapped in 500 μL RIPA buffer. For activity assessment, the media was removed and the cells washed twice with PBS. New media (media B) and 10 μM of the steroid substrate were added to cells and incubated at 37° C. At the indicated time points, cells were scrapped and removed with the media, extracted, and analyzed by RP-HPLC as described below.

Lentiviral Packaging

Lentiviral particles encoding the enzyme constructs were produced with HEK293FT cells using the third generation lentiviral packaging system (Addgene). Packaging vectors (7.5 μg PMDL, 3.75 μg RSV-REV, and 4.5 μg PMD2.G) and each transfer vector (3 μg pLenti-CMV-Blast (706-1) or pLenti-CMV-Puro (w118-1)) were diluted with 1.875 mL Opti-MEM (1 μg plasmid DNA/100 μL Opti-MEM) in a glass vial. DNA was mixed gently by tapping bottom of vial 30 times. For transfections using XtremeGene HP, a 2:1 ratio of XtremeGene HP to DNA (37.5 μL XtremeGene HP) was used. For transfections using XtremeGene 9, a 3:1 ratio of XtremeGene 9 to DNA (56.25 μL XtremeGene 9) was used. The transfection reagent was added to the glass vial and mixed gently by tapping 30 times. The DNA and transfection reagent mix were allowed to incubate at room temperature for 30 minutes. Following incubation, the DNA/transfection reagent was added to 12 mL of media A and mixed by inversion. The media containing the DNA/transfection reagent was added slowly to the side of the 0.10% gelatin coated T75 flask containing HEK293FT cells that were pre-seeded ($2\times10^6$ cells) and grown to 70% confluency. The flask was slowly laid flat to minimize disturbing the monolayer of cells. Cells were allowed to produce lentiviral particles for 48 hours. Following incubation, the viral supernatant was removed and subjected to centrifugation (1,625×g) for 2 minutes. Next, the supernatant was syringe filtered with a 0.45 μm polyethersulfone membrane and separated into 500 μL aliquots. Lastly the aliquots were flash frozen in a dry ice/ethanol bath and stored at −80° C.

Stable Expression of $\Delta^1$-KstD, KshAB, P450-FdxR-Fdx-P2A-HSD2, and P450-FdxRFdx-P2A-HSD2-T2A-KshA-P2A-KshB-T2A-$\Delta^1$-KstD in Hep3B and U-937 Cells Hep3B cells ($2.3\times10^5$ cells) were grown to 70% confluency in 60 mm dishes and U-937 monocytes ($1.0\times10^5$ cells/mL) were seeded in T25 flasks containing 5 mL media. Both Hep3B and U-937 cells were transduced with 0.5 mL of the total 13 mL of the viral supernatant. Cells were allowed to incubate with the viral supernatant for 48 hours prior to selection with 0.05 mg/mL hygromycin (pLenti-PGK-Hygro (w530-1)), 0.001 mg/mL puromycin (pLenti-CMV-Puro (w118-1)), or 0.012 mg/mL blasticidin (pLenti-CMVBlast (706-1)) antibiotic for two weeks prior to time course experiments.

SDS-PAGE and Western Blot of Eukaryotic Cell Lines

Cells were grown in 60 mm (Hep3B) or 100 mm (U-937 derived macrophages) dishes, washed with PBS (2×), and collected by scraping in 500 μL RIPA buffer. Cells were mechanically lysed on ice using a syringe with a 27 gauge needle. Protein samples were mixed with an equal volume of 2× Laemmli sample buffer, boiled for 5 minutes, and subjected to centrifugation at 15,000×g for 10 minutes at 4° C. Protein samples (25 μg) were separated using SDS-PAGE on a 10% polyacrylamide gel, transferred to a PVDF membrane, and probed with anti-FLAG (1:1000; Millipore MAB3118, from mouse), anti-HA (1:3000; Sigma H9658, from mouse), or anti-HSD3B2 (1:1000, Abcam ab80500, from rabbit). ECL anti-mouse IgG secondary antibody conjugated to HRP (1:10,000 GE Helathcare NA931VS, from sheep) or ECL anti-rabbit IgG (1:10,000, GE Healthcare UK Limited NA934V, from donkey) and SuperSignal West Femto Substrate were used for detection.

Enzyme Activity Assessment of Stable Hep3B and U-937 Cell Lines

Hep3B cells stably expressing enzyme constructs were seeded ($2.3\times10^5$ cells) into 60 mm dishes and grown to confluency in media A. At time 0, the media was removed and the cells were washed twice with PBS. New media (media B) and 10 μM of the steroid substrate were added to cells and incubated at 37° C. U-937 derived macrophages in 100 mm dishes coated with 0.1% gelatin were prepared as previously described. Five day old macrophages were given 5 mL media D and 10 μM of the steroid substrate or 50 μg C4-$^{14}$C cholesterol labeled LDLs (163 nCi C4-$^{14}$C—cholesterol). At the indicated time points, the cells were scraped and cells with media were removed from the dish. The steroids analytes were extracted and analyzed by RP-HPLC as described below.

Pregn-1,4-diene-3,20-dione (PDD) and 9-hydroxypregn-4-ene-3,20-dione (9-OHPD) Production and Isolation To produce and isolate the pregn-1,4-diene-3,20-dione (PDD) substrate, a reaction was assembled by adding 200 μL of elution fraction 20 from the $\Delta^1$-KstD IMAC isolation, 629 μg (100 μM) progesterone (PD), 200 μM resazurin, 10 μg/ml BSA, and the final volume brought to 20 mL with Tris-HCL pH 7.5. Following 24 hours of incubation at 25° C. on a rotator, the reaction was stopped and extracted using ethyl acetate (2:1; v/v), twice. The ethyl acetate was dried using nitrogen gas, and steroid analytes resuspended in 500 μL EtOH. The bioconversion analytes were analyzed as described below. RPHPLC analysis revealed a 95% conversion of progesterone (PD) to pregn-1,4-diene-3,20 dione (PDD). Based on the progesterone standard curve, the final concentration of the PDD stock was 2.54 mM.

To produce and isolate the 9-hydroxypregn-4-ene-3,20-dione (9-OHPD) substrate, a reaction was assembled by adding 7 mL of the bacterial KshAB clarified lysate, 1.25 mg progesterone, and 70 μNA NADH. Following 48 hours of incubation at 25° C. on a rotator, the reaction was stopped and extracted using ethyl acetate (2:1; v/v), thrice. The steroid analytes were dried using nitrogen gas, and resuspended in 500 μL EtOH. The bioconversion analytes were analyzed as described below. RP-HPLC analysis revealed a 76.6% conversion of progesterone (PD) to 9-hydroxypregn-4-ene-3,20-dione (9-OHPD). Based on the progesterone standard curve, the final concentration of the 9-OHPD stock was 5.8 mM.

C4-$^{14}$C-Progesterone and C4-$^{14}$C-Cholesterol Stocks (10 mM)

Stocks (10 mM at 20 nCi/μL) of C4-$^{14}$C-Progesterone were prepared by diluting 20 μL C4-$^{14}$C-Progesterone (ARC 1398A, Progesterone [4-13C], S.A. 55 mCi/mmol, 50 μCi/vial) with 50 μl . . . of 20 mM unlabeled progesterone (in EtOH) and 30 mL EtOH. Stocks (10 mM at 20 nCi/μL) of C4-$^{14}$C-cholesterol were prepared by diluting 50 μL C4-$^{14}$C-cholesterol (Perkin Elmer 250 μCi [9.25 mBq] 50.8 mCi/mmol [1.88 Gbq/mmol] in 6.25 mL EtOH) with 50 μL of 20 mM unlabeled cholesterol (in EtOH).

C4-$^{14}$C-Cholesterol LDL Labeling

C4-$^{14}$C-cholesterol (Perkin Elmer 250 μCi [9.25 mBq] 50.8 mCi/mmol [1.88 Gbq/mmol] in 6.25 mL EtOH) was used to radiolabel human low density lipoproteins (Alfa Aesar J65039 [BT-903] 5 mg/mL). First, 4.0 μCi of C4-$^{14}$C-cholesterol (60.8 μg in 200 μL EtOH) was added to a 2 mL glass vial. To reduce the volume of EtOH the C4-$^{14}$C-cholesterol was initially suspended in, the initial volume was dried down to approximately 20 μL. Next, a 250 μL aliquot containing 1.25 mg of human low density lipoproteins was added to the 4.0 μCi of C4-$^{14}$C-cholesterol (60.8 μg). The C4-$^{14}$C cholesterol was partitioned into the LDLs by placing the glass vial in an ultrasonic water bath for 10 minutes followed by incubation at room temperature on a rotator for three days. The final concentration of the C4-$^{14}$C-cholesterol labeled LDL stock was 4.6 μg/μL LDL labeled with 15 nCi/μL (225.19 ng/μL) C4-$^{14}$C-cholesterol.

C2,3,4-$^{13}$C3-Cholesterol LDL Labeling

C2,3,4-$^{13}$C3-cholesterol (Cambridge Isotopes, CLM-9139-0.002) was used to radiolabel human low density lipoproteins (Alfa Aesar J65039 [BT-903] 5 mg/mL). First 2 mg of C2,3,4-$^{13}$C3-cholesterol was resuspended in 517.26 uL EtOH to prepare a 10 mM stock. From this 10 mM stock of C2,3,4-$^{13}$C3-cholesterol, 60.75 μg (in 15.7 μL EtOH) was added to a 2 mL glass vial. Next, a 250 μL aliquot containing 1.25 mg of human low density lipoproteins was added to the 60.75 μg C2,3,4-$^{13}$C3-cholesterol. The C2,3,4 $^{13}$C3-cholesterol was partitioned into the LDLs by placing the glass vial in an ultrasonic water bath for 10 minutes followed by incubation at room temperature on a rotator for three days. The final concentration of the C2,3,4-$^{13}$C3-cholesterol labeled LDL stock was 4.7 μg/μL LDL labeled with 228.64 ng/μL C2,3,4-$^{13}$C3-cholesterol.

U-937-Derived Macrophage LDL Loading for C4-$^{14}$C—Cholesterol Efflux Analysis Five day old U-937-derived macrophages (prepared in 60 mm dishes as previously described) were incubated with 5 μg C4-$^{14}$C labeled LDLs (18 nCi C4-$^{14}$C—cholesterol) for 24 hours. Following incubation with C4-$^{14}$C labeled LDLs, the media was removed, cells were washed with PBS (2×), and new media (media D) was given for an additional two days. At the respective time points, media was removed, cells were washed with PBS (2×), and scraped in 500 μL RIPA buffer. Scintillation events from the media (250 μL of the 2 mL) and cells (250 μL of 500 μL) were suspended in 4 mL of Beckman Ready Safe scintillation fluid, mixed by vortexting, and analyzed with a Beckman LS 6500 multi-purpose scintillation counter for 10 minutes with luminex correction enabled. Scintillation events were normalized to total protein. Measurements were made with an N of 2 in quadruplicate.

U-937 Derived Macrophage LDL Loading for C2,3,4-$^{13}$C3—Cholesterol LC-MS Analysis Five day old macrophages (prepared in 100 mm dishes as previously described) were incubated with 50 μg C2,3,4-$^{13}$C3-cholesterol labeled LDLs (159.84 nCi C4-$^{14}$C—cholesterol) for 72 hours. Following incubation with C2,3,4-$^{13}$C3-cholesterol labeled LDLs, cells were scraped and removed with the media. Cells and media were extracted with ethyl acetate (2:1; v/v), twice. The ethyl acetate was dried under nitrogen gas and analyzed by LC-MS as described below.

BODIPY 493/503 Staining and Confocal Microscopy

U-937 derived macrophages were prepared as previously described in 35 mm glass bottom dishes. Following five days of differentiation, macrophages were given 50 μg/mL LDL (Alfa Aesar J65039 [BT-903] 5 mg/mL) or acetylated LDL ((Alfa Aesar J65029 [BT-906] 2.5 mg/mL) for 24 hours in media D. Following incubation with LDLs, cells were washed twice with PBS and stained with 20 μg/mL BODIPY 493/503 in PBS for 30 minutes at 37° C. BODIPY 493/503 (Difluoro{2-[1-3,5-dimethyl-2H-pyrrol-2- ylidene-N) ethyl]-3,5-dimethyl-1H-pyrrolato-N}boron) was prepared in DMF at a stock concentration of 2 μg/ml. Following staining, cells were washed with PBS (2×) and given 2 mL media D. Imaging was performed with a Nikon A1 Confocal Microscope using an excitation of 488 nm and emission of 525/50 nm at 60× magnification.

Steroid Isolation

Reactions were extracted twice with ethyl acetate (clarified lysates 5:1; v/v, isolated $\Delta^1$-KstD 2.5:1; v/v, Hep3B and U-937 cells 2:1; v/v). Samples were subjected to centrifugation between extractions at 3,100×g for 1 minute at 25° C. in order to minimize the interphase layer and improve extraction efficiency. The organic phase was collected and evaporated under nitrogen gas. Isolated pregnane analytes were reconstituted in an 80:20 mixture of 30% [vol/vol] acetonitrile in H2O and 80% [vol/vol] 2-propanol in $H_2O$. Isolated cholestane analytes were reconstituted in 90% [vol/vol] acetonitrile in $H_2O$. Clarified bacterial lysates and eukaryotic samples were resuspended in 250 mL and 500 mL, respectively, with the appropriate HPLC sample buffer. Samples were filtered with Millipore Ultrafree PVDF centrifugal filters (0.1 μm), and 80 μL of the sample was injected and analyzed by RP-HPLC.

Reverse Phase High Pressure Liquid Chromatography (RP-HPLC) Analysis

For separation and identification of steroid bioconversion analytes, an analytical RP-C18 column (Chromolith 100; end capped; 5 m; 100 by 4.6 mm; Merck, Darmstadt, Germany) was used with a Hitachi Elite LaChrom HPLC equipped with an in-line Perkin Elmer Radiomatic 150TR flow scintillation analyzer. For separation of pregnane based analytes, the mobile phase was comprised of a mixture of solvent A (30% [vol/vol] acetonitrile in $H_2O$) and solvent B (80% [vol/vol] 2-propanol in $H_2O$). Separation was performed at a flow rate of 0.8 ml $min^{-1}$ at room temperature with a linear gradient starting from 80:20 to 50:50 solvent A:B over 30 minutes. For separation of cholestane based analytes, the mobile phase was comprised of a mixture of solvent A (90% [vol/vol] acetonitrile in $H_2O$) and solvent B (85% [vol/vol] acetonitrile in 2-propanol). Separation was performed at a flow rate of 1.25 ml $min^{-1}$ at room temperature with an isocratic elution of 100:0 solvent A:B from time 0-25 minutes, a linear gradient of 100:0 to 0:100 solvent A:B from 25-35 minutes, and an isocratic elution of 0:100 solvent A:B from 35-45 minutes.

We claim:

1. A nucleic acid composition comprising:

a coding sequence, coding for one or more proteins selected from humanized forms of cholesterol dehydrogenase (coded for by nucleotides 166 to 1284 of SEQ ID NO:10; CholD), 3-ketosteroid Δ1-dehydrogenase (coded for by nucleotides 170 to 1704 of SEQ ID NO:13; Δ1-KstD), anoxic cholesterol metabolism B enzyme (coded for by nucleotides 74 to 1756 of SEQ ID NO:11; acmB), 3-ketosteroid 9α-hydroxylase (coded for by nucleotides 132 to 1316 and 1416 to 2483 of SEQ ID NO:17; KshAB), 3β-hydroxysteroid dehydrogenase 2 (coded for by nucleotides 3554 to 4672 of SEQ ID NO:12; HSD2), and a fusion protein of P450-ferredoxin reductase-ferredoxin fusion (SEQ ID NO:5; P450-FdxR-Fdx); and a control sequence, for regulating the transcription of one or more of the coding sequences in a eukaryotic cell.

2. The nucleic acid composition of claim 1, wherein the one or more proteins are selected from humanized forms of Δ1-KstD, KshAB, HSD2, and P450-FdxR-Fdx.

3. The nucleic acid composition of claim 2, comprising coding sequences for humanized proteins Δ1-KstD, KshAB, HSD2, and P450-FdxR-Fdx, and wherein the control sequence is a eukaryotic transcription promoter sequence.

4. The nucleic acid composition of claim 3, wherein the coding sequence comprises nucleotides 1007 to 9817 of the sequence SEQ ID NO: 27, and the eukaryotic transcription promoter sequence is a CMV promoter sequence.

5. A method of regulating a sterol concentration in a subject in need thereof, the method comprising the steps of:

modifying an immune cell of the subject by introducing the nucleic acid composition of claim 1;

allowing the immune cell to express one or more sequences from the nucleic acid, wherein the nucleic acid codes for one or more proteins involved in sterol metabolism;

administering the modified cell to the subject, and allowing the modified cell to degrade the sterol.

6. The method of claim 5, wherein the protein is selected from Δ1-KstD, KshAB, HSD2, and P450-FdxR-Fdx.

7. The method of claim 6, wherein the sequences code for humanized proteins Δ1-KstD, KshAB, HSD2, and (P450-FdxR-Fdx) and wherein expression is controlled by a eukaryotic promoter sequence.

8. The method of claim 7, wherein humanized KshAB is targeted to a mitochondrion of the cell by including a mitochondrial targeting sequence in the KshAB coding sequence.

9. The method of claim 7, wherein the nucleic acid comprises nucleotides 1007 to 9817 of sequence SEQ ID NO: 27, and the eukaryotic transcription promoter sequence is a CMV promoter sequence.

10. The method of claim 9, wherein the immune cell is a monocyte or macrophage.

11. A method of altering a eukaryotic cell that cannot catabolize a sterol comprising:

introducing an expression vector comprising the nucleic acid composition of claim 1 into the cell; and expressing one or more enzymes that catabolize the sterol from the vector.

12. The method of claim 11, wherein the sterol is cholesterol and the one or more enzymes are selected from Δ1-KstD, acmB, KshAB, HSD2, and P450-FdxR-Fdx.

13. The method of claim 12, wherein the enzymes are Δ1-KstD, KshAB, HSD2, and P450-FdxR-Fdx.

14. The method of claim 13, wherein humanized KshAB is targeted to a mitochondrion of the cell by including a mitochondrial targeting sequence in the KshAB coding sequence.

15. The method of claim 14, wherein the eukaryotic cell is an immune cell.

16. The method of claim 11, wherein the nucleic acid comprises at least one sequence selected from SEQ ID NOS: 10-27.

17. The method of claim 14, wherein the nucleic acid comprises nucleotides 1007 to 9817 of sequence SEQ ID NO: 27, and the eukaryotic transcription promoter sequence is a CMV promoter sequence.

* * * * *

UNITED STATES PATENT AND TRADEMARK OFFICE

CERTIFICATE OF CORRECTION

PATENT NO. : 11,612,619 B2
APPLICATION NO. : 16/672185
DATED : March 28, 2023
INVENTOR(S) : Richard Eric Honkanen, Brandon Marshall D'Arcy and Mark Raymond Swingle It is certified that error appears in the above-identified patent and that said Letters Patent is hereby corrected as shown below:

In the Specification

Column 6, Line 66:
"$A^1$-KstD"
Should be:
--$\Delta^1$-KstD--

Column 8, Line 49:
"E. co/clack the ability to metabolize"
Should be:
--E.coli lack the ability to metabolize--

Column 9, Line 65:
"the ring-A Cl-02 bond"
Should be:
--the ring-A Cl-C2 bond--

Column 11, Line 61:
"3p-hydroxyl oxidation"
Should be:
--3β-hydroxyl oxidation--

Column 13, Line 32:
"3p-hydroxyl"
Should be:
--3β-hydroxyl--

Column 13, Line 36:
"Purification outline for $£^1$-KstD"

Signed and Sealed this
Tenth Day of September, 2024

Katherine Kelly Vidal

Katherine Kelly Vidal
*Director of the United States Patent and Trademark Office*

Should be:
--Purification outline for $\Delta^1$-KstD--

Column 13, Line 42:
"KstDfusion protein"
Should be:
--KstD fusion protein--

Column 14, Line 51:
"Kst Dreaction"
Should be:
--KstD reaction--

Column 17, Line 38:
"formation from progesterone (PD) C1-02 ring-A"
Should be:
--formation from progesterone (PD) C1-C2 ring-A--

Column 17, Line 43:
"6=13.8 min"
Should be:
--$t_r$=13.8 min--

Column 18, Line 49:
"In Hep3B M-KstD cells"
Should be:
--In Hep3B Δ1-KstD cells--

Column 22, Line 58:
"1245 nm"
Should be:
--λ245 nm--

Column 23, Line 14:
"4-7.2 min"
Should be:
--$t_r$=7.2 min--

Column 29, Line 30:
"shine dalgarnosequence"
Should be:
--shine-delgarno sequence--

Column 30, Line 1:
"GeneOptimizersoftware"

Should be:
--GeneOptimizer software--

Column 30, Line 9:
"GeneOptimizersoftware"
Should be:
--GeneOptimizer software--

Column 33, Line 13:
"MTSKshAB-T2A-A1-KstD tricistronic vector."
Should be:
--MTSKshAB-T2A- Δ1-KstD tricistronic vector.--

Column 33, Line 15:
"A1-KstD"
Should be:
--Δ1-KstD--

Column 33, Line 22:
"A1-KstD"
Should be:
--Δ1-KstD--

Column 33, Line 34:
"A1-KstD"
Should be:
--Δ1-KstD--

Column 38, Line 45:
"E. Coll."
Should be:
--E. coli.--

Column 43, Line 40:
"3p-hydroxyl"
Should be:
--3β-hydroxyl--

Column 47, Line 2:
"Ata biochemical level"
Should be:
--At a biochemical level--

Column 49, Line 18:
"the C5-C6 double bond to C4-05"

Should be:
--the C5-C6 double bond to C4-C5--

Column 49, Line 25:
"incubated with 100 μNA"
Should be:
--incubated with 100 μM--

Column 49, Line 32:
"incubated with 100 WI cholesterol"
Should be:
--incubated with 100 μM cholesterol--

Column 49, Line 36:
"Analysis of 04-$^{14}$C scintillation events"
Should be:
--Analysis of C4-$^{14}$C scintillation events--

Column 49, Line 66:
"(CDN) ($\Delta_{max}$: 241 nm;"
Should be:
--(CDN) ($\lambda_{max}$: 241 nm;--

Column 51, Line 17:
"(PD) ($\Delta_{max}$: 245 nm;"
Should be:
--(PD) ($\lambda_{max}$: 245 nm;--

Column 67, Line 40:
"(11φ-11,21-dihydroxypregn-4-ene-3,20-dione (Corticosterone) (Sigma C-2505), (11p)"
Should be:
--(11β-11,21-dihydroxypregn-4-ene-3,20-dione (Corticosterone) (Sigma C-2505), (11β)--

Column 67, Line 50:
"(DH EA/Dehydroepiandrosterone)"
Should be:
--(DHEA/Dehydroepiandrosterone)--

Column 71, Line 3:
"($5\times10^6$ cells)"
Should be:
--($5\times10^5$ cells)--

Column 71, Line 22:
"($2.3\times10^6$ cells)"

Should be:
--(2.3×$10^5$ cells)--

Column 72, Line 63:
"70 μNA NADH"
Should be:
--70 μM NADH--

SEQUENCE LISTING

<160> NUMBER OF SEQ ID NOS: 27

<210> SEQ ID NO 1
<211> LENGTH: 1824
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
aaataatgat tttattttga ctgatagtga cctgttcgtt gcaacacatt gatgagcaat      60
gctttttat aatgccaact ttgtacaaaa aagcaggctt cgaattcaga tctagaagta     120
ctggcaccat ggccggcgac tacaaggacg acgacgataa gatgcaggac tggactagtg     180
aatgcgacgt gctggtcgtg ggctctggcg gaggcgctct gacaggcgct tatacagctg     240
ccgcccaggg cctgaccacc atcgtgctgg aaaagaccga cagattcggc ggcaccagcg     300
cctactctgg cgcctctatt tggctgcctg gcacccaggt gcaggaaaga gccggactgc     360
ctgacagcac cgagaacgcc agaacctacc tgagagccct gctgggcgac gccgagagcg     420
aaagacagga cgcctacgtg gaaaccgccc ctgctgtggt ggctctgctg gaacagaacc     480
ccaacatcga gttcgagttc cgggccttcc ccgactacta caaggccgag ggcagaatgg     540
acaccggccg cagcatcaac cccctggatc tggaccctgc cgacatcggc gatctggccg     600
gaaaagtgcg gcccgagctg gaccaggata gaaccggaca ggatcacgcc cctggcccca     660
tgattggagg cagagccctg atcggcagac tgctggctgc tgtgcagagc accggaaagg     720
ccgagctgag aaccgagagc gtgctgacca gcctgatcgt ggaagatggc agagtcgtgg     780
gcgccgaggt ggaatctggg ggcgagacac agcggatcaa ggccaacaga ggcgtgctga     840
tggccgctgg cggcatcgag ggaaacgccg agatgaggga acaggccgga acacccggca     900
aggccatctg gtctatgggc cccttcggag ccaataccgg cgacgccatc tctgccggaa     960
ttgccgtggg cggagctacc gcactgctgg atcaggcctg gttctgccct ggcgtggaac    1020
agcctgatgg cagcgccgcc tttatggtgg gagtgcgggg aggactggtg gtggattctg    1080
ccggggagag atacctgaac gagagcctgc cctacgacca gttcggcaga gctatggacg    1140
cccacgatga caacggctcc gccgtgccca gcttcatgat cttcgacagc agagagggcg    1200
gaggcctgcc cgccatctgc atccctaata ccgccccagc caagcacctg gaagccggaa    1260
catgggtggg agccgacaca ctggaagaac tggccgccaa gacaggcctg cctgccgatg    1320
ctctgagaag caccgtggaa aagttcaacg acgccgccaa gctgggcgtg gacgaagagt    1380
tccatagagg cgaggacccc tacgacgcct tcttctgccc acctaatggc ggagccaacg    1440
ccgccctgac cgccattgag aacggcccctt tttacgccgc cagaatcgtg ctgagcgacc   1500
tgggcacaaa gggcggcctc gtgaccgatg tgaacggcag agtgctgaga gccgacggca    1560
gcgccattga cggactgtat gccgccggaa ataccagcgc cagcctgagc ggcagattct    1620
accctggccc aggcgtgcca ctgggcaccg ctatggtgtt cagctacaga gctgcccagg    1680
acatggcgaa gtaattctag agagctcaag gtgaattcag atctgaccca gctttcttgt    1740
acaaagttgg cattataaga aagcattgct tatcaatttg ttgcaacgaa caggtcacta    1800
tcagtcaaaa taaaatcatt attt                                          1824
```

<210> SEQ ID NO 2
<211> LENGTH: 2852
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 2
aaataatgat tttattttga ctgatagtga cctgttcgtt gcaacaaatt gatgagcaat 60 gctttttat aatgccaact ttgtacaaaa aagcaggctt cgaattcaga tctagaagta 120
ctggcaccat ggccccatat agcctcctgg tgaccagact gcagaaagcc ctgggcgtgc 180
ggcagtacca tgtggcctct gtgctgtgcc agagggccaa ggtggccatg agcgactaca 240
aggacgacga cgacaaaggc ggcggaggca gcatgagcat cgacacagcc agaagcggca 300
gcgacgacga tgtggaaatc agagagatcc aggccgctgc cgcccctacc agatttgcca 360
gaggatggca ctgcctgggc ctgctgagag acttccagga cggcaagccc cacagcatcg 420
aggcctttgg caccaagctg gtggtgttcg ccgacagcaa gggccagctg aacgtgctgg 480
acgcctactg cagacacatg ggcggcgatc tgagcagagg cgaagtgaag ggcgactcta 540
tcgcctgccc cttccacgac tggcggtgga atggcaaggg caagtgcacc gacatccctt 600
acgccagacg ggtgcccccct atcgccaaga ccagagcctg gaccaccctg gaaagaaacg 660
gccagctgta tgtgtggaac gacccccagg gcaacccccc acctgaggat gtgaccatcc 720
ctgagatcgc cggctacggc accgacgagt ggacagactg gtcctggaaa agcctgcgga 780
tcaagggcag ccactgccgc gagatcgtgg acaacgtggt ggatatggcc cacttcttct 840
acatccacta cagcttcccc cggtacttca agaacgtgtt cgagggccac accgccaccc 900
agtacatgca ctctaccggc agagaagatg tgatcagcgg caccaactac gacgacccca 960
acgccgagct gagaagcgag gccacctact tcggccccag ctacatgatc gactggctgg 1020
aaagcgacgc caacggccag accatcgaga caatcctgat caactgccac taccccgtgt 1080
ccaacaacga gttcgtgctg cagtacggcg ccatcgtgaa gaaactgccc ggcgtgtccg 1140
acgagatcgc tgccggaatg gccgagcagt ttgccgaagg cgtgcagctg ggcttcgagc 1200
aggacgtgga aatctggaag aacaaggccc ccatcgacaa ccccctgctg agcgaagagg 1260
acggccctgt gtatcagctg cggcggtggt atcagcagtt ctacgtggac gtggaagata 1320
tcaccgagga catgaccaag cgcttcgagt tcgagatcga taccaccaga gccgtggcct 1380
cttggcagaa agaggtggcc gagaacctgg ccaagcaggc cgaaggctct acagccacac 1440
ctggcagcgg cgccaccaac ttcagcctgc tgaaacaggc cggggatgtg gaagagaacc 1500
caggccctat ggccccttac tctctgctcg tgacacggct gcagaaagct ctgggagtgc 1560
gccagtatca cgtggcaagc gtgctgtgtc agcgcgctaa agtggctatg agcggctacc 1620
cctacgatgt gcctgattat gctggcggcg gaggctccat gacagccgtg caggctcctg 1680
tgaccagcag agccacagtg ctgaccgtgt ctgccgtggt gcaggaaaca gccgatgccg 1740
tgtccctggt gttcgacgtg cccgacgaca gaagagagga cttcacctac agacccggcc 1800
agttcctgac cctgagaatc cccagcgaca ggacaggcag cgtggccaga tgttacagcc 1860
tggccagcag ccctttcacc ggcgagcctc caaaagtgac cgtgaagaga acagctggcg 1920
gctacggcag caactggctg tgcgacaata tcgtggccgg acggtccatc gaggtgctgc 1980
ctccagctgg cgtgttcacc cctgccgatc tgaccgagaa actggtgctg tttgctggcg 2040
gaagcggcat cacccccgtg atgagcatcc tggaatccgc cctgcacagc ggcaacaggg 2100
acgtggtgct gatctacggc aaccgcgacg agaagtccgt gatcttcgcc gagaagctga 2160
gagagctggc cgccagacac gctggcgctc tgacagtggt gcattggctg gaatcagtgc 2220
agggcctgcc cagccctcag cagctggcca cactgatcag ccccttcgcc gaccacaggg 2280
cctacatgtg tggcccaggc cccttcatgg acaccgtgcg ggaaggactg ctgctggctg 2340
gcgtgcccaa ggacagaatc cacgccgagg tgttcaccag cctgagcggc gatcctttcg 2400
ccgatgtgcc cctggtggaa atcgacgagt ccgacgccga tgccacctct gccacagtgc 2460
agctggatgg cgaggaacac gacctcgtgt ggcctagaag cgccacactg gtggacgtga 2520
tgctgtccaa gggcctggac gtgccctaca gctgcagaga aggcgagtgc ggcagctgcg 2580
cctgtactgt ggtggaaggc gacgtggaca gcctgcctag cgccatcctg gacgaagagg 2640
atatcgccaa tggctacgtg ctggcctgcc aggctagacc caagagcgat cacgtgcgga 2700
tcgagttctg ataaacccgg gtgataaaga gctcggatcc caattggcta gcgacccagc 2760
tttcttgtac aaagttggca ttataagaaa gcattgctta tcaatttgtt gcaacgaaca 2820
ggtcactatc agtcaaaata aaatcattat tt 2852

<210> SEQ ID NO 3
<211> LENGTH: 1980
<212> TYPE: DNA
<213> ORGANISM: Sterolibacterium denitrificans

<400> SEQUENCE: 3
aaataatgat tttattttga ctgatagtga cctgttcgtt gcaacaaatt gatgagcaat 60 gctttttat aatgccaact ttgtacaaaa aagcaggctt ccaattggga tccggtaccg 120
aaaacctgta cttccagggt accatgagca tcgagacaaa cacctacgac gtgatcgtcg 180
tgggctctgg cgctggcgct atgctggctg ctgctagagc ccatgatctg ggcctgagcg 240
tgctggtggt ggaaaagagc gataagtacg gcggcaccag cgccgtgtct ggcggagctg 300
tgtggattcc caacaacagc cagatgcaga tcaaggacag cttcgacgag gccctgacct 360
acctgaaggc cgccacacag ggactggtgg ccgaggatag actgctggcc tacctggaaa 420
gcgcccctca gatggtggag tacatcaacg ccaatatgac cctgcagtac ttcccctgcc 480
acagataccc cgactactac cagcatctgc ctggcgccaa gcctggcggc agaaccatgg 540
aacccatgct gttcgatgcc gccctgctgg gcgacgagtt cgccaatctg agaatggcct 600
acaccggcac cctgctgatg ggcaaggcca gcatgacagc cacagaggcc catgtgatgc 660
tggccaaaga acccggctgg atgctgcaag tgatcaagag cctgggccgg tactacctgg 720
acctgccctg gcggctgaag tcccggcacg atagaaagag aggcctgggc aacgccatgg 780
ccgctggact gagacacgct ctgctggaaa gaaaggtgcc cctgtggctg aacacccccct 840 tcgagagcct gatcacagag ggcgccgaga acaagcgcgt gaccggcatc gtcgtgaagc 900
ggaatggcca gacactgcag ctgaccgcca gacggggagt ggtgctggga gctggcggct 960
tcgagagaaa ccagcagatg agagagcagt acctgcccaa gcccaccaac gccgcttgga 1020
gcgctacccc ccctcacaat accggcgaca caatcagagc cgccatggac atcggagcca 1080
gagccgagct gatggactgg gcttggtggg tgccatccat ccacgtgcca ggcgaagccg 1140
ctcagaccgg actgttcgcc gagagaaatc tgcccggctg catcgtcgtg aatggcaagg 1200
gccagcggtt catcaacgag gccagccctt acctggaatt tggcgccgct atgtacgaga 1260
accacgccag atccggctct gccgtgcctg cctggctgat cttcgacggc aagttccggt 1320
acaactaccc catgggcccc ctgatgcctg gccagatcca gcctgataga aaggcctggc 1380
tgggcaaggt gtactggcgg gacgatacac tggaaggact ggccaagcag atcggcgtgg 1440
acgctgccgg actgaagcag tccgtggaac tgaacaacca gtacgcccag gacggcaagg 1500
acagagagtt cgacaagggc ggcaacgtgt tcgatcggta ctacggcgac tacaacgtga 1560
agcccaaccc ttgcctggcc cccatcggca agcctcccta ctacgccatg agagtggacg 1620
ccggggacat cggcacaaag ggcggactgc tgaccgacaa ggacgccaga gtgctggacg 1680
agagcgacag acctatcgag ggcctgtact gcatcggcaa caactccgcc agcgtgatgg 1740
gaaaagccta ccctggcgca ggcggcacac tgggacctgc catgaccttc ggctttaggg 1800
ccgccaacca cattgccgcc agcaagtacc cctacgatgt gcccgattac gccggctagt 1860
aacccgggga attcagatct gacccagctt tcttgtacaa agttggcatt ataagaaagc 1920
attgcttatc aatttgttgc aacgaacagg tcactatcag tcaaaataaa atcattattt 1980

<210> SEQ ID NO 4
<211> LENGTH: 1476
<212> TYPE: DNA
<213> ORGANISM: Mycobacterium tuberculosis

<400> SEQUENCE: 4
aaataatgat tttattttga ctgatagtga cctgttcgtt gcaacaaatt gatgagcaat 60 gctttttat aatgccaact ttgtacaaaa aagcaggctt ccaattggga tccctcgaga 120
acctgtactt ccagggccac caccaccacc accacggcac catggccggc ttcctgaact 180
gctgccccgg ctgctgcatg gagcccggcg ccagcgacta caaggacgac gacgacaaga 240
tgctgcggcg gatgggagat gccagcctga caacagagct gggccgggtg ctcgtgacag 300
gcggagctgg atttgtggga gccaacctcg tgaccaccct gctggataga ggacactggg 360
tgcgcagctt cgacagagcc ccttctctgc tgcctgccca ccctcagctg gaagtgctgc 420
agggcgatat caccgacgcc gatgtgtgtg ccgccgctgt ggatggcatc gacaccatct 480
ttcacaccgc cgccatcatc gagctgatgg gcggagccag cgtgaccgac gagtaccggc 540
agagaagctt cgccgtgaat gtgggcggca ccgagaatct gctgcacgcc ggacagaggg 600
ctggggtgca gagattcgtg tataccagca gcaacagcgt cgtgatggga ggccagaata 660
tcgctggcgg cgacgagaca ctgccctaca ccgacagatt caacgacctg tataccgaga 720
caaaagtggt ggccgagcgc ttcgtgctgg cccagaatgg cgtggacggc atgctgacct 780
gcgccatcag acctagcggc atctggggca acggcgacca gaccatgttc cggaagctgt 840
tcgagagcgt gctgaagggc cacgtgaagg tgctcgtggg cagaaagagc gccagactgg 900
acaacagcta cgtgcacaac ctgatccacg gcttcatcct ggccgctgcc cacctggtgc 960
ctgatggaac agctcctgga caggcctact tcatcaacga tgccgagccc atcaacatgt 1020
tcgagttcgc cagacccgtg ctggaagctt gcggccagag atggcccaag atgcggatct 1080
ctggacccgc cgtcagatgg gtcatgactg gctggcagcg gctgcacttc agattcggct 1140
ttcccgcccc tctgctggaa cccctggctg tggaaagact gtacctggac aactacttct 1200
ctatcgccaa ggccagacgg gacctgggct acgagcctct gtttaccaca cagcaggccc 1260
tgaccgagtg cctgccctac tacgtgtccc tgttcgagca gatgaagaac gaggccagag 1320
ccgagaaaac agccgccaca gtgaagcccg ggtagtaaac cggtgaattc agatctgacc 1380
cagctttctt gtacaaagtt ggcattataa gaaagcattg cttatcaatt tgttgcaacg 1440
aacaggtcac tatcagtcaa aataaaatca ttattt 1476

<210> SEQ ID NO 5

-continued

<211> LENGTH: 1144
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Leu Ala Lys Gly Leu Pro Pro Arg Ser Val Leu Val Lys Gly Cys
1               5                   10                  15

Gln Thr Phe Leu Ser Ala Pro Arg Glu Gly Leu Gly Arg Leu Arg Val
            20                  25                  30

Pro Thr Gly Glu Gly Ala Gly Ile Ser Thr Arg Ser Pro Arg Pro Phe
        35                  40                  45

Asn Glu Ile Pro Ser Pro Gly Asp Asn Gly Trp Leu Asn Leu Tyr His
    50                  55                  60

Phe Trp Arg Glu Thr Gly Thr His Lys Val His Leu His His Val Gln
65                  70                  75                  80

Asn Phe Gln Lys Tyr Gly Pro Ile Tyr Arg Glu Lys Leu Gly Asn Val
                85                  90                  95

Glu Ser Val Tyr Val Ile Asp Pro Glu Asp Val Ala Leu Leu Phe Lys
            100                 105                 110

Ser Glu Gly Pro Asn Pro Glu Arg Phe Leu Ile Pro Pro Trp Val Ala
        115                 120                 125

Tyr His Gln Tyr Tyr Gln Arg Pro Ile Gly Val Leu Leu Lys Lys Ser
    130                 135                 140

Ala Ala Trp Lys Lys Asp Arg Val Ala Leu Asn Gln Glu Val Met Ala
145                 150                 155                 160

Pro Glu Ala Thr Lys Asn Phe Leu Pro Leu Leu Asp Ala Val Ser Arg
                165                 170                 175

Asp Phe Val Ser Val Leu His Arg Arg Ile Lys Lys Ala Gly Ser Gly
            180                 185                 190

Asn Tyr Ser Gly Asp Ile Ser Asp Asp Leu Phe Arg Phe Ala Phe Glu
        195                 200                 205

Ser Ile Thr Asn Val Ile Phe Gly Glu Arg Gln Gly Met Leu Glu Glu
    210                 215                 220

Val Val Asn Pro Glu Ala Gln Arg Phe Ile Asp Ala Ile Tyr Gln Met
225                 230                 235                 240

Phe His Thr Ser Val Pro Met Leu Asn Leu Pro Pro Asp Leu Phe Arg
                245                 250                 255

Leu Phe Arg Thr Lys Thr Trp Lys Asp His Val Ala Ala Trp Asp Val
            260                 265                 270

Ile Phe Ser Lys Ala Asp Ile Tyr Thr Gln Asn Phe Tyr Trp Glu Leu
        275                 280                 285

Arg Gln Lys Gly Ser Val His His Asp Tyr Arg Gly Ile Leu Tyr Arg
    290                 295                 300

Leu Leu Gly Asp Ser Lys Met Ser Phe Glu Asp Ile Lys Ala Asn Val
305                 310                 315                 320

Thr Glu Met Leu Ala Gly Gly Val Asp Thr Thr Ser Met Thr Leu Gln
                325                 330                 335

Trp His Leu Tyr Glu Met Ala Arg Asn Leu Lys Val Gln Asp Met Leu
            340                 345                 350

Arg Ala Glu Val Leu Ala Ala Arg His Gln Ala Gln Gly Asp Met Ala
        355                 360                 365

Thr Met Leu Gln Leu Val Pro Leu Leu Lys Ala Ser Ile Lys Glu Thr
```

-continued

```
    370                 375                 380

Leu Arg Leu His Pro Ile Ser Val Thr Leu Gln Arg Tyr Leu Val Asn
385                 390                 395                 400

Asp Leu Val Leu Arg Asp Tyr Met Ile Pro Ala Lys Thr Leu Val Gln
                405                 410                 415

Val Ala Ile Tyr Ala Leu Gly Arg Glu Pro Thr Phe Phe Phe Asp Pro
            420                 425                 430

Glu Asn Phe Asp Pro Thr Arg Trp Leu Ser Lys Asp Lys Asn Ile Thr
        435                 440                 445

Tyr Phe Arg Asn Leu Gly Phe Gly Trp Gly Val Arg Gln Cys Leu Gly
    450                 455                 460

Arg Arg Ile Ala Glu Leu Glu Met Thr Ile Phe Leu Ile Asn Met Leu
465                 470                 475                 480

Glu Asn Phe Arg Val Glu Ile Gln His Leu Ser Asp Val Gly Thr Thr
                485                 490                 495

Phe Asn Leu Ile Leu Met Pro Glu Lys Pro Ile Ser Phe Thr Phe Trp
            500                 505                 510

Pro Phe Asn Gln Glu Ala Thr Gln Gln Thr Asp Gly Thr Ser Ser Thr
        515                 520                 525

Gln Glu Lys Thr Pro Gln Ile Cys Val Val Gly Ser Gly Pro Ala Gly
    530                 535                 540

Phe Tyr Thr Ala Gln His Leu Leu Lys His Pro Gln Ala His Val Asp
545                 550                 555                 560

Ile Tyr Glu Lys Gln Pro Val Pro Phe Gly Leu Val Arg Phe Gly Val
                565                 570                 575

Ala Pro Asp His Pro Glu Val Lys Asn Val Ile Asn Thr Phe Thr Gln
            580                 585                 590

Thr Ala His Ser Gly Arg Cys Ala Phe Trp Gly Asn Val Glu Val Gly
        595                 600                 605

Arg Asp Val Thr Val Pro Glu Leu Arg Glu Ala Tyr His Ala Val Val
    610                 615                 620

Leu Ser Tyr Gly Ala Glu Asp His Arg Ala Leu Glu Ile Pro Gly Glu
625                 630                 635                 640

Glu Leu Pro Gly Val Cys Ser Ala Arg Ala Phe Val Gly Trp Tyr Asn
                645                 650                 655

Gly Leu Pro Glu Asn Gln Glu Leu Glu Pro Asp Leu Ser Cys Asp Thr
            660                 665                 670

Ala Val Ile Leu Gly Gln Gly Asn Val Ala Leu Asp Val Ala Arg Ile
        675                 680                 685

Leu Leu Thr Pro Pro Glu His Leu Glu Arg Thr Asp Ile Thr Lys Ala
    690                 695                 700

Ala Leu Gly Val Leu Arg Gln Ser Arg Val Lys Thr Val Trp Leu Val
705                 710                 715                 720

Gly Arg Arg Gly Pro Leu Gln Val Ala Phe Thr Ile Lys Glu Leu Arg
                725                 730                 735

Glu Met Ile Gln Leu Pro Gly Ala Arg Pro Ile Leu Asp Pro Val Asp
            740                 745                 750

Phe Leu Gly Leu Gln Asp Lys Ile Lys Glu Val Pro Arg Pro Arg Lys
        755                 760                 765

Arg Leu Thr Glu Leu Leu Leu Arg Thr Ala Thr Glu Lys Pro Gly Pro
    770                 775                 780

Ala Glu Ala Ala Arg Gln Ala Ser Ala Ser Arg Ala Trp Gly Leu Arg
785                 790                 795                 800
```

```
Phe Phe Arg Ser Pro Gln Gln Val Leu Pro Ser Pro Asp Gly Arg Arg
                805                 810                 815

Ala Ala Gly Val Arg Leu Ala Val Thr Arg Leu Glu Gly Val Asp Glu
            820                 825                 830

Ala Thr Arg Ala Val Pro Thr Gly Asp Met Glu Asp Leu Pro Cys Gly
        835                 840                 845

Leu Val Leu Ser Ser Ile Gly Tyr Lys Ser Arg Pro Val Asp Pro Ser
    850                 855                 860

Val Pro Phe Asp Ser Lys Leu Gly Val Ile Pro Asn Val Glu Gly Arg
865                 870                 875                 880

Val Met Asp Val Pro Gly Leu Tyr Cys Ser Gly Trp Val Lys Arg Gly
                885                 890                 895

Pro Thr Gly Val Ile Ala Thr Thr Met Thr Asp Ser Phe Leu Thr Gly
            900                 905                 910

Gln Met Leu Leu Gln Asp Leu Lys Ala Gly Leu Leu Pro Ser Gly Pro
        915                 920                 925

Arg Pro Gly Tyr Ala Ala Ile Gln Ala Leu Leu Ser Ser Arg Gly Val
    930                 935                 940

Arg Pro Val Ser Phe Ser Asp Trp Glu Lys Leu Asp Ala Glu Glu Val
945                 950                 955                 960

Ala Arg Gly Gln Gly Thr Gly Lys Pro Arg Glu Lys Leu Val Asp Pro
                965                 970                 975

Gln Glu Met Leu Arg Leu Leu Gly His Thr Asp Gly Ala Ser Ser Ser
            980                 985                 990

Ser Glu Asp Lys Ile Thr Val His  Phe Ile Asn Arg Asp  Gly Glu Thr
        995                 1000                1005

Leu Thr  Thr Lys Gly Lys Val  Gly Asp Ser Leu Leu  Asp Val Val
    1010                 1015                 1020

Val Glu  Asn Asn Leu Asp Ile  Asp Gly Phe Gly Ala  Cys Glu Gly
    1025                 1030                 1035

Thr Leu  Ala Cys Ser Thr Cys  His Leu Ile Phe Glu  Asp His Ile
    1040                 1045                 1050

Tyr Glu  Lys Leu Asp Ala Ile  Thr Asp Glu Glu Asn  Asp Met Leu
    1055                 1060                 1065

Asp Leu  Ala Tyr Gly Leu Thr  Asp Arg Ser Arg Leu  Gly Cys Gln
    1070                 1075                 1080

Ile Cys  Leu Thr Lys Ser Met  Asp Asn Met Thr Val  Arg Val Pro
    1085                 1090                 1095

Glu Thr  Val Ala Asp Ala Arg  Gln Ser Ile Asp Val  Gly Lys Thr
    1100                 1105                 1110

Ser Asp  Tyr Lys Asp Asp Asp  Asp Lys Gly Ser Gly  Ala Thr Asn
    1115                 1120                 1125

Phe Ser  Leu Leu Lys Gln Ala  Gly Asp Val Glu Glu  Asn Pro Gly
    1130                 1135                 1140

Pro


<210> SEQ ID NO 6
<211> LENGTH: 521
<212> TYPE: PRT
<213> ORGANISM: Homo sapiens

<400> SEQUENCE: 6

Met Leu Ala Lys Gly Leu Pro Pro Arg Ser Val Leu Val Lys Gly Cys
1               5                   10                  15
```

-continued

```
Gln Thr Phe Leu Ser Ala Pro Arg Glu Gly Leu Gly Arg Leu Arg Val
            20                  25                  30

Pro Thr Gly Glu Gly Ala Gly Ile Ser Thr Arg Ser Pro Arg Pro Phe
        35                  40                  45

Asn Glu Ile Pro Ser Pro Gly Asp Asn Gly Trp Leu Asn Leu Tyr His
    50                  55                  60

Phe Trp Arg Glu Thr Gly Thr His Lys Val His Leu His His Val Gln
65                  70                  75                  80

Asn Phe Gln Lys Tyr Gly Pro Ile Tyr Arg Glu Lys Leu Gly Asn Val
                85                  90                  95

Glu Ser Val Tyr Val Ile Asp Pro Glu Asp Val Ala Leu Leu Phe Lys
            100                 105                 110

Ser Glu Gly Pro Asn Pro Glu Arg Phe Leu Ile Pro Pro Trp Val Ala
        115                 120                 125

Tyr His Gln Tyr Tyr Gln Arg Pro Ile Gly Val Leu Leu Lys Lys Ser
    130                 135                 140

Ala Ala Trp Lys Lys Asp Arg Val Ala Leu Asn Gln Glu Val Met Ala
145                 150                 155                 160

Pro Glu Ala Thr Lys Asn Phe Leu Pro Leu Leu Asp Ala Val Ser Arg
                165                 170                 175

Asp Phe Val Ser Val Leu His Arg Arg Ile Lys Lys Ala Gly Ser Gly
            180                 185                 190

Asn Tyr Ser Gly Asp Ile Ser Asp Asp Leu Phe Arg Phe Ala Phe Glu
        195                 200                 205

Ser Ile Thr Asn Val Ile Phe Gly Glu Arg Gln Gly Met Leu Glu Glu
    210                 215                 220

Val Val Asn Pro Glu Ala Gln Arg Phe Ile Asp Ala Ile Tyr Gln Met
225                 230                 235                 240

Phe His Thr Ser Val Pro Met Leu Asn Leu Pro Pro Asp Leu Phe Arg
                245                 250                 255

Leu Phe Arg Thr Lys Thr Trp Lys Asp His Val Ala Ala Trp Asp Val
            260                 265                 270

Ile Phe Ser Lys Ala Asp Ile Tyr Thr Gln Asn Phe Tyr Trp Glu Leu
        275                 280                 285

Arg Gln Lys Gly Ser Val His His Asp Tyr Arg Gly Ile Leu Tyr Arg
    290                 295                 300

Leu Leu Gly Asp Ser Lys Met Ser Phe Glu Asp Ile Lys Ala Asn Val
305                 310                 315                 320

Thr Glu Met Leu Ala Gly Gly Val Asp Thr Thr Ser Met Thr Leu Gln
                325                 330                 335

Trp His Leu Tyr Glu Met Ala Arg Asn Leu Lys Val Gln Asp Met Leu
            340                 345                 350

Arg Ala Glu Val Leu Ala Ala Arg His Gln Ala Gln Gly Asp Met Ala
        355                 360                 365

Thr Met Leu Gln Leu Val Pro Leu Leu Lys Ala Ser Ile Lys Glu Thr
    370                 375                 380

Leu Arg Leu His Pro Ile Ser Val Thr Leu Gln Arg Tyr Leu Val Asn
385                 390                 395                 400

Asp Leu Val Leu Arg Asp Tyr Met Ile Pro Ala Lys Thr Leu Val Gln
                405                 410                 415

Val Ala Ile Tyr Ala Leu Gly Arg Glu Pro Thr Phe Phe Phe Asp Pro
            420                 425                 430
```

-continued

```
Glu Asn Phe Asp Pro Thr Arg Trp Leu Ser Lys Asp Lys Asn Ile Thr
        435                 440                 445

Tyr Phe Arg Asn Leu Gly Phe Gly Trp Gly Val Arg Gln Cys Leu Gly
    450                 455                 460

Arg Arg Ile Ala Glu Leu Glu Met Thr Ile Phe Leu Ile Asn Met Leu
465                 470                 475                 480

Glu Asn Phe Arg Val Glu Ile Gln His Leu Ser Asp Val Gly Thr Thr
                485                 490                 495

Phe Asn Leu Ile Leu Met Pro Glu Lys Pro Ile Ser Phe Thr Phe Trp
            500                 505                 510

Pro Phe Asn Gln Glu Ala Thr Gln Gln
        515                 520
```

<210> SEQ ID NO 7
<211> LENGTH: 491
<212> TYPE: PRT
<213> ORGANISM: Homo sapiens

<400> SEQUENCE: 7

```
Met Ala Ser Arg Cys Trp Arg Trp Trp Gly Trp Ser Ala Trp Pro Arg
1               5                   10                  15

Thr Arg Leu Pro Pro Ala Gly Ser Thr Pro Ser Phe Cys His His Phe
            20                  25                  30

Ser Thr Gln Glu Lys Thr Pro Gln Ile Cys Val Val Gly Ser Gly Pro
        35                  40                  45

Ala Gly Phe Tyr Thr Ala Gln His Leu Leu Lys His Pro Gln Ala His
    50                  55                  60

Val Asp Ile Tyr Glu Lys Gln Pro Val Pro Phe Gly Leu Val Arg Phe
65                  70                  75                  80

Gly Val Ala Pro Asp His Pro Glu Val Lys Asn Val Ile Asn Thr Phe
                85                  90                  95

Thr Gln Thr Ala His Ser Gly Arg Cys Ala Phe Trp Gly Asn Val Glu
            100                 105                 110

Val Gly Arg Asp Val Thr Val Pro Glu Leu Arg Glu Ala Tyr His Ala
        115                 120                 125

Val Val Leu Ser Tyr Gly Ala Glu Asp His Arg Ala Leu Glu Ile Pro
    130                 135                 140

Gly Glu Glu Leu Pro Gly Val Cys Ser Ala Arg Ala Phe Val Gly Trp
145                 150                 155                 160

Tyr Asn Gly Leu Pro Glu Asn Gln Glu Leu Glu Pro Asp Leu Ser Cys
                165                 170                 175

Asp Thr Ala Val Ile Leu Gly Gln Gly Asn Val Ala Leu Asp Val Ala
            180                 185                 190

Arg Ile Leu Leu Thr Pro Pro Glu His Leu Glu Arg Thr Asp Ile Thr
        195                 200                 205

Lys Ala Ala Leu Gly Val Leu Arg Gln Ser Arg Val Lys Thr Val Trp
    210                 215                 220

Leu Val Gly Arg Arg Gly Pro Leu Gln Val Ala Phe Thr Ile Lys Glu
225                 230                 235                 240

Leu Arg Glu Met Ile Gln Leu Pro Gly Ala Arg Pro Ile Leu Asp Pro
                245                 250                 255

Val Asp Phe Leu Gly Leu Gln Asp Lys Ile Lys Glu Val Pro Arg Pro
            260                 265                 270

Arg Lys Arg Leu Thr Glu Leu Leu Leu Arg Thr Ala Thr Glu Lys Pro
        275                 280                 285
```

Gly Pro Ala Glu Ala Ala Arg Gln Ala Ser Ala Ser Arg Ala Trp Gly
290 295 300

Leu Arg Phe Phe Arg Ser Pro Gln Gln Val Leu Pro Ser Pro Asp Gly
305 310 315 320

Arg Arg Ala Ala Gly Val Arg Leu Ala Val Thr Arg Leu Glu Gly Val
325 330 335

Asp Glu Ala Thr Arg Ala Val Pro Thr Gly Asp Met Glu Asp Leu Pro
340 345 350

Cys Gly Leu Val Leu Ser Ser Ile Gly Tyr Lys Ser Arg Pro Val Asp
355 360 365

Pro Ser Val Pro Phe Asp Ser Lys Leu Gly Val Ile Pro Asn Val Glu
370 375 380

Gly Arg Val Met Asp Val Pro Gly Leu Tyr Cys Ser Gly Trp Val Lys
385 390 395 400

Arg Gly Pro Thr Gly Val Ile Ala Thr Thr Met Thr Asp Ser Phe Leu
405 410 415

Thr Gly Gln Met Leu Leu Gln Asp Leu Lys Ala Gly Leu Leu Pro Ser
420 425 430

Gly Pro Arg Pro Gly Tyr Ala Ala Ile Gln Ala Leu Leu Ser Ser Arg
435 440 445

Gly Val Arg Pro Val Ser Phe Ser Asp Trp Glu Lys Leu Asp Ala Glu
450 455 460

Glu Val Ala Arg Gly Gln Gly Thr Gly Lys Pro Arg Glu Lys Leu Val
465 470 475 480

Asp Pro Gln Glu Met Leu Arg Leu Leu Gly His
485 490

<210> SEQ ID NO 8
<211> LENGTH: 184
<212> TYPE: PRT
<213> ORGANISM: Homo sapiens

<400> SEQUENCE: 8

Met Ala Ala Ala Gly Gly Ala Arg Leu Leu Arg Ala Ala Ser Ala Val
1 5 10 15

Leu Gly Gly Pro Ala Gly Arg Trp Leu His His Ala Gly Ser Arg Ala
20 25 30

Gly Ser Ser Gly Leu Leu Arg Asn Arg Gly Pro Gly Gly Ser Ala Glu
35 40 45

Ala Ser Arg Ser Leu Ser Val Ser Ala Arg Ala Arg Ser Ser Ser Glu
50 55 60

Asp Lys Ile Thr Val His Phe Ile Asn Arg Asp Gly Glu Thr Leu Thr
65 70 75 80

Thr Lys Gly Lys Val Gly Asp Ser Leu Leu Asp Val Val Val Glu Asn
85 90 95

Asn Leu Asp Ile Asp Gly Phe Gly Ala Cys Glu Gly Thr Leu Ala Cys
100 105 110

Ser Thr Cys His Leu Ile Phe Glu Asp His Ile Tyr Glu Lys Leu Asp
115 120 125

Ala Ile Thr Asp Glu Glu Asn Asp Met Leu Asp Leu Ala Tyr Gly Leu
130 135 140

Thr Asp Arg Ser Arg Leu Gly Cys Gln Ile Cys Leu Thr Lys Ser Met
145 150 155 160

Asp Asn Met Thr Val Arg Val Pro Glu Thr Val Ala Asp Ala Arg Gln 165 170 175

Ser Ile Asp Val Gly Lys Thr Ser
180

<210> SEQ ID NO 9
<211> LENGTH: 13
<212> TYPE: PRT
<213> ORGANISM: Human immunodeficiency virus

<400> SEQUENCE: 9

Met Gly Tyr Gly Arg Lys Lys Arg Arg Gln Arg Arg Arg
1 5 10

<210> SEQ ID NO 10
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10
acaagtttgt acaaaaaagc aggcttccaa ttgggatccc tcgagaacct gtacttccag 60
ggccaccacc accaccacca cggcaccatg gccggcttcc tgaactgctg ccccggctgc 120
tgcatggagc ccggcgccag cgactacaag gacgacgacg acaagatgct gcggcggatg 180
ggagatgcca gcctgacaac agagctgggc cgggtgctcg tgacaggcgg agctggattt 240
gtgggagcca acctcgtgac caccctgctg gatagaggac actgggtgcg cagcttcgac 300
agagcccctt ctctgctgcc tgcccaccct cagctggaag tgctgcaggg cgatatcacc 360
gacgccgatg tgtgtgccgc cgctgtggat ggcatcgaca ccatctttca caccgccgcc 420
atcatcgagc tgatgggcgg agccagcgtg accgacgagt accggcagag aagcttcgcc 480
gtgaatgtgg gcggcaccga gaatctgctg cacgccggac agagggctgg ggtgcagaga 540
ttcgtgtata ccagcagcaa cagcgtcgtg atgggaggcc agaatatcgc tggcggcgac 600
gagacactgc cctacaccga cagattcaac gacctgtata ccgagacaaa agtggtggcc 660
gagcgcttcg tgctggccca gaatggcgtg gacggcatgc tgacctgcgc catcagacct 720
agcggcatct ggggcaacgg cgaccagacc atgttccgga agctgttcga gagcgtgctg 780
aagggccacg tgaaggtgct cgtgggcaga aagagcgcca gactggacaa cagctacgtg 840
cacaacctga tccacggctt catcctggcc gctgcccacc tggtgcctga tggaacagct 900
cctggacagg cctacttcat caacgatgcc gagcccatca acatgttcga gttcgccaga 960
cccgtgctgg aagcttgcgg ccagagatgg cccaagatgc ggatctctgg acccgccgtc 1020
agatgggtca tgactggctg gcagcggctg cacttcagat tcggctttcc cgcccctctg 1080
ctggaacccc tggctgtgga aagactgtac ctggacaact acttctctat cgccaaggcc 1140
agacgggacc tgggctacga gcctctgttt accacacagc aggccctgac cgagtgcctg 1200
ccctactacg tgtccctgtt cgagcagatg aagaacgagg ccagagccga gaaaacagcc 1260
gccacagtga agcccgggta gtaaaccggt gaattcagat ctgacccagc tttcttgtac 1320
aaagtggtg 1329

<210> SEQ ID NO 11
<211> LENGTH: 1840
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 11

```
ggggacaagt ttgtacaaaa aagcaggctt ccaattggga tccggtaccg aaaacctgta     60

cttccagggt accatgagca tcgagacaaa cacctacgac gtgatcgtcg tgggctctgg    120

cgctggcgct atgctggctg ctgctagagc ccatgatctg ggcctgagcg tgctggtggt    180

ggaaaagagc gataagtacg gcggcaccag cgccgtgtct ggcggagctg tgtggattcc    240

caacaacagc cagatgcaga tcaaggacag cttcgacgag gccctgacct acctgaaggc    300

cgccacacag ggactggtgg ccgaggatag actgctggcc tacctggaaa gcgcccctca    360

gatggtggag tacatcaacg ccaatatgac cctgcagtac ttcccctgcc acagataccc    420

cgactactac cagcatctgc ctggcgccaa gcctggcggc agaaccatgg aacccatgct    480

gttcgatgcc gccctgctgg gcgacgagtt cgccaatctg agaatggcct acaccggcac    540

cctgctgatg ggcaaggcca gcatgacagc cacagaggcc catgtgatgc tggccaaaga    600

acccggctgg atgctgcaag tgatcaagag cctgggccgg tactacctgg acctgccctg    660

gcggctgaag tcccggcacg atagaaagag aggcctgggc aacgccatgg ccgctggact    720

gagacacgct ctgctggaaa gaaaggtgcc cctgtggctg aacacccccct tcgagagcct    780

gatcacagag ggcgccgaga acaagcgcgt gaccggcatc gtcgtgaagc ggaatggcca    840

gacactgcag ctgaccgcca gacggggagt ggtgctggga gctggcggct tcgagagaaa    900

ccagcagatg agagagcagt acctgcccaa gcccaccaac gccgcttgga gcgctacccc    960

ccctcacaat accggcgaca caatcagagc cgccatggac atcggagcca gagccgagct   1020

gatggactgg gcttggtggg tgccatccat ccacgtgcca ggcgaagccg ctcagaccgg   1080

actgttcgcc gagagaaatc tgcccggctg catcgtcgtg aatggcaagg gccagcggtt   1140

catcaacgag gccagccctt acctggaatt tggcgccgct atgtacgaga accacgccag   1200

atccggctct gccgtgcctg cctggctgat cttcgacggc aagttccggt acaactaccc   1260

catgggcccc ctgatgcctg gccagatcca gcctgataga aaggcctggc tgggcaaggt   1320

gtactggcgg gacgatacac tggaaggact ggccaagcag atcggcgtgg acgctgccgg   1380

actgaagcag tccgtggaac tgaacaacca gtacgcccag gacggcaagg acagagagtt   1440

cgacaagggc ggcaacgtgt tcgatcggta ctacggcgac tacaacgtga agcccaaccc   1500

ttgcctggcc cccatcggca agcctcccta ctacgccatg agagtggacg ccggggacat   1560

cggcacaaag ggcggactgc tgaccgacaa ggacgccaga gtgctggacg agagcgacag   1620

acctatcgag ggcctgtact gcatcggcaa caactccgcc agcgtgatgg gaaaagccta   1680

ccctggcgca ggcggcacac tgggacctgc catgaccttc ggctttaggg ccgccaacca   1740

cattgccgcc agcaagtacc cctacgatgt gcccgattac gccggctagt aacccgggga   1800

attcagatct gacccagctt tcttgtacaa agtggtcccc                          1840
```

<210> SEQ ID NO 12
<211> LENGTH: 4820
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12

```
tcttaagctc gggccccaaa taatgatttt attttgactg atagtgacct gttcgttgca     60
```

-continued

```
acaaattgat gagcaatgct tttttataat gccaactttg tacaaaaaag caggctccac    120
catgctggcc aagggcctgc ctcctagaag cgtgctcgtg aagggctgcc agaccttcct    180
gagcgcccct agagaaggcc tgggcagact gagagtgcct acaggcgaag gcgccggaat    240
cagcaccaga agccccagac ccttcaacga gatccccagc cctggcgaca acggctggct    300
gaacctgtac cacttctggc gggaaaccgg cacccacaaa gtgcatctgc accacgtgca    360
gaacttccag aagtacggcc ccatctaccg cgagaagctg ggcaacgtgg aaagcgtgta    420
cgtgatcgac cccgaggacg tggccctgct gtttaagagc gagggcccca accccgagcg    480
gttcctgatt cctccttggg tggcctacca ccagtactac cagaggccca tcggcgtgct    540
gctgaagaag tccgccgcct ggaagaaaga ccgggtggcc ctgaaccagg aagtgatggc    600
ccctgaggcc accaagaact ttctgcccct gctggacgcc gtgtccagag actttgtgtc    660
cgtgctgcac cggcggatca agaaggccgg cagcggcaat tacagcggcg acatcagcga    720
cgacctgttc agattcgcct tcgagagcat caccaacgtg atcttcggcg agcggcaggg    780
catgctggaa gaggtcgtga atcccgaggc ccagcggttc atcgacgcca tctaccagat    840
gttccacacc agcgtgccca tgctgaatct gccccccgac ctgtttcggc tgttccggac    900
caagacctgg aaggaccatg tggccgcctg ggatgtgatc ttcagcaagg ccgacatcta    960
cacccagaac ttctactggg agctgcggca gaaaggcagc gtgcaccacg actaccgggg   1020
catcctgtac agactgctgg gcgacagcaa gatgagcttc gaggacatca aggccaacgt   1080
gaccgagatg ctggctggcg gcgtggacac caccagcatg actctgcagt ggcacctgta   1140
cgagatggcc cggaacctga aggtgcagga catgctgaga gccgaggtgc tggccgccag   1200
acatcaggct cagggcgata tggccacaat gctgcagctg gtgcctctgc tgaaggccag   1260
catcaaagag acactgcggc tgcaccccat cagcgtgacc ctgcagagat acctcgtgaa   1320
cgacctggtg ctgcgggact acatgatccc cgccaagacc ctggtgcagg tggccatcta   1380
tgccctggga agagagccta cattcttctt cgaccctgaa aacttcgacc ccacccggtg   1440
gctgagcaag gacaagaaca tcacctactt ccgcaacctg ggcttcggct ggggcgtgcg   1500
gcagtgtctg ggcagaagaa tcgccgagct ggaaatgacc atcttcctga tcaatatgct   1560
ggaaaacttc cgggtggaaa tccagcacct gagcgacgtg ggcaccacct tcaacctgat   1620
cctgatgccc gagaagccta tcagcttcac cttctggccc ttcaatcagg aagccaccca   1680
gcagaccgac ggcaccagca gcacccagga aaagaccccc cagatctgcg tcgtgggctc   1740
tggacctgcc ggcttttaca cagcccagca tctgctgaaa cacccccagg cccacgtgga   1800
catctacgag aagcagcccg tgcccttcgg cctggtgcgc tttggagtgg ccccagatca   1860
ccccgaagtg aagaacgtga tcaacacctt cacccagacc gcccacagcg gcagatgtgc   1920
cttctggggc aatgtggaag tgggccggga tgtgaccgtg cccgaactga gggaagccta   1980
ccatgccgtg gtgctgagct acggcgccga ggatcatcgg gccctggaaa tccctggcga   2040
ggaactgcct ggcgtgtgta gcgccagagc cttcgtgggc tggtacaacg gcctgcccga   2100
aaaccaggaa ctggaacccg acctgagctg cgacaccgcc gtgattctgg gccagggaaa   2160
tgtggccctg gatgtggcca gaatcctgct gacccctccc gagcacctgg aaagaaccga   2220
catcaccaag gccgccctgg gcgtgctgag acagagcaga gtgaaaaccg tgtggctcgt   2280
gggcagacgg ggacctctgc aggtggcatt caccatcaaa gaactgcgcg agatgatcca   2340
gctgccaggc gccagaccca tcctggaccc tgtggatttc ctgggactgc aggacaagat   2400
```

-continued

```
caaagaggtg cccagacccc ggaagcggct gacagaactg ctgctgagaa ccgccacaga   2460
gaagcctggc cctgccgaag ctgctagaca ggcctctgcc tctagagcct ggggcctgcg   2520
gttcttcaga tcccctcagc aggtgctgcc tagccccgat gggagaaggg cagctggcgt   2580
gcgcctggct gtgactagac tggaaggcgt ggacgaggcc acaagagccg tgccaacagg   2640
ggacatggaa gatctgccct gcggactggt gctgtccagc atcggctaca agagcagacc   2700
cgtggacccc tccgtgcctt tcgatagcaa gctgggcgtg atccctaacg tggaaggcag   2760
agtgatggac gtgcccggcc tgtactgttc cggctgggtc aaaaggggcc ccacaggcgt   2820
gatcgccaca acaatgaccg acagcttcct gaccggccag atgctgctgc aggacctgaa   2880
agccggcctg ctgccatctg gccctagacc tggatatgcc gccatccagg ctctgctgtc   2940
ctcacgggga gtgcggcctg tgtccttcag cgactgggag aaactggatg ccgaagaggt   3000
ggccagggga cagggcactg gcaagcccag agaaaagctg gtggaccctc aggaaatgct   3060
gcgcctgctg ggccatacag atggcgccag cagcagctcc gaggataaga tcaccgtgca   3120
cttcatcaac cgggacggcg agacactgac caccaagggc aaagtgggcg actctctgct   3180
ggacgtggtg gtggaaaaca acctggacat cgacggcttc ggcgcctgcg agggaacact   3240
ggcctgtagc acctgtcacc tgatcttcga ggatcacatc tacgaaaagc tggacgccat   3300
caccgacgaa gagaacgaca tgctggacct ggcctacggc ctgaccgata gaagcagact   3360
gggctgtcag atctgcctga ccaagagcat ggacaacatg accgtgcggg tgcccgagac   3420
agtggccgat gccagacagt ccatcgatgt gggcaagacc agcgactaca aggacgacga   3480
cgacaagggc tccggcgcca ccaatttcag cctgctgaag caggcaggcg acgtggaaga   3540
gaaccccgga cctatgggct ggtcctgcct cgtgacaggc gctggcgggc tgctggggca   3600
gagaattgtg cggctgctgg tggaagaaaa agagctgaaa gagatccgcg ccctggacaa   3660
ggccttcaga cccgagctgc gggaagagtt cagcaagctg cagaacagga ccaagctgac   3720
cgtgctggaa ggggatatcc tggacgagcc cttcctgaag cgggcctgcc aggacgtgtc   3780
cgtcgtgatc cacaccgcct gcatcatcga cgtgttcgga gtgacccacc gcgagtccat   3840
catgaatgtg aacgtgaagg gaacccagct gctgctggaa gcctgtgtgc aggcctcagt   3900
gcccgtgttt atctacacca gctccatcga ggtggccgga cccaacagct acaaagagat   3960
catccagaac ggccacgagg aagaacccct ggaaaacaca tggcccaccc cctaccccta   4020
cagcaagaag ctggccgaga aagccgtgct ggctgccaat ggctggaatc tgaaaaacgg   4080
cgacaccctg tacacatgcg ccctgcggcc cacctacatc tatggcgagg gcggaccttt   4140
cctgtccgcc tccatcaacg aagccctgaa caacaacggc atcctgagca gcgtggggaa   4200
gttcagcacc gtgaaccctg tgtacgtggg aaacgtggcc tgggcccaca tcctggctct   4260
gagagccctg cgggacccca agaaagctcc ttctgtgcgg ggccagttct actacatctc   4320
cgacgacacc ccccaccaga gctacgacaa cctgaactac atcctgtcca aagagttcgg   4380
cctgagactg gacagccggt ggtccctgcc actgacactg atgtactgga tcggcttcct   4440
gctggaagtg gtgtccttcc tgctgagccc tatctacagc taccagcccc ccttcaaccg   4500
gcacaccgtg acactgagca acagcgtgtt caccttcagc tataagaagg cccagagaga   4560
tctggcctac aagcccctgt acagctggga ggaagccaag cagaaaacag tggaatgggt   4620
gggaagcctg gtggacagac acaaagaaac cctgaagtcc aagacccagt gataaaggca   4680
ctagagtacc ggcgcgtccc aggacccagc tttcttgtac aaagttggca ttataagaaa   4740
gcattgctta tcaatttgtt gcaacgaaca ggtcactatc agtcaaaata aaatcattat   4800
```

ttgccatcca gctgatatcc 4820

<210> SEQ ID NO 13
<211> LENGTH: 1762
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
ggggacaagt ttgtacaaaa aagcaggctt ccaattggga tccctcgaga acctgtactt 60
ccagggtcac caccaccacc accacggcac catggccggc tttctgaatt gctgccccgg 120
ctgctgtatg gaacccgggg ctagcgacta caaggacgac gacgacaaga tgcaggactg 180
gactagtgaa tgcgacgtgc tggtcgtggg ctctggcgga ggcgctctga caggcgctta 240
tacagctgcc gcccagggcc tgaccaccat cgtgctggaa aagaccgaca gattcggcgg 300
caccagcgcc tactctggcg cctctatttg gctgcctggc acccaggtgc aggaaagagc 360
cggactgcct gacagcaccg agaacgccag aacctacctg agagccctgc tgggcgacgc 420
cgagagcgaa agacaggacg cctacgtgga aaccgcccct gctgtggtgg ctctgctgga 480
acagaacccc aacatcgagt tcgagttccg ggccttcccc gactactaca aggccgaggg 540
cagaatggac accggccgca gcatcaaccc cctggatctg gaccctgccg acatcggcga 600
tctggccgga aaagtgcggc ccgagctgga ccaggataga accggacagg atcacgcccc 660
tggccccatg attggaggca gagccctgat cggcagactg ctggctgctg tgcagagcac 720
cggaaaggcc gagctgagaa ccgagagcgt gctgaccagc ctgatcgtgg aagatggcag 780
agtcgtgggc gccgaggtgg aatctggggg cgagacacag cggatcaagg ccaacagagg 840
cgtgctgatg gccgctggcg gcatcgaggg aaacgccgag atgagggaac aggccggaac 900
acccggcaag gccatctggt ctatgggccc cttcggagcc aataccggcg acgccatctc 960
tgccggaatt gccgtgggcg gagctaccgc actgctggat caggcctggt tctgccctgg 1020
cgtggaacag cctgatggca gcgccgcctt tatggtggga gtgcggggag gactggtggt 1080
ggattctgcc ggggagagat acctgaacga gagcctgccc tacgaccagt tcggcagagc 1140
tatggacgcc cacgatgaca acggctccgc cgtgcccagc ttcatgatct tcgacagcag 1200
agagggcgga ggcctgcccg ccatctgcat ccctaatacc gccccagcca agcacctgga 1260
agccggaaca tgggtgggag ccgacacact ggaagaactg gccgccaaga caggcctgcc 1320
tgccgatgct ctgagaagca ccgtggaaaa gttcaacgac gccgccaagc tgggcgtgga 1380
cgaagagttc catagaggcg aggaccccta cgacgccttc ttctgcccac ctaatggcgg 1440
agccaacgcc gccctgaccg ccattgagaa cggccctttt tacgccgcca gaatcgtgct 1500
gagcgacctg ggcacaaagg gcggcctcgt gaccgatgtg aacggcagag tgctgagagc 1560
cgacggcagc gccattgacg gactgtatgc cgccggaaat accagcgcca gcctgagcgg 1620
cagattctac cctggcccag gcgtgccact gggcaccgct atggtgttca gctacagagc 1680
tgcccaggac atggcgaagt aattctagag agctcaaggt gaattcagat ctgacccagc 1740
tttcttgtac aaagtggtcc cc 1762

<210> SEQ ID NO 14
<211> LENGTH: 504
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14

```
cacccacaca aaggaaaagg gcctttccgt cctcagccgt cgcttcatgt gactccacgg     60

agtaccgggc gccgtccagg cacctcgatt agttctcgag cttttggagt acgtcgtctt    120

taggttgggg ggaggggttt tatgcgatgg agtttcccca cactgagtgg gtggagactg    180

aagttaggcc agcttggcac ttgatgtaat tctccttgga atttgccctt tttgagtttg    240

gatcttggtt cattctcaag cctcagacag tggttcaaag tttttttctt ccatttcagg    300

tgtcgtgagg aattagcttg gtactaatac gactcactat agggagaccc aagctggcta    360

ggtaagcttg atcaacaagt ttgtacaaaa aagcaggctt cgaattcaga tctagaagta    420

ctggcaccat ggccggcgac tacaaggacg acgacgataa gatgcaggac tggactagtg    480

aatgcgacgt gctggtcgtg ggct                                           504
```

<210> SEQ ID NO 15
<211> LENGTH: 7435
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15

```
tcaatattat tgaagcattt atcagggtta ttgtctcatg agcggataca tatttgaatg     60

tatttagaaa aataaacaaa taggggttcc gcgcacattt ccccgaaaag tgccacctga    120

cgtcgacgga tcgggagatc tcccgatccc ctatggtcga ctctcagtac aatctgctct    180

gatgccgcat agttaagcca gtatctgctc cctgcttgtg tgttggaggt cgctgagtag    240

tgcgcgagca aaatttaagc tacaacaagg caaggcttga ccgacaattg catgaagaat    300

ctgcttaggg ttaggcgttt tgcgctgctt cgcgatgtac gggccagata tacgcgttga    360

cattgattat tgactaggct tttgcaaaaa gctttgcaaa gatggataaa gttttaaaca    420

gagaggaatc tttgcagcta atggaccttc taggtcttga aaggagtgcc tcgtgaggct    480

ccggtgcccg tcagtgggca gagcgcacat cgcccacagt ccccgagaag ttggggggag    540

gggtcggcaa ttgaaccggt gcctagagaa ggtggcgcgg ggtaaactgg gaaagtgatg    600

tcgtgtactg gctccgcctt tttcccgagg gtgggggaga accgtatata agtgcagtag    660

tcgccgtgaa cgttcttttt cgcaacgggt ttgccgccag aacacaggta agtgccgtgt    720

gtggttcccg cgggcctggc ctctttacgg gttatggccc ttgcgtgcct tgaattactt    780

ccacctggct gcagtacgtg attcttgatc ccgagcttcg ggttggaagt gggtgggaga    840

gttcgaggcc ttgcgcttaa ggagcccctt cgcctcgtgc ttgagttgag gcctggcctg    900

ggcgctgggg ccgccgcgtg cgaatctggt ggcaccttcg cgcctgtctc gctgctttcg    960

ataagtctct agccatttaa aatttttgat gacctgctgc gacgcttttt ttctggcaag   1020

atagtcttgt aaatgcgggc caagatctgc acactggtat ttcggttttt ggggccgcgg   1080

gcggcgacgg ggcccgtgcg tcccagcgca catgttcggc gaggcggggc ctgcgagcgc   1140

ggccaccgag aatcggacgg gggtagtctc aagctggccg gcctgctctg gtgcctggcc   1200

tcgcgccgcc gtgtatcgcc ccgccctggg cggcaaggct ggcccggtcg gcaccagttg   1260

cgtgagcgga aagatggccg cttcccggcc ctgctgcagg gagctcaaaa tggaggacgc   1320
```

-continued

```
ggcgctcggg agagcgggcg ggtgagtcac ccacacaaag gaaaagggcc tttccgtcct   1380
cagccgtcgc ttcatgtgac tccacggagt accgggcgcc gtccaggcac ctcgattagt   1440
tctcgagctt ttggagtacg tcgtctttag gttgggggga ggggttttat gcgatggagt   1500
ttccccacac tgagtgggtg gagactgaag ttaggccagc ttggcacttg atgtaattct   1560
ccttggaatt tgcccttttt gagtttggat cttggttcat tctcaagcct cagacagtgg   1620
ttcaaagttt ttttcttcca tttcaggtgt cgtgaggaat tagcttggta ctaatacgac   1680
tcactatagg gagacccaag ctggctaggt aagcttgatc aacaagtttg tacaaaaaag   1740
caggcttcga attcagatct agaagtactg gcaccatggc cggcgactac aaggacgacg   1800
acgataagat gcaggactgg actagtgaat gcgacgtgct ggtcgtgggc tctggcggag   1860
gcgctctgac aggcgcttat acagctgccg cccagggcct gaccaccatc gtgctggaaa   1920
agaccgacag attcggcggc accagcgcct actctggcgc ctctatttgg ctgcctggca   1980
cccaggtgca ggaaagagcc ggactgcctg acagcaccga gaacgccaga acctacctga   2040
gagccctgct gggcgacgcc gagagcgaaa gacaggacgc ctacgtggaa accgcccctg   2100
ctgtggtggc tctgctggaa cagaacccca acatcgagtt cgagttccgg gccttccccg   2160
actactacaa ggccgagggc agaatggaca ccggccgcag catcaacccc ctggatctgg   2220
accctgccga catcggcgat ctggccggaa aagtgcggcc cgagctggac caggatagaa   2280
ccggacagga tcacgcccct ggccccatga ttggaggcag agccctgatc ggcagactgc   2340
tggctgctgt gcagagcacc ggaaaggccg agctgagaac cgagagcgtg ctgaccagcc   2400
tgatcgtgga agatggcaga gtcgtgggcg ccgaggtgga atctgggggc gagacacagc   2460
ggatcaaggc caacagaggc gtgctgatgg ccgctggcgg catcgaggga aacgccgaga   2520
tgagggaaca ggccggaaca cccggcaagg ccatctggtc tatgggcccc ttcggagcca   2580
ataccggcga cgccatctct gccggaattg ccgtgggcgg agctaccgca ctgctggatc   2640
aggcctggtt ctgccctggc gtggaacagc ctgatggcag cgccgccttt atggtgggag   2700
tgcggggagg actggtggtg gattctgccg gggagagata cctgaacgag agcctgccct   2760
acgaccagtt cggcagagct atggacgccc acgatgacaa cggctccgcc gtgcccagct   2820
tcatgatctt cgacagcaga gagggcggag gcctgcccgc catctgcatc cctaataccg   2880
ccccagccaa gcacctggaa gccggaacat gggtgggagc cgacacactg gaagaactgg   2940
ccgccaagac aggcctgcct gccgatgctc tgagaagcac cgtggaaaag ttcaacgacg   3000
ccgccaagct gggcgtggac gaagagttcc atagaggcga ggacccctac gacgccttct   3060
tctgcccacc taatggcgga gccaacgccg ccctgaccgc cattgagaac ggcccttttt   3120
acgccgccag aatcgtgctg agcgacctgg gcacaaaggg cggcctcgtg accgatgtga   3180
acggcagagt gctgagagcc gacggcagcg ccattgacgg actgtatgcc gccggaaata   3240
ccagcgccag cctgagcggc agattctacc ctggcccagg cgtgccactg ggcaccgcta   3300
tggtgttcag ctacagagct gcccaggaca tggcgaagta attctagaga gctcaaggtg   3360
aattcagatc tgacccagct ttcttgtaca aagtggttga tctagagggc ccgcggttcg   3420
aaggtaagcc tatccctaac cctctcctcg gtctcgattc tacgcgtacc ggtcatcatc   3480
accatcacca ttgagtttaa acccgctgat cagcctcgac tgtgccttct agttgccagc   3540
catctgttgt ttgcccctcc cccgtgcctt ccttgaccct ggaaggtgcc actcccactg   3600
tcctttccta ataaaatgag gaaattgcat cgcattgtct gagtaggtgt cattctattc   3660
tggggggtgg ggtggggcag gacagcaagg gggaggattg ggaagacaat agcaggcatg   3720
```

-continued

```
ctggggatgc ggtgggctct atggcttctg aggcggaaag aaccagctgg ggctctaggg   3780
ggtatcccca cgcgccctgt agcggcgcat taagcgcggc gggtgtggtg gttacgcgca   3840
gcgtgaccgc tacacttgcc agcgccctag cgcccgctcc tttcgctttc ttcccttcct   3900
ttctcgccac gttcgccggc tttccccgtc aagctctaaa tcggggcatc cctttagggt   3960
tccgatttag tgctttacgg cacctcgacc ccaaaaaact tgattagggt gatggttcac   4020
gtagtgggcc atcgccctga tagacggttt ttcgcccttt gacgttggag tccacgttct   4080
ttaatagtgg actcttgttc caaactggaa caacactcaa ccctatctcg gtctattctt   4140
ttgatttata agggattttg gggatttcgg cctattggtt aaaaaatgag ctgatttaac   4200
aaaaatttaa cgcgaattaa ttctgtggaa tgtgtgtcag ttagggtgtg gaaagtcccc   4260
aggctcccca ggcaggcaga agtatgcaaa gcatgcatct caattagtca gcaaccaggt   4320
gtggaaagtc cccaggctcc ccagcaggca gaagtatgca aagcatgcat ctcaattagt   4380
cagcaaccat agtcccgccc ctaactccgc ccatcccgcc cctaactccg cccagttccg   4440
cccattctcc gccccatggc tgactaattt tttttattta tgcagaggcc gaggccgcct   4500
ctgcctctga gctattccag aagtagtgag gaggcttttt tggaggccta ggcttttgca   4560
aaaagctccc gggagcttgt atatccattt tcggatctga tcagcacgtg ttgacaatta   4620
atcatcggca tagtatatcg gcatagtata atacgacaag gtgaggaact aaaccatggc   4680
caagcctttg tctcaagaag aatccaccct cattgaaaga gcaacggcta caatcaacag   4740
catccccatc tctgaagact acagcgtcgc cagcgcagct ctctctagcg acggccgcat   4800
cttcactggt gtcaatgtat atcattttac tgggggacct tgtgcagaac tcgtggtgct   4860
gggcactgct gctgctgcgg cagctggcaa cctgacttgt atcgtcgcga tcggaaatga   4920
gaacaggggc atcttgagcc cctgcggacg gtgtcgacag gtgcttctcg atctgcatcc   4980
tgggatcaaa gcgatagtga aggacagtga tggacagccg acggcagttg ggattcgtga   5040
attgctgccc tctggttatg tgtgggaggg ctaagcactt cgtggccgag gagcaggact   5100
gacacgtgct acgagatttc gattccaccg ccgccttcta tgaaaggttg ggcttcggaa   5160
tcgttttccg ggacgccggc tggatgatcc tccagcgcgg ggatctcatg ctggagttct   5220
tcgcccaccc caacttgttt attgcagctt ataatggtta caaataaagc aatagcatca   5280
caaatttcac aaataaagca tttttttcac tgcattctag ttgtggtttg tccaaactca   5340
tcaatgtatc ttatcatgtc tgtataccgt cgacctctag ctagagcttg gcgtaatcat   5400
ggtcatagct gtttcctgtg tgaaattgtt atccgctcac aattccacac aacatacgag   5460
ccggaagcat aaagtgtaaa gcctggggtg cctaatgagt gagctaactc acattaattg   5520
cgttgcgctc actgcccgct ttccagtcgg gaaacctgtc gtgccagctg cattaatgaa   5580
tcggccaacg cgcggggaga ggcggtttgc gtattgggcg ctcttccgct tcctcgctca   5640
ctgactcgct gcgctcggtc gttcggctgc ggcgagcggt atcagctcac tcaaaggcgg   5700
taatacggtt atccacagaa tcaggggata acgcaggaaa gaacatgtga gcaaaaggcc   5760
agcaaaaggc caggaaccgt aaaaaggccg cgttgctggc gtttttccat aggctccgcc   5820
cccctgacga gcatcacaaa aatcgacgct caagtcagag gtggcgaaac ccgacaggac   5880
tataaagata ccaggcgttt ccccctggaa gctccctcgt gcgctctcct gttccgaccc   5940
tgccgcttac cggatacctg tccgcctttc tcccttcggg aagcgtggcg ctttctcaat   6000
gctcacgctg taggtatctc agttcggtgt aggtcgttcg ctccaagctg ggctgtgtgc   6060
```

```
acgaaccccc cgttcagccc gaccgctgcg ccttatccgg taactatcgt cttgagtcca   6120

acccggtaag acacgactta tcgccactgg cagcagccac tggtaacagg attagcagag   6180

cgaggtatgt aggcggtgct acagagttct tgaagtggtg gcctaactac ggctacacta   6240

gaaggacagt atttggtatc tgcgctctgc tgaagccagt taccttcgga aaaagagttg   6300

gtagctcttg atccggcaaa caaaccaccg ctggtagcgg tggttttttt gtttgcaagc   6360

agcagattac gcgcagaaaa aaaggatctc aagaagatcc tttgatcttt tctacggggt   6420

ctgacgctca gtggaacgaa aactcacgtt aagggatttt ggtcatgaga ttatcaaaaa   6480

ggatcttcac ctagatcctt ttaaattaaa aatgaagttt taaatcaatc taaagtatat   6540

atgagtaaac ttggtctgac agttaccaat gcttaatcag tgaggcacct atctcagcga   6600

tctgtctatt tcgttcatcc atagttgcct gactccccgt cgtgtagata actacgatac   6660

gggagggctt accatctggc cccagtgctg caatgatacc gcgagaccca cgctcaccgg   6720

ctccagattt atcagcaata aaccagccag ccggaagggc cgagcgcaga agtggtcctg   6780

caactttatc cgcctccatc cagtctatta attgttgccg ggaagctaga gtaagtagtt   6840

cgccagttaa tagtttgcgc aacgttgttg ccattgctac aggcatcgtg gtgtcacgct   6900

cgtcgtttgg tatggcttca ttcagctccg gttcccaacg atcaaggcga gttacatgat   6960

cccccatgtt gtgcaaaaaa gcggttagct ccttcggtcc tccgatcgtt gtcagaagta   7020

agttggccgc agtgttatca ctcatggtta tggcagcact gcataattct cttactgtca   7080

tgccatccgt aagatgcttt tctgtgactg gtgagtactc aaccaagtca ttctgagaat   7140

agtgtatgcg gcgaccgagt tgctcttgcc cggcgtcaat acgggataat accgcgccac   7200

atagcagaac tttaaaagtg ctcatcattg gaaaacgttc ttcggggcga aaactctcaa   7260

ggatcttacc gctgttgaga tccagttcga tgtaacccac tcgtgcaccc aactgatctt   7320

cagcatcttt tactttcacc agcgtttctg ggtgagcaaa aacaggaagg caaaatgccg   7380

caaaaaaggg aataagggcg acacggaaat gttgaatact catactcttc ctttt        7435
```

<210> SEQ ID NO 16
<211> LENGTH: 2564
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
cactataggg cgaattggcg gaaggccgtc aaggccgcat ggggacaagt ttgtacaaaa     60

aagcaggctt cggatcctaa ggaggtaaca tctatgggtt atggtcgtaa aaaacgtcgt    120

cagcgtcgtc gtggtgcaag ccatcatcat caccatcatg gtagcatgag cattgatacc    180

gcacgtagcg gttcagatga tgacgttgaa attcgtgaaa ttcaggcagc agcagcaccg    240

acccgttttg cacgtggttg gcattgtctg ggtctgctgc gtgattttca ggatggtaaa    300

ccgcatagca ttgaagcatt tggcaccaaa ctggttgttt ttgcagatag caaaggtcag    360

ctgaatgttc tggatgcata ttgtcgtcat atgggtggtg atctgagccg tggtgaagtt    420

aaaggtgata gcattgcatg tccgtttcat gattggcgtt ggaatggtaa aggtaaatgt    480

accgatattc cgtatgcacg tcgtgttccg cctattgcca aaacccgtgc atggaccacc    540

ctggaacgta atggccagct gtatgtttgg aatgatccgc agggtaatcc gcctccggaa    600

gatgtgacca ttccggaaat tgcaggttat ggcaccgatg aatggaccga ttggagctgg    660
```

```
aaaagcctgc gtattaaagg tagccattgc cgtgaaattg ttgataatgt tgttgatatg    720

gcccacttct tctatatcca ttatagcttt ccgcgttatt tcaaaaacgt gtttgagggt    780

cataccgcaa cccagtatat gcatagcacc ggtcgtgaag atgttattag cggcaccaat    840

tatgatgatc cgaatgcaga actgcgtagc gaagcaacct attttggtcc gagctatatg    900

attgattggc tggaaagtga tgcaaatggc cagaccattg aaaccattct gattaattgt    960

cattacccgg tgagcaacaa tgagtttgtt ctgcaatatg gtgccatcgt gaaaaaactg   1020

cctggtgtta gtgatgaaat tgccgcaggt atggcagaac agtttgcaga aggtgttcag   1080

ctgggttttg aacaggatgt tgaaatttgg aaaaacaaag caccgattga taatccgctg   1140

ctgagcgaag aagatggtcc ggtttatcag ctgcgtcgtt ggtatcagca gttttatgtt   1200

gatgtggaag atatcaccga ggatatgacc aaacgctttg aatttgaaat tgataccacc   1260

cgtgcagttg caagctggca gaaagaagtt gcagaaaatc tggcaaaaca ggcagaaggt   1320

agcaccgcca ccccgtaaga attctaagga ggtaacatct atgggctacg gacgcaaaaa   1380

acgccgtcaa cggcgtcgcg gagcaagtca ccaccaccat caccatggta gtatgaccgc   1440

agttcaggca ccggttacca gccgtgcaac cgttctgacc gttagcgcag ttgttcaaga   1500

aaccgcagat gcagttagcc tggtttttga tgttccggat gatcgtcgcg aagattttac   1560

ctatcgtccg ggtcagtttc tgaccctgcg cattccgagc gatcgtaccg gtagcgttgc   1620

acgttgttat agcctggcaa gcagcccgtt taccggtgaa ccgcctaaag ttaccgttaa   1680

acgtaccgca ggcggttatg gtagcaattg gctgtgtgat aatattgtgg caggtcgtag   1740

tattgaagtt ctgcctccgg caggcgtttt tacaccggca gatctgaccg aaaaactggt   1800

tctgtttgcc ggtggtagcg gtattacacc ggttatgagc attctggaaa gcgcactgca   1860

tagcggtaat cgtgatgttg ttctgattta tggtaatcgc gacgaaaaaa gcgttatctt   1920

tgcggaaaaa ctgcgtgaac tggcagcacg tcatgccggt gcactgaccg ttgttcactg   1980

gctggaatca gttcagggtc tgccgagtcc gcagcagctg gcaaccctga ttagcccgtt   2040

tgcagatcat cgtgcatata tgtgtggtcc gggtcctttt atggataccg ttcgtgaagg   2100

cctgctgctg gctggtgttc cgaaagatcg tattcatgca gaagtttttta ccagcctgag  2160

cggtgatccg tttgccgatg ttccgctggt tgaaatcgat gaatcagatg cagatgcaac   2220

cagcgccacc gtgcagctgg atggtgaaga acatgatctg gtttggcctc gtagcgcaac   2280

cctggttgat gttatgctga gtaaaggtct ggatgttccg tatagctgtc gtgaaggtga   2340

atgtggtagc tgtgcgtgta ccgttgttga aggtgatgtt gatagcctgc cgagcgcaat   2400

tctggatgaa gaagatattg caaacggtta tgttctggca tgtcaggcac gtccgaaaag   2460

cgatcatgtg cgtattgaat tttgataact gcaggaccca gctttcttgt acaaagtggt   2520

ccccctgggc ctcatgggcc ttccgctcac tgcccgcttt ccag                     2564
```

<210> SEQ ID NO 17
<211> LENGTH: 2594
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
cactataggg cgaattggcg gaaggccgtc aaggccgcat ggggacaagt ttgtacaaaa     60

aagcaggctt cgaattcaga tctagaagta ctggcaccat ggccggcgac tacaaggacg    120
```

-continued

```
acgacgataa gggcggaggc ggcagcatga gcatcgacac agccagatcc ggcagcgacg    180
atgacgtgga aatcagagag atccaggccg ctgccgcccc taccagattt gccagaggat    240
ggcactgcct gggcctgctg agagacttcc aggacggcaa gccccacagc atcgaggcct    300
ttggcaccaa gctggtggtg ttcgccgaca gcaagggcca gctgaacgtg ctggacgcct    360
actgcagaca catgggcggc gatctgagca gaggcgaagt gaagggcgac tctatcgcct    420
gccccttcca cgactggcgg tggaatggca agggcaagtg caccgacatc ccttacgcca    480
gacgggtgcc ccctatcgcc aagaccagag cctggaccac cctggaaaga aacggccagc    540
tgtatgtgtg gaacgacccc cagggcaacc ccccacctga ggatgtgacc atccctgaga    600
tcgccggata cggcaccgac gagtggaccg actggtcctg gaaaagcctg cggatcaagg    660
gcagccactg ccgcgagatc gtggacaacg tggtggatat ggcccacttc ttctacatcc    720
actacagctt cccccggtac ttcaagaacg tgttcgaggg ccacaccgcc acccagtaca    780
tgcactctac cggcagagaa gatgtgatca gcggcaccaa ctacgacgac cccaacgccg    840
agctgagaag cgaggccacc tacttcggcc ccagctacat gatcgactgg ctggaaagcg    900
acgccaacgg ccagaccatc gagacaatcc tgatcaactg ccactacccc gtgtccaaca    960
acgagttcgt gctgcagtac ggcgccatcg tgaagaaact gcccggcgtg tccgacgaga   1020
ttgccgccgg aatggccgag cagtttgccg aaggcgtgca gctgggcttc gagcaggatg   1080
tggaaatctg gaagaacaag gcccccatcg acaacccccct gctgagcgaa gaggacggcc   1140
ctgtgtatca gctgcggcgg tggtatcagc agttctacgt ggacgtggaa gatatcaccg   1200
aggacatgac caagcgcttc gagttcgaga tcgataccac cagagccgtg gcctcttggc   1260
agaaagaggt ggccgagaac ctggccaagc aggccgaagg ctctacagct acacccggga   1320
gcggcgccac caacttcagc ctgctgaaac aggctgggga tgtggaagag aaccctggcc   1380
ctgccggcta cccctacgat gtgcctgatt atgctggcgg cggaggctcc atgacagccg   1440
tgcaggctcc tgtgaccagc agagccacag tgctgaccgt gtctgccgtg gtgcaggaaa   1500
cagccgatgc cgtgtccctg gtgttcgacg tgcccgacga cagaagagag gacttcacct   1560
acagacccgg ccagttcctg accctgagaa tccccagcga caggacaggc agcgtggcca   1620
gatgttacag cctggccagc agccctttca ccggcgagcc tccaaaagtg accgtgaaga   1680
gaacagctgg cggctacggc agcaactggc tgtgcgacaa tatcgtggcc ggacggtcca   1740
tcgaggtgct gcctccagct ggcgtgttca cccctgccga tctgaccgag aaactggtgc   1800
tgtttgctgg cggaagcggc atcacccccg tgatgagcat cctggaatcc gccctgcaca   1860
gcggcaacag ggacgtggtg ctgatctacg gcaaccgcga cgagaagtcc gtgatcttcg   1920
ccgagaagct gagagagctg gccgccagac acgctggcgc tctgacagtg gtgcattggc   1980
tggaatcagt gcagggcctg cccagccctc agcagctggc cacactgatc agccccttcg   2040
ccgaccacag ggcctacatg tgtggcccag gccccttcat ggacaccgtg cgggaaggac   2100
tgctgctggc tggcgtgccc aaggacagaa tccacgccga ggtgttcacc agcctgagcg   2160
gcgatccttt cgccgatgtg cccctggtgg aaatcgacga gtccgacgcc gatgccacct   2220
ctgccacagt gcagctggat ggcgaggaac acgacctcgt gtggcctaga agcgccacac   2280
tggtggacgt gatgctgtcc aagggcctgg acgtgcccta cagctgcaga gaaggcgagt   2340
gcggcagctg cgcctgtact gtggtggaag gcgacgtgga cagcctgcct agcgccatcc   2400
tggacgaaga ggatatcgcc aatggctacg tgctggcctg ccaggctaga cccaagagcg   2460
atcacgtgcg gatcgagttc tgataaaccc gggtgataaa gagctcggat cccaattggc   2520
```

tagcgaccca gctttcttgt acaaagtggt ccccctgggc ctcatgggcc ttccgctcac 2580
tgcccgcttt ccag 2594

<210> SEQ ID NO 18
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gcaggcttcg aattcagatc tagaagtact ggcaccatgg ccccatatag cctcctggtg 60
accagactgc agaaagccct gggcgtgcgg cagtaccatg tggcctctgt gctgtgccag 120
agggccaagg tggccatgag cgactacaag gacgacgacg acaaaggcgg cggaggcagc 180
atgagcatcg acacagccag aagcggcagc gacgacgatg tggaaatcag agagatccag 240
gccgctgccg cccctaccag atttgccaga ggatggcact gcctgggcct gctgagagac 300
ttccaggacg gcaagcccca cagcatcgag gcctttggca ccaagctggt ggtgttcgcc 360
gacagcaagg gccagctgaa cgtgctggac gcctactgca gacacatggg cggcgatctg 420
agcagaggcg aagtgaaggg cgactctatc gcctgcccct tccacgactg gcggtggaat 480
ggcaagggca agtgcaccga catcccttac gccagacggg tgccccctat cgccaagacc 540
agagcctgga ccaccctgga aagaaacggc cagctgtatg tgtggaacga cccccagggc 600
aaccccccac ctgaggatgt gaccatccct gagatcgccg gctacggcac cgacgagtgg 660
acagactggt cctggaaaag cctgcggatc aagggcagcc actgccgcga gatcgtggac 720
aacgtggtgg atatggccca cttcttctac atccactaca gcttccccccg gtacttcaag 780 aacgtgttcg agggccacac cgccacccag tacatgcact ctaccggcag agaagatgtg 840
atcagcggca ccaactacga cgaccccaac gccgagctga gaagcgaggc cacctacttc 900
ggccccagct acatgatcga ctggctggaa agcgacgcca acggccagac catcgagaca 960
atcctgatca actgccacta ccccgtgtcc aacaacgagt 1000

<210> SEQ ID NO 19
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
ctgatcaact gccactaccc cgtgtccaac aacgagttcg tgctgcagta cggcgccatc 60
gtgaagaaac tgcccggcgt gtccgacgag atcgctgccg gaatggccga gcagtttgcc 120
gaaggcgtgc agctgggctt cgagcaggac gtggaaatct ggaagaacaa ggcccccatc 180
gacaaccccc tgctgagcga agaggacggc cctgtgtatc agctgcggcg gtggtatcag 240
cagttctacg tggacgtgga agatatcacc gaggacatga ccaagcgctt cgagttcgag 300
atcgatacca ccagagccgt ggcctcttgg cagaaagagg tggccgagaa cctggccaag 360
caggccgaag gctctacagc cacacctggc agcggcgcca ccaacttcag cctgctgaaa 420
caggccgggg atgtggaaga gaacccaggc cctatggccc cttactctct gctcgtgaca 480
cggctgcaga aagctctggg agtgcgccag tatcacgtgg caagcgtgct gtgtcagcgc 540
gctaaagtgg ctatgagcgg ctacccctac gatgtgcctg attatgctgg cggcggaggc 600

<210> SEQ ID NO 20
<211> LENGTH: 5197
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
gtctttcctg cgttatcccc tgattctgtg gataaccgta ttaccgcctt tgagtgagct 60
gataccgctc gccgcagccg aacgaccgag cgcagcgagt cagtgagcga ggaagcggaa 120
gagcgcccaa tacgcaaacc gcctctcccc gcgcgttggc cgattcatta atgcagctgg 180
cacgacaggt ttcccgactg gaaagcgggc agtgagcgca acgcaattaa tacgcgtacc 240
gctagccagg aagagtttgt agaaacgcaa aaaggccatc cgtcaggatg gccttctgct 300
tagtttgatg cctggcagtt tatggcgggc gtcctgcccg ccaccctccg ggccgttgct 360
tcacaacgtt caaatccgct cccggcggat ttgtcctact caggagagcg ttcaccgaca 420
aacaacagat aaaacgaaag gcccagtctt ccgactgagc ctttcgtttt atttgatgcc 480
tggcagttcc ctactctcgc gttaacgcta gcatggatgt tttcccagtc acgacgttgt 540
aaaacgacgg ccagtcttaa gctcgggccc caaataatga ttttattttg actgatagtg 600
acctgttcgt tgcaacaaat tgatgagcaa tgctttttta taatgccaac tttgtacaaa 660
aaagcaggct tcgaattcag atctagaagt actggcacca tggccccata tagcctcctg 720
gtgaccagac tgcagaaagc cctgggcgtg cggcagtacc atgtggcctc tgtgctgtgc 780
cagagggcca aggtggccat gagcgactac aaggacgacg acgacaaagg cggcggaggc 840
agcatgagca tcgacacagc cagaagcggc agcgacgacg atgtggaaat cagagagatc 900
caggccgctg ccgcccctac cagatttgcc agaggatggc actgcctggg cctgctgaga 960
gacttccagg acggcaagcc ccacagcatc gaggcctttg gcaccaagct ggtggtgttc 1020
gccgacagca agggccagct gaacgtgctg gacgcctact gcagacacat gggcggcgat 1080
ctgagcagag gcgaagtgaa gggcgactct atcgcctgcc ccttccacga ctggcggtgg 1140
aatggcaagg gcaagtgcac cgacatccct tacgccagac gggtgccccc tatcgccaag 1200
accagagcct ggaccaccct ggaaagaaac ggccagctgt atgtgtggaa cgacccccag 1260
ggcaaccccc cacctgagga tgtgaccatc cctgagatcg ccggctacgg caccgacgag 1320
tggacagact ggtcctggaa aagcctgcgg atcaagggca gccactgccg cgagatcgtg 1380
gacaacgtgg tggatatggc ccacttcttc tacatccact acagcttccc ccggtacttc 1440
aagaacgtgt tcgagggcca caccgccacc cagtacatgc actctaccgg cagagaagat 1500
gtgatcagcg gcaccaacta cgacgacccc aacgccgagc tgagaagcga ggccacctac 1560
ttcggcccca gctacatgat cgactggctg gaaagcgacg ccaacggcca gaccatcgag 1620
acaatcctga tcaactgcca ctaccccgtg tccaacaacg agttcgtgct gcagtacggc 1680
gccatcgtga agaaactgcc cggcgtgtcc gacgagatcg ctgccggaat ggccgagcag 1740
tttgccgaag gcgtgcagct gggcttcgag caggacgtgg aaatctggaa gaacaaggcc 1800
cccatcgaca accccctgct gagcgaagag gacggccctg tgtatcagct gcggcggtgg 1860
tatcagcagt tctacgtgga cgtggaagat atcaccgagg acatgaccaa gcgcttcgag 1920
ttcgagatcg ataccaccag agccgtggcc tcttggcaga aagaggtggc cgagaacctg 1980

-continued

```
gccaagcagg ccgaaggctc tacagccaca cctggcagcg gcgccaccaa cttcagcctg   2040
ctgaaacagg ccggggatgt ggaagagaac ccaggcccta tggcccctta ctctctgctc   2100
gtgacacggc tgcagaaagc tctgggagtg cgccagtatc acgtggcaag cgtgctgtgt   2160
cagcgcgcta aagtggctat gagcggctac ccctacgatg tgcctgatta tgctggcggc   2220
ggaggctcca tgacagccgt gcaggctcct gtgaccagca gagccacagt gctgaccgtg   2280
tctgccgtgg tgcaggaaac agccgatgcc gtgtccctgg tgttcgacgt gcccgacgac   2340
agaagagagg acttcaccta cagacccggc cagttcctga ccctgagaat ccccagcgac   2400
aggacaggca gcgtggccag atgttacagc ctggccagca gcccctttcac cggcgagcct  2460
ccaaaagtga ccgtgaagag aacagctggc ggctacggca gcaactggct gtgcgacaat   2520
atcgtggccg gacggtccat cgaggtgctg cctccagctg gcgtgttcac ccctgccgat   2580
ctgaccgaga aactggtgct gtttgctggc ggaagcggca tcacccccgt gatgagcatc   2640
ctggaatccg ccctgcacag cggcaacagg gacgtggtgc tgatctacgg caaccgcgac   2700
gagaagtccg tgatcttcgc cgagaagctg agagagctgg ccgccagaca cgctggcgct   2760
ctgacagtgg tgcattggct ggaatcagtg cagggcctgc ccagccctca gcagctggcc   2820
acactgatca gccccttcgc cgaccacagg gcctacatgt gtggcccagg ccccttcatg   2880
gacaccgtgc gggaaggact gctgctggct ggcgtgccca aggacagaat ccacgccgag   2940
gtgttcacca gcctgagcgg cgatcccttc gccgatgtgc cctggtgga aatcgacgag    3000
tccgacgccg atgccacctc tgccacagtg cagctggatg gcgaggaaca cgacctcgtg   3060
tggcctagaa gcgccacact ggtggacgtg atgctgtcca agggcctgga cgtgccctac   3120
agctgcagag aaggcgagtg cggcagctgc gcctgtactg tggtggaagg cgacgtggac   3180
agcctgccta gcgccatcct ggacgaagag gatatcgcca atggctacgt gctggcctgc   3240
caggctagac ccaagagcga tcacgtgcgg atcgagttct gataaacccg ggtgataaag   3300
agctcggatc ccaattggct agcgacccag ctttcttgta caaagttggc attataagaa   3360
agcattgctt atcaatttgt tgcaacgaac aggtcactat cagtcaaaat aaaatcatta   3420
tttgccatcc agctgatatc ccctatagtg agtcgtatta catggtcata gctgtttcct   3480
ggcagctctg gcccgtgtct caaaatctct gatgttacat tgcacaagat aaaaatatat   3540
catcatgaac aataaaactg tctgcttaca taaacagtaa tacaaggggt gttatgagcc   3600
atattcaacg ggaaacgtcg aggccgcgat taaattccaa catggatgct gatttatatg   3660
ggtataaatg ggctcgcgat aatgtcgggc aatcaggtgc gacaatctat cgcttgtatg   3720
ggaagcccga tgcgccagag ttgtttctga aacatggcaa aggtagcgtt gccaatgatg   3780
ttacagatga gatggtcaga ctaaactggc tgacggaatt tatgcctctt ccgaccatca   3840
agcattttat ccgtactcct gatgatgcat ggttactcac cactgcgatc cccggaaaaa   3900
cagcattcca ggtattagaa gaatatcctg attcaggtga aaatattgtt gatgcgctgg   3960
cagtgttcct gcgccggttg cattcgattc ctgtttgtaa ttgtcctttt aacagcgatc   4020
gcgtatttcg tctcgctcag gcgcaatcac gaatgaataa cggtttggtt gatgcgagtg   4080
attttgatga cgagcgtaat ggctggcctg ttgaacaagt ctggaaagaa atgcataaac   4140
ttttgccatt ctcaccggat tcagtcgtca ctcatggtga tttctcactt gataacctta   4200
tttttgacga ggggaaatta ataggttgta ttgatgttgg acgagtcgga atcgcagacc   4260
gataccagga tcttgccatc ctatggaact gcctcggtga gttttctcct tcattacaga   4320
aacggctttt tcaaaaatat ggtattgata atcctgatat gaataaattg cagtttcatt   4380
```

tgatgctcga tgagtttttc taatcagaat tggttaattg gttgtaacac tggcagagca 4440
ttacgctgac ttgacgggac ggcgcaagct catgaccaaa atcccttaac gtgagttacg 4500
cgtcgttcca ctgagcgtca gaccccgtag aaaagatcaa aggatcttct tgagatcctt 4560
tttttctgcg cgtaatctgc tgcttgcaaa caaaaaaacc accgctacca gcggtggttt 4620
gtttgccgga tcaagagcta ccaactcttt ttccgaaggt aactggcttc agcagagcgc 4680
agataccaaa tactgttctt ctagtgtagc cgtagttagg ccaccacttc aagaactctg 4740
tagcaccgcc tacatacctc gctctgctaa tcctgttacc agtggctgct gccagtggcg 4800
ataagtcgtg tcttaccggg ttggactcaa gacgatagtt accggataag gcgcagcggt 4860
cgggctgaac ggggggttcg tgcacacagc ccagcttgga gcgaacgacc tacaccgaac 4920
tgagatacct acagcgtgag ctatgagaaa gcgccacgct tcccgaaggg agaaaggcgg 4980
acaggtatcc ggtaagcggc agggtcggaa caggagagcg cacgagggag cttccagggg 5040
gaaacgcctg gtatctttat agtcctgtcg ggtttcgcca cctctgactt gagcgtcgat 5100
ttttgtgatg ctcgtcaggg gggcggagcc tatggaaaaa cgccagcaac gcggcctttt 5160
tacggttcct ggccttttgc tggccttttg ctcacat 5197

<210> SEQ ID NO 21
<211> LENGTH: 656
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
tggtgcattg gctggaatca gtgcagggcc tgcccagccc tcagcagctg gccacactga 60
tcagcccctt cgccgaccac agggcctaca tgtgtggccc aggccccttc atggacaccg 120
tgcgggaagg actgctgctg gctggcgtgc ccaaggacag aatccacgcc gaggtgttca 180
ccagcctgag cggcgatcct ttcgccgatg tgcccctggt ggaaatcgac gagtccgacg 240
ccgatgccac ctctgccaca gtgcagctgg atggcgagga acacgacctc gtgtggccta 300
gaagcgccac actggtggac gtgatgctgt ccaagggcct ggacgtgccc tacagctgca 360
gagaaggcga gtgcggcagc tgcgcctgta ctgtggtgga aggcgacgtg gacagcctgc 420
ctagcgccat cctggacgaa gaggatatcg ccaatggcta cgtgctggcc tgccaggcta 480
gacccaagag cgatcacgtg cggatcgagt tcggcagcgg cgagggaaga ggcagcctgc 540
tgacatgcgg agatgtggaa gagaaccctg gccccgacta caaggacgac gacgataaga 600
tgcaggactg gactagtgaa tgcgacgtgc tggtcgtggg ctctggcgga ggcgct 656

<210> SEQ ID NO 22
<211> LENGTH: 659
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22
tggtgcattg gctggaatca gtgcagggcc tgcccagccc tcagcagctg gccacactga 60
tcagcccctt cgccgaccac agggcctaca tgtgtggccc aggccccttc atggacaccg 120
tgcgggaagg actgctgctg gctggcgtgc ccaaggacag aatccacgcc gaggtgttca 180

```
ccagcctgag cggcgatcct ttcgccgatg tgcccctggt ggaaatcgac gagtccgacg    240

ccgatgccac ctctgccaca gtgcagctgg atggcgagga acacgacctc gtgtggccta    300

gaagcgccac actggtggac gtgatgctgt ccaagggcct ggacgtgccc tacagctgca    360

gagaaggcga gtgcggcagc tgcgcctgta ctgtggtgga aggcgacgtg gacagcctgc    420

ctagcgccat cctggacgaa gaggatatcg ccaatggcta cgtgctggcc tgccaggcta    480

gacccaagag cgatcacgtg cggatcgagt tcggcagcgg cgccaccaac ttcagcctgc    540

tgaaacaggc cggggatgtg gaagagaacc caggccctga ctacaaggac gacgacgata    600

agatgcagga ctggactagt gaatgcgacg tgctggtcgt gggctctggc ggaggcgct     659


<210> SEQ ID NO 23
<211> LENGTH: 6803
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

ccagcttgga gcgaacgacc tacaccgaac tgagatacct acagcgtgag ctatgagaaa     60

gcgccacgct tcccgaaggg agaaaggcgg acaggtatcc ggtaagcggc agggtcggaa    120

caggagagcg cacgagggag cttccagggg gaaacgcctg gtatctttat agtcctgtcg    180

ggtttcgcca cctctgactt gagcgtcgat ttttgtgatg ctcgtcaggg gggcggagcc    240

tatggaaaaa cgccagcaac gcggcctttt tacggttcct ggccttttgc tggccttttg    300

ctcacatgtc tttcctgcgt tatcccctga ttctgtggat aaccgtatta ccgcctttga    360

gtgagctgat accgctcgcc gcagccgaac gaccgagcgc agcgagtcag tgagcgagga    420

agcggaagag cgcccaatac gcaaaccgcc tctccccgcg cgttggccga ttcattaatg    480

cagctggcac gacaggtttc ccgactggaa agcgggcagt gagcgcaacg caattaatac    540

gcgtaccgct agccaggaag agtttgtaga aacgcaaaaa ggccatccgt caggatggcc    600

ttctgcttag tttgatgcct ggcagtttat ggcgggcgtc ctgcccgcca ccctccgggc    660

cgttgcttca caacgttcaa atccgctccc ggcggatttg tcctactcag gagagcgttc    720

accgacaaac aacagataaa acgaaaggcc cagtcttccg actgagcctt tcgttttatt    780

tgatgcctgg cagttcccta ctctcgcgtt aacgctagca tggatgtttt cccagtcacg    840

acgttgtaaa acgacggcca gtcttaagct cgggccccaa ataatgattt tattttgact    900

gatagtgacc tgttcgttgc aacaaattga tgagcaatgc ttttttataa tgccaacttt    960

gtacaaaaaa gcaggcttcg aattcagatc tagaagtact ggcaccatgg ccccatatag   1020

cctcctggtg accagactgc agaaagccct gggcgtgcgg cagtaccatg tggcctctgt   1080

gctgtgccag agggccaagg tggccatgag cgactacaag gacgacgacg acaaaggcgg   1140

cggaggcagc atgagcatcg acacagccag aagcggcagc gacgacgatg tggaaatcag   1200

agagatccag gccgctgccg cccctaccag atttgccaga ggatggcact gcctgggcct   1260

gctgagagac ttccaggacg gcaagcccca cagcatcgag gcctttggca ccaagctggt   1320

ggtgttcgcc gacagcaagg gccagctgaa cgtgctggac gcctactgca gacacatggg   1380

cggcgatctg agcagaggcg aagtgaaggg cgactctatc gcctgcccct tccacgactg   1440

gcggtggaat ggcaagggca agtgcaccga catcccttac gccagacggg tgccccctat   1500

cgccaagacc agagcctgga ccaccctgga aagaaacggc cagctgtatg tgtggaacga   1560
```

-continued

```
cccccagggc aaccccccac ctgaggatgt gaccatccct gagatcgccg gctacggcac   1620
cgacgagtgg acagactggt cctggaaaag cctgcggatc aagggcagcc actgccgcga   1680
gatcgtggac aacgtggtgg atatggccca cttcttctac atccactaca gcttccccg    1740
gtacttcaag aacgtgttcg agggccacac cgccacccag tacatgcact ctaccggcag   1800
agaagatgtg atcagcggca ccaactacga cgaccccaac gccgagctga gaagcgaggc   1860
cacctacttc ggccccagct acatgatcga ctggctggaa agcgacgcca acggccagac   1920
catcgagaca atcctgatca actgccacta ccccgtgtcc aacaacgagt tcgtgctgca   1980
gtacggcgcc atcgtgaaga aactgcccgg cgtgtccgac gagatcgctg ccggaatggc   2040
cgagcagttt gccgaaggcg tgcagctggg cttcgagcag gacgtggaaa tctggaagaa   2100
caaggccccc atcgacaacc ccctgctgag cgaagaggac ggccctgtgt atcagctgcg   2160
gcggtggtat cagcagttct acgtggacgt ggaagatatc accgaggaca tgaccaagcg   2220
cttcgagttc gagatcgata ccaccagagc cgtggcctct tggcagaaag aggtggccga   2280
gaacctggcc aagcaggccg aaggctctac agccacacct ggcagcggcg ccaccaactt   2340
cagcctgctg aaacaggccg gggatgtgga agagaaccca ggccctatgg ccccttactc   2400
tctgctcgtg acacggctgc agaaagctct gggagtgcgc cagtatcacg tggcaagcgt   2460
gctgtgtcag cgcgctaaag tggctatgag cggctacccc tacgatgtgc ctgattatgc   2520
tggcggcgga ggctccatga cagccgtgca ggctcctgtg accagcagag ccacagtgct   2580
gaccgtgtct gccgtggtgc aggaaacagc cgatgccgtg tccctggtgt tcgacgtgcc   2640
cgacgacaga agagaggact tcacctacag acccggccag ttcctgaccc tgagaatccc   2700
cagcgacagg acaggcagcg tggccagatg ttacagcctg gccagcagcc ctttcaccgg   2760
cgagcctcca aaagtgaccg tgaagagaac agctggcggc tacggcagca actggctgtg   2820
cgacaatatc gtggccggac ggtccatcga ggtgctgcct ccagctggcg tgttcacccc   2880
tgccgatctg accgagaaac tggtgctgtt tgctggcgga agcggcatca cccccgtgat   2940
gagcatcctg gaatccgccc tgcacagcgg caacagggac gtggtgctga tctacggcaa   3000
ccgcgacgag aagtccgtga tcttcgccga gaagctgaga gagctggccg ccagacacgc   3060
tggcgctctg acagtggtgc attggctgga atcagtgcag ggcctgccca gccctcagca   3120
gctggccaca ctgatcagcc ccttcgccga ccacagggcc tacatgtgtg gcccaggccc   3180
cttcatggac accgtgcggg aaggactgct gctggctggc gtgcccaagg acagaatcca   3240
cgccgaggtg ttcaccagcc tgagcggcga tcctttcgcc gatgtgcccc tggtggaaat   3300
cgacgagtcc gacgccgatg ccacctctgc cacagtgcag ctggatggcg aggaacacga   3360
cctcgtgtgg cctagaagcg ccacactggt ggacgtgatg ctgtccaagg gcctggacgt   3420
gccctacagc tgcagagaag gcgagtgcgg cagctgcgcc tgtactgtgg tggaaggcga   3480
cgtggacagc ctgcctagcg ccatcctgga cgaagaggat atcgccaatg gctacgtgct   3540
ggcctgccag gctagaccca agagcgatca cgtgcggatc gagttcggca gcggcgaggg   3600
aagaggcagc ctgctgacat gcggagatgt ggaagagaac cctggccccg actacaagga   3660
cgacgacgat aagatgcagg actggactag tgaatgcgac gtgctggtcg tgggctctgg   3720
cggaggcgct ctgacaggcg cttatacagc tgccgcccag ggcctgacca ccatcgtgct   3780
ggaaaagacc gacagattcg gcggcaccag cgcctactct ggcgcctcta tttggctgcc   3840
tggcacccag gtgcaggaaa gagccggact gcctgacagc accgagaacg ccagaaccta   3900
cctgagagcc ctgctgggcg acgccgagag cgaaagacag gacgcctacg tggaaaccgc   3960
```

ccctgctgtg gtggctctgc tggaacagaa ccccaacatc gagttcgagt tccgggcctt 4020
ccccgactac tacaaggccg agggcagaat ggacaccggc cgcagcatca acccccctgga 4080
tctggaccct gccgacatcg gcgatctggc cggaaaagtg cggcccgagc tggaccagga 4140
tagaaccgga caggatcacg cccctggccc catgattgga ggcagagccc tgatcggcag 4200
actgctggct gctgtgcaga gcaccggaaa ggccgagctg agaaccgaga gcgtgctgac 4260
cagcctgatc gtggaagatg gcagagtcgt gggcgccgag gtggaatctg gggcgagac 4320
acagcggatc aaggccaaca gaggcgtgct gatggccgct ggcggcatcg agggaaacgc 4380
cgagatgagg gaacaggccg gaacacccgg caaggccatc tggtctatgg gccccttcgg 4440
agccaatacc ggcgacgcca tctctgccgg aattgccgtg ggcggagcta ccgcactgct 4500
ggatcaggcc tggttctgcc ctggcgtgga acagcctgat ggcagcgccg cctttatggt 4560
gggagtgcgg ggaggactgg tggtggattc tgccggggag agatacctga acgagagcct 4620
gccctacgac cagttcggca gagctatgga cgcccacgat gacaacggct ccgccgtgcc 4680
cagcttcatg atcttcgaca gcagagaggg cggaggcctg cccgccatct gcatccctaa 4740
taccgcccca gccaagcacc tggaagccgg aacatgggtg ggagccgaca cactggaaga 4800
actggccgcc aagacaggcc tgcctgccga tgctctgaga agcaccgtgg aaaagttcaa 4860
cgacgccgcc aagctgggcg tggacgaaga gttccataga ggcgaggacc cctacgacgc 4920
cttcttctgc ccacctaatg gcggagccaa cgccgccctg accgccattg agaacggccc 4980
tttttacgcc gccagaatcg tgctgagcga cctgggcaca aagggcggcc tcgtgaccga 5040
tgtgaacggc agagtgctga gagccgacgg cagcgccatt gacggactgt atgccgccgg 5100
aaataccagc gccagcctga gcggcagatt ctaccctggc ccaggcgtgc cactgggcac 5160
cgctatggtg ttcagctaca gagctgccca ggacatggcg aagtaattct agagagctca 5220
aggtgaattg gctagcgacc cagctttctt gtacaaagtt ggcattataa gaaagcattg 5280
cttatcaatt tgttgcaacg aacaggtcac tatcagtcaa aataaaatca ttatttgcca 5340
tccagctgat atcccctata gtgagtcgta ttacatggtc atagctgttt cctggcagct 5400
ctggcccgtg tctcaaaatc tctgatgtta cattgcacaa gataaaaata tatcatcatg 5460
aacaataaaa ctgtctgctt acataaacag taatacaagg ggtgttatga gccatattca 5520
acgggaaacg tcgaggccgc gattaaattc caacatggat gctgatttat atgggtataa 5580
atgggctcgc gataatgtcg ggcaatcagg tgcgacaatc tatcgcttgt atgggaagcc 5640
cgatgcgcca gagttgtttc tgaaacatgg caaaggtagc gttgccaatg atgttacaga 5700
tgagatggtc agactaaact ggctgacgga atttatgcct cttccgacca tcaagcattt 5760
tatccgtact cctgatgatg catggttact caccactgcg atccccggaa aaacagcatt 5820
ccaggtatta gaagaatatc ctgattcagg tgaaaatatt gttgatgcgc tggcagtgtt 5880
cctgcgccgg ttgcattcga ttcctgtttg taattgtcct tttaacagcg atcgcgtatt 5940
tcgtctcgct caggcgcaat cacgaatgaa taacggtttg gttgatgcga gtgattttga 6000
tgacgagcgt aatggctggc ctgttgaaca agtctggaaa gaaatgcata aacttttgcc 6060
attctcaccg gattcagtcg tcactcatgg tgatttctca cttgataacc ttatttttga 6120
cgaggggaaa ttaataggtt gtattgatgt tggacgagtc ggaatcgcag accgatacca 6180
ggatcttgcc atcctatgga actgcctcgg tgagttttct ccttcattac agaaacggct 6240
ttttcaaaaa tatggtattg ataatcctga tatgaataaa ttgcagtttc atttgatgct 6300

-continued cgatgagttt ttctaatcag aattggttaa ttggttgtaa cactggcaga gcattacgct 6360
gacttgacgg gacggcgcaa gctcatgacc aaaatccctt aacgtgagtt acgcgtcgtt 6420
ccactgagcg tcagaccccg tagaaaagat caaaggatct tcttgagatc cttttttct 6480 gcgcgtaatc tgctgcttgc aaacaaaaaa accaccgcta ccagcggtgg tttgtttgcc 6540
ggatcaagag ctaccaactc tttttccgaa ggtaactggc ttcagcagag cgcagatacc 6600
aaatactgtt cttctagtgt agccgtagtt aggccaccac ttcaagaact ctgtagcacc 6660
gcctacatac ctcgctctgc taatcctgtt accagtggct gctgccagtg gcgataagtc 6720
gtgtcttacc gggttggact caagacgata gttaccggat aaggcgcagc ggtcgggctg 6780
aacggggggt tcgtgcacac agc 6803

<210> SEQ ID NO 24
<211> LENGTH: 474
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24
aaaagcaggc ttcgaattca gatctagaag tactggcacc atgctggcca agggcctgcc 60
tcctagaagc gtgctcgtga agggctgcca gaccttcctg agcgccccta gagaaggcct 120
gggcagactg agagtgccta caggcgaagg cgccggaatc agcaccagaa gccccagacc 180
cttcaacgag atccccagcc ctggcgacaa cggctggctg aacctgtacc acttctggcg 240
ggaaaccggc acccacaaag tgcatctgca ccacgtgcag aacttccaga agtacggccc 300
catctaccgc gagaagctgg gcaacgtgga aagcgtgtac gtgatcgacc ccgaggacgt 360
ggccctgctg tttaagagcg agggccccaa ccccgagcgg ttcctgattc ctccttgggt 420
ggcctaccac cagtactacc agaggcccat cggcgtgctg ctgaagaagt ccgc 474

<210> SEQ ID NO 25
<211> LENGTH: 3221
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25
actaccagag gcccatcggc gtgctgctga agaagtccgc cgcctggaag aaagaccggg 60
tggccctgaa ccaggaagtg atggcccctg aggccaccaa gaactttctg cccctgctgg 120
acgccgtgtc cagagacttt gtgtccgtgc tgcaccggcg gatcaagaag gccggcagcg 180
gcaattacag cggcgacatc agcgacgacc tgttcagatt cgccttcgag agcatcacca 240
acgtgatctt cggcgagcgg cagggcatgc tggaagaggt cgtgaatccc gaggcccagc 300
ggttcatcga cgccatctac cagatgttcc acaccagcgt gcccatgctg aatctgcccc 360
ccgacctgtt tcggctgttc cggaccaaga cctggaagga ccatgtggcc gcctgggatg 420
tgatcttcag caaggccgac atctacaccc agaacttcta ctgggagctg cggcagaaag 480
gcagcgtgca ccacgactac cggggcatcc tgtacagact gctgggcgac agcaagatga 540
gcttcgagga catcaaggcc aacgtgaccg agatgctggc tggcggcgtg gacaccacca 600
gcatgactct gcagtggcac ctgtacgaga tggcccggaa cctgaaggtg caggacatgc 660
tgagagccga ggtgctggcc gccagacatc aggctcaggg cgatatggcc acaatgctgc 720

```
agctggtgcc tctgctgaag gccagcatca aagagacact gcggctgcac cccatcagcg    780
tgaccctgca gagatacctc gtgaacgacc tggtgctgcg ggactacatg atccccgcca    840
agaccctggt gcaggtggcc atctatgccc tgggaagaga gcctacattc ttcttcgacc    900
ctgaaaactt cgaccccacc cggtggctga gcaaggacaa gaacatcacc tacttccgca    960
acctgggctt cggctggggc gtgcggcagt gtctgggcag aagaatcgcc gagctggaaa   1020
tgaccatctt cctgatcaat atgctggaaa acttccgggt ggaaatccag cacctgagcg   1080
acgtgggcac caccttcaac ctgatcctga tgcccgagaa gcctatcagc ttcaccttct   1140
ggcccttcaa tcaggaagcc acccagcaga ccgacggcac cagcagcacc caggaaaaga   1200
ccccccagat ctgcgtcgtg ggctctggac ctgccggctt ttacacagcc cagcatctgc   1260
tgaaacaccc ccaggcccac gtggacatct acgagaagca gcccgtgccc ttcggcctgg   1320
tgcgctttgg agtggcccca gatcaccccg aagtgaagaa cgtgatcaac accttcaccc   1380
agaccgccca cagcggcaga tgtgccttct ggggcaatgt ggaagtgggc cgggatgtga   1440
ccgtgcccga actgagggaa gcctaccatg ccgtggtgct gagctacggc gccgaggatc   1500
atcgggccct ggaaatccct ggcgaggaac tgcctggcgt gtgtagcgcc agagccttcg   1560
tgggctggta caacggcctg cccgaaaacc aggaactgga acccgacctg agctgcgaca   1620
ccgccgtgat tctgggccag ggaaatgtgg ccctggatgt ggccagaatc ctgctgaccc   1680
ctcccgagca cctggaaaga accgacatca ccaaggccgc cctgggcgtg ctgagacaga   1740
gcagagtgaa aaccgtgtgg ctcgtgggca gacggggacc tctgcaggtg gcattcacca   1800
tcaaagaact gcgcgagatg atccagctgc caggcgccag acccatcctg gaccctgtgg   1860
atttcctggg actgcaggac aagatcaaag aggtgcccag accccggaag cggctgacag   1920
aactgctgct gagaaccgcc acagagaagc ctggccctgc cgaagctgct agacaggcct   1980
ctgcctctag agcctggggc ctgcggttct tcagatcccc tcagcaggtg ctgcctagcc   2040
ccgatgggag aagggcagct ggcgtgcgcc tggctgtgac tagactggaa ggcgtggacg   2100
aggccacaag agccgtgcca acaggggaca tggaagatct gccctgcgga ctggtgctgt   2160
ccagcatcgg ctacaagagc agacccgtgg acccctccgt gcctttcgat agcaagctgg   2220
gcgtgatccc taacgtggaa ggcagagtga tggacgtgcc cggcctgtac tgttccggct   2280
gggtcaaaag gggccccaca ggcgtgatcg ccacaacaat gaccgacagc ttcctgaccg   2340
gccagatgct gctgcaggac ctgaaagccg gcctgctgcc atctggccct agacctggat   2400
atgccgccat ccaggctctg ctgtcctcac ggggagtgcg gcctgtgtcc ttcagcgact   2460
gggagaaact ggatgccgaa gaggtggcca ggggacaggg cactggcaag cccagagaaa   2520
agctggtgga ccctcaggaa atgctgcgcc tgctgggcca tacagatggc gccagcagca   2580
gctccgagga taagatcacc gtgcacttca tcaaccggga cggcgagaca ctgaccacca   2640
agggcaaagt gggcgactct ctgctggacg tggtggtgga aaacaacctg gacatcgacg   2700
gcttcggcgc ctgcgaggga acactggcct gtagcacctg tcacctgatc ttcgaggatc   2760
acatctacga aaagctggac gccatcaccg acgaagagaa cgacatgctg gacctggcct   2820
acggcctgac cgatagaagc agactgggct gtcagatctg cctgaccaag agcatggaca   2880
acatgaccgt gcgggtgccc gagacagtgg ccgatgccag acagtccatc gatgtgggca   2940
agaccagcga ctacaaggac gacgacgaca agggctccgg cgccaccaat ttcagcctgc   3000
tgaagcaggc aggcgacgtg gaagagaacc ccggacctat gggctggtcc tgcctcgtga   3060
```

caggcgctgg cgggctgctg gggcagagaa ttgtgcggct gctggtggaa gaaaaagagc 3120
tgaaagagat ccgcgccctg gacaaggcct tcagacccga gctgcgggaa gagttcagca 3180
agctgcagaa caggaccaag ctgaccgtgc tggaagggga t 3221

<210> SEQ ID NO 26
<211> LENGTH: 1079
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
gctgcagaac aggaccaagc tgaccgtgct ggaaggggat atcctggacg agcccttcct 60
gaagagggcc tgccaggatg tgtccgtcgt gatccacacc gcctgcatca tcgacgtgtt 120
cggcgtgacc caccgcgaga gcatcatgaa tgtgaacgtg aagggcaccc agctgctgct 180
ggaagcctgt gtgcaggcca gcgtgcccgt gttcatctac accagcagca tcgaggtggc 240
cggacccaac agctacaaag agatcatcca gaacggccac gaggaagaac ccctggaaaa 300
cacctggccc accccctacc cctacagcaa gaagctggcc gagaaagccg tgctggccgc 360
caacggctgg aacctgaaga acggcgacac cctgtacacc tgtgccctgc ggcccaccta 420
catctatggc gagggcggac ctttcctgag cgccagcatc aacgaggccc tgaacaacaa 480
cggcatcctg agcagcgtgg gcaagttcag caccgtgaac cccgtgtacg tgggcaatgt 540
ggcctgggcc cacattctgg ctctgagagc cctgcgggac cccaagaaag ctccttctgt 600
gcggggccag ttctactaca tcagcgacga caccccccac cagagctacg acaacctgaa 660
ctacatcctg tccaaagagt tcggcctgcg gctggacagc agatggtccc tgcctctgac 720
cctgatgtac tggatcggct tcctgctgga agtggtgtcc ttcctgctga gccccatcta 780
cagctaccag ccccccttca accggcacac cgtgaccctg agcaacagcg tgttcacctt 840
cagctacaag aaggcccagc gggacctggc ctacaagccc ctgtactctt gggaggaagc 900
caagcagaaa accgtggaat gggtgggaag cctggtggac cggcacaaag agacactgaa 960
gtccaagacc cagggcagcg gcgagggcag aggatctctg ctgacatgcg gcgacgtgga 1020
agagaaccct ggccccatgg ccccatatag cctcctggtg accagactgc agaaagccc 1079

<210> SEQ ID NO 27
<211> LENGTH: 11414
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27
ccagcttgga gcgaacgacc tacaccgaac tgagatacct acagcgtgag ctatgagaaa 60
gcgccacgct tcccgaaggg agaaaggcgg acaggtatcc ggtaagcggc agggtcggaa 120
caggagagcg cacgagggag cttccagggg gaaacgcctg gtatctttat agtcctgtcg 180
ggtttcgcca cctctgactt gagcgtcgat ttttgtgatg ctcgtcaggg gggcggagcc 240
tatggaaaaa cgccagcaac gcggcctttt tacggttcct ggccttttgc tggccttttg 300
ctcacatgtc tttcctgcgt tatcccctga ttctgtggat aaccgtatta ccgcctttga 360
gtgagctgat accgctcgcc gcagccgaac gaccgagcgc agcgagtcag tgagcgagga 420
agcggaagag cgcccaatac gcaaaccgcc tctccccgcg cgttggccga ttcattaatg 480

-continued

```
cagctggcac gacaggtttc ccgactggaa agcgggcagt gagcgcaacg caattaatac    540
gcgtaccgct agccaggaag agtttgtaga aacgcaaaaa ggccatccgt caggatggcc    600
ttctgcttag tttgatgcct ggcagtttat ggcgggcgtc ctgcccgcca ccctccgggc    660
cgttgcttca caacgttcaa atccgctccc ggcggatttg tcctactcag gagagcgttc    720
accgacaaac aacagataaa acgaaaggcc cagtcttccg actgagcctt tcgttttatt    780
tgatgcctgg cagttcccta ctctcgcgtt aacgctagca tggatgtttt cccagtcacg    840
acgttgtaaa acgacggcca gtcttaagct cgggccccaa ataatgattt tattttgact    900
gatagtgacc tgttcgttgc aacaaattga tgagcaatgc tttttttataa tgccaacttt    960
gtacaaaaaa gcaggcttcg aattcagatc tagaagtact ggcaccatgc tggccaaggg   1020
cctgcctcct agaagcgtgc tcgtgaaggg ctgccagacc ttcctgagcg cccctagaga   1080
aggcctgggc agactgagag tgcctacagg cgaaggcgcc ggaatcagca ccagaagccc   1140
cagacccttc aacgagatcc ccagccctgg cgacaacggc tggctgaacc tgtaccactt   1200
ctggcgggaa accggcaccc acaaagtgca tctgcaccac gtgcagaact tccagaagta   1260
cggccccatc taccgcgaga agctgggcaa cgtggaaagc gtgtacgtga tcgaccccga   1320
ggacgtggcc ctgctgttta agagcgaggg ccccaacccc gagcggttcc tgattcctcc   1380
ttgggtggcc taccaccagt actaccagag gcccatcggc gtgctgctga agaagtccgc   1440
cgcctggaag aaagaccggg tggccctgaa ccaggaagtg atggcccctg aggccaccaa   1500
gaactttctg cccctgctgg acgccgtgtc cagagacttt gtgtccgtgc tgcaccggcg   1560
gatcaagaag gccggcagcg gcaattacag cggcgacatc agcgacgacc tgttcagatt   1620
cgccttcgag agcatcacca acgtgatctt cggcgagcgg cagggcatgc tggaagaggt   1680
cgtgaatccc gaggcccagc ggttcatcga cgccatctac cagatgttcc acaccagcgt   1740
gcccatgctg aatctgcccc ccgacctgtt tcggctgttc cggaccaaga cctggaagga   1800
ccatgtggcc gcctgggatg tgatcttcag caaggccgac atctacaccc agaacttcta   1860
ctgggagctg cggcagaaag gcagcgtgca ccacgactac cggggcatcc tgtacagact   1920
gctgggcgac agcaagatga gcttcgagga catcaaggcc aacgtgaccg agatgctggc   1980
tggcggcgtg gacaccacca gcatgactct gcagtggcac ctgtacgaga tggcccggaa   2040
cctgaaggtg caggacatgc tgagagccga ggtgctggcc gccagacatc aggctcaggg   2100
cgatatggcc acaatgctgc agctggtgcc tctgctgaag gccagcatca aagagacact   2160
gcggctgcac cccatcagcg tgaccctgca gagatacctc gtgaacgacc tggtgctgcg   2220
ggactacatg atccccgcca agaccctggt gcaggtggcc atctatgccc tgggaagaga   2280
gcctacattc ttcttcgacc ctgaaaactt cgaccccacc cggtggctga gcaaggacaa   2340
gaacatcacc tacttccgca acctgggctt cggctggggc gtgcggcagt gtctgggcag   2400
aagaatcgcc gagctggaaa tgaccatctt cctgatcaat atgctggaaa acttccgggt   2460
ggaaatccag cacctgagcg acgtgggcac caccttcaac ctgatcctga tgcccgagaa   2520
gcctatcagc ttcaccttct ggcccttcaa tcaggaagcc acccagcaga ccgacggcac   2580
cagcagcacc caggaaaaga ccccccagat ctgcgtcgtg ggctctggac ctgccggctt   2640
ttacacagcc cagcatctgc tgaaacaccc ccaggcccac gtggacatct acgagaagca   2700
gcccgtgccc ttcggcctgg tgcgctttgg agtggcccca gatcaccccg aagtgaagaa   2760
cgtgatcaac accttcaccc agaccgccca cagcggcaga tgtgccttct ggggcaatgt   2820
```

-continued

```
ggaagtgggc cgggatgtga ccgtgcccga actgagggaa gcctaccatg ccgtggtgct   2880
gagctacggc gccgaggatc atcgggccct ggaaatccct ggcgaggaac tgcctggcgt   2940
gtgtagcgcc agagccttcg tgggctggta caacggcctg cccgaaaacc aggaactgga   3000
acccgacctg agctgcgaca ccgccgtgat tctgggccag ggaaatgtgg ccctggatgt   3060
ggccagaatc ctgctgaccc ctcccgagca cctggaaaga accgacatca ccaaggccgc   3120
cctgggcgtg ctgagacaga gcagagtgaa aaccgtgtgg ctcgtgggca gacggggacc   3180
tctgcaggtg gcattcacca tcaaagaact gcgcgagatg atccagctgc caggcgccag   3240
acccatcctg gaccctgtgg atttcctggg actgcaggac aagatcaaag aggtgcccag   3300
accccggaag cggctgacag aactgctgct gagaaccgcc acagagaagc ctggccctgc   3360
cgaagctgct agacaggcct ctgcctctag agcctggggc ctgcggttct tcagatcccc   3420
tcagcaggtg ctgcctagcc ccgatgggag aagggcagct ggcgtgcgcc tggctgtgac   3480
tagactggaa ggcgtggacg aggccacaag agccgtgcca acaggggaca tggaagatct   3540
gccctgcgga ctggtgctgt ccagcatcgg ctacaagagc agacccgtgg accccctccgt   3600
gcctttcgat agcaagctgg gcgtgatccc taacgtggaa ggcagagtga tggacgtgcc   3660
cggcctgtac tgttccggct gggtcaaaag gggccccaca ggcgtgatcg ccacaacaat   3720
gaccgacagc ttcctgaccg gccagatgct gctgcaggac ctgaaagccg gcctgctgcc   3780
atctggccct agacctggat atgccgccat ccaggctctg ctgtcctcac ggggagtgcg   3840
gcctgtgtcc ttcagcgact gggagaaact ggatgccgaa gaggtggcca ggggacaggg   3900
cactggcaag cccagagaaa agctggtgga ccctcaggaa atgctgcgcc tgctgggcca   3960
tacagatggc gccagcagca gctccgagga taagatcacc gtgcacttca tcaaccggga   4020
cggcgagaca ctgaccacca agggcaaagt gggcgactct ctgctggacg tggtggtgga   4080
aaacaacctg gacatcgacg gcttcggcgc ctgcgaggga acactggcct gtagcacctg   4140
tcacctgatc ttcgaggatc acatctacga aaagctggac gccatcaccg acgaagagaa   4200
cgacatgctg gacctggcct acggcctgac cgatagaagc agactgggct gtcagatctg   4260
cctgaccaag agcatggaca acatgaccgt gcgggtgccc gagacagtgg ccgatgccag   4320
acagtccatc gatgtgggca agaccagcga ctacaaggac gacgacgaca agggctccgg   4380
cgccaccaat ttcagcctgc tgaagcaggc aggcgacgtg gaagagaacc ccggacctat   4440
gggctggtcc tgcctcgtga caggcgctgg cgggctgctg ggcagagaa ttgtgcggct   4500
gctggtggaa gaaaaagagc tgaaagagat ccgcgccctg gacaaggcct tcagacccga   4560
gctgcgggaa gagttcagca agctgcagaa caggaccaag ctgaccgtgc tggaagggga   4620
tatcctggac gagcccttcc tgaagagggc ctgccaggat gtgtccgtcg tgatccacac   4680
cgcctgcatc atcgacgtgt tcggcgtgac ccaccgcgag agcatcatga atgtgaacgt   4740
gaagggcacc cagctgctgc tggaagcctg tgtgcaggcc agcgtgcccg tgttcatcta   4800
caccagcagc atcgaggtgg ccggacccaa cagctacaaa gagatcatcc agaacggcca   4860
cgaggaagaa cccctggaaa acacctggcc caccccctac ccctacagca agaagctggc   4920
cgagaaagcc gtgctggccg ccaacggctg gaacctgaag aacggcgaca ccctgtacac   4980
ctgtgccctg cggcccacct acatctatgg cgagggcgga cctttcctga gcgccagcat   5040
caacgaggcc ctgaacaaca acggcatcct gagcagcgtg ggcaagttca gcaccgtgaa   5100
ccccgtgtac gtgggcaatg tggcctgggc ccacattctg gctctgagag ccctgcggga   5160
ccccaagaaa gctccttctg tgcggggcca gttctactac atcagcgacg acacccccca   5220
```

-continued

```
ccagagctac gacaacctga actacatcct gtccaaagag ttcggcctgc ggctggacag   5280
cagatggtcc ctgcctctga ccctgatgta ctggatcggc ttcctgctgg aagtggtgtc   5340
cttcctgctg agccccatct acagctacca gcccccccttc aaccggcaca ccgtgaccct   5400
gagcaacagc gtgttcacct tcagctacaa gaaggcccag cgggacctgg cctacaagcc   5460
cctgtactct tgggaggaag ccaagcagaa aaccgtggaa tgggtgggaa gcctggtgga   5520
ccggcacaaa gagacactga agtccaagac ccagggcagc ggcgagggca gaggatctct   5580
gctgacatgc ggcgacgtgg aagagaaccc tggccccatg gccccatata gcctcctggt   5640
gaccagactg cagaaagccc tgggcgtgcg gcagtaccat gtggcctctg tgctgtgcca   5700
gagggccaag gtggccatga gcgactacaa ggacgacgac gacaaaggcg gcggaggcag   5760
catgagcatc gacacagcca gaagcggcag cgacgacgat gtggaaatca gagagatcca   5820
ggccgctgcc gcccctacca gatttgccag aggatggcac tgcctgggcc tgctgagaga   5880
cttccaggac ggcaagcccc acagcatcga ggcctttggc accaagctgg tggtgttcgc   5940
cgacagcaag ggccagctga acgtgctgga cgcctactgc agacacatgg gcggcgatct   6000
gagcagaggc gaagtgaagg gcgactctat cgcctgcccc ttccacgact ggcggtggaa   6060
tggcaagggc aagtgcaccg acatccctta cgccagacgg gtgcccccta tcgccaagac   6120
cagagcctgg accaccctgg aaagaaacgg ccagctgtat gtgtggaacg acccccaggg   6180
caacccccca cctgaggatg tgaccatccc tgagatcgcc ggctacggca ccgacgagtg   6240
gacagactgg tcctggaaaa gcctgcggat caagggcagc cactgccgcg agatcgtgga   6300
caacgtggtg gatatggccc acttcttcta catccactac agcttccccc ggtacttcaa   6360
gaacgtgttc gagggccaca ccgccaccca gtacatgcac tctaccggca gagaagatgt   6420
gatcagcggc accaactacg acgaccccaa cgccgagctg agaagcgagg ccacctactt   6480
cggccccagc tacatgatcg actggctgga aagcgacgcc aacggccaga ccatcgagac   6540
aatcctgatc aactgccact accccgtgtc caacaacgag ttcgtgctgc agtacggcgc   6600
catcgtgaag aaactgcccg gcgtgtccga cgagatcgct gccggaatgg ccgagcagtt   6660
tgccgaaggc gtgcagctgg gcttcgagca ggacgtggaa atctggaaga acaaggcccc   6720
catcgacaac cccctgctga gcgaagagga cggccctgtg tatcagctgc ggcggtggta   6780
tcagcagttc tacgtggacg tggaagatat caccgaggac atgaccaagc gcttcgagtt   6840
cgagatcgat accaccagag ccgtggcctc ttggcagaaa gaggtggccg agaacctggc   6900
caagcaggcc gaaggctcta cagccacacc tggcagcggc gccaccaact tcagcctgct   6960
gaaacaggcc ggggatgtgg aagagaaccc aggccctatg gccccttact ctctgctcgt   7020
gacacggctg cagaaagctc tgggagtgcg ccagtatcac gtggcaagcg tgctgtgtca   7080
gcgcgctaaa gtggctatga gcggctaccc ctacgatgtg cctgattatg ctggcggcgg   7140
aggctccatg acagccgtgc aggctcctgt gaccagcaga gccacagtgc tgaccgtgtc   7200
tgccgtggtg caggaaacag ccgatgccgt gtccctggtg ttcgacgtgc ccgacgacag   7260
aagagaggac ttcacctaca gacccggcca gttcctgacc ctgagaatcc ccagcgacag   7320
gacaggcagc gtggccagat gttacagcct ggccagcagc cctttcaccg gcgagcctcc   7380
aaaagtgacc gtgaagagaa cagctggcgg ctacggcagc aactggctgt gcgacaatat   7440
cgtggccgga cggtccatcg aggtgctgcc tccagctggc gtgttcaccc ctgccgatct   7500
gaccgagaaa ctggtgctgt ttgctggcgg aagcggcatc acccccgtga tgagcatcct   7560
```

-continued

```
ggaatccgcc ctgcacagcg gcaacaggga cgtggtgctg atctacggca accgcgacga   7620
gaagtccgtg atcttcgccg agaagctgag agagctggcc gccagacacg ctggcgctct   7680
gacagtggtg cattggctgg aatcagtgca gggcctgccc agccctcagc agctggccac   7740
actgatcagc cccttcgccg accacagggc ctacatgtgt ggcccaggcc ccttcatgga   7800
caccgtgcgg gaaggactgc tgctggctgg cgtgcccaag gacagaatcc acgccgaggt   7860
gttcaccagc ctgagcggcg atcctttcgc cgatgtgccc ctggtggaaa tcgacgagtc   7920
cgacgccgat gccacctctg ccacagtgca gctggatggc gaggaacacg acctcgtgtg   7980
gcctagaagc gccacactgg tggacgtgat gctgtccaag ggcctggacg tgccctacag   8040
ctgcagagaa ggcgagtgcg gcagctgcgc ctgtactgtg gtggaaggcg acgtggacag   8100
cctgcctagc gccatcctgg acgaagagga tatcgccaat ggctacgtgc tggcctgcca   8160
ggctagaccc aagagcgatc acgtgcggat cgagttcggc agcggcgagg gaagaggcag   8220
cctgctgaca tgcggagatg tggaagagaa ccctggcccc gactacaagg acgacgacga   8280
taagatgcag gactggacta gtgaatgcga cgtgctggtc gtgggctctg gcggaggcgc   8340
tctgacaggc gcttatacag ctgccgccca gggcctgacc accatcgtgc tggaaaagac   8400
cgacagattc ggcggcacca gcgcctactc tggcgcctct atttggctgc ctggcaccca   8460
ggtgcaggaa agagccggac tgcctgacag caccgagaac gccagaacct acctgagagc   8520
cctgctgggc gacgccgaga gcgaaagaca ggacgcctac gtggaaaccg cccctgctgt   8580
ggtggctctg ctggaacaga accccaacat cgagttcgag ttccgggcct tccccgacta   8640
ctacaaggcc gagggcagaa tggacaccgg ccgcagcatc aacccccctgg atctggaccc   8700
tgccgacatc ggcgatctgg ccggaaaagt gcggcccgag ctggaccagg atagaaccgg   8760
acaggatcac gcccctggcc ccatgattgg aggcagagcc ctgatcggca gactgctggc   8820
tgctgtgcag agcaccggaa aggccgagct gagaaccgag agcgtgctga ccagcctgat   8880
cgtggaagat ggcagagtcg tgggcgccga ggtggaatct gggggcgaga cacagcggat   8940
caaggccaac agaggcgtgc tgatggccgc tggcggcatc gagggaaacg ccgagatgag   9000
ggaacaggcc ggaacacccg gcaaggccat ctggtctatg ggccccttcg gagccaatac   9060
cggcgacgcc atctctgccg gaattgccgt gggcggagct accgcactgc tggatcaggc   9120
ctggttctgc cctggcgtgg aacagcctga tggcagcgcc gcctttatgg tgggagtgcg   9180
gggaggactg gtggtggatt ctgccgggga gagatacctg aacgagagcc tgccctacga   9240
ccagttcggc agagctatgg acgcccacga tgacaacggc tccgccgtgc ccagcttcat   9300
gatcttcgac agcagagagg gcggaggcct gcccgccatc tgcatcccta ataccgcccc   9360
agccaagcac ctggaagccg gaacatgggt gggagccgac acactggaag aactggccgc   9420
caagacaggc ctgcctgccg atgctctgag aagcaccgtg gaaaagttca acgacgccgc   9480
caagctgggc gtggacgaag agttccatag aggcgaggac ccctacgacg ccttcttctg   9540
cccacctaat ggcggagcca acgccgccct gaccgccatt gagaacggcc ctttttacgc   9600
cgccagaatc gtgctgagcg acctgggcac aaagggcggc ctcgtgaccg atgtgaacgg   9660
cagagtgctg agagccgacg gcagcgccat tgacggactg tatgccgccg gaaataccag   9720
cgccagcctg agcggcagat tctaccctgg cccaggcgtg ccactgggca ccgctatggt   9780
gttcagctac agagctgccc aggacatggc gaagtaattc tagagagctc aaggtgaatt   9840
ggctagcgac ccagctttct tgtacaaagt tggcattata agaaagcatt gcttatcaat   9900
ttgttgcaac gaacaggtca ctatcagtca aaataaaatc attatttgcc atccagctga   9960
```

-continued

```
tatcccctat agtgagtcgt attacatggt catagctgtt tcctggcagc tctggcccgt  10020
gtctcaaaat ctctgatgtt acattgcaca agataaaaat atatcatcat gaacaataaa  10080
actgtctgct tacataaaca gtaatacaag gggtgttatg agccatattc aacgggaaac  10140
gtcgaggccg cgattaaatt ccaacatgga tgctgattta tatgggtata aatgggctcg  10200
cgataatgtc gggcaatcag gtgcgacaat ctatcgcttg tatgggaagc ccgatgcgcc  10260
agagttgttt ctgaaacatg gcaaaggtag cgttgccaat gatgttacag atgagatggt  10320
cagactaaac tggctgacgg aatttatgcc tcttccgacc atcaagcatt ttatccgtac  10380
tcctgatgat gcatggttac tcaccactgc gatccccgga aaaacagcat tccaggtatt  10440
agaagaatat cctgattcag gtgaaaatat tgttgatgcg ctggcagtgt tcctgcgccg  10500
gttgcattcg attcctgttt gtaattgtcc ttttaacagc gatcgcgtat ttcgtctcgc  10560
tcaggcgcaa tcacgaatga ataacggttt ggttgatgcg agtgattttg atgacgagcg  10620
taatggctgg cctgttgaac aagtctggaa agaaatgcat aaacttttgc cattctcacc  10680
ggattcagtc gtcactcatg gtgatttctc acttgataac cttatttttg acgaggggaa  10740
attaataggt tgtattgatg ttggacgagt cggaatcgca gaccgatacc aggatcttgc  10800
catcctatgg aactgcctcg gtgagttttc tccttcatta cagaaacggc tttttcaaaa  10860
atatggtatt gataatcctg atatgaataa attgcagttt catttgatgc tcgatgagtt  10920
tttctaatca gaattggtta attggttgta acactggcag agcattacgc tgacttgacg  10980
ggacggcgca agctcatgac caaaatccct taacgtgagt tacgcgtcgt tccactgagc  11040
gtcagacccc gtagaaaaga tcaaaggatc ttcttgagat cctttttttc tgcgcgtaat  11100
ctgctgcttg caaacaaaaa aaccaccgct accagcggtg gtttgtttgc cggatcaaga  11160
gctaccaact ctttttccga aggtaactgg cttcagcaga gcgcagatac caaatactgt  11220
tcttctagtg tagccgtagt taggccacca cttcaagaac tctgtagcac cgcctacata  11280
cctcgctctg ctaatcctgt taccagtggc tgctgccagt ggcgataagt cgtgtcttac  11340
cgggttggac tcaagacgat agttaccgga taaggcgcag cggtcgggct gaacgggggg  11400
ttcgtgcaca cagc                                                    11414
```